(12) United States Patent
Armani et al.

(10) Patent No.: US 9,199,980 B2
(45) Date of Patent: Dec. 1, 2015

(54) COMPOUNDS

(71) Applicant: CHIESI FARMACEUTICI S.p.A., Parma (IT)

(72) Inventors: Elisabetta Armani, Parma (IT); Gabriele Amari, Parma (IT); Mauro Riccaboni, Parma (IT); Andrea Rizzi, Parma (IT); Charles Baker-Glenn, Essex (GB); Wesley Blackaby, Essex (GB); Herve' Van de Poel, Essex (GB); Ben Whittaker, Essex (GB)

(73) Assignee: Chiesi Farmaceutici S.p.A., Parma (IT)

( * ) Notice: Subject to any disclaimer, the term of this patent is extended or adjusted under 35 U.S.C. 154(b) by 78 days.

(21) Appl. No.: 14/097,586

(22) Filed: Dec. 5, 2013

(65) Prior Publication Data

US 2014/0155427 A1    Jun. 5, 2014

(30) Foreign Application Priority Data

Dec. 5, 2012  (EP) .................................. 12195725

(51) Int. Cl.
| | |
|---|---|
| *A61K 31/44* | (2006.01) |
| *A61K 9/14* | (2006.01) |
| *C07D 453/02* | (2006.01) |
| *C07D 421/00* | (2006.01) |
| *C07D 401/14* | (2006.01) |
| *C07D 401/12* | (2006.01) |
| *C07D 453/00* | (2006.01) |
| *A61K 31/439* | (2006.01) |
| *A61K 9/00* | (2006.01) |

(52) U.S. Cl.
CPC ............ *C07D 453/02* (2013.01); *C07D 401/12* (2013.01); *C07D 401/14* (2013.01); *C07D 453/00* (2013.01); *A61K 9/0075* (2013.01); *A61K 31/439* (2013.01)

(58) Field of Classification Search
CPC .. C07D 453/02; C07D 401/12; C07D 401/14; A61K 31/439; A61K 9/0075
USPC ........... 546/137, 268.1; 514/305; 424/489, 46
See application file for complete search history.

(56) References Cited

U.S. PATENT DOCUMENTS

| | | | |
|---|---|---|---|
| 7,820,698 | B2 | 10/2010 | Rizzi et al. |
| 7,923,565 | B2 | 4/2011 | Delcanale et al. |
| 7,968,724 | B2 | 6/2011 | Armani et al. |
| 8,203,000 | B2 | 6/2012 | Delcanale et al. |
| 8,383,826 | B2 | 2/2013 | Delcanale et al. |
| 8,440,834 | B2 | 5/2013 | Amari et al. |
| 8,648,204 | B2 | 2/2014 | Amari et al. |
| 2011/0144075 | A1 | 6/2011 | Delcanale et al. |
| 2013/0005716 | A1 | 1/2013 | Armani et al. |
| 2013/0012487 | A1 | 1/2013 | Amari et al. |
| 2013/0079313 | A1 | 3/2013 | Armani et al. |
| 2013/0137648 | A1 | 5/2013 | Delcanale et al. |
| 2013/0324501 | A1 | 12/2013 | Armani et al. |

OTHER PUBLICATIONS

U.S. Appl. No. 14/097,693, filed Dec. 5, 2013, Armani, et al.
U.S. Appl. No. 14/097,397, filed Dec. 5, 2013, Armani, et al.
U.S. Appl. No. 14/097,445, filed Dec. 5, 2013, Armani, et al.
U.S. Appl. No. 14/048,651, filed Oct. 8, 2013, Armani, et al.
U.S. Appl. No. 14/164,527, filed Jan. 27, 2014, Armani, et al.
U.S. Appl. No. 14/560,140, filed Dec. 4, 2014, Amari, et al.
U.S. Appl. No. 14/560,009, filed Dec. 4, 2014, Amari, et al.

*Primary Examiner* — Shengjun Wang
(74) *Attorney, Agent, or Firm* — Oblon, McClelland, Maier & Neustadt, L.L.P.

(57) ABSTRACT

Compounds of formula (I) described herein are inhibitors of the phosphodiesterase 4 (PDE4) enzyme and muscarinic M3 receptor antagonists and are useful for the prevention and/or treatment of diseases of the respiratory tract characterized by airway obstruction.

13 Claims, No Drawings

COMPOUNDS

CROSS REFERENCES TO RELATED APPLICATIONS

This application claims priority to European Patent Application No. 12195725.2 filed on Dec. 5, 2012, which is incorporated herein by reference in its entirety.

BACKGROUND OF THE INVENTION

1. Field of the Invention

The present invention relates to novel compounds which are both inhibitors of the phosphodiesterase 4 (PDE4) enzyme and muscarinic M3 receptor antagonists. The present invention also relates to methods of preparing such a compound, compositions which contain such a compound, and therapeutic uses of such a compound.

2. Discussion of the Background

Chronic obstructive pulmonary disease (COPD) is a respiratory disorder characterized by progressive, not fully reversible, airflow limitation associated with an abnormal pulmonary inflammatory response to noxious particles or gases. For this reason, bronchial relaxation and inflammatory response suppression represent a mechanistic approach to the treatment of COPD that might improve symptoms such as dyspnea, wheezing, chest tightness, cough and mucus secretion, improve health status and reduce exacerbations.

Nowadays, the drug therapy options for COPD fall into 2 general classes: bronchodilators, (β2-adrenoceptor agonists, antimuscarinic agents and methylxanthines) and antiinflammatory agents (glucocorticosteroids and selective phosphodiesterase-4 (PDE4) inhibitors). Bronchodilator drugs are the current mainstay of treatment for symptoms' relief.

As anticholinergic bronchodilators, the efficacy of muscarinic M3 antagonists is based on the fact that the major reversible component of airflow narrowing in COPD patients is the increase of acetylcholine (ACh) released to airway smooth muscle, by the bronchial postganglionic vagal efferent in some pathological conditions. Therefore, compounds that antagonize the action of ACh at muscarinic receptors are able to counteract the bronchoconstriction and thus improve lung function in these patients.

Muscarinic antagonists block the effects of ACh at muscarinic receptors. Currently, there are five known muscarinic receptor subtypes (M1-M5); human airway smooth muscle contains M1, M2, and M3 receptors. M1 receptors facilitate neurotransmission through parasympathetic ganglia and are weakly expressed on submucosal glands in human airways. The M2 receptors are located on the smooth-muscle fibers. Some studies have suggested a small role of M2 mediating the inhibition of airway smooth-muscle relaxation caused by adenylyl cyclase activation by compounds such as beta agonists. In addition, presynaptic M2 receptors are found on postganglionic parasympathetic nerves that project to airway smooth muscle and mucus-producing cells. These presynaptic M2 autoreceptors provide a negative feedback mechanism, which, when stimulated, inhibit further release of ACh. Postsynaptic M3 receptors are known to mediate both contraction of smooth muscle in the respiratory tract and mucus secretion, making them a major target for symptomatic relief of COPD. Consequently, in the airways, the major effects of muscarinic antagonists are bronchodilation and reduction of mucus secretion via blockage of ACh-induced effects in the parasympathetic nervous system.

Given the distribution of muscarinic receptors, systemically available agents that bind to muscarinic receptors outside of the respiratory tract have the potential to produce unwanted side effects such as tachycardia, dry mouth, urinary retention and constipation. Whereas dry mouth is the most common systemic anticholinergic side effect associated with the use of antimuscarinic antagonists as a result of the systemic blockade of M1 and M3 receptors, the most potentially serious systemic effect is tachycardia, which results from the blockade of cardiac M2 receptors.

Inhaled anticholinergic antimuscarinic drugs approved for the treatment of COPD include ipratropium bromide (Atrovent®), oxitropium bromide (Oxivent®) and tiotropium bromide (Spiriva®). Both ipratropium and oxitropium are short-acting agents. In contrast, tiotropium bromide is the only long-acting antimuscarinic agent (LAMA) currently marketed for COPD, proved to be suitable for one-daily administration as a dry powder. Several others newer LAMAs are newly registered for the treatment of COPD, including aclidinium bromide and glycopyrrolate bromide, or are currently in phase III development, including umeclidinium.

Although bronchodilators are quite effective to improve symptoms, they do not address the underlying chronic inflammation or the changes in airway structure. Standard treatment with glucocorticosteroids as antiinflammatory agents has demonstrated limited efficacy. However, among the antiinflammatory agents currently being developed, PDE4 inhibitors proved to be effective in attenuating the responses of various inflammatory cells, through their ability to elevate cAMP levels.

PDE4 is the predominant PDE expressed in neutrophils and T cells, suggesting that PDE4 inhibitors would be effective in controlling inflammation in COPD. Inhibition of PDE4 in inflammatory cells influences various specific responses, such as the production and/or release of pro-inflammatory mediators including cytokines and reactive oxygen species, with a well-documented efficacy in animal models mimicking certain aspects of asthma and COPD, as well as inflammatory bowel disease, atopic dermatitis, psoriasis and rheumatoid arthritis.

The selective PDE4 inhibitor, roflumilast (Daxas®) is an approved phosphodiesterase-4 inhibitor for the treatment of COPD associated with chronic bronchitis and a history of exacerbations. Roflumilast inhibits lung inflammation and emphysema in a smoking model of COPD in mice. In COPD patients, oral roflumilast given over 4 weeks significantly reduces the numbers of neutrophils (by 36%) and CXCL8 concentrations in sputum. In clinical trials roflumilast (500 mg once daily) given over 12 months improved lung function in COPD patients to a small extent but had little effect in reducing exacerbations or improving quality of life. More recently roflumilast has been shown to significantly improve FEV 1 (by approximately 50 ml) and reduce exacerbation (by about 15%) in patients with severe disease who have frequent exacerbations and mucus hypersecretion. Roflumilast provides clinical benefit when added to salmeterol or tiotropium and so may be used as an additional treatment in patients with severe disease.

However, the clinical utility of PDE4 inhibitors has so far been compromised by the occurrence of mechanism-associated side effects, including headache, nausea and emesis, which often limited the maximally tolerated dose. This problem could be overcome by inhaled delivery and designing compounds with a potentially more advantageous therapeutic window.

Since bronchial relaxation and inflammatory response suppression represent a mechanistic approach to the treatment of COPD, the combination of muscarinic M3 antagonism with selective PDE4 inhibition may lead to a new class of drugs, combining both bronchodilating and antiinflammatory properties in one molecule, which may open new perspectives in the management of COPD.

SUMMARY OF THE INVENTION

Accordingly, it is one object of the present invention to provide novel compounds which act as inhibitors of the phosphodiesterase 4 (PDE4) enzyme and as muscarinic M3 receptor antagonists.

It is another object of the present invention to provide novel methods of preparing such a compound.

It is another object of the present invention to provide novel compositions which contain such a compound.

It is another object of the present invention to provide novel methods of treating and/or prevention certain diseases and conditions by administering such a compound.

These and other objects, which will become apparent during the following detailed description, have been achieved by the inventors' discovery of compounds of formula (I):

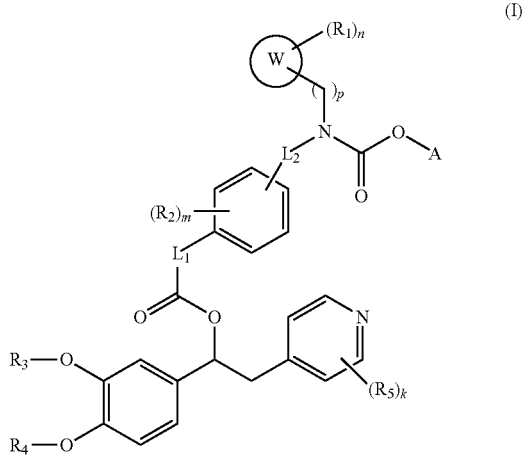

(I)

wherein:

W is selected from an aryl and a heteroaryl;

each $R_1$ is independently hydrogen or is selected in the group consisting of: halogen, $(C_1-C_4)$ alkyl, $(C_1-C_4)$ alkoxy, $(C_1-C_4)$ haloalkyl, hydroxy, —$SO_2NR_6R_7$, —CN, —$NR_8SO_2R_9$, —$NR_6R_7$, —$CONR_6R_7$ and —$NR_8COR_9$ and wherein $(C_1-C_4)$ alkyl is optionally substituted by one or more groups selected from $(C_3-C_7)$ cycloalkyl, hydroxyl, and —$NR_6R_7$ and wherein $(C_1-C_4)$ alkoxy is optionally substituted by one or more halogens or groups $(C_3-C_7)$ cycloalkyl wherein, $R_6$ is hydrogen or $(C_1-C_6)$ alkyl;
$R_7$ is hydrogen or $(C_1-C_6)$ alkyl;
$R_8$ is hydrogen or $(C_1-C_6)$ alkyl;
$R_9$ is hydrogen or $(C_1-C_6)$ alkyl;
n is an integer ranging from 1 to 3;

each $R_2$ is independently hydrogen or is selected in the group consisting of: halogen, $(C_1-C_4)$ alkyl, $(C_1-C_4)$ alkoxy, $(C_1-C_4)$haloalkyl, hydroxy, —$SO_2NR_{10}R_{11}$, —CN, and —$NR_{12}SO_2R_{13}$ and wherein $(C_1-C_4)$ alkyl and $(C_1-C_4)$ alkoxy are optionally substituted by one group $(C_3-C_7)$ cycloalkyl, $R_{10}$ is hydrogen or $(C_1-C_6)$ alkyl;
$R_{11}$ is hydrogen or $(C_1-C_6)$ alkyl;
$R_{12}$ is hydrogen or $(C_1-C_6)$ alkyl;
$R_{13}$ is hydrogen or $(C_1-C_6)$ alkyl;
m is an integer ranging from 1 to 3;
p is zero or 1;

$L_1$ is a group $(CH_2)_t$ wherein t is 0 or an integer ranging from 1 to 3;

$L_2$ is:
$(CH_2)_q$ wherein q is an integer ranging from 1 to 3,
divalent ortho-benzyl (o-$C_6H_4$—$CH_2$—),
divalent meta-benzyl (m-$C_6H_4$—$CH_2$—),
divalent para-benzyl (p-$C_6H_4$—$CH_2$—),
divalent ortho-methyleneoxy-benzyl (o-$CH_2$—O—$C_6H_4$—$CH_2$—),
divalent meta-methyleneoxy-benzyl (m-$CH_2$—O—$C_6H_4$—$CH_2$—), or
divalent para-methylenoxy-benzyl (p-$CH_2$—O—$C_6H_4$—$CH_2$—), wherein the carbon chain atom of the benzyl group is linked to the nitrogen atom and the respective aromatic carbon atom or the methylene carbon atom of the methylene oxy group is linked to the phenyl group;

$R_3$ and $R_4$ are different or the same and are independently selected from the group consisting of:
H;
$(C_3-C_7)$ cycloalkylcarbonyl;
$(C_1-C_6)$ alkyl, optionally substituted by one or more substituents selected from
$(C_3-C_7)$ cycloalkyl and $(C_5-C_7)$ cycloalkenyl;
$(C_1-C_6)$ haloalkyl;
$(C_3-C_7)$ cycloalkyl;
$(C_5-C_7)$ cycloalkenyl;
$(C_2-C_6)$ alkenyl; and
$(C_2-C_6)$ alkynyl;
or $R_3$ and $R_4$, together with the interconnecting atoms, form a 2,2-difluoro-1,3-dioxolane ring of formula (r) fused to the phenyl moiety which bears groups —$OR_3$ and —$OR_4$, wherein asterisks indicate carbon atoms shared with the phenyl ring to which it is attached:

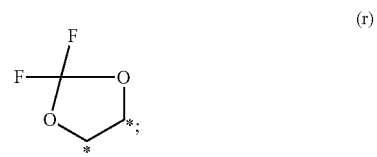

(r)

each $R_5$ is independently selected from the group consisting of: CN, $NO_2$, $CF_3$ and a halogen atom;
k is an integer ranging from 1 to 3; and
A is a nitrogen containing group which may be:
a group (a) which is —$(CH_2)_s$—$NR_{14}R_{15}$ wherein s is an integer ranging from 1 to 4 and $R_{14}$ and $R_{15}$ are independently hydrogen or $(C_1-C_4)$ alkyl; or
a group (b) which is a saturated monocyclic, bicyclic or tricyclic heterocyclic ring system optionally substituted by one or two groups $R_{16}$ which are at each occurrence independently $(C_1-C_4)$ alkyl or benzyl;
their N-oxides on the pyridine ring, deuterated derivatives, and pharmaceutically acceptable salts, and solvates thereof The present invention further provides the corresponding N-oxides on the pyridine ring of compounds of formula (I).

The present invention further provides the corresponding deuterated derivatives of compounds of formula (I) wherein at least one hydrogen atom is substituted by corresponding atoms of deuterium.

The present invention also provides pharmaceutically acceptable salts and/or solvates thereof.

The term "pharmaceutically acceptable salts", as used herein, refers to derivatives of compounds of formula (I) or of their corresponding N-oxides on the pyridine ring wherein the parent compound is suitably modified by converting any of the free acid or basic group, if present, into the corresponding addition salt with any base or acid conventionally intended as being pharmaceutically acceptable. Suitable examples of said salts may thus include mineral or organic acid addition salts of basic residues such as amino groups, as well as mineral or organic acid residues such as carboxylic groups.

Cations of inorganic bases which can be suitably used to prepare salts within the invention comprise ions of alkali or alkaline earth metals such as potassium, sodium, calcium or magnesium. Those obtained by reacting the main compound, functioning as a base, with an inorganic or organic acid to form a salt comprise, for example, salts of hydrochloric acid, hydrobromic acid, sulfuric acid, phosphoric acid, acetic acid, methane sulfonic acid, camphor sulfonic acid, oxalic acid, maleic acid, fumaric acid, succinic acid and citric acid.

Those skilled in the art of organic chemistry will appreciate that many organic compounds can form complexes with solvents in which they are reacted or from which they are precipitated or crystallized. These complexes are known as "solvates." Pharmaceutically acceptable solvates of compound of the invention are within the scope of the invention.

Included within the scope of the present invention are also polymorphs and crystalline forms of compounds of formula (I), of their N-oxides on the pyridine ring, or of pharmaceutically acceptable salts, or solvates thereof Hereinafter, compounds of formula (I), (IA), (IB), (IC), (ID), (IE), (Ia), (Ib), (Ic), (Id) and (I)', corresponding N—Oxides on the pyridine ring, enantiomers, diastereoisomers thereof, their pharmaceutically acceptable salts and solvates, and polymorphs or crystalline forms thereof defined in any aspect of the invention (except intermediate compounds described in the chemical processes) are referred to as "compounds of the invention."

The present invention further provides processes for the preparation of compounds of the invention.

The present invention also provides pharmaceutical compositions of compounds of the invention either alone or in combination with another active ingredient, in admixture with one or more pharmaceutically acceptable carriers.

In a further aspect, the present invention provides the use of the compounds of the invention as a medicament.

In another aspect, the present invention provides the use of the compounds of the invention for the manufacture of a medicament.

In particular the present invention provides the use of the compounds of the invention for the prevention and/or treatment of any disease wherein an inhibition of PDE4 activity along with muscarinic M3 receptor antagonism is desirable.

In particular the compounds of the invention alone or combined with other active ingredients may be administered for the prevention and/or treatment of a disease of the respiratory tract characterized by airway obstruction such as asthma and COPD. In one embodiment, the compounds of the invention may be administered for the prevention and/or treatment of COPD.

In a further aspect the present invention provides the use of compounds of the invention for the preparation of a medicament for the prevention and/or treatment of any disease wherein an inhibition of PDE4 activity along with muscarinic M3 receptor antagonism is desirable.

Moreover the present invention provides a method for prevention and/or treatment of any disease wherein an inhibition of PDE4 activity along with muscarinic M3 receptor antagonism is desirable, said method comprises administering to a patient in need of such treatment a therapeutically effective amount of a compound of the invention.

A further aspect of the present invention provides a suitable inhalation device, comprising a pharmaceutical composition of a compound of the invention, which may be respectively selected from a single- or multi-dose dry powder inhaler, a pressurized metered dosed inhaler, or a nebulizer and in particular a soft mist nebulizer.

A further aspect of the present invention provides a kit comprising a pharmaceutical composition of a compound of the present invention either alone or in combination with one or more active ingredient and a device which may be a single- or multi-dose dry powder inhaler, a metered dose inhaler, or a nebulizer.

DETAILED DESCRIPTION OF THE PREFERRED EMBODIMENTS

The term "halogen atoms" as used herein includes fluorine, chlorine, bromine, and iodine, preferably chlorine.

As used herein, the term "$(C_1-C_x)$ alkyl" where x is an integer greater than 1, refers to straight-chained and branched alkyl groups wherein the number of constituent carbon atoms is in the range 1 to x. Particular alkyl groups are methyl, ethyl, n-propyl, isopropyl, and t-butyl.

By analogy, the term "$(C_1-C_x)$alkylene" refers to a divalent $(C_1-C_x)$alkyl radical, wherein $(C_1-C_x)$alkyl is as above defined.

The term "$(C_1-C_x)$ alkoxy" where x is an integer greater than 1, refers to straight-chained and branched alkoxy groups wherein the number of constituent carbon atoms is in the range 1 to x. Particular alkoxy groups are methoxy, ethoxy, n-propoxy, isopropoxy, and t-butoxy.

The expressions "$(C_1-C_x)$haloalkyl" refer to the above defined "$(C_1-C_x)$alkyl" groups wherein one or more hydrogen atoms are replaced by one or more halogen atoms, which can be the same or different from each other. Non-limiting examples of said $(C_1-C_6)$haloalkyl groups may thus include halogenated, poly-halogenated, and fully halogenated alkyl groups wherein all of the hydrogen atoms are replaced by halogen atoms, e.g. trifluoromethyl or difluoro methyl groups.

The term "$(C_3-C_y)$ cycloalkyl" where y is an integer greater than or equal to 3 refers to saturated cyclic hydrocarbon groups containing from 3 to y ring carbon atoms. Non-limiting examples include cyclopropyl, cyclobutyl, cyclopentyl, cyclohexyl, and cycloheptyl.

The derived expression "$(C_3-C_y)$heterocycloalkyl" refers to monocyclic $(C_3-C_y)$cycloalkyl groups, in which at least one ring carbon atom is replaced by a heteroatom (e.g. N, NH, S or O). Non-limiting examples of $(C_3-C_y)$heterocycloalkyl are represented by: pyrrolidinyl, thiazolidinyl, piperazinyl, piperidinyl, morpholinyl, thiomorpholinyl, azetidinyl.

By analogy, the term "$(C_3-C_y)$heterocycloalkylene", refers to a divalent $(C_3-C_y)$heterocycloalkyl radical, wherein $(C_3-C_y)$heterocycloalkyl is as above defined.

The expression "$(C_3-C_y)$cycloalkylcarbonyl" refers to $(C_3-C_y)$cycloalkylCO— groups wherein the group "$(C_3-C_y)$cycloalkyl" has the meaning above defined.

The term "$(C_2-C_6)$alkenyl" refers to straight or branched, conjugated or non-conjugated, carbon chains with one or more double bonds, in cis or trans configuration, wherein the number atoms is in the range 2 to 6.

The term "$(C_5-C_z)$ cycloalkenyl" where z is an integer greater than or equal to 5 refers to cyclic hydrocarbon groups containing from 5 to z ring carbon atoms and one or more double bonds.

The term "$(C_2-C_6)$alkynyl" refers to straight or branched carbon chains with one or more triple bonds wherein the number atoms is in the range 2 to 6.

The term "aryl" refers to mono or bi-cyclic systems which have 6 to 10 ring atoms, wherein at least one ring is aromatic.

The expression "heteroaryl" refers to mono or bi-cyclic systems with 5 to 11 ring atoms, in which at least one ring is aromatic and in which at least one ring atom is a heteroatom (e.g. N, NH, S or O).

Non-limiting examples of suitable aryl or 5 or 6-membered heteroaryl monocyclic systems include, for instance, benzene (phenyl), thiophene (thiophenyl), pyrrole (pyrrolyl), pyrazole (pyrazolyl), imidazole (imidazolyl), triazole (triazolyl), tetrazole (tetrazolyl), isoxazole (isoxaolyl), oxazole (oxazolyl), isothiazole (isothiazolyl), thiazole (thiazolyl), pyridine (pyridinyl), furan (furanyl) derived radicals, and the like.

Non-limiting examples of suitable aryl or heteroaryl bicyclic systems include naphthalene (naphthyl), biphenylene (biphenylenyl), purine (purinyl), pteridine (pteridinyl), benzimidazole (benzimidazolyl), benzotriazole (benzotriazolyl), quinoline (quinolinyl), isoquinoline (isoquinolinyl), indole (indolyl), isoindole (isoindolyl), indazole (indazolyl), benzothiophene (benzthiophenyl), dihydrobenzo dioxin, dihydrobenzo dioxepin, benzo oxazin radicals, and the like.

As used herein, the expression "heterocyclic ring system" refers to optionally substituted mono- bi- or tri-cyclic ring systems which may be saturated, partially unsaturated or unsaturated, such as ($C_3$-$C_7$) heterocycloalkyl or heteroaryl, having 5 to 11 ring atoms in which at least one ring atom is a heteroatom (e.g. N, S or O). Non-limiting examples of "heterocyclic ring system" are represented by: pyrrolidinyl, imidazolidinyl, piperazinyl, piperidinyl, quinuclidinyl, 8-azabicyclo[3.2.1]octanyl or dehydroxylate scopine radicals all optionally substituted by ($C_1$-$C_4$) alkyl or benzyl on a nitrogen atom.

The phrase "the carbon chain atom of the benzyl group is linked to the nitrogen atom" means that the —$CH_2$— group linked to the phenyl ring of —$C_6H_4$—$CH_2$— or of —$CH_2$—O—$C_6H_4$—$CH_2$— is bonded to the nitrogen atom in formula (I) or (IE).

The phrase "the respective aromatic carbon atom or the methylene carbon atom is linked to the phenyl group" means that, in the case of —$C_6H_4$—$CH_2$—, an aromatic carbon atom is bonded to the phenyl group of compound of formula (I) or (IE), and in the case of —$CH_2$—O—$C_6H_4$—$CH_2$—, the methylene group of —$CH_2$—O—$C_6H_4$—$CH_2$— is bonded to the phenyl group of compound of formula (I) or (IE).

The present invention is directed to a class of compounds which act both as inhibitors of the phosphodiesterase 4 (PDE4) enzyme and as muscarinic M3 receptor antagonists.

The present invention relates to derivatives of general formula (I), N-oxides on the pyridine ring, deuterated derivatives and pharmaceutically acceptable salts and solvates thereof:

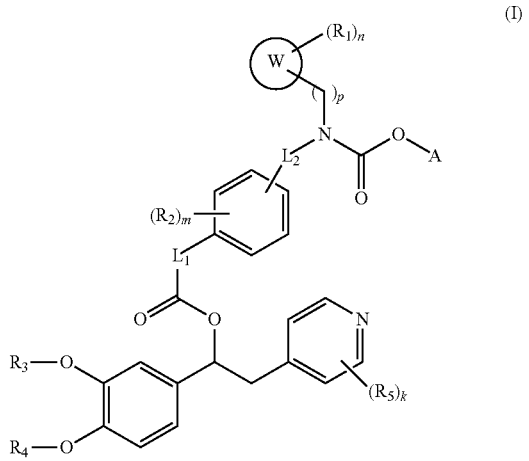

(I)

wherein $R_1$, $R_2$, $R_3$, $R_4$, $R_5$, A, W, $L_1$, $L_2$, m, n, p, and k are as above defined.

It will be apparent to those skilled in the art that compounds of general formula (I) contain at least one stereogenic center, namely represented by the carbon atom (1) and therefore exist as optical stereoisomers:

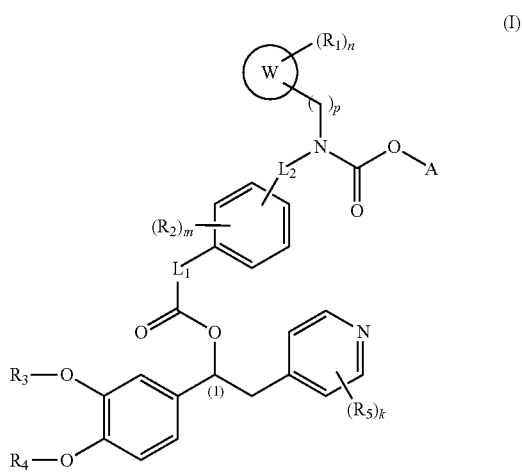

(I)

Since the compounds according to the present invention have at least one stereogenic center, they may accordingly exist as enantiomers. When the compounds according to the invention possess two or more stereogenic centers, they may additionally exist as diastereoisomers. It is to be understood that all such isomers and mixtures thereof in any proportion are encompassed within the scope of the present invention.

In a preferred embodiment, the present invention is directed to compounds of formula (I)', which are compounds of formula (I) as above defined where the absolute configuration of carbon (1) is that shown herebelow:

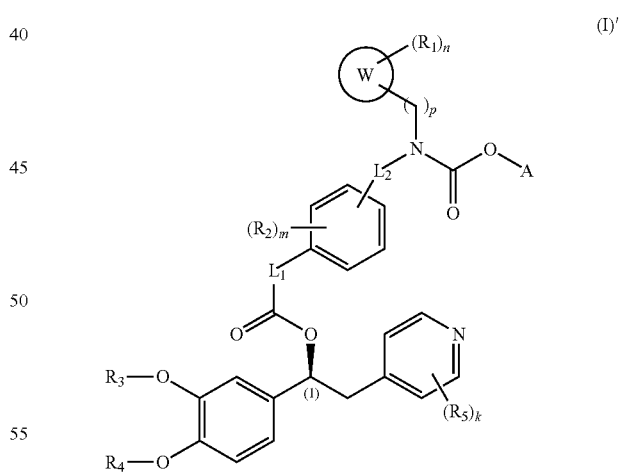

(I)'

The absolute configuration for carbon (1) is assigned on the basis of Cahn-Ingold-Prelog nomenclature based on groups' priorities.

In one preferred embodiment, for compounds of formula (I), absolute configuration at carbon (1) is (S).

When the compounds of formula (I) possess a second stereogenic center, they exist as at least four diastereoisomers; the four diastereoisomers thereof are comprised within the scope of the present invention.

In one embodiment, when A is a group of formula (i), as below defined, compounds of formula (I) may exist as at least four diastereoisomers (Ia), (Ib), (Ic), and (Id) herebelow reported, which are comprised within the scope of the present invention:

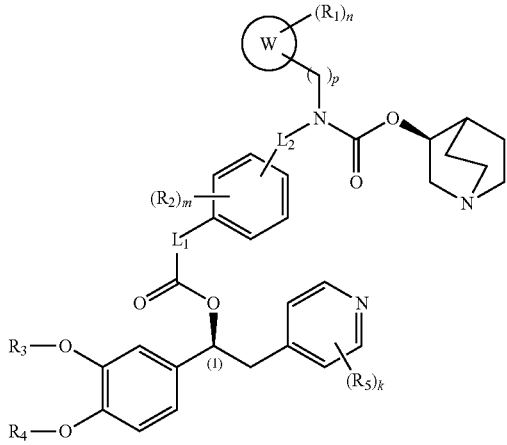

Ia

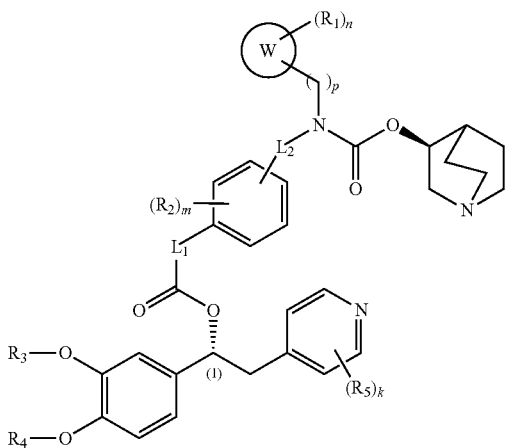

Ib

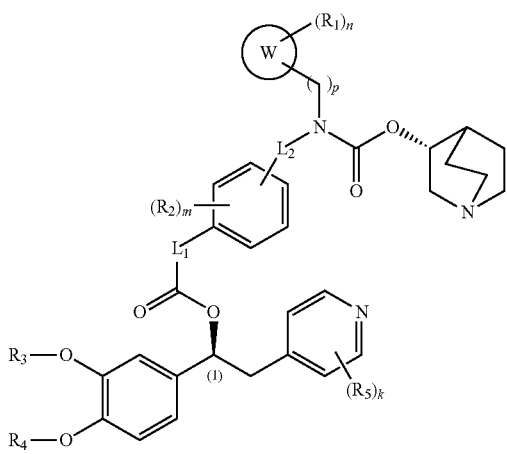

Ic

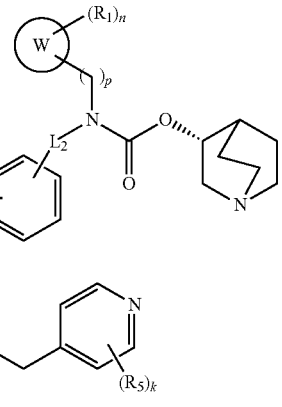

Id

In one embodiment, compounds of formula (Ic) are provided as above reported.

It is to be understood that all preferred groups or embodiments described herebelow and hereabove for compounds of formula (I) may be combined among each other and apply to compounds of formula (IA), (IB), (IC), (ID), (Ia), (Ib), (Ic), (Id), and (I)' as well mutatis mutandis.

In one embodiment, the invention provides compounds of formula (IA), which are N-oxides on the pyridine ring of compounds of formula (I), deuterated derivatives and pharmaceutically acceptable salts and solvate thereof:

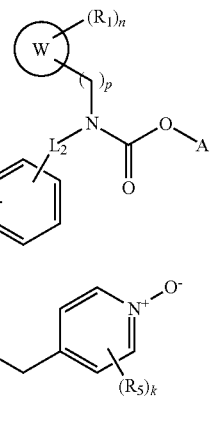

(IA)

wherein $R_1$, $R_2$, $R_3$, $R_4$, $R_5$, A, W, $L_1$, $L_2$, m, n, p, and k are as defined above.

In one embodiment, 4-pyridinyl ring has two $R_5$ substituents which are halogen atom. In a further preferred embodiment, such $R_5$ substituents are two chlorine atoms at positions 3 and 5 of the pyridine ring.

In one embodiment, $R_4$ is selected from ($C_1$-$C_6$) haloalkyl and ($C_1$-$C_6$) alkyl.

In one embodiment, $R_3$ is selected from ($C_3$-$C_7$) cycloalkyl and ($C_1$-$C_6$) alkyl optionally substituted by ($C_3$-$C_7$) cycloalkyl.

In another embodiment, $R_3$ and $R_4$, together with the interconnecting atoms, form a 2,2-difluoro-1,3-dioxolane ring of formula (r) fused to the phenyl moiety which bears groups —OR₃ and —OR₄, wherein asterisks indicate carbon atoms shared with the phenyl ring:

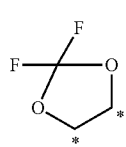

(r)

In a further embodiment, R₄ is (C₁-C₆) haloalkyl and R₃ is (C₁-C₆) alkyl which is substituted by (C₃-C₇) cycloalkyl.

In a still further embodiment, R₃ is (C₁-C₆) alkyl and R₄ is (C₁-C₆) alkyl.

In one embodiment, compounds of general formula (I) are provided wherein the 4-pyridinyl ring is substituted at the 3 and 5 positions with two atoms of chlorine, according to formula (IB)

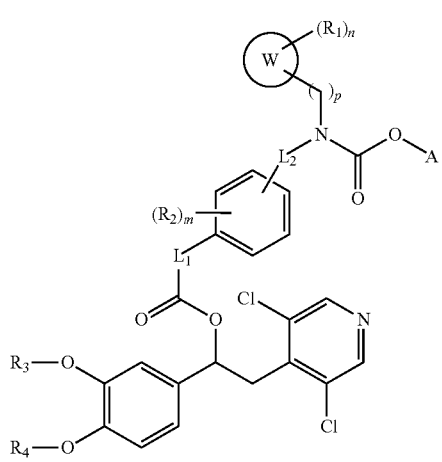

(IB)

wherein $R_1, R_2, R_3, R_4, A, W, L_1, L_2$, m, n, and p are as above defined; and the corresponding N-oxides on the pyridine ring, deuterated derivatives, and pharmaceutically acceptable salts and solvates thereof In one embodiment, another group of compounds of formula (I) is provided which is that shown below according to formula (IC):

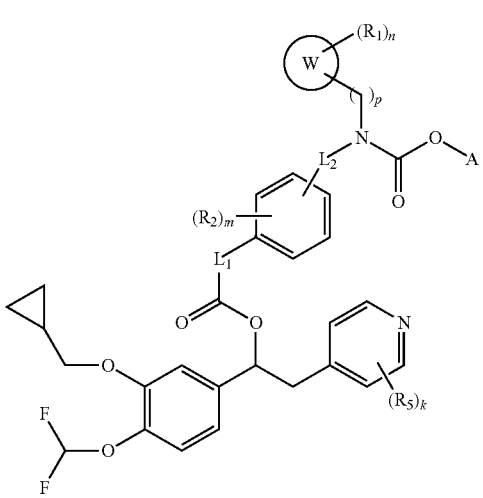

(IC)

wherein $R_1, R_2, R_5, A, W, L_1, L_2$, m, n, p, and k are as above defined; and the corresponding N-oxides on the pyridine ring, and pharmaceutically acceptable salts and solvates thereof.

In a still further embodiment, a group of compounds of formula (I) is provided which is shown below according to formula (ID):

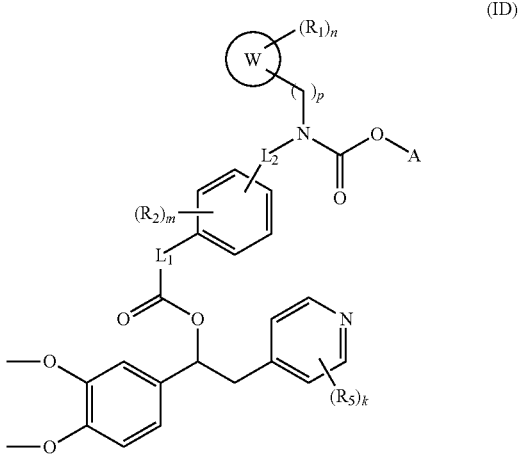

(ID)

wherein $R_1, R_2, R_5, A, W, L_1, L_2$, m, n, p, and k are as above defined; and the corresponding N-oxides on the pyridine ring, and pharmaceutically acceptable salts and solvates thereof.

In a still further embodiment, a group of compounds of formula (I) is provided which is shown below according to formula (IE):

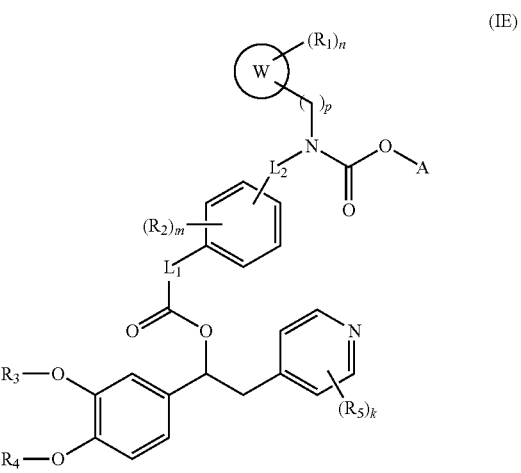

(IE)

wherein $L_2$ and $L_1$ are located in the ortho, meta or para position on the phenyl ring they are linked to, $L_1$ is selected from a group $(CH_2)_t$ wherein t is 0 or an integer ranging from 1 to 3;

$L_2$ is:

$(CH_2)_q$ wherein q is an integer ranging from 1 to 3, divalent meta-benzyl (m-C₆H₄—CH₂—), divalent para-benzyl (p-C₆H₄—CH₂—), divalent meta-methyleneoxy-benzyl (m-CH₂—O—C₆H₄—CH₂—), or divalent para-methyleneoxy-benzyl (p-CH₂—O—C₆H₄—CH₂—), wherein the carbon chain atom of the benzyl group is linked to the nitrogen atom and the respective aromatic carbon atom or the methylene carbon atom of the methylene oxy group is linked to the phenyl group;

and wherein $R_1, R_2, R_3, R_4, R_5, A, W$, m, n, p, and k are as above defined; and the corresponding N-oxides on the pyridine ring, and pharmaceutically acceptable salts and solvates thereof.

In one embodiment, A is a group (b) represented by a group of formula (i), (ii), (iii) or (iv):

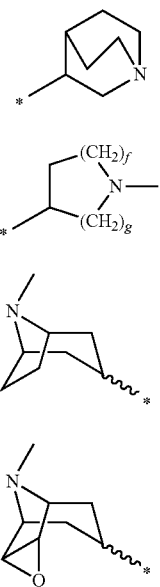

wherein
f=1, 2 or 3;
g=1, 2 or 3.
In another embodiment, A is a group (b) represented by a group of formula (i):

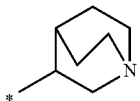

According to one embodiment, the present invention provides a compound selected in the list consisting of:
(1S)-2-(3,5-dichloro-1-oxido-pyridin-1-ium-4-yl)-1-(3,4-dimethoxyphenyl)ethyl]3-[(4-fluoro-N-[(3R)-quinuclidin-3-yl]oxycarbonyl-anilino)methyl]benzoate;
[(1S)-2-(3,5-dichloro-1-oxido-pyridin-1-ium-4-yl)-1-(3,4-dimethoxyphenyl)ethyl]3-[(2-fluoro-N-[(3R)-quinuclidin-3-yl]oxycarbonyl-anilino)methyl]benzoate;
[(1S)-2-(3,5-dichloro-1-oxido-pyridin-1-ium-4-yl)-1-(3,4-dimethoxyphenyl)ethyl]3-[(3-fluoro-N-[(3R)-quinuclidin-3-yl]oxycarbonyl-anilino)methyl]benzoate;
[(1S)-2-(3,5-dichloro-1-oxido-pyridin-1-ium-4-yl)-1-(3,4-dimethoxyphenyl)ethyl]3-[(2-methoxy-N-[(3R)-quinuclidin-3-yl]oxycarbonyl-anilino)methyl]benzoate;
[(1S)-2-(3,5-dichloro-1-oxido-pyridin-1-ium-4-yl)-1-(3,4-dimethoxyphenyl)ethyl]3-[(3-methoxy-N-[(3R)-quinuclidin-3-yl]oxycarbonyl-anilino)methyl]benzoate;
[(1S)-2-(3,5-dichloro-1-oxido-pyridin-1-ium-4-yl)-1-(3,4-dimethoxyphenyl)ethyl]3-[(4-methoxy-N-[(3R)-quinuclidin-3-yl]oxycarbonyl-anilino)methyl]benzoate;
[(1S)-2-(3,5-dichloro-1-oxido-pyridin-1-ium-4-yl)-1-(3,4-dimethoxyphenyl)ethyl]4-[(N-[(3R)-quinuclidin-3-yl]oxycarbonylanilino)methyl]benzoate;
[(1S)-2-(3,5-dichloro-1-oxido-pyridin-1-ium-4-yl)-1-(3,4-dimethoxyphenyl)ethyl]4-[(2-fluoro-N-[(3R)-quinuclidin-3-yl]oxycarbonyl-anilino)methyl]benzoate;
[(1S)-2-(3,5-dichloro-1-oxido-pyridin-1-ium-4-yl)-1-(3,4-dimethoxyphenyl)ethyl]4-[(4-fluoro-N-[(3R)-quinuclidin-3-yl]oxycarbonyl-anilino)methyl]benzoate;
[(1S)-2-(3,5-dichloro-1-oxido-pyridin-1-ium-4-yl)-1-(3,4-dimethoxyphenyl)ethyl]4-[(2-methoxy-N-[(3R)-quinuclidin-3-yl]oxycarbonyl-anilino)methyl]benzoate;
[(1S)-2-(3,5-dichloro-1-oxido-pyridin-1-ium-4-yl)-1-(3,4-dimethoxyphenyl)ethyl]4-[(3-methoxy-N-[(3R)-quinuclidin-3-yl]oxycarbonyl-anilino)methyl]benzoate;
[(1S)-2-(3,5-dichloro-1-oxido-pyridin-1-ium-4-yl)-1-(3,4-dimethoxyphenyl)ethyl]4-[(2-methyl-N-[(3R)-quinuclidin-3-yl]oxycarbonyl-anilino)methyl]benzoate;
[(1S)-2-(3,5-dichloro-1-oxido-pyridin-1-ium-4-yl)-1-(3,4-dimethoxyphenyl)ethyl]3-[(N-[(3R)-quinuclidin-3-yl]oxycarbonylanilino)methyl]benzoate;
[(1R)-2-(3,5-dichloro-1-oxido-pyridin-1-ium-4-yl)-1-(3,4-dimethoxyphenyl)ethyl]3-[(N-[(3R)-quinuclidin-3-yl]oxycarbonylanilino)methyl]benzoate;
[(1S)-2-(3,5-dichloro-1-oxido-pyridin-1-ium-4-yl)-1-(3,4-dimethoxyphenyl)ethyl]4-[(3-fluoro-N-[(3R)-quinuclidin-3-yl]oxycarbonyl-anilino)methyl]benzoate;
[(1R)-2-(3,5-dichloro-1-oxido-pyridin-1-ium-4-yl)-1-(3,4-dimethoxyphenyl)ethyl]4-[(3-fluoro-N-[(3R)-quinuclidin-3-yl]oxycarbonyl-anilino)methyl]benzoate;
[(1S)-2-(3,5-dichloro-1-oxido-pyridin-1-ium-4-yl)-1-(3,4-dimethoxyphenyl)ethyl]4-[(4-methoxy-N-[(3R)-quinuclidin-3-yl]oxycarbonyl-anilino)methyl]benzoate;
[(1R)-2-(3,5-dichloro-1-oxido-pyridin-1-ium-4-yl)-1-(3,4-dimethoxyphenyl)ethyl]4-[(4-methoxy-N-[(3R)-quinuclidin-3-yl]oxycarbonyl-anilino)methyl]benzoate;
[2-(3,5-dichloro-1-oxido-pyridin-1-ium-4-yl)-1-(3,4-dimethoxyphenyl)ethyl]3-[(N-[(3R)-quinuclidin-3-yl]oxycarbonylanilino)methyl]benzoate;
[(1S)-2-(3,5-dichloro-1-oxido-pyridin-1-ium-4-yl)-1-(3,4-dimethoxyphenyl)ethyl]3-bromo-5-[(2-fluoro-N-[(3R)-quinuclidin-3-yl]oxycarbonyl-anilino)methyl]benzoate;
[(1S)-2-(3,5-dichloro-1-oxido-pyridin-1-ium-4-yl)-1-(3,4-dimethoxyphenyl)ethyl]2-[4-[(N-[(3R)-quinuclidin-3-yl]oxycarbonylanilino)methyl]phenyl]acetate;
[(1S)-1-[3-(cyclopropylmethoxy)-4-(difluoromethoxy)phenyl]-2-(3,5-dichloro-1-oxido-pyridin-1-ium-4-yl)ethyl]2-[4-[(N-[(3R)-quinuclidyl]oxycarbonylanilino)-methyl]phenyl]acetate;
[(1S)-2-(3,5-dichloro-1-oxido-pyridin-1-ium-4-yl)-1-(3,4-dimethoxyphenyl)ethyl]2-[4-[(2-fluoro-N-[(3R)-quinuclidin-3-yl]oxycarbonyl-anilino)methyl]phenyl]acetate;
[(1S)-2-(3,5-dichloro-1-oxido-pyridin-1-ium-4-yl)-1-(3,4-dimethoxyphenyl)ethyl]3-[(3-chloro-N-[(3R)-quinuclidin-3-yl]oxycarbonyl-anilino)methyl]benzoate;
[(1S)-2-(3,5-dichloro-1-oxido-pyridin-1-ium-4-yl)-1-(3,4-dimethoxyphenyl)ethyl]3-[(2,3-difluoro-N-[(3R)-quinuclidin-3-yl]oxycarbonyl-anilino)methyl]benzoate;
[(1S)-2-(3,5-dichloro-1-oxido-pyridin-1-ium-4-yl)-1-(3,4-dimethoxyphenyl)ethyl]3-[(2,5-difluoro-N-[(3R)-quinuclidin-3-yl]oxycarbonyl-anilino)methyl]benzoate;
[(1S)-2-(3,5-dichloro-1-oxido-pyridin-1-ium-4-yl)-1-(3,4-dimethoxyphenyl)ethyl]3-[(3-methyl-N-[(3R)-quinuclidin-3-yl]oxycarbonyl-anilino)methyl]benzoate;
[(1S)-2-(3,5-dichloro-1-oxido-pyridin-1-ium-4-yl)-1-(3,4-dimethoxyphenyl)ethyl]3-[[N-[(3R)-quinuclidin-3-yl]oxycarbonyl-3-(trifluoromethyl)anilino]methyl]benzoate;
[(1S)-2-(3,5-dichloro-1-oxido-pyridin-1-ium-4-yl)-1-(3,4-dimethoxyphenyl)ethyl]3-[(2-methyl-N-[(3R)-quinuclidin-3-yl]oxycarbonyl-anilino)methyl]benzoate;
[(1S)-2-(3,5-dichloro-1-oxido-pyridin-1-ium-4-yl)-1-(3,4-dimethoxyphenyl)ethyl]3-[(3-cyano-N-[(3R)-quinuclidin-3-yl]oxycarbonyl-anilino)methyl]benzoate;

[(1S)-2-(3,5-dichloro-1-oxido-pyridin-1-ium-4-yl)-1-[4-(difluoromethoxy)-3-methoxy-phenyl]ethyl]3-[(2-fluoro-N-[(3R)-quinuclidin-3-yl]oxycarbonyl-anilino)methyl]benzoate;

[(1S)-2-(3,5-dichloro-1-oxido-pyridin-1-ium-4-yl)-1-[4-(difluoromethoxy)-3-isopropoxy-phenyl]ethyl]3-[(2-fluoro-N-[(3R)-quinuclidin-3-yl]oxycarbonyl-anilino)methyl]benzoate;

[(1S)-2-(3,5-dichloro-1-oxido-pyridin-1-ium-4-yl)-1-[4-(difluoromethoxy)-3-ethoxy-phenyl]ethyl]3-[(2-fluoro-N-[(3R)-quinuclidin-3-yl]oxycarbonyl-anilino)methyl]benzoate;

[(1S)-2-(3,5-dichloro-1-oxido-pyridin-1-ium-4-yl)-1-[4-(difluoromethoxy)-3-methoxy-phenyl]ethyl]3-[(3-fluoro-N-[(3R)-quinuclidin-3-yl]oxycarbonyl-anilino)methyl]benzoate;

[(1S)-2-(3,5-dichloro-1-oxido-pyridin-1-ium-4-yl)-1-[4-(difluoromethoxy)-3-isopropoxy-phenyl]ethyl]3-[(3-fluoro-N-[(3R)-quinuclidin-3-yl]oxycarbonyl-anilino)methyl]benzoate;

[(1S)-2-(3,5-dichloro-1-oxido-pyridin-1-ium-4-yl)-1-[4-(difluoromethoxy)-3-ethoxy-phenyl]ethyl]3-[(3-fluoro-N-[(3R)-quinuclidin-3-yl]oxycarbonyl-anilino)methyl]benzoate;

[(1S)-2-(3,5-dichloro-1-oxido-pyridin-1-ium-4-yl)-1-[4-(difluoromethoxy)-3-methoxy-phenyl]ethyl]4-[(2-methoxy-N-[(3R)-quinuclidin-3-yl]oxycarbonyl-anilino)methyl]benzoate;

[(1S)-2-(3,5-dichloro-1-oxido-pyridin-1-ium-4-yl)-1-[4-(difluoromethoxy)-3-isopropoxy-phenyl]ethyl]4-[(2-methoxy-N-[(3R)-quinuclidin-3-yl]oxycarbonyl-anilino)methyl]benzoate;

[(1S)-2-(3,5-dichloro-1-oxido-pyridin-1-ium-4-yl)-1-[4-(difluoromethoxy)-3-ethoxy-phenyl]ethyl]4-[(2-methoxy-N-[(3R)-quinuclidin-3-yl]oxycarbonyl-anilino)methyl]benzoate;

[(1S)-2-(3,5-dichloro-1-oxido-pyridin-1-ium-4-yl)-1-(3,4-dimethoxylphenyl)ethyl]4-[(2,3-difluoro-N-[(3R)-quinuclidin-3-yl]oxycarbonyl-anilino)methyl]benzoate;

[(1S)-2-(3,5-dichloro-1-oxido-pyridin-1-ium-4-yl)-1-(3,4-dimethoxylphenyl)ethyl]4-[(2,4-difluoro-N-[(3R)-quinuclidin-3-yl]oxycarbonyl-anilino)methyl]benzoate;

[(1S)-2-(3,5-dichloro-1-oxido-pyridin-1-ium-4-yl)-1-(3,4-dimethoxylphenyl)ethyl]4-[(2,5-difluoro-N-[(3R)-quinuclidin-3-yl]oxycarbonyl-anilino)methyl]benzoate;

[(1S)-2-(3,5-dichloro-1-oxido-pyridin-1-ium-4-yl)-1-(3,4-dimethoxylphenyl)ethyl]4-[(2,5-difluoro-N-[(3R)-quinuclidin-3-yl]oxycarbonyl-anilino)methyl]benzoate;

[(1S)-2-(3,5-dichloro-1-oxido-pyridin-1-ium-4-yl)-1-(3,4-dimethoxylphenyl)ethyl]4-[(3-methyl-N-[(3R)-quinuclidin-3-yl]oxycarbonyl-anilino)methyl]benzoate;

[(1S)-2-(3,5-dichloro-1-oxido-pyridin-1-ium-4-yl)-1-(3,4-dimethoxylphenyl)ethyl]4-[(3-methyl-N-[(3R)-quinuclidin-3-yl]oxycarbonyl-anilino)methyl]benzoate;

[(1S)-2-(3,5-dichloro-1-oxido-pyridin-1-ium-4-yl)-1-(3,4-dimethoxylphenyl)ethyl]4-[(3-cyano-N-[(3R)-quinuclidin-3-yl]oxycarbonyl-anilino)methyl]benzoate;

[(1S)-2-(3,5-dichloro-1-oxido-pyridin-1-ium-4-yl)-1-(3,4-dimethoxylphenyl)ethyl]2-fluoro-4-[(2-fluoro-N-[(3R)-quinuclidin-3-yl]oxycarbonyl-anilino)methyl]benzoate;

[(1S)-2-(3,5-dichloro-1-oxido-pyridin-1-ium-4-yl)-1-(3,4-dimethoxylphenyl)ethyl]2-fluoro-4-[(N-[(3R)-quinuclidin-3-yl]oxycarbonylanilino)methyl]benzoate;

[(1S)-2-(3,5-dichloro-1-oxido-pyridin-1-ium-4-yl)-1-(3,4-dimethoxylphenyl)ethyl]3-fluoro-5-[(2-fluoro-N-[(3R)-quinuclidin-3-yl]oxycarbonyl-anilino)methyl]benzoate;

[(1S)-2-(3,5-dichloro-1-oxido-pyridin-1-ium-4-yl)-1-(3,4-dimethoxylphenyl)ethyl]3-fluoro-4-[(2-fluoro-N-[(3R)-quinuclidin-3-yl]oxycarbonyl-anilino)methyl]benzoate;

[(1S)-2-(3,5-dichloro-1-oxido-pyridin-1-ium-4-yl)-1-[4-(difluoromethoxy)-3-(trideuteriomethoxy)phenyl]ethyl]3-[(2-fluoro-N-[(3R)-quinuclidin-3-yl]oxycarbonyl-anilino)methyl]benzoate;

[(1S)-2-(3,5-dichloro-1-oxido-pyridin-1-ium-4-yl)-1-[4-(difluoromethoxy)-3-(trideuteriomethoxy)phenyl]ethyl]3-[(3-fluoro-N-[(3R)-quinuclidin-3-yl]oxycarbonyl-anilino)methyl]benzoate;

[(1S)-2-(3,5-dichloro-1-oxido-pyridin-1-ium-4-yl)-1-[4-(difluoromethoxy)-3-(trideuteriomethoxy)phenyl]ethyl]4-[(2-methoxy-N-[(3R)-quinuclidin-3-yl]oxycarbonyl-anilino)methyl]benzoate;

[(1S)-2-(3,5-dichloro-1-oxido-pyridin-1-ium-4-yl)-1-(3,4-dimethoxylphenyl)-ethyl]4-[[2-pyridyl-[(3R)-quinuclidin-3-yl]oxycarbonyl-amino]methyl]benzoate;

[(1S)-1-[3-(cyclopropylmethoxy)-4-(difluoromethoxy)phenyl]-2-(3,5-dichloro-1-oxido-pyridin-1-ium-4-yl)ethyl]4-[[2-pyridyl-[(3R)-quinuclidin-3-yl]oxycarbonyl-amino]methyl]benzoate;

[(1S)-2-(3,5-dichloro-1-oxido-pyridin-1-ium-4-yl)-1-(3,4-dimethoxylphenyl)ethyl]4-[[3-pyridyl-[(3R)-quinuclidin-3-yl]oxycarbonyl-amino]methyl]benzoate;

[(1S)-1-[3-(cyclopentoxy)-4-(difluoromethoxy)phenyl]-2-(3,5-dichloro-1-oxido-pyridin-1-ium-4-yl)ethyl]3-[(2-fluoro-N-[(3R)-quinuclidin-3-yl]oxycarbonyl-anilino)methyl]benzoate;

[(1S)-1-[3-(cyclopentoxy)-4-(difluoromethoxy)phenyl]-2-(3,5-dichloro-1-oxido-pyridin-1-ium-4-yl)ethyl]4-[(2-fluoro-N-[(3R)-quinuclidin-3-yl]oxycarbonyl-anilino)methyl]benzoate;

[(1S)-2-(3,5-dichloro-1-oxido-pyridin-1-ium-4-yl)-1-(3,4-dimethoxylphenyl)ethyl]3-[[3-(N-[(3R)-quinuclidin-3-yl]oxycarbonylanilino)methyl]phenoxy]methyl]benzoate;

[(1S)-2-(3,5-dichloro-1-oxido-pyridin-1-ium-4-yl)-1-(3,4-dimethoxylphenyl)ethyl]4-[[3-(N-[(3R)-quinuclidin-3-yl]oxycarbonylanilino)methyl]phenoxy]methyl]benzoate;

[(1S)-2-(3,5-dichloro-1-oxido-pyridin-1-ium-4-yl)-1-(3,4-dimethoxylphenyl)ethyl]3-[[4-(N-[(3R)-quinuclidin-3-yl]oxycarbonylanilino)methyl]phenoxy]methyl]benzoate;

[(1S)-2-(3,5-dichloro-1-oxido-pyridin-1-ium-4-yl)-1-(3,4-dimethoxylphenyl)ethyl]4-[[4-(N-[(3R)-quinuclidin-3-yl]oxycarbonylanilino)methyl]phenoxy]methyl]benzoate;

[(1S)-1-[3-(cyclopropylmethoxy)-4-(difluoromethoxy)phenyl]-2-(3,5-dichloro-1-oxido-pyridin-1-ium-4-yl)ethyl]4-[(2-fluoro-N-[(3R)-quinuclidin-3-yl]oxycarbonyl-anilino)methyl]benzoate;

[(1S)-2-(3,5-dichloro-1-oxido-pyridin-1-ium-4-yl)-1-[4-(difluoromethoxy)-3-isopropoxy-phenyl]ethyl]4-[[2-pyridyl-[(3R)-quinuclidin-3-yl]oxycarbonyl-amino]methyl]benzoate;

[(1S)-2-(3,5-dichloro-1-oxido-pyridin-1-ium-4-yl)-1-[4-(difluoromethoxy)-3-(trideuteriomethoxy)phenyl]ethyl]4-[(2-fluoro-N-[(3R)-quinuclidin-3-yl]oxycarbonyl-anilino)methyl]benzoate;

[(1S)-2-(3,5-dichloro-1-oxido-pyridin-1-ium-4-yl)-1-[4-(difluoromethoxy)-3-methoxy-phenyl]ethyl]4-[(2-fluoro-N-[(3R)-quinuclidin-3-yl]oxycarbonyl-anilino)methyl]benzoate;

[(1S)-2-(3,5-dichloro-1-oxido-pyridin-1-ium-4-yl)-1-[4-(difluoromethoxy)-3-ethoxy-phenyl]ethyl]4-[(2-fluoro-N-[(3R)-quinuclidin-3-yl]oxycarbonyl-anilino)methyl]benzoate;

[(1S)-2-(3,5-dichloro-1-oxido-pyridin-1-ium-4-yl)-1-[4-(difluoromethoxy)-3-isopropoxy-phenyl]ethyl]4-[(2-fluoro-N-[(3R)-quinuclidin-3-yl]oxycarbonyl-anilino)methyl]benzoate;

[(1S)-2-(3,5-dichloro-1-oxido-pyridin-1-ium-4-yl)-1-(3,4-dimethoxyphenyl)ethyl]2-fluoro-5-[(2-fluoro-N-[(3R)-quinuclidin-3-yl]oxycarbonyl-anilino)methyl]benzoate;

[(1S)-2-(3,5-dichloro-1-oxido-pyridin-1-ium-4-yl)-1-(3,4-dimethoxyphenyl)ethyl]4-[2-(2-fluoro-N-[(3R)-quinuclidin-3-yl]oxycarbonyl-anilino)ethyl]benzoate;

[2-(3,5-dichloro-4-pyridyl)-1-(3,4-dimethoxyphenyl)ethyl]4-[(2-fluoro-N-[(3R)-quinuclidin-3-yl]oxycarbonyl-anilino)methyl]benzoate;

[2-(3,5-dichloro-4-pyridyl)-1-(3,4-dimethoxyphenyl)ethyl]3-[(2-fluoro-N-[(3R)-quinuclidin-3-yl]oxycarbonyl-anilino)methyl]benzoate;

[(1S)-2-(3,5-dichloro-1-oxido-pyridin-1-ium-4-yl)-1-(3,4-dimethoxyphenyl)ethyl]3-[(2-fluoro-N-[(3R)-quinuclidin-3-yl]oxycarbonyl-anilino)methyl]-5-methyl-benzoate;

[(1S)-1-[3-(cyclopropylmethoxy)-4-(difluoromethoxy)phenyl]-2-(3,5-dichloro-1-oxido-pyridin-1-ium-4-yl)ethyl]2-[3-[(N-[(3R)-quinuclidin-3-yl]oxycarbonylanilino)methyl]phenyl]acetate;

[(1S)-2-(3,5-dichloro-1-oxido-pyridin-1-ium-4-yl)-1-(3,4-dimethoxyphenyl)ethyl]2-[3-[(2-fluoro-N-[(3R)-quinuclidin-3-yl]oxycarbonyl-anilino)methyl]phenyl]acetate;

[(1R)-1-[3-(cyclopropylmethoxy)-4-methoxy-phenyl]-2-(3,5-dichloro-1-oxido-pyridin-1-ium-4-yl)ethyl]4-[(2-fluoro-N-[(3R)-quinuclidin-3-yl]oxycarbonyl-anilino)methyl]benzoate;

[(1S)-1-[3-(cyclopropylmethoxy)-4-methoxy-phenyl]-2-(3,5-dichloro-1-oxido-pyridin-1-ium-4-yl)ethyl]4-[(2-fluoro-N-[(3R)-quinuclidin-3-yl]oxycarbonyl-anilino)methyl]benzoate;

[(1R)-1-[3,4-bis(difluoromethoxy)phenyl]-2-(3,5-dichloro-1-oxido-pyridin-1-ium-4-yl)ethyl]3-[(2-fluoro-N-[(3R)-quinuclidin-3-yl]oxycarbonyl-anilino)methyl]benzoate;

[(1S)-1-[3,4-bis(difluoromethoxy)phenyl]-2-(3,5-dichloro-1-oxido-pyridin-1-ium-4-yl)ethyl]3-[(2-fluoro-N-[(3R)-quinuclidin-3-yl]oxycarbonyl-anilino)methyl]benzoate;

[(1R)-1-[3,4-bis(difluoromethoxy)phenyl]-2-(3,5-dichloro-1-oxido-pyridin-1-ium-4-yl)ethyl]4-[(2-fluoro-N-[(3R)-quinuclidin-3-yl]oxycarbonyl-anilino)methyl]benzoate;

[(1S)-1-[3,4-bis(difluoromethoxy)phenyl]-2-(3,5-dichloro-1-oxido-pyridin-1-ium-4-yl)ethyl]4-[(2-fluoro-N-[(3R)-quinuclidin-3-yl]oxycarbonyl-anilino)methyl]benzoate;

[(1R)-1-[3-(cyclopentoxy)-4-methoxy-phenyl]-2-(3,5-dichloro-1-oxido-pyridin-1-ium-4-yl)ethyl]4-[(2-fluoro-N-[(3R)-quinuclidin-3-yl]oxycarbonyl-anilino)methyl]benzoate;

[(1S)-1-[3-(cyclopentoxy)-4-methoxy-phenyl]-2-(3,5-dichloro-1-oxido-pyridin-1-ium-4-yl)ethyl]4-[(2-fluoro-N-[(3R)-quinuclidin-3-yl]oxycarbonyl-anilino)methyl]benzoate;

[(1R)-1-[3-(cyclopentoxy)-4-methoxy-phenyl]-2-(3,5-dichloro-1-oxido-pyridin-1-ium-4-yl)ethyl]3-[(2-fluoro-N-[(3R)-quinuclidin-3-yl]oxycarbonyl-anilino)methyl]benzoate;

[(1R)-1-[3-(cyclopropylmethoxy)-4-methoxy-phenyl]-2-(3,5-dichloro-1-oxido-pyridin-1-ium-4-yl)ethyl]3-[(2-fluoro-N-[(3R)-quinuclidin-3-yl]oxycarbonyl-anilino)methyl]benzoate;

[(1R)-1-[3-(cyclopentoxy)-4-methoxy-phenyl]-2-(3,5-dichloro-1-oxido-pyridin-1-ium-4-yl)ethyl]4-[[2-pyridyl-[(3R)-quinuclidin-3-yl]oxycarbonyl-amino]methyl]benzoate;

[(1S)-1-[3-(cyclopentoxy)-4-methoxy-phenyl]-2-(3,5-dichloro-1-oxido-pyridin-1-ium-4-yl)ethyl]4-[[2-pyridyl-[(3R)-quinuclidin-3-yl]oxycarbonyl-amino]methyl]benzoate;

[(1S)-1-[3-(cyclopentoxy)-4-methoxy-phenyl]-2-(3,5-dichloro-1-oxido-pyridin-1-ium-4-yl)ethyl]4-[[3-pyridyl-[(3R)-quinuclidin-3-yl]oxycarbonyl-amino]methyl]benzoate;

[(1R)-1-[3-(cyclopentoxy)-4-methoxy-phenyl]-2-(3,5-dichloro-1-oxido-pyridin-1-ium-4-yl)ethyl]4-[[3-pyridyl-[(3R)-quinuclidin-3-yl]oxycarbonyl-amino]methyl]benzoate;

[(1S)-1-[3-(cyclopropylmethoxy)-4-methoxy-phenyl]-2-(3,5-dichloro-1-oxido-pyridin-1-ium-4-yl)ethyl]4-[[3-pyridyl-[(3R)-quinuclidin-3-yl]oxycarbonyl-amino]methyl]benzoate;

[(1R)-1-[3-(cyclopropylmethoxy)-4-methoxy-phenyl]-2-(3,5-dichloro-1-oxido-pyridin-1-ium-4-yl)ethyl]4-[[3-pyridyl-[(3R)-quinuclidin-3-yl]oxycarbonyl-amino]methyl]benzoate;

[(1S)-1-[3-(cyclopropylmethoxy)-4-methoxy-phenyl]-2-(3,5-dichloro-1-oxido-pyridin-1-ium-4-yl)ethyl]4-[[2-pyridyl-[(3R)-quinuclidin-3-yl]oxycarbonyl-amino]methyl]benzoate;

[(1R)-1-[3-(cyclopropylmethoxy)-4-methoxy-phenyl]-2-(3,5-dichloro-1-oxido-pyridin-1-ium-4-yl)ethyl]4-[[2-pyridyl-[(3R)-quinuclidin-3-yl]oxycarbonyl-amino]methyl]benzoate;

[(1S)-2-(3,5-dichloro-1-oxido-pyridin-1-ium-4-yl)-1-(3,4-dimethoxyphenyl)ethyl]3-[(2-chloro-N-[(3R)-quinuclidin-3-yl]oxycarbonyl-anilino)methyl]benzoate;

[(1S)-2-(3,5-dichloro-1-oxido-pyridin-1-ium-4-yl)-1-(3,4-dimethoxyphenyl)ethyl]3-[(2,4-difluoro-N-[(3R)-quinuclidin-3-yl]oxycarbonyl-anilino)methyl]benzoate;

[(1S)-2-(3,5-dichloro-1-oxido-pyridin-1-ium-4-yl)-1-(3,4-dimethoxyphenyl)ethyl]4-fluoro-3-[(2-fluoro-N-[(3R)-quinuclidin-3-yl]oxycarbonyl-anilino)methyl]benzoate;

[(1S)-2-(3,5-dichloro-1-oxido-pyridin-1-ium-4-yl)-1-(3,4-dimethoxyphenyl)ethyl]4-fluoro-3-[(N-[(3R)-quinuclidin-3-yl]oxycarbonylanilino)methyl]benzoate;

[(1S)-2-(3,5-dichloro-1-oxido-pyridin-1-ium-4-yl)-1-(3,4-dimethoxyphenyl)ethyl]4-[(2-fluoro-4-methoxy-N-[(3R)-quinuclidin-3-yl]oxycarbonyl-anilino)methyl]benzoate;

[(1S)-2-(3,5-dichloro-1-oxido-pyridin-1-ium-4-yl)-1-(3,4-dimethoxyphenyl)ethyl]4-[[2-(difluoromethoxy)-N-[(3R)-quinuclidin-3-yl]oxycarbonyl-anilino]methyl]benzoate;

[(1S)-2-(3,5-dichloro-1-oxido-pyridin-1-ium-4-yl)-1-(3,4-dimethoxyphenyl)ethyl]4-[(2-fluoro-6-methoxy-N-[(3R)-quinuclidin-3-yl]oxycarbonyl-anilino)methyl]benzoate;

[(1S)-2-(3,5-dichloro-1-oxido-pyridin-1-ium-4-yl)-1-(3,4-dimethoxyphenyl)ethyl]4-[(2-hydroxy-N-[(3R)-quinuclidin-3-yl]oxycarbonyl-anilino)methyl]benzoate;

[(1S)-2-(3,5-dichloro-1-oxido-pyridin-1-ium-4-yl)-1-(3,4-dimethoxyphenyl)ethyl]4-[(3-hydroxy-N-[(3R)-quinuclidin-3-yl]oxycarbonyl-anilino)methyl]benzoate;

[(1S)-2-(3,5-dichloro-1-oxido-pyridin-1-ium-4-yl)-1-(3,4-dimethoxyphenyl)ethyl]4-[[(5-fluoro-3-pyridyl)-[(3R)-quinuclidin-3-yl]oxycarbonyl-amino]methyl]benzoate;

[(1S)-2-(3,5-dichloro-1-oxido-pyridin-1-ium-4-yl)-1-(3,4-dimethoxylphenyl)ethyl]4-[[(4-fluoro-2-pyridyl)-[(3R)-quinuclidin-3-yl]oxycarbonyl-amino]methyl]benzoate;

[(1S)-2-(3,5-dichloro-1-oxido-pyridin-1-ium-4-yl)-1-(3,4-dimethoxylphenyl)ethyl]4-[[3-(dimethylcarbamoyl)-N-[(3R)-quinuclidin-3-yl]oxycarbonyl-anilino]methyl]benzoate;

[(1S)-2-(3,5-dichloro-1-oxido-pyridin-1-ium-4-yl)-1-(3,4-dimethoxylphenyl)ethyl]4-[[(2-methoxy-3-pyridyl)-[(3R)-quinuclidin-3-yl]oxycarbonyl-amino]methyl]benzoate;

[(1S)-2-(3,5-dichloro-1-oxido-pyridin-1-ium-4-yl)-1-(3,4-dimethoxylphenyl)ethyl]4-[[(5-methoxy-3-pyridyl)-[(3R)-quinuclidin-3-yl]oxycarbonyl-amino]methyl]benzoate;

[(1S)-2-(3,5-dichloro-1-oxido-pyridin-1-ium-4-yl)-1-(3,4-dimethoxylphenyl)ethyl]4-[[(6-hydroxy-3-pyridyl)-[(3R)-quinuclidin-3-yl]oxycarbonyl-amino]methyl]benzoate;

[(1S)-2-(3,5-dichloro-1-oxido-pyridin-1-ium-4-yl)-1-(3,4-dimethoxylphenyl)ethyl]4-[(2-cyano-N-[(3R)-quinuclidin-3-yl]oxycarbonyl-anilino)methyl]benzoate;

[(1S)-1-[3-(cyclopropylmethoxy)-4-(difluoromethoxy)phenyl]-2-(3,5-dichloro-1-oxido-pyridin-1-ium-4-yl)ethyl]4-[[3-pyridyl-[(3R)-quinuclidin-3-yl]oxycarbonyl-amino]methyl]benzoate;

[(1S)-2-(3,5-dichloro-1-oxido-pyridin-1-ium-4-yl)-1-[4-(difluoromethoxy)-3-isopropoxy-phenyl]ethyl]4-[[3-pyridyl-[(3R)-quinuclidin-3-yl]oxycarbonyl-amino]methyl]benzoate;

[1-[3-(cyclopropylmethoxy)-4-methoxy-phenyl]-2-(3,5-dichloro-1-oxido-pyridin-1-ium-4-yl)ethyl]4-[[3-pyridyl-[(3R)-quinuclidin-3-yl]oxycarbonyl-amino]methyl]benzoate;

[1-[3-(cyclopentoxy)-4-methoxy-phenyl]-2-(3,5-dichloro-1-oxido-pyridin-1-ium-4-yl)ethyl]4-[[3-pyridyl-[(3R)-quinuclidin-3-yl]oxycarbonyl-amino]methyl]benzoate;

[(1S)-2-(3,5-dichloro-1-oxido-pyridin-1-ium-4-yl)-1-(3,4-dimethoxylphenyl)ethyl]4-3-[(2-fluoro-N-[(3R)-quinuclidin-3-yl]oxycarbonyl-anilino)methyl]phenyl]benzoate;

[(1S)-2-(3,5-dichloro-1-oxido-pyridin-1-ium-4-yl)-1-(3,4-dimethoxylphenyl)ethyl]3-3-[(2-fluoro-N-[(3R)-quinuclidin-3-yl]oxycarbonyl-anilino)methyl]phenyl]benzoate;

[(1S)-2-(3,5-dichloro-1-oxido-pyridin-1-ium-4-yl)-1-(3,4-dimethoxylphenyl)ethyl]4-[4-[(2-fluoro-N-[(3R)-quinuclidin-3-yl]oxycarbonyl-anilino)methyl]phenyl]benzoate;

[(1S)-2-(3,5-dichloro-1-oxido-pyridin-1-ium-4-yl)-1-(3,4-dimethoxylphenyl)ethyl]3-[4-[(2-fluoro-N-[(3R)-quinuclidin-3-yl]oxycarbonyl-anilino)methyl]phenyl]benzoate;

[(1S)-2-(3,5-dichloro-1-oxido-pyridin-1-ium-4-yl)-1-(3,4-dimethoxylphenyl)ethyl]4-[[[(3R)-quinuclidin-3-yl]oxycarbonyl-thiazol-2-yl-amino]methyl]benzoate;

[(1S)-2-(3,5-dichloro-1-oxido-pyridin-1-ium-4-yl)-1-(3,4-dimethoxylphenyl)ethyl]4-[[1H-indazol-7-yl-[(3R)-quinuclidin-3-yl]oxycarbonyl-amino]methyl]benzoate;

[(1S)-2-(3,5-dichloro-1-oxido-pyridin-1-ium-4-yl)-1-(3,4-dimethoxylphenyl)ethyl]4-[[1H-indazol-7-yl-[(3R)-quinuclidin-3-yl]oxycarbonyl-amino]methyl]benzoate;

[(1S)-2-(3,5-dichloro-1-oxido-pyridin-1-ium-4-yl)-1-(3,4-dimethoxylphenyl)ethyl]4-[[1H-indol-7-yl-[(3R)-quinuclidin-3-yl]oxycarbonyl-amino]methyl]benzoate;

[(1S)-1-[3-(cyclopropylmethoxy)-4-(difluoromethoxy)phenyl]-2-(3,5-dichloro-1-oxido-pyridin-1-ium-4-yl)ethyl]4-[(2-hydroxy-N-[(3R)-quinuclidin-3-yl]oxycarbonyl-anilino)methyl]benzoate;

[(1S)-1-[3-(cyclopropylmethoxy)-4-(difluoromethoxy)phenyl]-2-(3,5-dichloro-1-oxido-pyridin-1-ium-4-yl)ethyl]3-[(2-hydroxy-N-[(3R)-quinuclidin-3-yl]oxycarbonyl-anilino)methyl]benzoate;

[(1S)-2-(3,5-dichloro-1-oxido-pyridin-1-ium-4-yl)-1-(3,4-dimethoxylphenyl)ethyl]4-[[3-(difluoromethyl)-N-[(3R)-quinuclidin-3-yl]oxycarbonyl-anilino]methyl]benzoate;

[(1S)-2-(3,5-dichloro-1-oxido-pyridin-1-ium-4-yl)-1-(3,4-dimethoxylphenyl)ethyl]4-[(3-fluoro-5-hydroxy-N-[(3R)-quinuclidin-3-yl]oxycarbonyl-anilino)methyl]benzoate;

[(1S)-2-(3,5-dichloro-1-oxido-pyridin-1-ium-4-yl)-1-(3,4-dimethoxylphenyl)ethyl]4-[(2-methoxy-3-hydroxy-N-[(3R)-quinuclidin-3-yl]oxycarbonyl-anilino)methyl]benzoate;

[(1S)-2-(3,5-dichloro-1-oxido-pyridin-1-ium-4-yl)-1-(3,4-dimethoxylphenyl)ethyl]4-[(2-methyl-3-hydroxy-N-[(3R)-quinuclidin-3-yl]oxycarbonyl-anilino)methyl]benzoate;

[(1S)-2-(3,5-dichloro-1-oxido-pyridin-1-ium-4-yl)-1-(3,4-dimethoxylphenyl)ethyl]4-[(2-chloro-5-hydroxy-N-[(3R)-quinuclidin-3-yl]oxycarbonyl-anilino)methyl]benzoate;

[(1S)-2-(3,5-dichloro-1-oxido-pyridin-1-ium-4-yl)-1-(3,4-dimethoxylphenyl)ethyl]4-[(2-fluoro-5-hydroxy-N-[(3R)-quinuclidin-3-yl]oxycarbonyl-anilino)methyl]benzoate;

[(1S)-2-(3,5-dichloro-1-oxido-pyridin-1-ium-4-yl)-1-(3,4-dimethoxylphenyl)ethyl]4-[(5-hydroxy-2-methyl-N-[(3R)-quinuclidin-3-yl]oxycarbonyl-anilino)methyl]benzoate;

[(1S)-2-(3,5-dichloro-1-oxido-pyridin-1-ium-4-yl)-1-(3,4-dimethoxylphenyl)ethyl]4-[(2-chloro-3-hydroxy-N-[(3R)-quinuclidin-3-yl]oxycarbonyl-anilino)methyl]benzoate;

[(1S)-2-(3,5-Dichloro-1-oxido-pyridin-1-ium-4-yl)-1-(3,4-dimethoxylphenyl)ethyl]3-(3-hydroxy-N-[(3R)-quinuclidin-3-yl]oxycarbonyl-anilino)methyl]benzoate;

[(1S)-2-(3,5-dichloro-1-oxido-pyridin-1-ium-4-yl)-1-(3,4-dimethoxylphenyl)ethyl]3-[(2,6-difluoro-N-[(3R)-quinuclidin-3-yl]oxycarbonyl-anilino)methyl]benzoate;

[(1S)-1-[3-(cyclopropylmethoxy)-4-(difluoromethoxy)phenyl]-2-(3,5-dichloro-1-oxido-pyridin-1-ium-4-yl)ethyl]3-[(3-fluoro-N-[(3R)-quinuclidin-3-yl]oxycarbonyl-anilino)methyl]benzoate;

[(1S)-2-(3,5-dichloro-1-oxido-pyridin-1-ium-4-yl)-1-(3,4-dimethoxylphenyl)ethyl]3-[[2-pyridyl-[(3R)-quinuclidin-3-yl]oxycarbonyl-amino]methyl]benzoate;

[(1S)-2-(3,5-dichloro-1-oxido-pyridin-1-ium-4-yl)-1-(3,4-dimethoxylphenyl)ethyl]4-[(2-chloro-N-[(3R)-quinuclidin-3-yl]oxycarbonyl-anilino)methyl]benzoate;

[(1S)-2-(3,5-dichloro-1-oxido-pyridin-1-ium-4-yl)-1-(3,4-dimethoxylphenyl)ethyl]4-[(2,6-difluoro-N-[(3R)-quinuclidin-3-yl]oxycarbonyl-anilino)methyl]benzoate;

[(1S)-2-(3,5-dichloro-1-oxido-pyridin-1-ium-4-yl)-1-(3,4-dimethoxylphenyl)ethyl]3-[[3-pyridyl-[(3R)-quinuclidin-3-yl]oxycarbonyl-amino]methyl]benzoate;

[(1S)-2-(3,5-dichloro-1-oxido-pyridin-1-ium-4-yl)-1-(3,4-dimethoxylphenyl)ethyl]3-[(2-fluoro-4-hydroxy-N-[(3R)-quinuclidin-3-yl]oxycarbonyl-anilino)methyl]benzoate;

[(1S)-2-(3,5-dichloro-1-oxido-pyridin-1-ium-4-yl)-1-(3,4-dimethoxylphenyl)ethyl]3-[(4-hydroxy-N-[(3R)-quinuclidin-3-yl]oxycarbonyl-anilino)methyl]benzoate;

[(1S)-2-(3,5-dichloro-1-oxido-pyridin-1-ium-4-yl)-1-(3,4-dimethoxylphenyl)ethyl]3-[[4-(methanesulfonamido)-N-[(3R)-quinuclidin-3-yl]oxycarbonyl-anilino]methyl]benzoate;

[(1S)-2-(3,5-dichloro-1-oxido-pyridin-1-ium-4-yl)-1-(3,4-dimethoxylphenyl)ethyl]3-[(3-tert-butyl-N-[(3R)-quinuclidin-3-yl]oxycarbonyl-anilino)methyl]benzoate;

[(1S)-2-(3,5-dichloro-1-oxido-pyridin-1-ium-4-yl)-1-[4-(difluoromethoxy)-3-propoxy-phenyl]ethyl]4-[(2-fluoro-N-[(3R)-quinuclidin-3-yl]oxycarbonyl-anilino)methyl]benzoate;

[(1S)-2-(3,5-dichloro-1-oxido-pyridin-1-ium-4-yl)-1-[4-(difluoromethoxy)-3-propoxy-phenyl]ethyl]4-[(3-pyridyl-N-[(3R)-quinuclidin-3-yl]oxycarbonyl-anilino)methyl]benzoate;

[(1S)-2-(3,5-dichloro-1-oxido-pyridin-1-ium-4-yl)-1-(3,4-dimethoxylphenyl)ethyl]3-[[3-(methanesulfonamido)-N-[(3R)-quinuclidin-3-yl]oxycarbonyl-anilino]methyl]benzoate;

[(1S)-2-(3,5-dichloro-1-oxido-pyridin-1-ium-4-yl)-1-(3,4-dimethoxylphenyl)ethyl]4-[[4-(methanesulfonamido)-N-[(3R)-quinuclidin-3-yl]oxycarbonyl-anilino]methyl]benzoate;

[(1S)-2-(3,5-dichloro-1-oxido-pyridin-1-ium-4-yl)-1-(3,4-dimethoxylphenyl)ethyl]4-[[2-(cyclopropylmethoxy)-N-[(3R)-quinuclidin-3-yl]oxycarbonyl-anilino]methyl]benzoate;

[(1S)-2-(3,5-dichloro-1-oxido-pyridin-1-ium-4-yl)-1-(3,4-dimethoxylphenyl)ethyl]4-[[2-(cyclopropylmethoxy)-N-[(3R)-quinuclidin-3-yl]oxycarbonyl-anilino]methyl]benzoate;

[(1S)-2-(3,5-dichloro-1-oxido-pyridin-1-ium-4-yl)-1-(3,4-dimethoxylphenyl)ethyl]4-[(2-fluoro-6-hydroxy-N-[(3R)-quinuclidin-3-yl]oxycarbonyl-anilino)methyl]benzoate;

[(1S)-2-(3,5-dichloro-1-oxido-pyridin-1-ium-4-yl)-1-(3,4-dimethoxylphenyl)ethyl]4-[[3-(hydroxymethyl)-N-[(3R)-quinuclidin-3-yl]oxycarbonyl-anilino]methyl]benzoate;

[(1S)-2-(3,5-dichloro-1-oxido-pyridin-1-ium-4-yl)-1-(3,4-dimethoxylphenyl)ethyl]4-[(2-carbamoyl-N-[(3R)-quinuclidin-3-yl]oxycarbonyl-anilino)methyl]benzoate;

[(1S)-2-(3,5-dichloro-1-oxido-pyridin-1-ium-4-yl)-1-(3,4-dimethoxylphenyl)ethyl]4-[(2,3-dihydroxy-N-[(3R)-quinuclidin-3-yl]oxycarbonyl-anilino)methyl]benzoate;

[(1S)-2-(3,5-dichloro-1-oxido-pyridin-1-ium-4-yl)-1-(3,4-dimethoxylphenyl)ethyl]4-[(2,3-dihydroxy-N-[(3R)-quinuclidin-3-yl]oxycarbonyl-anilino)methyl]benzoate;

[(1S)-2-(3,5-dichloro-1-oxido-pyridin-1-ium-4-yl)-1-(3,4-dimethoxylphenyl)ethyl]4-[[[(3R)-quinuclidin-3-yl]oxycarbonyl-(1H-tetrazol-5-yl)amino]methyl]benzoate;

[(1S)-1-[3-(cyclopropylmethoxy)-4-(difluoromethoxy)phenyl]-2-(3,5-dichloro-1-oxido-pyridin-1-ium-4-yl)ethyl]3-[(2-fluoro-N-[(3R)-quinuclidin-3-yl]oxycarbonyl-anilino)methyl]benzoate;

[(1S)-1-[3-(cyclopropylmethoxy)-4-(difluoromethoxy)phenyl]-2-(3,5-dichloro-1-oxido-pyridin-1-ium-4-yl)ethyl]3-[(N-[(3R)-quinuclidin-3-yl]oxycarbonyl-anilino)methyl]benzoate;

[(1S)-1-[3-(cyclopropylmethoxy)-4-(difluoromethoxy)phenyl]-2-(3,5-dichloro-1-oxido-pyridin-1-ium-4-yl)ethyl]2-hydroxy-3-[(2-hydroxy-N-[(3R)-quinuclidin-3-yl]oxycarbonyl-anilino)methyl]benzoate and pharmaceutically acceptable salts and solvates thereof.

In one aspect of the present invention, processes for the preparation of compounds of the invention are provided.

Compounds of formula (I) can be obtained according to general synthetic routes reported in Scheme A or Scheme B or following the procedures of Scheme A and Scheme B starting from slightly modified reagents, easily identifiable by the skilled person and/or following slightly modified procedures that the skilled person can easily apply.

In Scheme A reference is made to specific synthetic schemes (S1/A to S7/A), and in Scheme B reference is made to specific synthetic schemes (S1/B to S3/B) which are better detailed in the following paragraphs.

Scheme A:

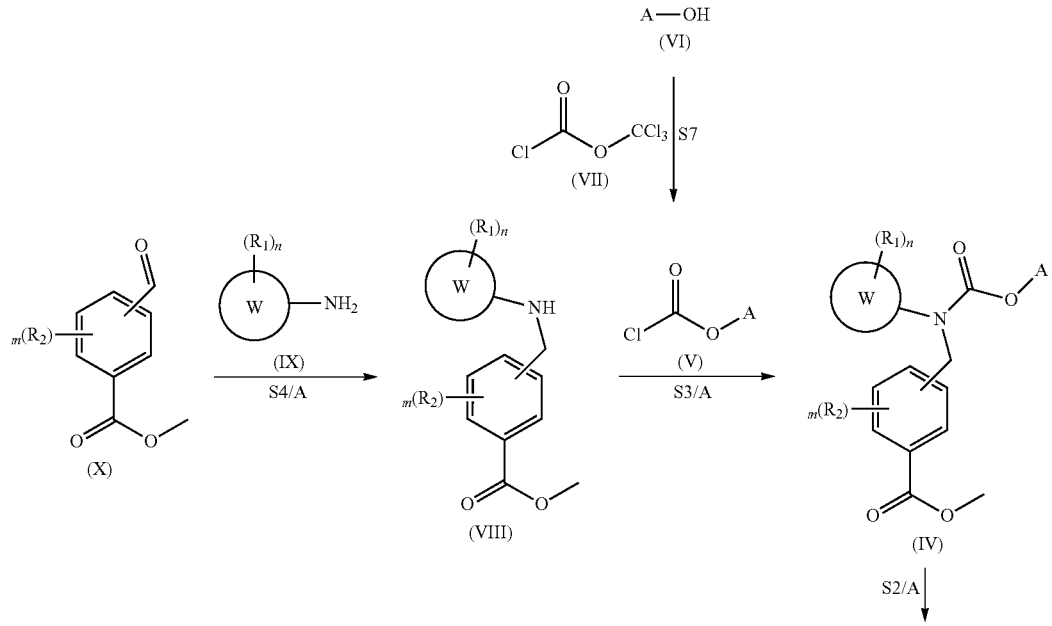

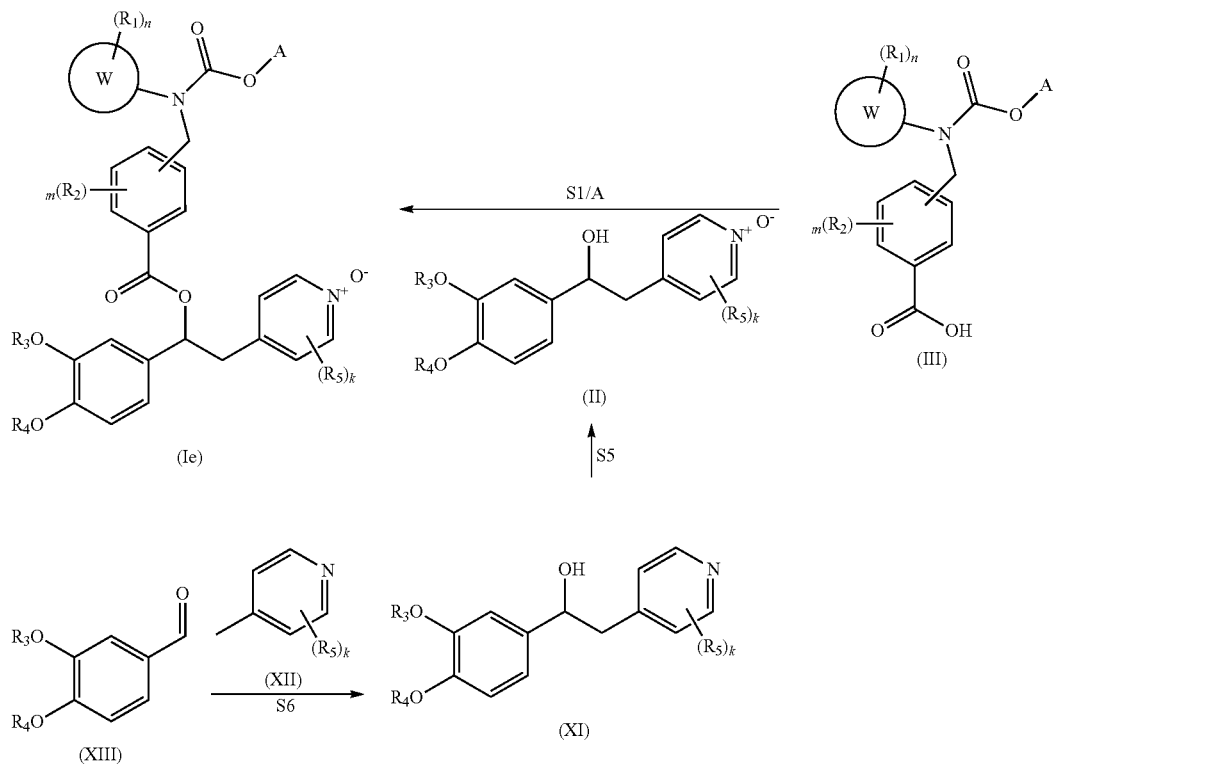

Processes which can be used and are described in Scheme A should not be viewed as limiting the scope of the synthetic methods available for the preparation of the compounds of the invention.

In the following Schemes, for compounds of formula (II) to (XIII), unless otherwise indicated, groups $R_1$, $R_2$, $R_3$, $R_4$, $R_5$, A, m, n and k have the same meanings as described for compounds of formula (I) above.

Compounds of formula (Ie), i.e. compounds of formula (I) which are in the form of N-oxide on the pyridine ring and wherein L1 is absent (i.e. $L_1$ is $(CH_2)_t$ and t is 0) and $L_2$ is $CH_2$, may be prepared according to Scheme S1/A (S1/A) below reported by reaction of a compound of formula (III) with an appropriate compound of formula (II) as below reported.

Scheme 1/A (S1/A):

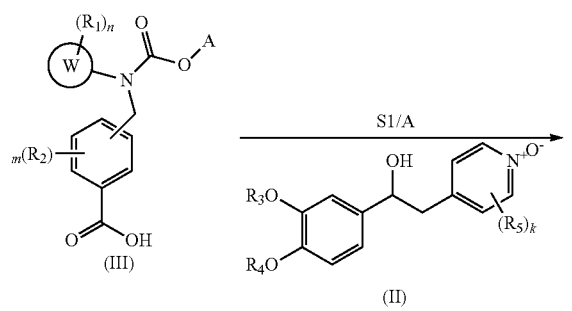

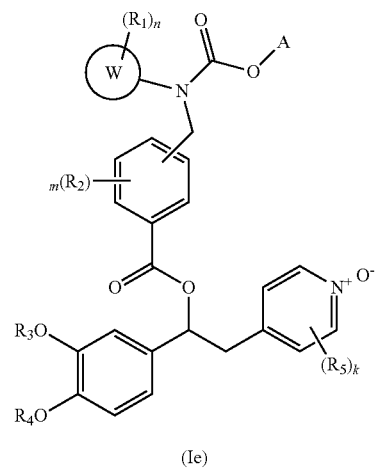

Typical reaction conditions comprise reacting a compound of formula (III) with a compound of formula (II) in a suitable solvent, such as DMF, in the presence of a coupling agent, such as EDC/DMAP or HATU, at an appropriate temperature such as room (or ambient) temperature or 40° C.

Compounds of formula (III) may be prepared according to Scheme 2/A (S2/A) below by reaction of a compound of formula (IV) as below reported.

Scheme 2/A (S2/A):

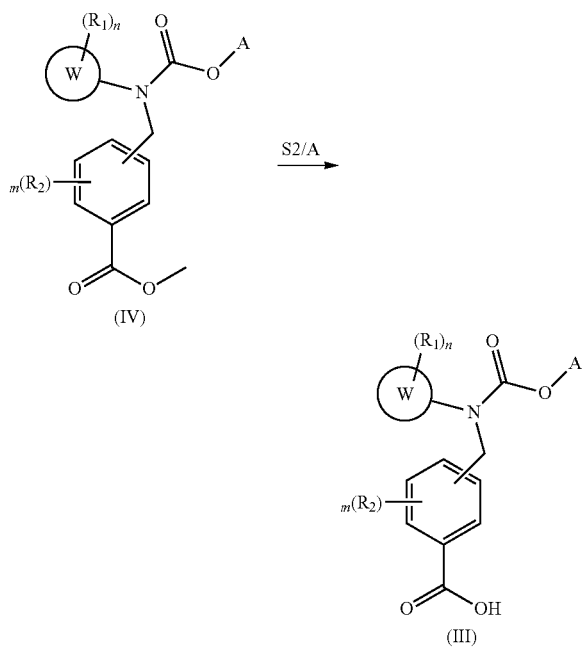

Typical reaction conditions comprise hydrolysis of a compound of formula (IV) in a suitable solvent mixture, such as THF/MeOH/water, in the presence of a suitable base, such as lithium hydroxide, at an appropriate temperature such as room temperature or 40° C.

Compounds of formula (IV) may be prepared according to Scheme 3/A (S3/A) below by reaction of a compound of formula (VIII) with an appropriate compound of formula (V) as below reported.

Scheme 3/A (S3/A):

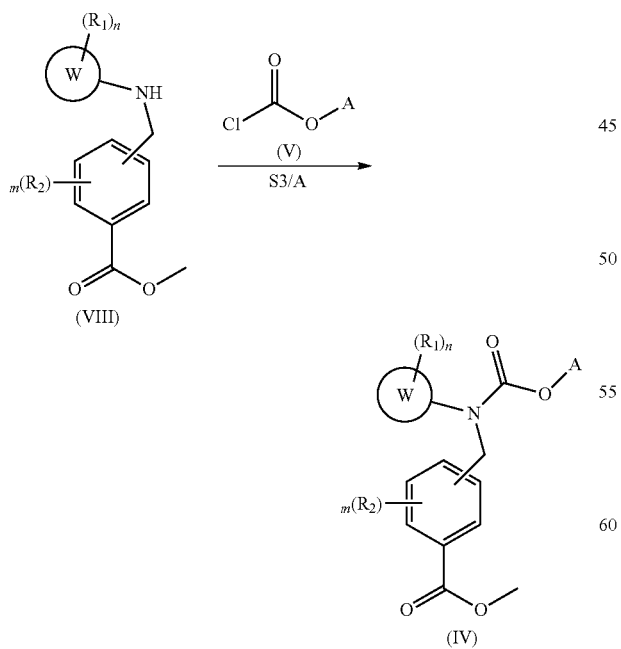

Typical reaction conditions comprise reacting a compound of formula (VIII) with a compound of formula (V) in a suitable solvent, such as THF or pyridine, in the presence of a base, such as LHMDS or pyridine, and an optional catalyst, such as DMAP, at an appropriate temperature such as room (or ambient) temperature or 0° C. or 40° C. or 50° C.

Compounds of formula (VIII) may be prepared according to Scheme 4/A (S4/A) by reaction of a compound of formula (X) with an appropriate compound of formula (IX) as below reported.

Scheme 4/A (S4/A):

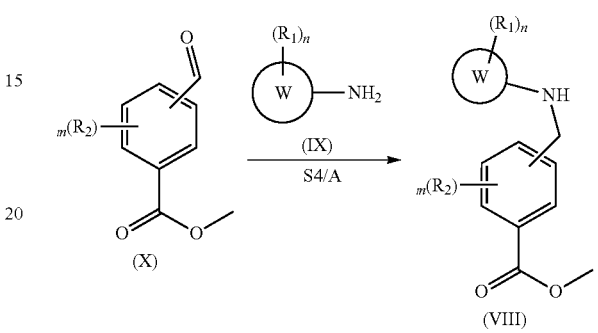

Typical reaction conditions comprise reacting a compound of formula (X) with a compound of formula (IX) in a suitable solvent, such as DCM, in the presence of an acid, such as acetic acid, under reducing conditions, for example with sodium borohydride, sodium triacetoxyborohydride, sodium cyanoborohydride or by catalytic hydrogenation, and an optional catalyst, such as DMAP, at an appropriate temperature such as room (or ambient) temperature or 0° C. or 40° C. or 50° C.

Compounds of formula (II) may be prepared according to Scheme 5 (S5) by reaction of a compound of formula (XI) as below reported.

Scheme 5 (S5):

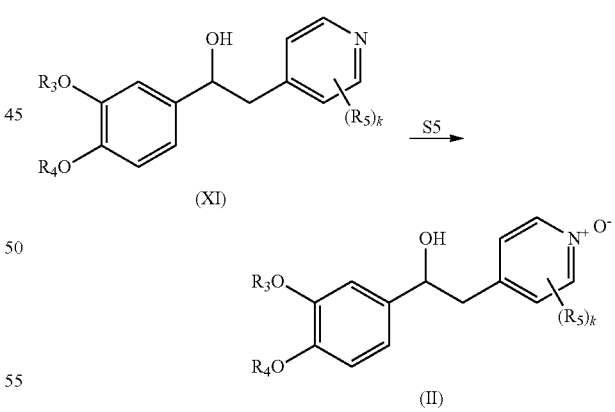

Typical reaction conditions comprise reacting a compound of formula (XI) with a suitable oxidizing agent, such as mCPBA or hydrogen peroxide or perbenzoic acid or peracetic acid, in a suitable solvent, such as DCM or chloroform, at an appropriate temperature, such as room (or ambient) temperature.

Compounds of formula (XI) may be prepared according to Scheme 6 (S6) by reaction of a compound of formula (XIII) with an appropriate compound of formula (XII) as below reported.

Scheme 6 (S6):

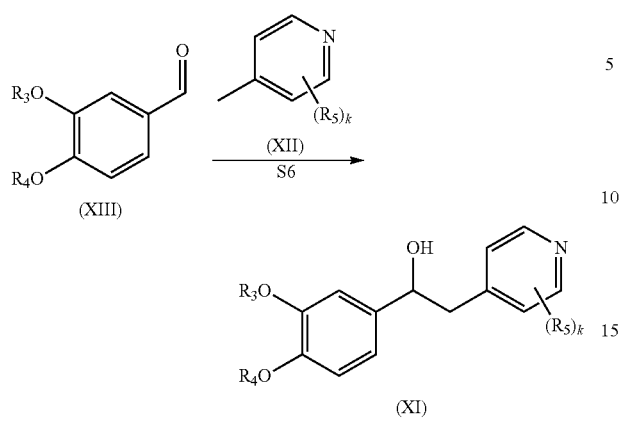

Typical reaction conditions comprise reacting a compound of formula (XIII) with a compound of formula (XII) in a suitable solvent, such as THF or other aprotic solvents, in the presence of a base, such as LHMDS or a similar strong base, at an appropriate temperature, such as −78° C.

Compounds of formula (V) may be prepared according to Scheme 7 (S7) by reaction of a compound of formula (VI) with a compound of formula (VII) as below reported.

Scheme 7 (S7):

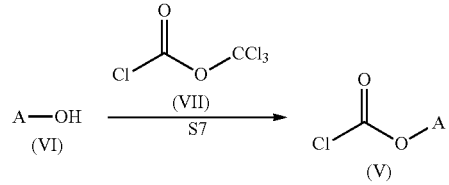

Typical reaction conditions comprise reacting a compound of formula (VI) with a compound of formula (VII) in a suitable solvent, such as MeCN, at an appropriate temperature, such as 0° C.

Scheme B:

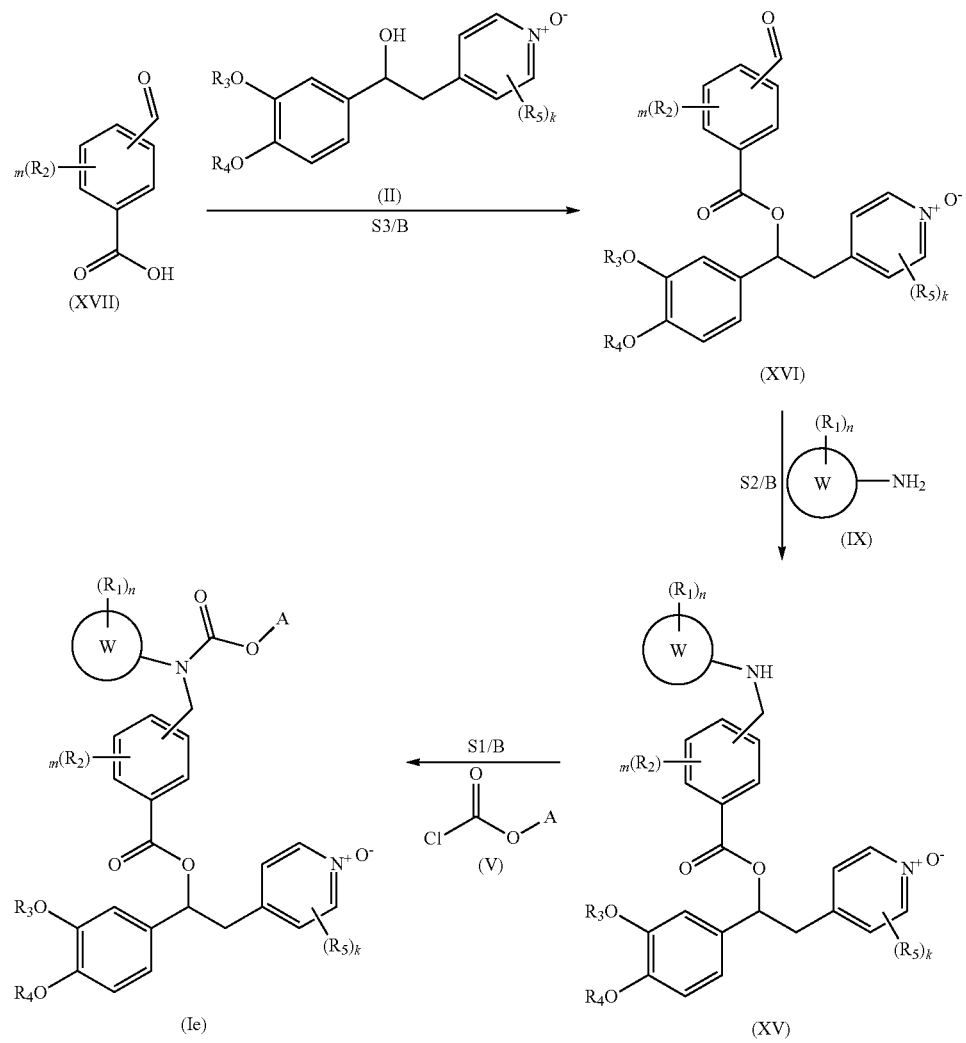

Processes which can be used and are described in Scheme B should not be viewed as limiting the scope of the synthetic methods available for the preparation of the compounds of the invention.

In the following Schemes, for compounds of formula (II), (V), (IX), (XV), (XVI), (XVII), unless otherwise indicated, groups $R_1$, $R_2$, $R_3$, $R_4$, $R_5$, A, m, n and k have the same meanings as described for compounds of formula (I) above.

Compounds of formula (Ie), i.e. compounds of formula (I) which are in the form of N-oxide on the pyridine ring and wherein $L_1$ is absent (i.e. $L_1$ is $(CH_2)_t$ and t is 0) and $L_2$ is $CH_2$, may be prepared according to Scheme S1/B (S1/B) below reported by reaction of a compound of formula (XV) with an appropriate compound of formula (V) as below reported.

Scheme 1/B (S1/B):

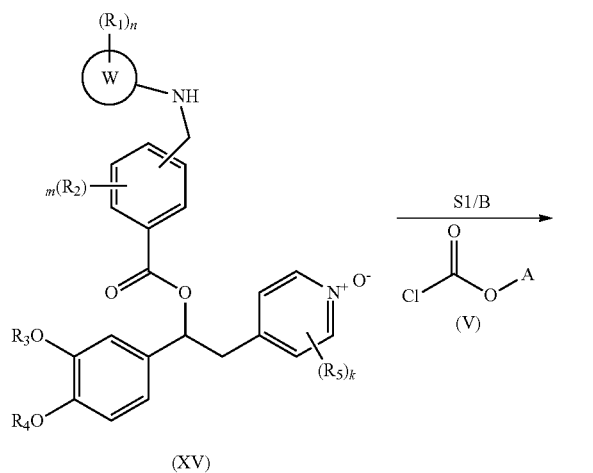

Typical reaction conditions comprise reacting a compound of formula (XV) with a compound of formula (V) in a suitable solvent, such as THF or pyridine or $CH_3CN$, at high temperatures, typically between 70° C. and 150° C.

Compounds of formula (XV) may be prepared according to Scheme 2/B(S2/B) by reaction of a compound of formula (XVI) with an appropriate compound of formula (IX) as below reported.

Scheme 2/B (S2/B):

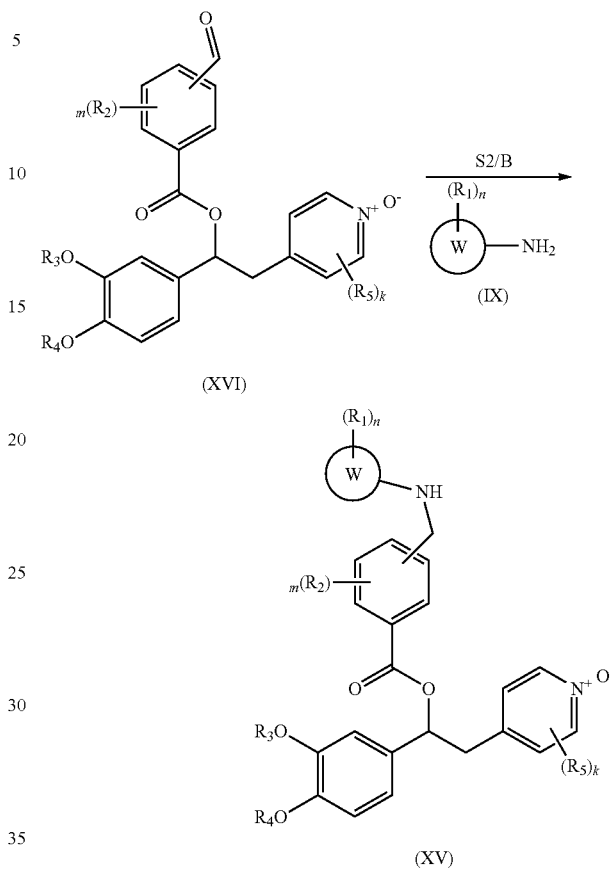

Typical reaction conditions comprise reacting a compound of formula (XVI) with a compound of formula (IX) in a suitable solvent, such as an alcoholic solvent or DCM or THF, in the presence of an acid, such as acetic acid, under reducing conditions, for example with sodium borohydride, sodium triacetoxyborohydride, sodium cyanoborohydride or by catalytic hydrogenation, and an optional catalyst, such as DMAP, at an appropriate temperature such as room (or ambient) temperature or 0° C. or 40° C. or 50° C.

Compounds of formula (XVI) may be prepared according to Scheme 3/B(S3/B) below by reaction of a compound of formula (XVII) with a compound of formula (II) as below reported.

Scheme 3/B (S3/B):

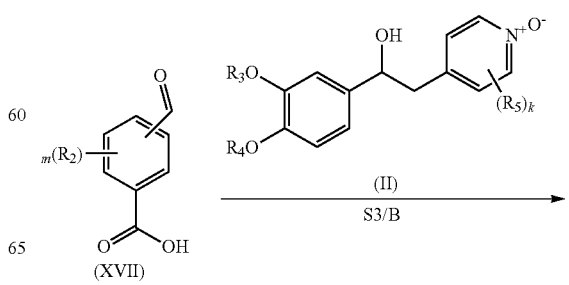

-continued

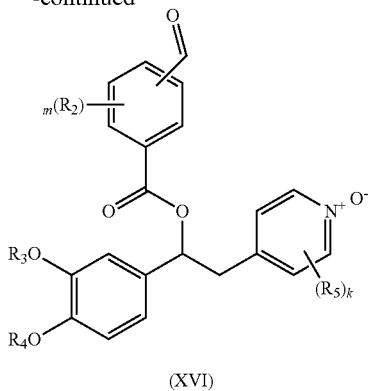

(XVI)

Typical reaction conditions comprise reacting a compound of formula (XVIII) with a compound of formula (II) in a suitable solvent, such as DMF, in the presence of a coupling agent, such as EDC/DMAP or HATU, at an appropriate temperature such as room (or ambient) temperature or 40° C.

The processes described are particularly advantageous as they are susceptible of being properly modulated, through any proper variant known to the skilled person, so as to obtain any of the desired compounds of the invention. Such variants are comprised within the scope of the present invention.

From all of the above, it should be clear to the skilled person that any of the described groups may be present as such or in any properly protected form. In particular, functional groups present in the compounds of formula (II), to (XVII) and which could generate unwanted side reaction and by-products, need to be properly protected before the alkylation, acylation, coupling, oxidation or sulfonylation takes place. Likewise, subsequent deprotection of those same protected groups may follow upon completion of the said reactions.

In the present invention, unless otherwise indicated, the term "protecting group" designates a protective group adapted to preserve the function of the group it is bound to. Typically, protective groups are used to preserve amino, hydroxy, or carboxyl functions. Appropriate protecting groups may thus include, for example, benzyl, benzyloxycarbonyl, t-butoxycarbonyl, alkyl or benzyl esters or the like, which are well known to those skilled in the art (see, for a general reference, T. W. Green; Protective Groups in Organic Synthesis (Wiley, N.Y. 1999), which is incorporated herein by reference in its entirety).

Likewise, selective protection and deprotection of any of the said groups, for instance including carbonyl, hydroxy or amino groups, may be accomplished according to very well-known methods commonly employed in organic synthetic chemistry.

The N-oxides on the 4-pyridinyl ring of the compounds of general formula (I) and embodiments thereof may be prepared according to methods available in the literature and well known to the skilled person. For instance they may be prepared by dissolving the compound of general formula (I) or embodiments thereof in $CH_2Cl_2$ or $CHCl_3$, then adding an oxidizing agent such as m-chloro perbenzoic acid (mCPBA) to the resulting solution. Other oxidizing agents which may be used are hydrogen peroxide, perbenzoic acid and peracetic acid.

Alternatively, in particular for those compounds comprising functional groups sensitive to oxidation, the corresponding N-oxides are prepared by carrying out the oxidation step before further functional groups are introduced, for example on compounds of formula (IX) as above reported. In a preferred embodiment, the process for preparation of compounds of formula (I) or embodiments thereof is performed starting from N-oxide on the pyridine ring of compound of formula (II), thus allowing the preparation of compound of formula (I) or embodiments thereof in the form of N-oxides on the pyridine ring.

Optional salification of the compounds of formula (I) or N-oxides on the pyridine ring thereof may be carried out by properly converting any of the free acidic or amino groups into the corresponding pharmaceutically acceptable salts. In this case too, the operative conditions being employed for the optional salification of the compounds of the invention are all within the ordinary knowledge of the skilled person.

From all of the above, it should be clear to the skilled person that the above process, comprehensive of any variant thereof for the preparation of suitable compounds of the invention, may be conveniently modified so that to adapt the reaction conditions to the specific needs, for instance by choosing appropriate condensing agents, solvents and protective groups, as the case may be.

The present invention also provides pharmaceutical compositions of compounds of the invention in admixture with one or more pharmaceutically acceptable carriers, for example those described in Remington's Pharmaceutical Sciences Handbook, XVII Ed., Mack Pub., N.Y., U.S.A., which is incorporated herein by reference in its entirety.

Administration of the compounds of the present invention or may be accomplished according to patient needs, for example, orally, nasally, parenterally (subcutaneously, intravenously, intramuscularly, intrasternally and by infusion), by inhalation, rectally, vaginally, topically, locally, transdermally, and by ocular administration. Various solid oral dosage forms may be used for administering compounds of the invention including such solid forms as tablets, gelcaps, capsules, caplets, granules, lozenges and bulk powders. The compounds of the present invention may be administered alone or combined with various pharmaceutically acceptable carriers, diluents (such as sucrose, mannitol, lactose, starches) and excipients known in the art, including but not limited to suspending agents, solubilizers, buffering agents, binders, disintegrants, preservatives, colorants, flavorants, lubricants and the like. Time release capsules, tablets and gels are also advantageous in administering the compounds of the present invention.

Various liquid oral dosage forms may also be used for administering compounds of the invention, including aqueous and non-aqueous solutions, emulsions, suspensions, syrups, and elixirs. Such dosage forms can also contain suitable inert diluents known in the art such as water and suitable excipients known in the art such as preservatives, wetting agents, sweeteners, flavorants, as well as agents for emulsifying and/or suspending the compounds of the invention. The compounds of the present invention may be injected, for example, intravenously, in the form of an isotonic sterile solution. Other preparations are also possible.

Suppositories for rectal administration of the compounds of the present invention may be prepared by mixing the compound with a suitable excipient such as cocoa butter, salicylates and polyethylene glycols.

Formulations for vaginal administration may be in the form of cream, gel, paste, foam, or spray formula containing, in addition to the active ingredient, such suitable carriers as are known in the art.

For topical administration, the pharmaceutical composition may be in the form of creams, ointments, liniments, lotions, emulsions, suspensions, gels, solutions, pastes, powders, sprays, and drops suitable for administration to the skin, eye, ear or nose. Topical administration may also involve transdermal administration via means such as transdermal patches.

For the treatment of the diseases of the respiratory tract, the compounds according to the invention are preferably administered by inhalation.

Inhalable preparations include inhalable powders, propellant-containing metered aerosols or propellant-free inhalable formulations and may be administered through a suitable inhalation device which may be respectively selected from dry powder inhaler, pressurized metered dosed inhaler, or a nebulizer.

For administration as a dry powder, single- or multi-dose inhalers known from the prior art may be utilized. In that case the powder may be filled in gelatine, plastic or other capsules, cartridges or blister packs or in a reservoir.

A diluent or carrier, generally non-toxic and chemically inert to the compounds of the invention, e.g. lactose or any other additive suitable for improving the respirable fraction may be added to the powdered compounds of the invention.

Inhalation aerosols containing propellant gas such as hydrofluoroalkanes may contain the compounds of the invention either in solution or in dispersed form. The propellant-driven formulations may also contain other ingredients such as co-solvents, stabilizers and optionally other excipients.

The propellant-free inhalable formulations comprising the compounds of the invention may be in form of solutions or suspensions in an aqueous, alcoholic or hydroalcoholic medium and they may be delivered by jet or ultrasonic nebulizers known from the prior art or by soft-mist nebulizers such as Respimat®.

The compounds of the invention may be administered as the sole active agent or in combination with other pharmaceutical active ingredients including those currently used in the treatment of respiratory disorders, e.g. beta2-agonists, antimuscarinic agents, corticosteroids, mitogen-activated protein kinases (P38 MAP kinase) inhibitors, nuclear factor kappa-B kinase subunit beta (IKK2) inhibitors, human neutrophil elastase (FINE) inhibitors, phosphodiesterase 4 (PDE4) inhibitors, leukotriene modulators, non-steroidal anti-inflammatory agents (NSAIDs), and mucus regulators.

The present invention also provides combinations of a compound of the invention, with a β2-agonist selected from the group consisting of carmoterol, vilanterol (GSK-642444), indacaterol, milveterol, arformoterol, formoterol, salbutamol, levalbuterol, terbutaline, AZD-3199, olodaterol (BI-1744-CL), abediterol (LAS-100977), bambuterol, isoproterenol, procaterol, clenbuterol, reproterol, fenoterol, and ASF-1020 and salts thereof.

The present invention also provides combinations of a compound of the invention, with a corticosteroid selected from the group consisting of fluticasone propionate, fluticasone furoate, mometasone furoate, beclometasone dipropionate, ciclesonide, budesonide, GSK 685698, and GSK 870086.

The present invention also provides combinations of a compound of the invention, with an antimuscarinic agent selected from the group consisting of aclidinium, tiotropium, ipratropium, trospium, glycopyrronium, and oxitropium salts.

The present invention also provides combinations of a compound of the invention, with a PDE4 inhibitor selected from the group consisting of AN-2728, AN-2898, CBS-3595, apremilast, ELB-353, KF-66490, K-34, LAS-37779, IBFB-211913, AWD-12-281, cipamfylline, cilomilast, roflumilast, BAY19-8004 and SCH-351591, AN-6415, indus-82010, TPI-PD3, ELB-353, CC-11050, GSK-256066, oglemilast, OX-914, tetomilast, MEM-1414, and RPL-554.

The present invention also provides combinations of a compound of the invention, with a P38 MAP kinase inhibitor selected from the group consisting of semapimod, talmapimod, pirfenidone, PH-797804, GSK-725, minokine, and losmapimod and salts thereof.

In a preferred embodiment, the present invention provides combinations of a compound of the invention with an IKK2 inhibitor.

The invention also provides combinations of a compound of the invention with a HNE inhibitor selected from the group consisting of AAT, ADC-7828, Aeriva, TAPI, AE-3763, KRP-109, AX-9657, POL-6014, AER-002, AGTC-0106, respriva, AZD-9668, zemaira, AAT IV, PGX-100, elafin, SPHD-400, prolastin C and prolastin inhaled.

The invention also provides combinations of a compound of the invention with a leukotriene modulator selected from the group consisting of montelukast, zafirlukast, and pranlukast.

The invention also provides combinations of a compound of the invention with a NSAID selected from the group consisting of ibuprofen and ketoprofen.

The invention also provides combinations of a compound of the invention with a mucus regulator selected from the group consisting of INS-37217, diquafosol, sibenadet, CS-003, talnetant, DNK-333, MSI-1956, and gefitinib.

The dosages of the compounds of the present invention depend upon a variety of factors including the particular disease to be treated, the severity of the symptoms, the route of administration, the frequency of the dosage interval, the particular compound utilized, the efficacy, toxicology profile, and pharmacokinetic profile of the compound.

Advantageously, the compounds of the invention may be administered for example, at a dosage comprised between 0.001 and 1000 mg/day, preferably between 0.1 and 500 mg/day.

When they are administered by inhalation route, the dosage of the compounds of the invention is advantageously comprised between 0.01 and 20 mg/day, preferably between 0.1 and 10 mg/day.

Preferably, the compounds of the invention alone or combined with other active ingredients may be administered for the prevention and/or treatment of any obstructive respiratory disease such as asthma, chronic bronchitis, and chronic obstructive pulmonary disease (COPD).

However the compounds of the invention may be administered for the prevention and/or treatment of any disease wherein PDE4 inhibition or M3 antagonism is required. Said disease include: allergic disease states such as atopic dermatitis, urticaria, allergic rhinitis, allergic conjunctivitis, vernal conjunctivitis, eosinophilic granuloma, psoriasis, inflammatory arthritis, rheumatoid arthritis, septic shock, ulcerative colitis, Crohn's disease, reperfusion injury of the myocardium and brain, chronic glomerulonephritis, endotoxic shock, cystic fibrosis, arterial restenosis, artherosclerosis, keratosis, rheumatoid spondylitis, osteoarthritis, pyresis, diabetes mellitus, pneumoconiosis, toxic and allergic contact eczema, atopic eczema, seborrheic eczema, lichen simplex, sunburn, pruritus in the anogenital area, alopecia areata, hypertrophic scars, discoid lupus erythematosus, systemic lupus erythematosus, follicular and wide-area pyodermias, endogenous and exogenous acne, acne rosacea, Behçet's disease, anaphylactoid purpura nephritis, inflammatory bowel disease, leukemia, multiple sclerosis, gastrointestinal diseases, autoimmune diseases and the like.

They also include neurological and psychiatric disorders such as Alzheimer's disease, multiple sclerosis, amylolaterosclerosis (ALS), multiple systems atrophy (MSA), schizophrenia, Parkinson's disease, Huntington's disease, Pick's disease, depression, stroke, and spinal cord injury.

Other features of the invention will become apparent in the course of the following descriptions of exemplary embodiments which are given for illustration of the invention and are not intended to be limiting thereof.

EXAMPLES

Abbreviations

EDC=1-ethyl-3-(3-dimethylaminopropyl)carbodiimide) hydrochloride;
DMAP=4-dimethylaminopyridine;
DMF=dimethylformamide;
EtOAc=ethyl acetate;
RT=room temperature;
THF=tetrahydrofuran;
DCM=dichloromethane;
MeOH=methyl alcohol;
EtOH=ethylic alcohol;
LHMDS=lithium bis(trimethylsilyl)amide;
m-CPBA=meta-chloroperoxybenzoic acid;
LC-MS=liquid chromatography/mass spectrometry;
HPLC=high pressure liquid chromatography;
MPLC=medium pressure liquid chromatography;
SFC=supercritical fluid chromatography;
HATU=(dimethylamino)-N,N-dimethyl(3H-[1,2,3]triazolo[4,5-b]pyridin-3-yloxy)methaniminium hexafluorophosphate.

General Experimental Details

Analytical Methods
Liquid Chromatography-Mass Spectrometry
Method 1:
LC-MS was performed on a Waters 2795 Alliance HT HPLC with Waters 2996 Diode Array Detector coupled to a Micromass ZQ, single quadrapole mass spectrometer using a Phenomenex Luna C18 (2) column (5 μm, 100×4.6 mm plus guard cartridge) with a linear gradient of 5-95% acetonitrile/water (with 0.1% formic acid in each mobile phase) within 3.5 minutes and held at 95% for 2.0 minutes.
Method 2:
LC-MS was performed on a Waters 2795 Alliance HT HPLC with Waters 2996 Diode Array Detector coupled to a Micromass ZQ, single quadrapole mass spectrometer using a Waters Xterra MS C18 column (5 μm, 100×4.6 mm plus guard cartridge) being initially held at 5% acetonitrile/water (with 10 mM ammonium bicarbonate in the aqueous mobile phase) for 0.5 minutes, followed by a linear gradient of 5-95% within 3.5 minutes and then held at 95% for 1.5 minutes.
NMR:
$^1$H Nuclear magnetic resonance (NMR) spectroscopy was carried out using a Bruker instrument operating at 400 MHz using the stated solvent at around room temperature unless otherwise stated. In all cases, NMR data were consistent with the proposed structures. Characteristic chemical shifts (δ) are given in parts-per-million using conventional abbreviations for designation of major peaks: e.g. s, singlet; d, doublet; t, triplet; q, quartet; dd, doublet of doublets; dt, doublet of triplets; m, multiplet; br, broad.

Preparative reverse-phase HPLC conditions
Preparative HPLC—Method 1:
Waters Micromass ZQ/Sample manager 2767
Photodiode array detector 2996;
Column: XTerra Prep MS C18 Column (5 μm, 19×150 mm, Waters)
Flow rate: 20 ml/min with MS detection
UV wavelength: 254 nm.
Mobile phase: Solvent A (water:MeCN:HCOOH 95:5:0.05); Solvent B (water:MeCN:HCOOH 5:95:0.05)
Gradient:

| Time (min) | % A | % B |
|---|---|---|
| 0.00 | 100.0 | 0.00 |
| 1.00 | 100 | 0.00 |
| 10.00 | 0.00 | 100.0 |
| 11.00 | 0.00 | 100.0 |
| 12.00 | 100.0 | 0.00 |

The above method, or slight modifications known to the skilled in the art, were used.
Compound Preparation:
Where the preparation of starting materials is not described, these are commercially available, known in the literature, or readily obtainable by those skilled in the art using standard procedures. Where it is stated that compounds were prepared "analogously" or "similarly" to earlier examples or intermediates, it will be appreciated by the skilled person that the reaction time, number of equivalents of reagents and temperature can be modified for each specific reaction and that it may be necessary or desirable to employ different work-up or purification techniques.

Flash chromatography refers to silica gel chromatography and is carried out using an Isolera MPLC system (manufactured by Biotage); pre-packed silica gel cartridges (supplied by Biotage); or using conventional glass column chromatography.

In the procedures that follow, after each starting material, reference to a compound number is made is typically provided. This is provided merely for assistance to the skilled chemist. The starting material may not necessarily have been prepared from the batch referred to.

Many of the Compounds described in the following Examples have been prepared from stereochemically pure starting materials, for example 95% ee. The stereochemistry of the compounds in the Examples, where indicated, has been assigned on the assumption that absolute configuration at resolved stereogenic centers of staring materials in maintained throughout any subsequent reaction conditions.

Intermediate 1 (R)-Quinuclidin-3-yl carbonochloridate hydrochloride (I-1)

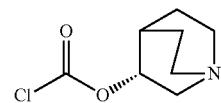

To a stirred solution of (R)-3-quinuclidinol (2.5 g, 19.66 mmol) in acetonitrile (200 mL) was added trichloromethyl chloroformate (3.06 mL, 25.57 mmol) dropwise at 0° C. and the mixture was allowed to stir at 0° C. for 1 hour. The reaction mixture was then stirred at RT for 16 hours and then the solvent was removed in vacuo to afford the title compound as a white solid (4.39 g, 98%).

$^1$H NMR (400 MHz, DMSO-d$_6$): δ 10.29 (s, 1H), 4.05-3.95 (m, 1H), 3.43 (t, J=10.8 Hz, 1H), 3.12 (m, 3H), 3.10-2.95 (m, 1H), 2.79 (d, J=13.3 Hz, 1H), 2.12-2.02 (m, 1H), 1.98 (m, J=3.4 Hz, 1H), 1.89-1.78 (m, 1H), 1.75-1.59 (m, 2H).

Intermediate 2. Methyl 3-(((4-fluorophenyl)amino)methyl)benzoate (I-2)

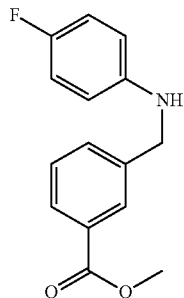 [SMILES: COC(=O)c1cccc(CNc2ccc(F)cc2)c1]

To a stirred solution of methyl 3-formylbenzoate (0.5 g, 3.046 mmol) in anhydrous DCM (15 mL) was added 4-fluoroaniline (0.303 mL, 3.198 mmol) followed by glacial acetic acid (0.174 mL, 3.046 mmol). The reaction was stirred at room temperature for 64 hours. Sodium triacetoxyborohydride (1.614 g, 7.615 mmol) was added, and the reaction was stirred at room temperature for 2 hours. Water was added to quench the reaction and the mixture was diluted with DCM. The organic layer was washed with brine, passed through a hydrophobic frit and the solvent was removed in vacuo to afford the title compound as a red oil (0.805 g, quantitative yield).

$^1$H NMR (400 MHz, CDCl3): δ 8.04 (s, 1H), 7.95 (d, J=7.8 Hz, 1H), 7.56 (d, J=7.7 Hz, 1H), 7.42 (t, J=7.7 Hz, 1H), 6.91-6.82 (m, 2H), 6.58-6.51 (m, 2H), 4.35 (s, 2H), 4.06-3.94 (br s, 1H), 3.91 (s, 3H). LCMS (Method 2): [MH+]=260 at 3.56 min.

The following intermediates were synthesised via a similar method as that described for intermediate 2.

| Structure | Intermediate number | Analytical Data |
|---|---|---|
| 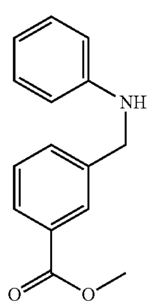 | Intermediate 3 | $^1$H NMR (400 MHz, CDCl3): δ 8.06 (s, 1 H), 7.95 (d, J = 7.8 Hz, 1 H), 7.58 (d, J = 7.7 Hz, 1 H), 7.45-7.36 (m, 1 H), 7.20-7.13 (m, 2 H), 6.78-6.65 (m, 1 H), 6.63 (dd, J = 7.5, 1.4 Hz, 2 H), 4.39 (s, 2 H), 4.16 (bs, 1 H), 3.91 (s, 3 H). |
| 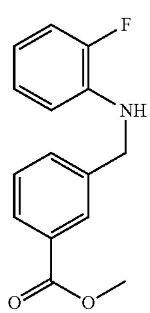 | Intermediate 4 | $^1$H NMR (400 MHz, CDCl3): δ 8.06 (s, 1 H), 7.96 (d, J = 7.8 Hz, 1 H), 7.58 (d, J = 7.7 Hz, 1 H), 7.43 (t, J = 7.7 Hz, 1 H), 7.02-6.90 (m, 2 H), 6.67-6.59 (m, 2 H), 4.45-4.41 (m, 2 H), 4.36 (bs, 1 H), 3.92 (s, 3 H). LCMS (Method 1): [MH+] = 260 at 4.33 min. |
| 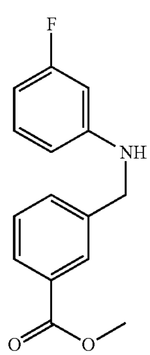 | Intermediate 5 | $^1$H NMR (400 MHz, CDCl3): δ 8.06-8.02 (m, 1 H), 7.98-7.93 (m, 1 H), 7.58-7.53 (m, 1 H), 7.42 (t, J = 7.7 Hz, 1 H), 7.12-7.04 (m, 1 H), 6.46-6.35 (m, 2 H), 6.33-6.27 (m, 1 H), 4.37 (s, 2 H), 3.92 (s, 3 H). LCMS (Method 1): [MH+] = 260 at 4.26 min. |

| Structure | Intermediate number | Analytical Data |
|---|---|---|
| 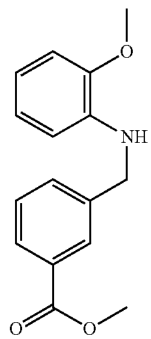 [SMILES: COC(=O)c1cccc(CNc2ccccc2OC)c1] | Intermediate 6 | $^1$H NMR (400 MHz, CDCl3): δ 8.06 (s, 1 H), 7.94 (d, J = 7.8 Hz, 1 H), 7.58 (d, J = 7.7 Hz, 1 H), 7.40 (t, J = 7.7 Hz, 1 H), 6.84-6.77 (m, 2 H), 6.75-6.65 (m, 1 H), 6.56-6.52 (m, 1 H), 4.41 (s, 2 H), 3.91 (s, 3 H), 3.86 (s, 3 H). LCMS (Method 2): [MH+] = 272 at 3.69 min. |
| 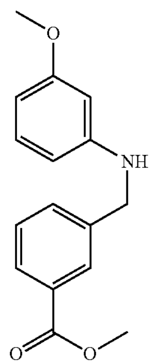 [SMILES: COC(=O)c1cccc(CNc2cccc(OC)c2)c1] | Intermediate 7 | $^1$H NMR (400 MHz, CDCl3): δ 8.05 (s, 1 H), 7.94 (d, J = 7.8 Hz, 1 H), 7.57 (d, J = 7.6 Hz, 1 H), 7.41 (t, J = 7.7 Hz, 1 H), 7.07 (t, J = 8.1 Hz, 1 H), 6.32-6.23 (m, 2 H), 6.18 (t, J = 2.3 Hz, 1 H), 4.37 (s, 2 H), 4.15 (bs, 1 H), 3.91 (s, 3 H), 3.74 (s, 3 H). LCMS (Method 2): [MH+] = 272 at 3.50 min. |
| 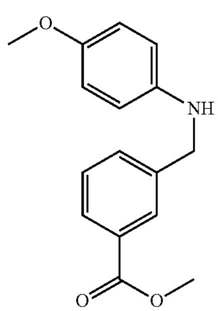 | Intermediate 8 | $^1$H NMR (400 MHz, CDCl3): δ 8.05 (s, 1 H), 7.94 (d, J = 7.8 Hz, 1 H), 7.58 (d, J = 7.7 Hz, 1 H), 7.41 (t, J = 7.7 Hz, 1 H), 6.79-6.74 (m, 2 H), 6.62-6.56 (m, 2 H), 4.34 (s, 2 H), 3.91 (s, 3 H), 3.74 (s, 3 H). LCMS (Method 2): [MH+] = 272 at 3.40 min. |
| 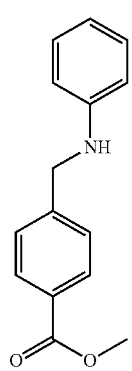 | Intermediate 9 | $^1$H NMR (400 MHz, DMSO): δ 7.95 (d, J = 8.0 Hz, 2 H), 7.52 (d, J = 7.9 Hz, 2 H), 7.10-7.01 (m, 2 H), 6.61-6.50 (m, 3 H), 6.36 (t, J = 7.9 Hz, 1 H), 4.38 (d, J = 8.1 Hz, 2 H), 3.87 (s, 3 H). LCMS (Method 2): [MH+] = 242 at 4.04 min. |

-continued

| Structure | Intermediate number | Analytical Data |
|---|---|---|
| 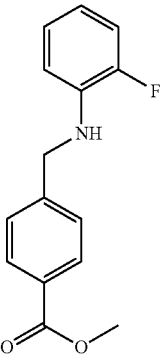 [SMILES: COC(=O)c1ccc(CNc2ccccc2F)cc1] | Intermediate 10 | Purified by chromatography using EtOAc/isohexane (1:9) as eluent.<br>$^1$H NMR (400 MHz, CDCl3): δ 8.04-7.99 (m, 2 H), 7.44 (d, J = 8.1 Hz, 2 H), 7.02-6.96 (m, 1 H), 6.93 (t, J = 7.9 Hz, 1 H), 6.72-6.61 (m, 1 H), 6.61-6.54 (m, 1 H), 4.45 (s, 2 H), 3.91 (s, 3 H), 3.71 (bs, 1 H).<br>LCMS (Method 1): [MH+] = 260 at 4.34 min. |
| 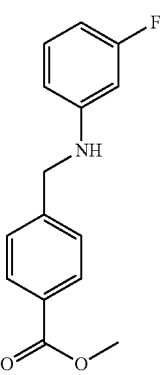 [SMILES: COC(=O)c1ccc(CNc2cccc(F)c2)cc1] | Intermediate 11 | $^1$H NMR (400 MHz, CDCl3): δ 8.05-7.99 (m, 2 H), 7.46-7.40 (m, 2 H), 7.13-7.05 (m, 1 H), 6.45-6.35 (m, 2 H), 6.32-6.25 (m, 1 H), 4.39 (s, 2 H), 3.91 (s, 3 H).<br>LCMS (Method 2): [MH+] = 260 at 3.60 min. |
| 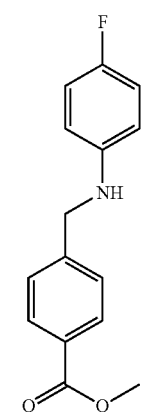 | Intermediate 12 | $^1$H NMR (400 MHz, CDCl3): δ 8.03-7.99 (m, 2 H), 7.45-7.41 (m, 2 H), 6.91-6.83 (m, 2 H), 6.56-6.49 (m, 2 H), 4.37 (s, 2 H), 4.07 (bs, 1 H), 3.91 (s, 3 H).<br>LCMS (Method 2): [MH+] = 260 at 3.55 min |
| 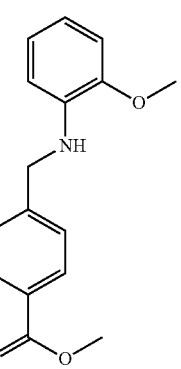 | Intermediate 13 | $^1$H NMR (400 MHz, CDCl3): δ 8.02-7.98 (m, 2 H), 7.47-7.42 (m, 2 H), 6.82-6.65 (m, 3 H), 6.51-6.48 (m, 1 H), 4.43 (s, 2 H), 3.91 (s, 3 H), 3.87 (s, 3 H).<br>LCMS (Method 2): [MH+] = 272 at 3.68 min. |

| Structure | Intermediate number | Analytical Data |
|---|---|---|
| 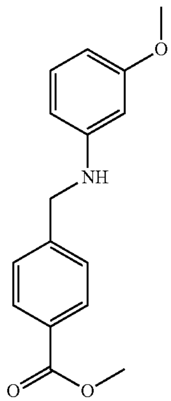 [SMILES: COC(=O)c1ccc(CNc2cccc(OC)c2)cc1] | Intermediate 14 | $^1$H NMR (400 MHz, CDCl3): δ 8.03-7.98 (m, 2 H), 7.46-7.41 (m, 2 H), 7.07 (t, J = 8.1 Hz, 1 H), 6.29 (dd, J = 8.2, 2.3 Hz, 1 H), 6.23 (dd, J = 8.1, 2.2 Hz, 1 H), 6.16 (t, J = 2.3 Hz, 1 H), 4.40 (s, 2 H), 3.91 (s, 3 H), 3.74 (s, 3 H). |
| 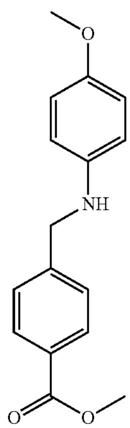 | Intermediate 15 | Purified by chromatography using EtOAc/isohexane (3:7) as eluent.<br>$^1$H NMR (400 MHz, CDCl3): δ 8.03-7.97 (m, 2 H), 7.44 (d, J = 8.1 Hz, 2 H), 6.79-6.74 (m, 2 H), 6.60-6.55 (m, 2 H), 4.36 (s, 2 H), 3.91 (s, 3 H), 3.74 (s, 3 H).<br>LCMS (Method 2): [MH+] = 272 at 3.40 min. |
| 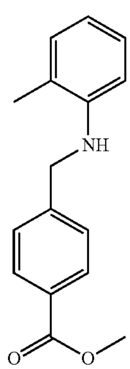 | Intermediate 16 | $^1$H NMR (400 MHz, CDCl3): δ 8.01 (d, J = 8.1 Hz, 2 H), 7.45 (d, J = 7.9 Hz, 2 H), 7.11-7.01 (m, 2 H), 6.73-6.65 (m, 1 H), 6.51 (d, J = 8.0 Hz, 1 H), 4.46 (s, 2 H), 3.91 (s, 3 H), 2.20 (s, 3 H). LCMS (Method 2): [MH+] = 256 at 3.76 min. |

Intermediate 17. (R)-methyl-3-(((4-fluorophenyl)((quinuclidin-3-yloxy)carbonyl)amino)-methyl)benzoate (I-17)

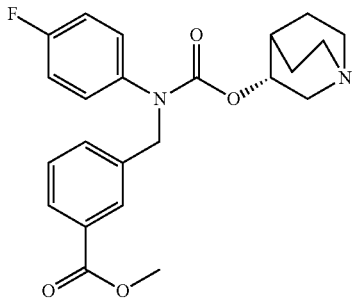 [SMILES: COC(=O)c1cccc(CN(C(=O)O[C@H]2CN3CCC2CC3)c2ccc(F)cc2)c1]

To a stirred solution of methyl 3-(((4-fluorophenyl)amino)methyl)benzoate (0.3 g, 1.157 mmol) in anhydrous pyridine (6 mL) at 0° C. under $N_2$ was added (R)-quinuclidin-3-yl carbonochloridate hydrochloride (0.314 g, 1.39 mmol) in one portion. After stirring at 0° C. for 1 hour the reaction was allowed to warm to room temperature. After 25 minutes, further (R)-quinuclidin-3-yl carbonochloridate (0.314 g, 1.39 mmol) was added, and the reaction was stirred at room temperature for 18 hours. The reaction was quenched by addition of 10% aqueous potassium carbonate solution and extracted with ethyl acetate (×3). The combined organic extracts were washed with brine and dried (sodium sulfate), filtered and the solvent was removed in vacuo to afford a red oil. The crude material was purified by silica gel column chromatography eluting sequentially with ethyl acetate, 10% methanol in ethyl acetate, 5% 7N methanolic ammonia in ethyl acetate and 10% 7N methanolic ammonia in ethyl acetate to afford the title compound as a yellow oil (0.471 g, 98%).

$^1$H NMR (400 MHz, CDCl3): δ 7.96-7.88 (m, 2H), 7.46-7.36 (m, 2H), 7.12-6.94 (m, 4H), 4.87 (s, 2H), 4.81-4.75 (m, 1H), 3.90 (s, 3H), 3.25-3.16 (m, 1H), 2.80-2.54 (m, 5H), 1.99-1.92 (m, 1H), 1.68-1.32 (m, 4H).

The following intermediates were synthesised via a similar method as that described for intermediate 17.

| Structure | Intermediate number | Precursor | Analytical Data |
|---|---|---|---|
| 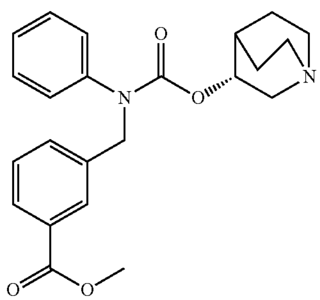 [SMILES: COC(=O)c1cccc(CN(C(=O)O[C@H]2CN3CCC2CC3)c2ccccc2)c1] | Intermediate 18 | Intermediate 3 | $^1$H NMR (400 MHz, CDCl3): δ 7.96-7.90 (m, 2 H), 7.46 (d, J = 7.7 Hz, 1 H), 7.38 (t, J = 7.9 Hz, 1 H), 7.30 (t, J = 7.6 Hz, 2 H), 7.21 (t, J = 7.4 Hz, 1 H), 7.14 (bs, 2 H), 4.97-4.86 (m, 2 H), 4.82-4.76 (m, 1 H), 3.90 (s, 3 H), 3.19 (ddd, J = 14.7, 8.2, 2.2 Hz, 1 H), 2.78-2.52 (m, 5 H), 1.96 (bs, 1 H), 1.67-1.58 (m, 1 H), 1.56-1.46 (m, 1 H), 1.45-1.35 (m, 1 H), 1.29-1.16 (m, 1 H). |
| 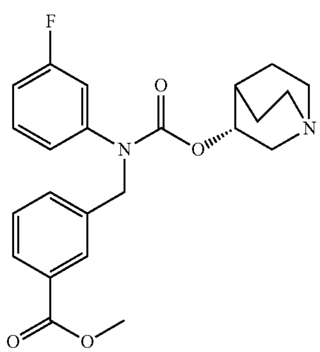 [SMILES: COC(=O)c1cccc(CN(C(=O)O[C@H]2CN3CCC2CC3)c2cccc(F)c2)c1] | Intermediate 19 | Intermediate 5 | $^1$H NMR (400 MHz, CDCl3): δ 7.97-7.90 (m, 2 H), 7.47-7.37 (m, 2 H), 7.29-7.22 (m, 1 H), 6.98-6.88 (m, 3 H), 4.97-4.87 (m, 2 H), 4.83-4.77 (m, 1 H), 3.90 (s, 3 H), 3.25-3.17 (m, 1 H), 2.81-2.54 (m, 5 H), 2.00-1.95 (m, 1 H), 1.69-1.47 (m, 2 H), 1.46-1.36 (m, 1 H), 1.30-1.20 (m, 1 H). |
| 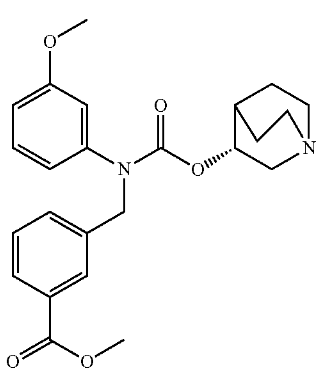 [SMILES: COC(=O)c1cccc(CN(C(=O)O[C@H]2CN3CCC2CC3)c2cccc(OC)c2)c1] | Intermediate 20 | Intermediate 7 | $^1$H NMR (400 MHz, CDCl3): δ 7.95-7.91 (m, 2 H), 7.49-7.44 (m, 1 H), 7.41-7.36 (m, 1 H), 7.20 (t, J = 8.1 Hz, 1 H), 6.78-6.67 (m, 3 H), 4.95-4.85 (m, 2 H), 4.82-4.76 (m, 1 H), 3.90 (s, 3 H), 3.74 (s, 3 H), 3.24-3.16 (m, 1 H), 2.82-2.55 (m, 5 H), 1.99-1.93 (m, 1 H), 1.67-1.37 (m, 3 H), 1.29-1.19 (m, 1 H). |

| Structure | Intermediate number | Precursor | Analytical Data |
|---|---|---|---|
| (structure) | Intermediate 21 | Intermediate 8 | ¹H NMR (400 MHz, CDCl3): δ 7.96-7.88 (m, 2 H), 7.48-7.42 (m, 1 H), 7.38 (t, J = 7.7 Hz, 1 H), 7.10-6.90 (m, 2 H), 6.88-6.75 (m, 2 H), 4.91-4.81 (m, 2 H), 4.80-4.74 (m, 1 H), 3.90 (s, 3 H), 3.78 (s, 3 H), 3.25-3.13 (m, 1 H), 2.78-2.53 (m, 5 H), 2.00-1.92 (m, 1 H), 1.69-1.33 (m, 3 H), 1.30-1.17 (m, 1 H). |
| (structure) | Intermediate 22 | Intermediate 9 | ¹H NMR (400 MHz, MeOD): δ 8.00 (d, J = 8.0 Hz, 2 H), 7.43-7.34 (m, 4 H), 7.30-7.20 (m, 3 H), 5.00 (s, 2 H), 4.85-4.80 (m, 1 H), 3.92 (s, 3 H), 3.21 (ddd, J = 14.7, 8.2, 2.4 Hz, 1 H), 2.82-2.66 (m, 3 H), 2.61 (dt, J = 14.7, 2.3 Hz, 1 H), 2.61-2.48 (m, 1 H), 2.00-1.95 (m, 1 H), 1.78-1.68 (m, 1 H), 1.66-1.56 (m, 1 H), 1.52-1.41 (m, 1 H), 1.40-1.29 (m, 1 H). LCMS (Method 2): [MH+] = 395 at 3.57 min. |
| (structure) | Intermediate 23 | Intermediate 10 | ¹H NMR (400 MHz, CDCl3): δ 7.96 (d, J = 7.8 Hz, 2 H), 7.33 (d, J = 7.9 Hz, 2 H), 7.28-7.19 (m, 1 H), 7.15-6.95 (m, 3 H), 4.89-4.74 (m, 3 H), 3.90 (s, 3 H), 3.23-3.14 (m, 1 H), 2.80-2.52 (m, 5 H), 1.96-1.83 (m, 1 H), 1.76-1.35 (m, 3 H), 1.30-1.13 (m, 1 H). |
| (structure) | Intermediate 24 | Intermediate 11 | ¹H NMR (400 MHz, CDCl3): δ 7.99 (d, J = 8.1 Hz, 2 H), 7.34-7.22 (m, 3 H), 6.99-6.88 (m, 3 H), 4.98-4.87 (m, 2 H), 4.82-4.77 (m, 1 H), 3.91 (s, 3 H), 3.24-3.16 (m, 1 H), 2.79-2.50 (m, 5 H), 1.98-1.93 (m, 1 H), 1.68-1.57 (m, 1 H), 1.56-1.46 (m, 1 H), 1.44-1.33 (m, 1 H), 1.29-1.19 (m, 1 H). |

| Structure | Intermediate number | Precursor | Analytical Data |
|---|---|---|---|
| (4-fluorophenyl structure) | Intermediate 25 | Intermediate 12 | ¹H NMR (400 MHz, CDCl3): δ 7.98 (d, J = 8.0 Hz, 2 H), 7.31 (d, J = 8.0 Hz, 2 H), 7.12-6.94 (m, 4 H), 4.93-4.82 (m, 2 H), 4.81-4.75 (m, 1 H), 3.91 (s, 3 H), 3.23-3.15 (m, 1 H), 2.82-2.51 (m, 5 H), 1.97-1.91 (m, 1 H), 1.68-1.19 (m, 4 H). |
| (3-methoxyphenyl structure) | Intermediate 26 | Intermediate 14 | ¹H NMR (400 MHz, CDCl3): δ 7.98 (d, J = 8.1 Hz, 2 H), 7.33 (d, J = 8.1 Hz, 2 H), 7.20 (t, J = 8.1 Hz, 1 H), 6.78-6.66 (m, 3 H), 4.96-4.85 (m, 2 H), 4.81-4.75 (m, 1 H), 3.91 (s, 3 H), 3.73 (s, 3 H), 3.23-3.15 (m, 1 H), 2.82-2.52 (m, 5 H), 1.98-1.92 (m, 1 H), 1.68-1.35 (m, 3 H), 1.29-1.18 (m, 1 H). LCMS (Method 2): [MH+] = 425 at 3.62 min. |
| (4-methoxyphenyl structure) | Intermediate 27 | Intermediate 15 | ¹H NMR (400 MHz, CDCl3): δ 7.97 (d, J = 7.8 Hz, 2 H), 7.32 (d, J = 8.0 Hz, 2 H), 6.95 (bs, 2 H), 6.80 (d, J = 8.2 Hz, 2 H), 4.85 (bs, 2 H), 4.77 (bs, 1 H), 3.91 (s, 3 H), 3.78 (s, 3 H), 3.18 (dd, J = 14.6, 8.2 Hz, 1 H), 2.74-2.66 (m, 3 H), 2.65-2.53 (m, 2 H), 1.94 (bs, 1 H), 1.67-1.57 (m, 1 H), 1.56-1.45 (m, 1 H), 1.45-1.30 (m, 1 H), 1.29-1.15 (m, 1 H). |

Intermediate 28. (R)-methyl 3-(((2-fluorophenyl)((quinuclidin-3-yloxy)carbonyl)amino)-methyl)benzoate (I-28)

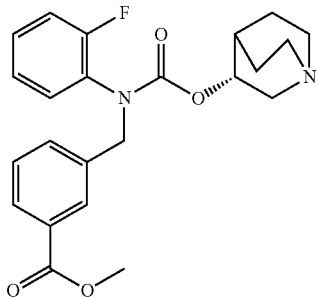 [SMILES: COC(=O)c1cccc(CN(C(=O)O[C@H]2CN3CCC2CC3)c2ccccc2F)c1]

To a stirred solution of methyl 3-(((2-fluorophenyl)amino) methyl)benzoate (0.3 g, 1.157 mmol) in anhydrous pyridine (6 mL) at 0° C. under $N_2$ was added 4-(dimethylamino)pyridine (0.014 g, 0.116 mmol) followed by (R)-quinuclidin-3-yl carbonochloridate hydrochloride (0.314 g, 1.39 mmol) in one portion. After stirring at 0° C. for 1 hour the reaction was allowed to warm to room temperature. After 2.5 hours, further (R)-quinuclidin-3-yl carbonochloridate (0.628 g, 2.777 mmol) was added, and the reaction was stirred at room temperature for 65 hours. The reaction was quenched by addition of 10% aqueous potassium carbonate solution and extracted with ethyl acetate (×3). The combined organic extracts were washed with brine and dried (sodium sulfate), filtered and the solvent was removed in vacuo to afford a brown oil. The crude material was purified by silica gel column chromatography eluting sequentially with ethyl acetate, 5% methanol in ethyl acetate, 5% 7N methanolic ammonia in ethyl acetate and 10% 7N methanolic ammonia in ethyl acetate to afford the title compound as a yellow oil (0.349 g, 73%).

$^1$H NMR (400 MHz, CDCl3): δ 7.97-7.86 (m, 2H), 7.53-7.45 (m, 1H), 7.37 (t, J=7.7 Hz, 1H), 7.27-7.19 (m, 1H), 7.16-6.96 (m, 3H), 4.90-4.74 (m, 3H), 3.89 (s, 3H), 3.24-3.14 (m, 1H), 2.84-2.53 (m, 5H), 1.96-1.83 (m, 1H), 1.66-1.36 (m, 3H), 1.33-1.13 (m, 1H).

The following intermediates were synthesized via a similar method as that described for intermediate 28:

| Structure | Intermediate number | Precursor | Analytical Data |
|---|---|---|---|
| 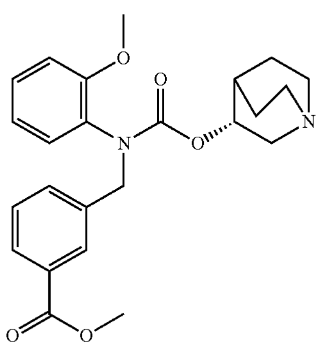 [SMILES: COC(=O)c1cccc(CN(C(=O)O[C@H]2CN3CCC2CC3)c2ccccc2OC)c1] | Intermediate 29 | Intermediate 6 | $^1$H NMR (400 MHz, CDCl3): δ 7.94-7.88 (m, 2 H), 7.52-7.42 (m, 1 H), 7.39-7.31 (m, 1 H), 7.28-7.17 (m, 1 H), 6.94-6.78 (m, 3 H), 5.12-4.45 (m, 3 H), 3.89 (s, 3 H), 3.83-3.69 (m, 3 H), 3.21-3.09 (m, 1 H), 2.83-2.43 (m, 5 H), 1.95-1.79 (m, 1 H), 1.76-1.36 (m, 3 H), 1.21-1.06 (m, 1 H). |
| 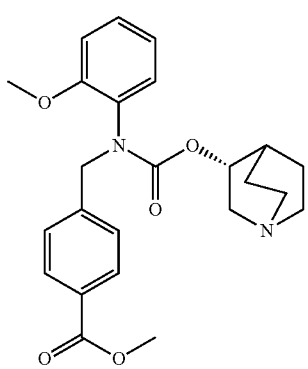 [SMILES: COC(=O)c1ccc(CN(C(=O)O[C@H]2CN3CCC2CC3)c2ccccc2OC)cc1] | Intermediate 30 | Intermediate 13 | $^1$H NMR (400 MHz, CDCl3): δ 7.94 (d, J = 8.0 Hz, 2 H), 7.33 (d, J = 8.0 Hz, 2 H), 7.25-7.18 (m, 1 H), 6.93-6.78 (m, 3 H), 5.13-4.41 (m, 3 H), 3.90 (s, 3 H), 3.84-3.69 (m, 3 H), 3.21-3.09 (m, 1 H), 2.85-2.43 (m, 5 H), 1.93-1.80 (m, 1 H), 1.66-1.37 (m, 3 H), 1.28-1.06 (m, 1 H). |

| Structure | Intermediate number | Precursor | Analytical Data |
|---|---|---|---|
| [structure image] | Intermediate 31 | Intermediate 16 | $^1$H NMR (400 MHz, CDCl3): δ 7.96 (d, J = 8.0 Hz, 2 H), 7.32 (d, J = 7.9 Hz, 2 H), 7.23-7.14 (m, 2 H), 7.13-7.04 (m, 1 H), 6.82 (dd, J = 13.5, 7.8 Hz, 1 H), 5.01 (d, J = 14.6 Hz, 1 H), 4.79-4.70 (m, 1 H), 4.53 (d, J = 14.7 Hz, 1 H), 3.93-3.88 (m, 3 H), 3.29-3.10 (m, 1 H), 2.95-2.40 (m, 5 H), 2.15-1.99 (m, 3 H), 1.90-1.81 (m, 1 H), 1.75-1.45 (m, 2 H), 1.21-1.07 (s, 2 H). |

Intermediate 32/A (I-32/A)

Step 1: Preparation of (R,S)-2-(3,5-dichloropyridin-4-yl)-1-(3,4-dimethoxylphenyl)ethanol (I-1/Aa)

3,5-dichloro-4-methylpyridine (54 g, 331 mmol) was dissolved in dry THF (480 mL) under argon atmosphere and cooled at −78° C. in dry-ice/acetone bath. LHMDS 1N THF solution (331 mL, 331 mmol) was added drop-wise keeping the temperature at −78°. The mixture was stirred at −78° for 1 hours. Thereafter, a solution of 3,4-dimethoxybenzaldehyde (50 g, 301 mmol) in dry THF (120 mL) was added drop-wise keeping the temperature at −78° C. When the addition was completed, the mixture was allowed to warm at RT. The reaction was poured into ice and water (1 L), and the mixture was stirred until a copious precipitate formed. The solid was filtered, and dissolved in ethyl acetate (500 mL), dried over Na$_2$SO$_4$ and the solvent evaporated under vacuum. The crude was crystallized in CHCl$_3$/hexane. The precipitate was filtered, washed with hexane and dried under vacuum at 40° C. for 8 hours to give 55 g of the title compound (45% yield). The mother liquor solution was evaporated under vacuum at 40° C., dissolved in ethyl acetate (200 mL) and extracted with 200 mL of water. The organic solution was dried over Na$_2$SO$_4$ and the solvent evaporated under vacuum at 40° C. The crude was crystallized in CHCl$_3$/hexane, and additional 15 g of the title product were obtained (70% overall yield).

Step 2: Preparation of (R,S)-2-(3,5-dichloropyridin-4-yl)-1-(3,4-dimethoxylphenyl)ethyl) (R)-2-(6-methoxynaphthalen-2-yl)propanoate (I-1/Ab)

(R,S)-2-(3,5-dichloropyridin-4-yl)-1-(3,4-dimethoxylphenyl)ethanol (50 g, 152 mmol), (R)-2-(6-methoxynaphthalen-2-yl)propanoic acid (38.6 g, 168 mmol), DMAP (20.5 g, 168 mmol), and EDC (43.8 g, 229 mmol) were dissolved in DMF (300 mL), and the reaction mixture was stirred at RT for 2 hours. Thereafter, water (500 mL) was added, and the solution stirred till complete precipitation occurs. The solid was filtered and dissolved in DCM (500 mL). The organic solution was washed with aqueous HCl 1N (2×500 mL), saturated aqueous NaHCO$_3$ solution (500 mL) and dried over Na$_2$SO$_4$. The solvent was evaporated under vacuum and the solid residue sonicated in EtOH (300 mL) and triturated for 1 hour. The resulting precipitate was collected by filtration and dried under vacuum at 40° C. for 4 hours to give 79 g (99% yield) of the title compound, as diastereoisomeric mixture.

Step 3: Preparation of (S)-2-(3,5-dichloropyridin-4-yl)-1-(3,4-dimethoxylphenyl)ethyl) (R)-(2-(6-methoxynaphthalen-2-yl)propanoate (I-1/Ac)

(R,S)-2-(3,5-dichloropyridin-4-yl)-1-(3,4-dimethoxylphenyl)ethyl) (R)-(6-methoxynaphthalen-2-yl)propanoate (diastereoisomeric mixture, 79 g, 146 mmol) was dissolved in CHCl$_3$ (100 mL), and MeOH (30 mL) was slowly added up to persistent opalescence and the mixture left at RT for 2 hours. The solid formed was collected by filtration and re-crystallized by CHCl$_3$/MeOH (70 mL/20 mL) solvent system to obtain 35 g of the desired compound (yield 88%, ee 98%). Chiral HPLC analysis: Chiralcel OD column, 10 μm, 250×4.6 mm; Flow=0.8 ml/min; eluent=hexane:isopropanol 97/3; R$_t$=42.33 min;

$^1$H NMR (600 MHz, CHLOROFORM-d) δ ppm 8.04 (s, 2H), 7.67 (d, J=8.79 Hz, 1H), 7.58 (d, J=8.52 Hz, 1H), 7.53 (m, 1H), 7.12-7.20 (m, 3H), 6.95 (dd, J=8.24, 1.92 Hz, 1H), 6.78-6.88 (m, 2H), 6.14 (dd, J=10.44, 4.12 Hz, 1H), 3.95 (s, 3H), 3.88 (s, 3H), 3.78-3.81 (m, 4H), 3.55 (dd, J=13.73, 10.44 Hz, 1H), 3.14 (dd, J=13.60, 4.26 Hz, 1H), 1.44 (d, J=7.14 Hz, 3H).

Step 4: Preparation of (S)-2-(3,5-dichloropyridin-4-yl)-1-(3,4-dimethoxylphenyl)ethanol, (I-1/Ad)

(S)-2-(3,5-dichloropyridin-4-yl)-1-(3,4-dimethoxyphenyl)ethyl) (R)-2-(6-methoxynaphthalen-2-yl)propanoate (30 g, 56 mmol) was dissolved in MeOH, and toluene was slowly added. Potassium tert-butoxide was slowly added to the suspension. The mixture was stirred for 24 hours at RT. The reaction was diluted with water (500 mL), and the aqueous mixture was extracted with CHCl$_3$ (500 mL). The organic layer was dried over Na$_2$SO$_4$ and the solvent was evaporated under vacuum. The residue was crystallized from CHCl$_3$ (100 mL) and hexane (20 mL) The mother liquor was concentrated and recrystallized with an analogous procedure giving a second crop of desired compound. In total, 16 g of the title compound (87% yield) were obtained. Chiral HPLC analysis: Chiralcel OD column, 10 μm, 250×4.6 mm; flow=0.8 ml/min; eluent=hexane:isopropanol 95/5; R$_t$=58.03 min; [α]$_D^{20}$=+10.21 (c=0.506, Methanol); $^1$H NMR (400 MHz, acetone) δ ppm 8.47 (s, 2H), 6.96-7.15 (m, 1H), 6.87 (m, 2H), 4.93-5.21

(m, 1H), 4.50 (d, J=3.97 Hz, 1H), 3.78 (s, 6H), 3.44 (dd, J=12.79, 8.38 Hz, 1H), 3.22 (dd, J=13.01, 5.51 Hz, 1H). MS/ESI⁺[MH]⁺: 328.19

Step 5: Preparation of (S)-3,5-dichloro-4-(2-(3,4-dimethoxylphenyl)-2-hydroxyethyl)pyridine 1-oxide (I-1/A)

(S)-2-(3,5-dichloropyridin-4-yl)-1-(3,4-dimethoxyphenyl)ethanol (4 g, 12 mmol) was dissolved in ethyl acetate, and m-CPBA was added to the solution. The mixture was stirred at RT for 5 hours. The formed solid was collected by filtration, washed with ethyl acetate and dried under vacuum to give 1.72 g of (S)-2-(3,5-dichloropyridin-4-yl)-1-(3,4-dimethoxyphenyl)ethanol (41% yield). Chiral HPLC analysis:Chiralcel OD column, 10 µm, 250×4.6 mm; Flow=0.8 ml/min; eluent=hexane:isopropanol 60/40; $R_t$=22.16 min; $[\alpha]_D^{20}$=+68.91 (c=0.253, Methanol/CHCl₃ 1:1); ¹H NMR (400 MHz, CHLOROFORM-d) δ ppm 8.15 (s, 2H), 6.99 (m, 1H), 6.79-6.88 (m, 2H), 5.03 (dd, J=8.50, 5.32 Hz, 1H), 3.75-3.98 (m, 6H), 3.42 (dd, J=13.57, 8.56 Hz, 1H), 3.19 (dd, J=13.51, 5.32 Hz, 1H), 2.06-2.15 (m, 1H); MS/ESI⁺ [MH]⁺: 344

Intermediates I-32/B, I-32/C, I-32/D, I-32/E, I-32/F

The racemic alcohol intermediates reported in table below are described in patent application WO2009/018909, which is incorporated herein by reference in its entirety, or may be obtained following the above procedure (only step 1 followed by step 5) substituting 3,4-dimethoxybenzaldehyde with the suitable 3,4-dialkoxybenzaldehyde.

| Table of racemic alcohol intermediates | | | |
|---|---|---|---|
| Structure | Name | Intermediate | Analytical data |
| [structure] | (R,S)-3,5-dichloro-4-(2-(3,4-dimethoxyphenyl)-2-hydroxyethyl)pyridine 1-oxide | I-32/B | ¹H NMR (400 MHz, (CDCl3) δ ppm 8.15 (s, 2 H), 6.99 (m, 1 H), 6.79-6.88 (m, 2 H), 5.03 (dd, J = 8.50, 5.32 Hz, 1 H), 3.75-3.98 (m, 6 H), 3.42 (dd, J = 13.57, 8.56 Hz, 1 H), 3.19 (dd, J = 13.51, 5.32 Hz, 1 H), 2.06-2.15 (m, 1 H); MS/ESI⁺ [MH]⁺: 344 |
| [structure] | (R,S)-3,5-dichloro-4-(2-(3-ethoxy-4-methoxyphenyl)-2-hydroxyethyl)pyridine 1-oxide | I-/32/C | MS/ESI⁺ [MH]⁺: 358 |
| [structure] | (R,S)-3,5-dichloro-4-(2-(3-cyclopropylmethoxy-4-methoxyphenyl)-2-hydroxyethyl)pyridine 1-oxide | I/32D | ¹H NMR (400 MHz, CDCl3): δ 8.13 (s, 2 H), 6.97 (s, 1 H), 6.83-6.81 (m, 2 H), 5.00-4.97 (m, 1 H), 3.87-3.84 (m, 5 H), 3.41-3.13 (m, 1 H), 3.18-3.13 (m, 1 H), 2.13-2.11 (br s, 1 H), 1.35-1.31 (m, 1 H), 0.68-0.63 (m, 2 H), 0.37-0.35 (m, 2 H). LCMS (Method 1): [MH+] = 384 at 3.21 min. |
| [structure] | (R,S)-3,5-dichloro-4-(2-(3-(cyclopentyloxy)-4-methoxyphenyl)-2-hydroxyethyl)pyridine 1-oxide | I/32E | ¹H NMR (400 MHz, CDCl₃): δ 8.13 (s, 2 H), 6.94 (s, 1 H), 6.82-6.81 (m , 2 H), 5.01-4.80 (m, 1 H), 4.79-4.76 (m, 1 H), 3.42 (s, 3 H), 3.41-3.36 (m, 1 H), 3.19-3.14 (m, 1 H), 1.95-1.79 (m, 6 H), 1.65-1.57 (m, 3 H). LCMS (Method 2): [MH+] = 398 at 3.13 min. |
| [structure] | (R,S)-4-(2-(3,4-bis(difluoromethoxy)phenyl)-2-hydroxyethyl)-3,5-dichloropyridine 1-oxide | I/32F | ¹H NMR (400 MHz, CDCl3): δ 8.15 (s, 2 H), 7.33 (s, 1 H), 7.28-7.19 (m, 2 H), 6.55 (t, J = 73.4 Hz, 1 H), 6.53 (t, J = 73.4 Hz, 1 H), 5.08 (app t, J = 6.4 Hz, 1 H), 3.38 (dd, J = 13.6, 8.7 Hz, 1 H), 3.17 (dd, J = 13.6, 5.2 Hz, 1 H), 2.29 (s, 1 H). LCMS (Method 1): [MH+] = 416 at 3.54 min. |

Intermediate 32/G (I-32/G). (S)-3,5-dichloro-4-(2-(3-(cyclopropylmethoxy)-4-(difluoromethoxy)phenyl)-2-hydroxyethyl)pyridine 1-oxide

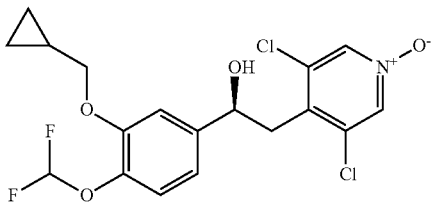 [SMILES: [O-][n+]1cc(Cl)c(C[C@H](O)c2ccc(OC(F)F)c(OCC3CC3)c2)c(Cl)c1]

The intermediate I-32/G may be obtained following the procedure described in patent application WO2010/089107 which is incorporated herein by reference in its entirety.

Intermediate 32/H (I-32/H). (S)-3,5-dichloro-4-(2-(4-(difluoromethoxy)-3-methoxylphenyl)-2-hydroxyethyl)pyridine 1-oxide

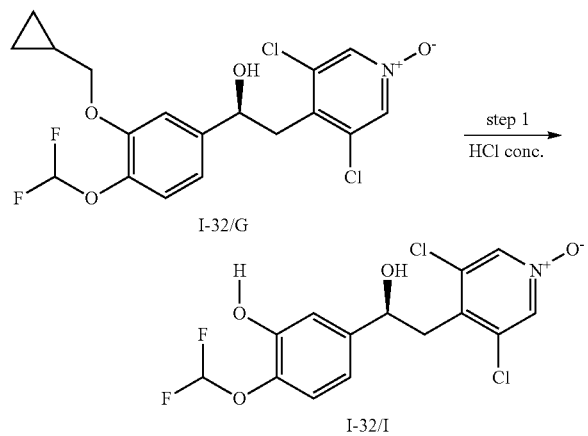

Step 1: (S)-3,5-dichloro-4-(2-(4-(difluoromethoxy)-3-hydroxylphenyl)-2-hydroxyethyl)pyridine 1-oxide (I-32/I)

(S)-3,5-dichloro-4-(2-(3-(cyclopropylmethoxy)-4-(difluoromethoxy)phenyl)-2-hydroxyethyl)pyridine 1-oxide (5 g, 11.90 mmol) was added to 100 mL of 37% HCl and stirred at room temperature for about 3 minutes, obtaining a yellow solution. After stirring for further 3 minutes the solution was poured into a solution of NaOH (48 g) in water (500 mL). The red solution was added with 1 M HCl to pH 1. The brown solid was filtered, washed with water, and triturated with hot EtOH (50 mL). After stirring at r.t. for 1 hour the solid was filtered, washed with EtOH and dried under vacuum at 40° C. yielding 2.4 of the title compound. MS/ESI+ [MH]+:366

Step 2: S)-3,5-dichloro-4-(2-(4-(difluoromethoxy)-3-methoxylphenyl)-2-hydroxyethyl)pyridine 1-oxide (I-32/H)

(S)-3,5-dichloro-4-(2-(4-(difluoromethoxy)-3-hydroxylphenyl)-2-hydroxyethyl-) pyridine 1-oxide (2 g, 5.46 mmol) was dissolved in DMF (16 mL), then $K_2CO_3$ (2 g, 14.47 mmol) and iodomethane (1.72 g, 12.12 mmol) were added, and the mixture was stirred at r.t. for 4 hours. The mixture was poured into 200 mL of water, filtered, washed with water and dried under vacuum at 40° C. 1.98 g of whitish solid was obtained.

$^1$H NMR (400 MHz, DMSO-d6): δ ppm 8.53 (s, 2H), 7.08-7.13 (m, 2H), 7.01 (t, J=75.00 Hz, 1H), 6.88 (dd, J=7.94, 1.76 Hz, 1H), 5.64 (d, J=4.41 Hz, 1H), 4.77-4.94 (m, 1H), 3.81 (s, 3H), 3.17 (d, J=8.38 Hz, 1H), 3.05 (d, J=5.73 Hz, 1H) MS/ESI+ [MH]+:380

Intermediates I-32/J, I-32/K, I-32/L, I-32/M, I-32/N

The intermediates reported in table below, I-32/J, I-32/K, I-32/L, I-32/M, I-32/N, may be obtained following the procedure described above for intermediate 32/H, by reacting intermediate I-32/I with a suitable alkylating agent.

| Structure | Name | Intermediate | Analytical data |
|---|---|---|---|
| (structure shown) | (S)-3,5-dichloro-4-(2-(4-(difluoromethoxy)-3-trideuteromethoxyphenyl)-2-hydroxyethyl)pyridine 1-oxide | I-32/J | $^1$H NMR (400 MHz, DMSO-d6): δ ppm 8.53 (s, 2 H), 7.06-7.13 (m, 2 H), 7.01 (t, J = 75.00 Hz, 1 H), 6.88 (dd, J = 8.38, 1.76 Hz, 1 H), 5.63 (d, J = 4.41 Hz, 1 H), 4.64-4.91 (m, 1 H), 3.19 (dd, J = 13.23, 8.38 Hz, 1 H), 3.05 (d, J = 5.73 Hz, 1 H) MS/ESI+ [MH]+: 383 |
| (structure shown) | (S)-3,5-dichloro-4-(2-(4-(difluoromethoxy)-3-ethoxyphenyl)-2-hydroxyethyl)pyridine 1-oxide | I-32/K | $^1$H NMR (400 MHz, DMSO-d6): δ ppm 8.53 (s, 2 H), 7.06-7.13 (m, 2 H), 7.01 (t, J = 75.00 Hz, 1 H), 6.86 (dd, J = 8.16, 1.54 Hz, 1 H), 5.62 (d, J = 3.97 Hz, 1 H), 4.72-4.97 (m, 1 H), 3.91-4.19 (m, 2 H), 3.18 (dd, J = 13.23, 8.38 Hz, 1 H), 3.02 (dd, J = 13.23, 5.29 Hz, 1 H), 1.33 (t, J = 7.06 Hz, 3 H) MS/ESI+ [MH]+: 394 |

| Structure | Name | Intermediate | Analytical data |
|---|---|---|---|
| [Structure: (S)-isomer with isopropoxy, difluoromethoxy phenyl, dichloro pyridine N-oxide] | (S)-3,5-dichloro-4-(2-(4-(difluoromethoxy)-3-isopropoxyphenyl)-2-hydroxyethyl)pyridine 1-oxide | I-32/L | ¹H NMR (400 MHz, DMSO-d6): δ ppm 8.52 (s, 2 H), 7.04-7.13 (m, 2 H), 6.97 (t, J = 75.00 Hz, 1 H), 6.86 (dd, J = 7.94, 1.76 Hz, 1 H), 5.63 (d, J = 3.53 Hz, 1 H), 4.81-4.90 (m, 1 H), 4.46-4.65 (m, 1 H), 3.16 (d, J = 7.94 Hz, 1 H), 3.04 (d, J = 6.17 Hz, 1 H), 1.26 (dd, J = 13.67, 6.17 Hz, 6 H) MS/ESI+ [MH]⁺: 408 |
| [Structure: (S)-isomer with propoxy, difluoromethoxy phenyl, dichloro pyridine N-oxide] | (S)-3,5-dichloro-4-(2-(4-(difluoromethoxy)-3-propoxyphenyl)-2-hydroxyethyl)pyridine 1-oxide | I-32/M | MS/ESI+ [MH]⁺: 408 |
| [Structure: (S)-isomer with cyclopentyloxy, difluoromethoxy phenyl, dichloro pyridine N-oxide] | (S)-3,5-dichloro-4-(2-(3-(cyclopentyloxy)-4-(difluoromethoxy)phenyl)-2-hydroxyethyl)pyridine 1-oxide | I-32/N | MS/ESI+ [MH]⁺: 434 |

The following intermediates I-33 to I-52 were prepared similarly to Intermediate 2.

| Structure | Intermediate number | Analytical Data |
|---|---|---|
| [3-chlorophenyl-NH-CH₂-phenyl-C(=O)-O-methyl] | Intermediate 33 | ¹H NMR (400 MHz, CDCl₃): δ 8.03 (s, 1 H), 7.96 (d, J = 7.8 Hz, 1 H), 7.55 (d, J = 7.8 Hz, 1 H), 7.42 (t, J = 7.7 Hz, 1 H), 7.06 (t, J = 8.0 Hz, 1 H), 6.72-6.66 (m, 1 H), 6.60 (t, J = 2.1 Hz, 1 H), 6.48 (dd, J = 8.2, 2.3 Hz, 1 H), 4.37 (s, 2 H), 3.92 (s, 3 H). LCMS (Method 1): [MH+] = 276 at 4.42 min. |
| [2,3-difluorophenyl-NH-CH₂-phenyl-C(=O)-O-methyl] | Intermediate 34 | ¹H NMR (400 MHz, CDCl₃): δ 8.04 (s, 1 H), 7.97 (d, J = 7.8 Hz, 1 H), 7.56 (d, J = 7.7 Hz, 1 H), 7.43 (t, J = 7.7 Hz, 1 H), 6.88-6.80 (m, 1 H), 6.55-6.45 (m, 1 H), 6.37 (t, J = 7.9 Hz, 1 H), 4.50-4.41 (m, 3 H), 3.92 (s, 3 H). LCMS (Method 1): [MH+] = 278 at 4.33 min. |
| [2,5-difluorophenyl-NH-CH₂-phenyl-C(=O)-O-methyl] | Intermediate 35 | ¹H NMR (400 MHz, CDCl₃): δ 8.04 (s, 1 H), 7.97 (d, J = 7.8 Hz, 1 H), 7.56 (d, J = 7.7 Hz, 1 H), 7.44 (t, J = 7.7 Hz, 1 H), 6.94-6.85 (m, 1 H), 6.39-6.25 (m, 2 H), 4.39 (d, J = 5.7 Hz, 2 H), 3.92 (s, 3 H), 3.81 (br s, 1 H). LCMS (Method 6): [MH+] = 278 at 3.69 min. |
| [3-methylphenyl-NH-CH₂-phenyl-C(=O)-O-methyl] | Intermediate 36 | ¹H NMR (400 MHz, CDCl₃): δ 8.05 (s, 1 H), 7.94 (d, J = 7.6 Hz, 1 H), 7.57 (d, J = 7.7 Hz, 1 H), 7.41 (t, J = 7.7 Hz, 1 H), 7.06 (t, J = 7.7 Hz, 1 H), 6.55 (d, J = 7.5 Hz, 1 H), 6.47-6.40 (m, 2 H), 4.37 (s, 2 H), 4.12 (br s, 1 H), 3.91 (s, 3 H), 2.26 (s, 3 H). LCMS (Method 1): [MH+] = 256 at 4.31 min. |

| Structure | Intermediate number | Analytical Data |
|---|---|---|
| (3-CF₃-phenyl-NH-CH₂-phenyl-3-CO₂Me) | Intermediate 37 | ¹H NMR (400 MHz, CDCl₃): δ 8.05 (s, 1 H), 7.97 (d, J = 7.8 Hz, 1 H), 7.56 (d, J = 7.7 Hz, 1 H), 7.46-7.40 (m, 1 H), 7.27-7.21 (m, 1 H), 6.95 (d, J = 7.7 Hz, 1 H), 6.84 (s, 1 H), 6.74 (dd, J = 8.2, 2.3 Hz, 1 H), 4.41 (s, 2 H), 4.35 (br s, 1 H), 3.92 (s, 3 H). LCMS (Method 1): [MH+] = 310 at 4.47 min. |
| (2-Me-phenyl-NH-CH₂-phenyl-3-CO₂Me) | Intermediate 38 | ¹H NMR (400 MHz, CDCl₃): δ 8.07 (s, 1 H), 7.95 (d, J = 7.8 Hz, 1 H), 7.59 (d, J = 7.7 Hz, 1 H), 7.42 (t, J = 7.7 Hz, 1 H), 7.10-7.05 (m, 2 H), 6.68 (t, J = 7.4 Hz, 1 H), 6.56 (d, J = 8.3 Hz, 1 H), 4.43 (s, 2 H), 3.96 (br s, 1 H), 3.92 (s, 3 H), 2.19 (s, 3 H). LCMS (Method 1): [MH+] = 256 at 4.37 min. |
| (3-CN-phenyl-NH-CH₂-phenyl-3-CO₂Me) | Intermediate 39 | ¹H NMR (400 MHz, CDCl₃): δ 8.03 (s, 1 H), 7.97 (d, J = 7.8 Hz, 1 H), 7.54 (d, J = 7.7 Hz, 1 H), 7.47-7.41 (m, 1 H), 7.25-7.19 (m, 1 H), 6.98 (dt, J = 7.6, 1.2 Hz, 1 H), 6.83-6.77 (m, 2 H), 4.39 (s, 2 H), 4.30 (br s, 1 H), 3.92 (s, 3 H). LCMS (Method 1): [MH+] = 267 at 4.05 min. |
| (2,3-diF-phenyl-NH-CH₂-phenyl-4-CO₂Me) | Intermediate 40 | ¹H NMR (400 MHz, CDCl₃): δ 8.02 (d, J = 7.6 Hz, 2 H), 7.43 (d, J = 7.6 Hz, 2 H), 6.86-6.79 (m, 1 H), 6.49 (dd, J = 17.1, 8.5 Hz, 1 H), 6.33 (t, J = 7.8 Hz, 1 H), 4.78 (d, J = 5.6 Hz, 1 H), 4.46 (d, J = 5.6 Hz, 2 H), 3.91 (s, 3 H). LCMS (Method 1): [MH+] = 278 at 4.32 min. |
| (2,4-diF-phenyl-NH-CH₂-phenyl-4-CO₂Me) | Intermediate 41 | ¹H NMR (400 MHz, CDCl₃): δ 8.02 (d, J = 8.0 Hz, 2 H), 7.43 (d, J = 8.0 Hz, 2 H), 6.84-6.76 (m, 1 H), 6.71-6.64 (m, 1 H), 6.49 (td, J = 9.3, 5.3 Hz, 1 H), 4.42 (s, 2 H), 3.91 (s, 3 H). Note: NH not visible. LCMS (Method 6): [MH+] = 278 at 3.71 min. |
| (2-F-phenyl-NH-CH₂-phenyl-2-F-4-CO₂Me) | Intermediate 42 | ¹H NMR (400 MHz, CDCl₃): δ 7.93 (dd, J = 6.8, 2.4 Hz, 1 H), 7.51 (ddd, J = 8.5, 4.6, 2.5 Hz, 1 H), 7.09 (dd, J = 10.5, 8.5 Hz, 1 H), 6.97 (ddd, J = 11.9, 8.0, 1.4 Hz, 1 H), 6.93 (t, J = 7.8 Hz, 1 H), 6.63 (tdd, J = 7.8, 4.9, 1.6 Hz, 1 H), 6.58 (dt, J = 7.9, 1.4 Hz, 1 H), 4.72-4.01 (m, 3 H), 3.91 (s, 3 H). LCMS (Method 6) [M + H] = 278 at 4.07 min. |
| (2,5-diF-phenyl-NH-CH₂-phenyl-4-CO₂Me) | Intermediate 43 | ¹H NMR (400 MHz, CDCl₃): δ 8.01 (d, J = 8.1 Hz, 2 H), 7.40 (d, J = 8.1 Hz, 2 H), 6.93-6.81 (m, 1 H), 6.31-6.22 (m, 2 H), 4.57 (br s, 1 H), 4.38 (d, J = 5.9 Hz, 2 H), 3.90 (s, 3 H). LCMS (Method 6): [MH+] = 278 at 3.68 min. |
| (3-Cl-phenyl-NH-CH₂-phenyl-4-CO₂Me) | Intermediate 44 | ¹H NMR (400 MHz, CDCl₃): δ 8.02 (d, J = 8.1 Hz, 2 H), 7.42 (d, J = 8.1 Hz, 2 H), 7.06 (t, J = 8.0 Hz, 1 H), 6.68 (d, J = 8.6 Hz, 1 H), 6.59 (t, J = 2.2 Hz, 1 H), 6.47 (dd, J = 8.2, 2.4 Hz, 1 H), 4.39 (s, 2 H), 4.22 (s, 1 H), 3.91 (s, 3 H). LCMS (Method 1): [MH+] = 276 at 4.42 min. |

| Structure | Intermediate number | Analytical Data |
|---|---|---|
| 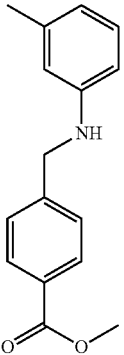 | Intermediate 45 | $^1$H NMR (400 MHz, CDCl$_3$): δ 8.00 (d, J = 8.0 Hz, 2 H), 7.43 (d, J = 8.0 Hz, 2 H), 7.05 (t, J = 7.7 Hz, 1 H), 6.55 (d, J = 7.7 Hz, 1 H), 6.46-6.40 (m, 2 H), 4.40 (s, 2 H), 3.91 (s, 3 H), 2.26 (s, 3 H). LCMS (Method 6): [MH+] = 256 at 3.73 min. |
| 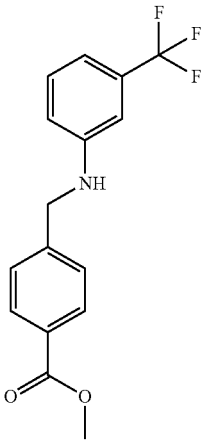 [SMILES: COC(=O)c1ccc(CNc2cccc(C(F)(F)F)c2)cc1] | Intermediate 46 | $^1$H NMR (400 MHz, CDCl$_3$): δ 8.02 (d, J = 8.1 Hz, 2 H), 7.43 (d, J = 8.1 Hz, 2 H), 7.29-7.21 (m, 1 H), 6.96 (d, J = 7.8 Hz, 1 H), 6.83 (s, 1 H), 6.72 (d, J = 8.4 Hz, 1 H), 4.43 (s, 2 H), 4.24 (br s, 1 H), 3.92 (s, 3 H). LCMS (Method 1): [MH+] = 310 at 4.43 min. |
| 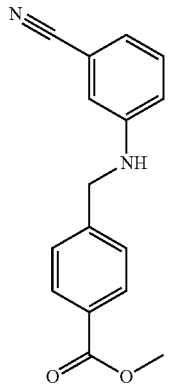 [SMILES: COC(=O)c1ccc(CNc2cccc(C#N)c2)cc1] | Intermediate 47 | $^1$H NMR (400 MHz, CDCl$_3$): δ 8.03 (d, J = 8.0 Hz, 2 H), 7.41 (d, J = 8.1 Hz, 2 H), 7.22 (t, J = 7.8 Hz, 1 H), 6.99 (d, J = 7.5 Hz, 1 H), 6.82-6.77 (m, 2 H), 4.42 (s, 2 H), 3.92 (s, 3 H). LCMS (Method 6): [MH+] = 267 at 3.41 min. |
| 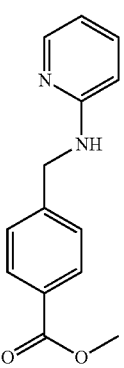 | Intermediate 48 | $^1$H NMR (400 MHz, CDCl$_3$): δ 8.11 (d, J = 5.1 Hz, 1 H), 8.00 (d, J = 8.1 Hz, 2 H), 7.44-7.41 (m, 3 H), 6.61 (dd, J = 7.1, 5.1 Hz, 1 H), 6.36 (d, J = 8.4 Hz, 1 H), 4.95 (br s, 1 H), 4.59 (d, J = 6.0 Hz, 2 H), 3.91 (s, 3 H). LCMS (Method 6): [MH+] = 243 at 3.02 min. |
| 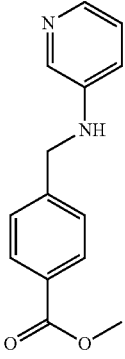 [SMILES: COC(=O)c1ccc(CNc2cccnc2)cc1] | Intermediate 49 | $^1$H NMR (400 MHz, CDCl$_3$): δ 8.30 (s, 1 H), 8.02 (d, J = 8.0 Hz, 2 H), 7.93 (d, J = 5.0 Hz, 1 H), 7.43 (d, J = 8.0 Hz, 2 H), 7.18 (dd, J = 8.4, 4.9 Hz, 1 H), 6.94 (dd, J = 8.5, 2.7 Hz, 1 H), 4.46 (s, 2 H), 3.91 (s, 3 H). LCMS (Method 6): [MH+] = 243 at 2.61 min. |
| 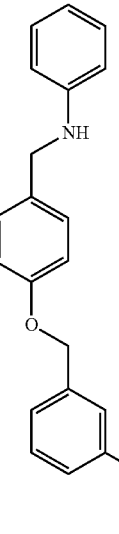 | Intermediate 50 | $^1$H NMR (400 MHz, CDCl$_3$): δ 8.11 (s, 1 H), 8.00 (d, J = 8.0 Hz, 1 H), 7.62 (d, J = 8.0 Hz, 1 H), 7.48-7.44 (m, 1 H), 7.30-7.25 (m, 2 H), 7.19-7.15 (m, 2 H), 6.96-6.93 (m, 2 H), 6.73-6.69 (m, 1 H), 6.64-6.62 (m, 2 H), 5.10 (s, 2 H), 4.31 (s, 2 H), 4.25 (brs, 1 H), 3.92 (s, 3 H). LCMS (Method 1): [MNa+] = 370 at 4.60 min. |
| 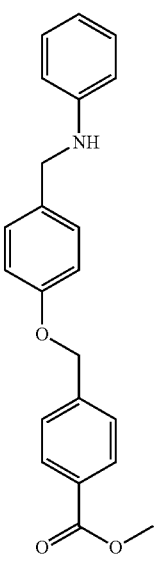 [SMILES: COC(=O)c1ccc(COc2ccc(CNc3ccccc3)cc2)cc1] | Intermediate 51 | $^1$H NMR (400 MHz, CDCl$_3$): δ 8.06-8.04 (m, 2 H), 7.51-7.49 (m, 2 H), 7.30-7.26 (m, 2 H), 7.19-7.15 (m, 2 H), 6.94-6.92 (m, 2 H), 6.73-6.69 (m, 1 H), 6.64-6.62 (m, 2 H), 5.12 (s, 2 H), 4.25 (s, 2 H), 3.94 (brs, 1 H), 3.90 (s, 3 H). |

| Structure | Intermediate number | Analytical Data |
|---|---|---|
| 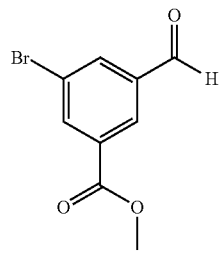 | Intermediate 52 | $^1$H NMR (400 MHz, CDCl$_3$): δ 8.00-7.98 (m, 2 H), 7.30-7.25 (m, 2 H), 7.02-6.93 (m, 2 H), 6.75-6.71 (m, 1 H), 6.66-6.60 (m, 1 H), 3.91-3.89 (m, 4 H), 3.51-3.43 (m, 2 H), 3.00-2.97 (m, 2 H). LCMS (Method 1): [MH+] = 274 at 4.45 min. |

Intermediate 53. Methyl 3-bromo-5-formylbenzoate (I-53)

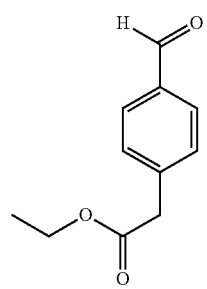

To a mixture of methyl 3-formylbenzoate (5.0 g, 30.5 mmol) in concentrated sulfuric acid (50 mL) was added N-bromosuccinimide (5.4 g, 30.5 mmol) in one portion at 0° C. After warming to room temperature, the reaction mixture was stirred for 2 days before being poured into 400 mL of ice/water. Once the ice had melted, the aqueous phase was extracted with DCM (2×400 mL). The combined organic phases were passed through a hydrophobic fit. The solvent was removed in vacuo and the residue was purified via silica gel chromatography, eluting with 0-10% EtOAc in isohexane, to give the title compound as an oil that solidified upon standing (4.6 g, 63%). $^1$H NMR (400 MHz, CDCl$_3$): δ 10.02 (s, 1H), 8.45 (t, J=1.5 Hz, 1H), 8.41 (t, J=1.7 Hz, 1H), 8.20 (t, J=1.7 Hz, 1H), 3.98 (s, 3H).

Intermediate 54

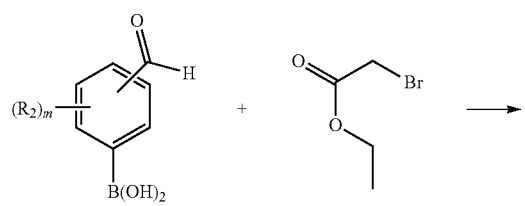

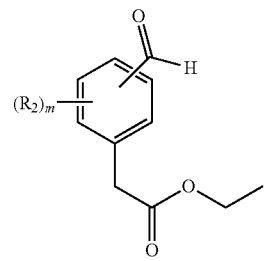

Ethyl 2-(4-formylphenyl)acetate (I-54)

A screw cap tube was loaded with (4-formylphenyl)boronic acid (450 mg, 3 mmol), ethylbromoacetate (0.22 mL, 2 mmol), potassium carbonate (830 mg, 6 mmol), Pd$_2$(dba)$_3$ (46 mg, 0.05 mmol), tri-1-naphtylphosphine (62 mg, 0.15 mmol), H$_2$O (0.5 mL), and THF (4.5 mL). The mixture was degased with nitrogen for 5 minutes and then heated to 65° C. for 18 hours. The reaction was cooled to room temperature and diluted with ethyl acetate (50 mL) and washed with water (2×50 mL). The organic phase was filtered through a phase separator and the solvent was removed in vacuo. The residue was purified by silica gel chromatography, eluting with 0-20% EtOAc in isohexane, to yield ethyl 2-(4-formylphenyl) acetate as colourless oil (327 mg, 57%).

$^1$H NMR (400 MHz, CDCl$_3$): δ 9.99 (s, 1H), 7.83 (d, J=8.0 Hz, 2H), 7.45 (d, J=8.0 Hz, 2H), 4.19-4.12 (m, 2H), 3.70 (s, 2H), 1.28-1.20 (m, 3H). LCMS (Method 1):

[MH+]=193 at 3.58 min.

Intermediate 55

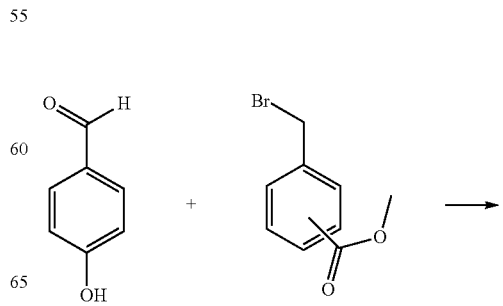

-continued

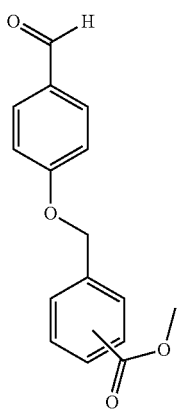

Methyl 4-((4-formylphenoxy)methyl)benzoate (I-55)

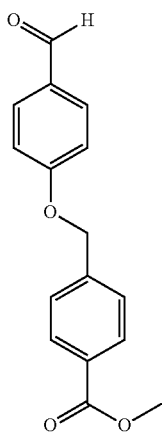 [SMILES: COC(=O)c1ccc(COc2ccc(C=O)cc2)cc1]

To a suspension of 4-hydroxybenzaldehyde (244.2 mg, 2 mmol) and cesium carbonate (445 mg, 1.36 mmol) in anhydrous DMF (8 mL) was added methyl-4-(bromomethyl)benzoate (481 mg, 2.1 mmol). The resulting mixture was stirred for 24 hours at room temperature, after which time the mixture was concentrated under reduced pressure. The resulting crude was partitioned between dichloromethane (30 mL) and water (10 mL). The mixture was filtered through a phase separator, washed with dichloromethane and the solvent was removed in vacuo to yield the title compound as an off-white solid (520 mg, 96%).

$^1$H NMR (400 MHz, CDCl$_3$): δ 9.89 (s, 1H), 8.08-8.06 (m, 2H), 7.86-7.83 (m, 2H), 7.51-7.49 (m, 2H), 7.07-6.98 (m, 2H), 5.23 (s, 2H), 3.93 (s, 3H). LCMS (Method 1): [MH+]=271 at 4.12 min.

The following intermediate was synthesized via the same method as that of I-55.

| Structure | Intermediate number | Analytical Data |
|---|---|---|
| 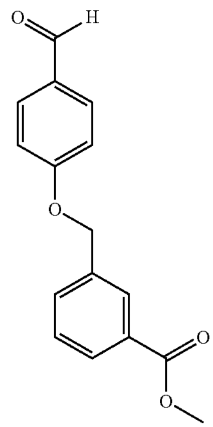 [SMILES: COC(=O)c1cccc(COc2ccc(C=O)cc2)c1] | Intermediate 56 | $^1$H NMR (400 MHz, CDCl$_3$): δ 9.89 (s, 1 H), 8.12 (s, 1 H), 8.04-8.02 (m, 1 H), 7.87-7.84 (m, 2 H), 7.64-7.63 (m, 1 H), 7.50-7.47 (m, 1 H), 7.10-7.06 (m, 2 H), 5.19 (s, 2 H), 3.93 (s, 3 H). |

The following intermediates (I-57 to I-61) were synthesized via procedure as used for intermediate 2.

| Structure | Intermediate number | Precursor | Analytical Data |
|---|---|---|---|
| 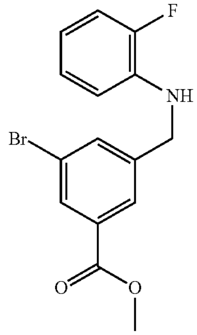 [SMILES: COC(=O)c1cc(Br)cc(CNc2ccccc2F)c1] | Intermediate 57 | Intermediate 53 | $^1$H NMR (400 MHz, CDCl$_3$): δ 8.08 (t, J = 1.7 Hz, 1 H), 7.97 (s, 1 H), 7.72 (t, J = 1.7 Hz, 1 H), 7.00 (ddd, J = 11.8, 8.0, 1.4 Hz, 1 H), 6.93 (t, J = 7.8 Hz, 1 H), 6.65 (tdd, J = 7.8, 4.9, 1.6 Hz, 1 H), 6.55 (td, J = 8.4, 1.5 Hz, 1 H), 4.40 (s, 3 H), 3.91 (s, 3 H). HPLC (Method 1): [MH+] = 338 at 4.62 min. |

| Structure | Intermediate number | Precursor | Analytical Data |
|---|---|---|---|
| 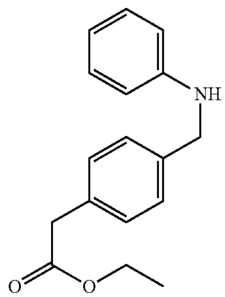 [SMILES: CCOC(=O)Cc1ccc(CNc2ccccc2)cc1] | Intermediate 58 | Intermediate 54 | $^1$H NMR (400 MHz, CDCl$_3$): δ 7.49-7.09 (m, 6 H), 6.80-6.66 (m, 3 H), 5.92-5.63 (brs, 1 H), 4.29 (s, 2 H), 4.16-4.11 (m, 2 H), 3.58 (s, 2 H), 1.26-1.22 (m, 3 H). LCMS (Method 1): [MH+] = 270 at 4.20 min. |
| 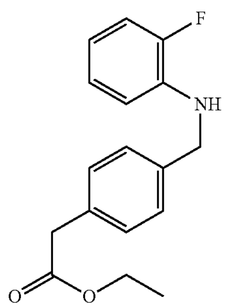 [SMILES: CCOC(=O)Cc1ccc(CNc2ccccc2F)cc1] | Intermediate 59 | Intermediate 54 | $^1$H NMR (400 MHz, CDCl$_3$): δ 7.41-7.12 (m, 5 H), 6.71-6.59 (m, 3 H), 5.90-5.64 (brs, 1 H), 4.31 (s, 2 H), 4.16-4.10 (m, 2 H), 3.59 (s, 2 H), 1.26-1.21 (m, 3 H). |
| 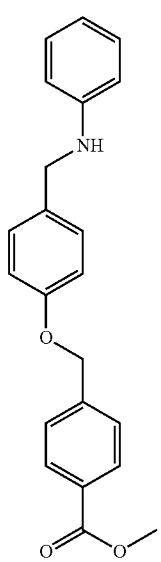 [SMILES: COC(=O)c1ccc(COc2ccc(CNc3ccccc3)cc2)cc1] | Intermediate 60 | Intermediate 55 | $^1$H NMR (400 MHz, CDCl$_3$): δ 8.06-8.04 (m, 2 H), 7.51-7.49 (m, 2 H), 7.30-7.26 (m, 2 H), 7.19-7.15 (m, 2 H), 6.94-6.92 (m, 2 H), 6.73-6.69 (m, 1 H), 6.64-6.62 (m, 2 H), 5.12 (s, 2 H), 4.25 (s, 2 H), 3.94 (brs, 1 H), 3.90 (s, 3 H). |

-continued

| Structure | Intermediate number | Precursor | Analytical Data |
|---|---|---|---|
| 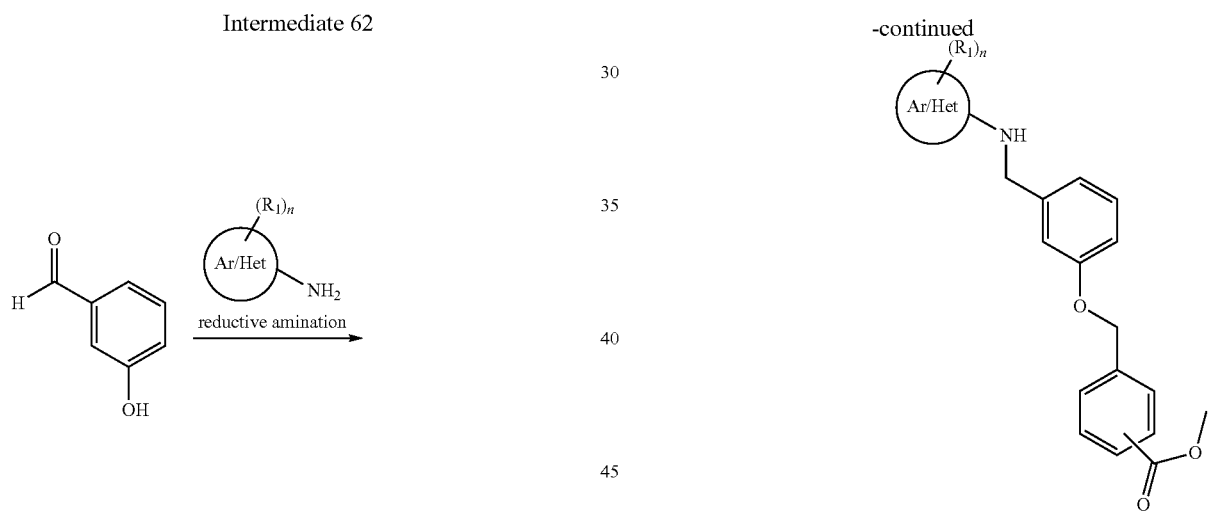 | Intermediate 61 | Intermediate 56 | $^1$H NMR (400 MHz CDCl$_3$): δ 8.11 (s, 1 H), 8.00 (d, J = 8.0 Hz, 1 H), 7.62 (d, J = 8.0 Hz, 1 H), 7.48-7.44 (m, 1 H), 7.30-7.25 (m, 2 H), 7.19-7.15 (m, 2 H), 6.96-6.93 (m, 2 H), 6.73-6.69 (m, 1 H), 6.64-6.62 (m, 2 H), 5.10 (s, 2 H), 4.31 (s, 2 H), 4.25 (brs, 1 H), 3.92 (s, 3 H). LCMS (Method 1): [MNa+] = 370 at 4.60 min. |

Intermediate 62

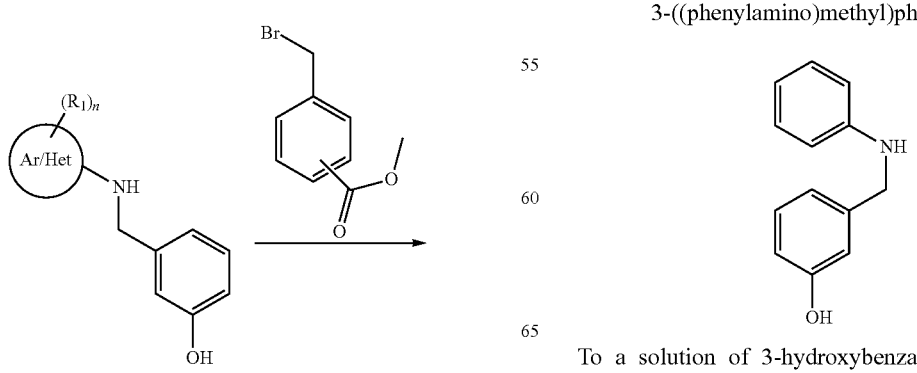

Methyl 4-((3-((phenylamino)methyl)phenoxy)methyl)benzoate (I-62)

Step 1: Preparation of 3-((phenylamino)methyl)phenol (I-62a)

To a solution of 3-hydroxybenzaldehyde (1.05 g, 8.6 mmol) and aniline (821 μL, 9.0 mmol) in dichloromethane (35 mL) was added acetic acid (516 μL, 9.0 mmol). The reaction mixture was stirred at room temperature for 24 hours. Sodium triacetoxyborohydride (4.55 g, 21.5 mmol) was added, and the reaction was stirred at room temperature for 24 hours. Water was added to quench the reaction and the mixture was diluted with dichloromethane. The organic layer was washed with brine, passed through a hydrophobic frit and the solvent was removed in vacuo to afford the title compound as a brown oil (1.7 g, quantitative yield).

$^1$H NMR (400 MHz, CDCl$_3$): δ 7.25-7.15 (m, 3H), 6.94-6.92 (m, 1H), 6.85 (s, 1H), 6.74-6.69 (m, 2H), 6.63-6.60 (m, 2H), 4.71 (brs, 1H), 4.29 (s, 2H), 4.11 (brs, 1H). LCMS (Method 1): [MH+]=200 at 3.48 min.

Step 2: Preparation of methyl 4-((3-((phenylamino)methyl)phenoxy)methyl)benzoate (I-62b)

| Structure | Intermediate number | Analytical Data |
|---|---|---|
| 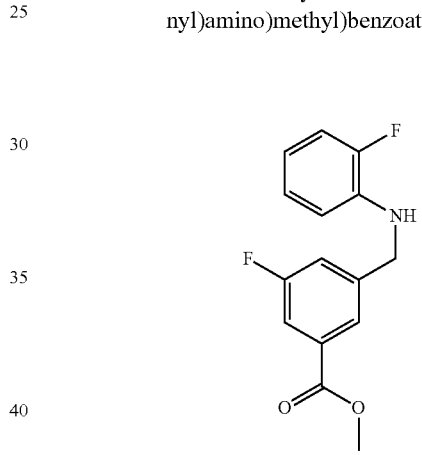 | Intermediate 63 | $^1$H NMR (400 MHz, CDCl$_3$): δ 8.10 (s, 1 H), 7.99 (d, J = 8.0 Hz, 1 H), 7.61 (d, J = 8.0 Hz, 1 H), 7.47-7.43 (m, 1 H), 7.28-7.24 (m, 1 H), 7.18-7.14 (m, 2 H), 7.01-6.97 (m, 2 H), 6.89-6.86 (m, 1 H), 6.73-6.69 (m, 1 H), 6.63-6.61 (m, 2 H), 5.08 (s, 2 H), 4.31 (s, 2 H), 4.03 (brs, 1 H), 3.92 (s, 3 H). |

Intermediate 64. Methyl 3-fluoro-5-(((2-fluorophenyl)amino)methyl)benzoate (I-64)

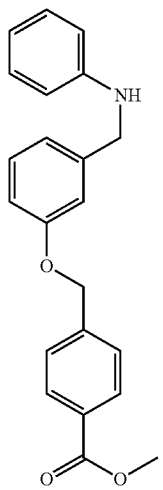 [SMILES: COC(=O)c1ccc(COc2cccc(CNc3ccccc3)c2)cc1]

To a suspension of 3-((phenylamino)methyl)phenol (398 mg, 2 mmol) and cesium carbonate (651 mg, 2 mmol) in anhydrous DMF (8 mL) was added methyl-4-(bromomethyl)benzoate (481 mg, 2.1 mmol). The resulting mixture was stirred for 22 hours at room temperature, after which time the solvent was removed in vacuo. The residue was partitioned between dichloromethane (30 mL) and water (10 mL). The mixture was passed through a phase separator, washed with dichloromethane and solvent was removed in vacuo to afford a brown oil. The crude material was purified by silica gel chromatography eluting with 25% ethyl acetate in iso-hexane to afford the title compound as a yellow oil (133 mg, 19%).

$^1$H NMR (400 MHz, CDCl$_3$): δ 8.04-8.02 (m, 2H), 7.48 (d, J=8.0 Hz, 2H), 7.27-7.14 (m, 3H), 7.00-6.97 (m, 2H), 6.88-6.85 (m, 1H), 6.73-6.69 (m, 1H), 6.63-6.60 (m, 2H), 5.10 (s, 2H), 4.30 (s, 2H), 4.03 (brs, 1H), 3.90 (s, 3H).

The following intermediate was synthesized via the same method as that of I-62.

A mixture of methyl 3-fluoro-5-methylbenzoate (1.0 g, 5.95 mmol), N-bromosuccinimide (1.27 g, 7.14 mmol), and dibenzoylperoxide (145 mg, 0.60 mmol) in CHCl$_3$ (50 mL) was heated to reflux for 6 hours. After cooling to room temperature, the reaction mixture was quenched with saturated aqueous NaHCO$_3$ (50 mL), and the layers were separated. The organic phase was washed with saturated aqueous NaHCO$_3$ (50 mL) and then passed through a hydrophobic frit. The solvent was removed in vacuo and the residue was used directly in the next step without any further purification. To the residue was added 2-fluoroaniline (0.23 mL, 2.41 mmol) and potassium carbonate (454 mg, 3.29 mmL) in DMF (5.5 mL). The mixture was stirred at room temperature for 18 hours and then partitioned between EtOAc (30 mL) and water (20 mL). The layers were separated and the aqueous phase extracted with EtOAc (3×30 mL) The combined organic phases were washed with brine (20 mL) and dried over Na$_2$SO$_4$. The mixture was filtered and the solvent was removed in vacuo. The residue was purified on an SCX cartridge washing with MeOH and eluting with 3 to 10% NH$_3$ in DCM. Further purification via silica gel chromatography, eluting with 0-20% EtOAc in isohexane, gave methyl 3-fluoro-5-(((2-fluorophenyl)amino)methyl)benzoate (CD6) as a yellow oil (133 mg, 8.1% over two steps).

$^1$H NMR (400 MHz, CDCl$_3$): δ 7.85 (s, 1H), 7.63-7.59 (m, 1H), 7.30 (d, J=9.2 Hz, 1H), 7.00 ddd, J=11.8, 8.0, 1.4 Hz, 1H), 6.93 (t, J=7.8 Hz, 1H), 6.68-6.61 (m, 1H), 6.59-6.51 (m, 1H), 4.43 (s, 2H), 3.92 (s, 3H). LCMS (Method 1): [MH+]= 278 at 4.37 min.

The following compound was synthesized using the above procedure used for I-64.

| Structure | Intermediate number | Analytical Data |
|---|---|---|
| 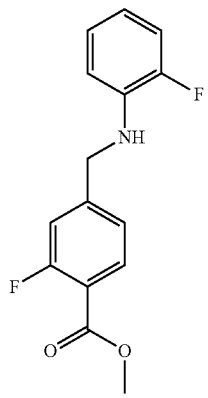 [SMILES: COC(=O)c1ccc(CNc2ccccc2F)cc1F] | Intermediate 65 | $^1$H NMR (400 MHz, CDCl$_3$): δ 7.77 (dd, J = 8.0, 1.5 Hz, 1 H), 7.72 (dd, J = 10.5, 1.6 Hz, 1 H), 7.48-7.39 (m, 1 H), 7.03-6.94 (m, 1 H), 6.96-6.90 (m, 1 H), 6.67-6.60 (m, 1 H), 6.61-6.56 (m, 1 H), 4.49 (d, J = 5.9 Hz, 2 H), 4.43 (s, 1 H), 3.90 (s, 3 H). |

Intermediate 66. Methyl 2-fluoro-4-[(2-fluoroanilino)methyl]benzoate (I-66)

To a mixture of 2-fluoroaniline (0.12 mL, 1.2 mmol) and potassium carbonate (207 mg, 1.5 mL) in DMF (5 mL) was added methyl 4-(bromomethyl)-2-fluoro-benzoate (247 mg, 1 mmol). The mixture was heated to 60° C. for 18 hours. The solvent was removed in vacuo. The mixture was partitioned between DCM (15 mL) and water (15 mL), the layers were separated and the organic phase was passed through a hydrophobic frit. The solvent was removed in vacuo and the residue was used directly in the next step without any further purification. LCMS (Method 2): [MH+]=278 at 3.60 min.

The following intermediate was synthesized via a similar method as that for 1-66.

| Structure | Intermediate number | Analytical Data |
|---|---|---|
| 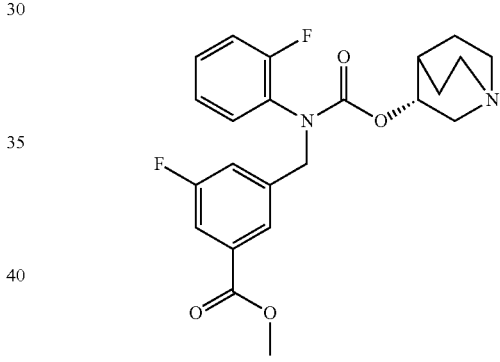 | Intermediate 67 | LCMS (Method 2): [MH+] = 260 at 3.51 min. |

Intermediate 68. Methyl 3-fluoro-5-[(2-fluoro-N-[(3R)-quinuclidin-3-yl]oxycarbonyl-anilino)methyl]benzoate (I-68)

A suspension of methyl 3-fluoro-5-(((2-fluorophenyl)amino)methyl)benzoate (133 mg, 0.48 mmol) and (R)-quinuclidin-3-yl carbonochloridate hydrochloride (163 mg, 0.72 mmol) in anhydrous CH$_3$CN (6 mL) was heated to 100° C. for 30 minutes under microwave irradiation. After cooling to room temperature, the mixture was diluted with EtOAc (30 mL) and saturated aqueous NaHCO$_3$ (20 mL). The layers were separated and the organic phase was dried over Na$_2$SO$_4$. The mixture was filtered and the solvent was removed in vacuo to yield the title compound which was used directly in the next step without any further purification.

$^1$H NMR (400 MHz, CDCl$_3$): δ 7.75-7.65 (m, 1H), 7.61 (d, J=9.0 Hz, 1H), 7.29-7.20 (m, 2H), 7.14-7.03 (m, 3H), 4.85 (s, 2H), 4.82-4.74 (m, 1H), 3.90 (s, 3H), 3.28-3.11 (m, 1H), 2.83-2.46 (m, 5H), 2.03-1.96 (m, 1H), 1.69-1.57 (m, 1H), 1.56-1.45 (m, 1H), 1.37-1.25 (m, 1H), 1.25-1.13 (m, 1H). LCMS (Method 2) [MH+]=431 at 3.36 min The following compounds (I-69 to I-92) were synthesized using the above procedure used for 1-68.

| Structure | Intermediate number | Precursor | Analytical Data |
|---|---|---|---|
| 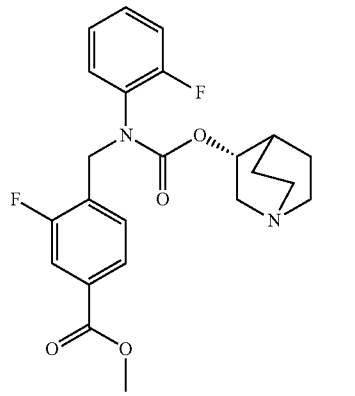 [SMILES: COC(=O)c1ccc(CN(C(=O)O[C@H]2CN3CCC2CC3)c2ccccc2F)c(F)c1] | Intermediate 69 | Intermediate 65 | ¹H NMR (400 MHz, CDCl₃): δ 7.78 (d, J = 8.0 Hz, 1 H), 7.63 (d, J = 10.3 Hz, 1 H), 7.53-7.46 (m, 1 H), 7.27-7.21 (m, 1 H), 7.14-7.02 (m, 3 H), 4.94 (s, 2 H), 4.79 (bs, 1 H), 3.91 (s, 3 H), 3.27-3.14 (m, 1 H), 2.83-2.52 (m, 4 H), 1.97-1.90 (m, 1 H), 1.78-1.67 (m, 2 H), 1.56-1.47 (m, 1 H), 1.36-1.27 (m, 1 H), 1.24-1.15 (m, 1 H). HPLC (Method 1): [MH+] = 431 at 2.65 min |
| 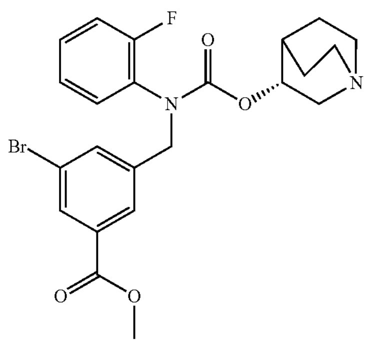 [SMILES: COC(=O)c1cc(Br)cc(CN(C(=O)O[C@H]2CN3CCC2CC3)c2ccccc2F)c1] | Intermediate 70 | Intermediate 57 | ¹H NMR (400 MHz, CDCl₃): δ 8.06 (s, 1 H), 7.84 (s, 1 H), 7.63 (s, 1 H), 7.32-7.20 (m, 1 H), 7.14-7.05 (m, 3 H), 4.83 (s, 2 H), 3.90 (s, 3 H), 3.28-3.16 (m, 1 H), 2.79-2.59 (m, 5 H), 2.03-1.93 (m, 1 H), 1.71-1.59 (m, 1 H), 1.59-1.47 (m, 1 H), 1.39-1.28 (m, 1 H), 1.28-1.16 (m, 1 H). LCMS (Method 1): [MH+] = 491 at 2.78 min. |
| 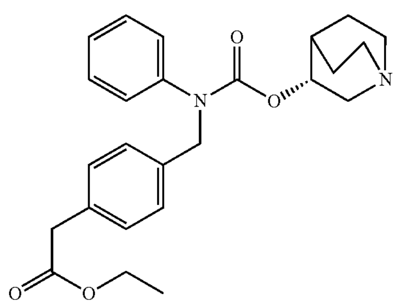 [SMILES: CCOC(=O)Cc1ccc(CN(C(=O)O[C@H]2CN3CCC2CC3)c2ccccc2)cc1] | Intermediate 71 | Intermediate 58 | LCMS (Method 2): [MH+] = 423 at 3.73 min. |
| 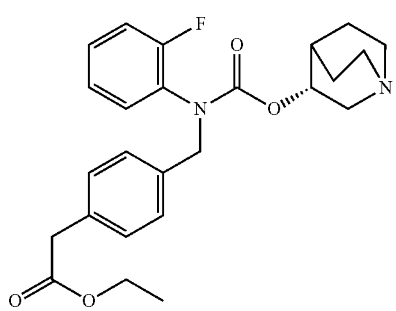 [SMILES: CCOC(=O)Cc1ccc(CN(C(=O)O[C@H]2CN3CCC2CC3)c2ccccc2F)cc1] | Intermediate 72 | Intermediate 59 | ¹H NMR (400 MHz, CDCl₃): δ 7.23-6.99 (m, 8 H), 4.84-4.82 (m, 3 H), 4.16-4.11 (m, 2 H), 3.57 (s, 2 H), 3.11-3.47 (m, 1 H), 2.87-2.52 (m, 4 H), 2.09-2.07 (m, 1 H), 1.72-1.71 (m, 1 H), 1.69-1.48 (m, 4 H), 1.23-1.21 (m, 3 H). |

| Structure | Intermediate number | Precursor | Analytical Data |
|---|---|---|---|
| 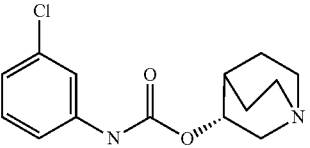 | Intermediate 73 | Intermediate 33 | $^1$H NMR (400 MHz, CDCl$_3$): δ 7.97-7.90 (m, 2 H), 7.47-7.37 (m, 2 H), 7.26-7.16 (m, 3 H), 7.04 (br s, 1 H), 4.91 (d, J = 3.2 Hz, 2 H), 4.82-4.77 (m, 1 H), 3.90 (s, 3 H), 3.21 (ddd, J = 14.8, 8.2, 2.3 Hz, 1 H), 2.81-2.55 (m, 5 H), 2.00-1.95 (m, 1 H), 1.69-1.59 (m, 1 H), 1.57-1.47 (m, 1 H), 1.47-1.37 (m, 1 H), 1.32-1.21 (m, 1 H). |
| 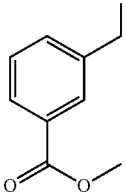 | Intermediate 74 | Intermediate 42 | $^1$H NMR (400MHz, CD$_3$CN): δ 7.82 (br s, 1 H), 7.53-7.46 (m, 1 H), 7.37-7.21 (m, 2 H), 7.20-7.09 (m, 3 H), 4.87 (t, J = 16.1 Hz, 2 H), 4.77-4.68 (m, 1 H), 3.87 (s, 3 H), 3.13 (dd, J = 14.8, 8.1 Hz, 1 H), 2.79-2.42 (m, 5 H), 1.95-1.73 (m, 1 H), 1.72-1.58 (m, 1 H), 1.58-1.42 (m, 1 H), 1.39-1.07 (m, 2 H). LCMS (Method 2): [MH+] = 431 at 3.60 min. |
| 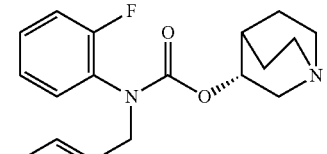 | Intermediate 75 | Intermediate 34 | $^1$H NMR (400 MHz, CDCl$_3$): δ 7.97-7.87 (m, 2 H), 7.48 (d, J = 7.7 Hz, 1 H), 7.39 (t, J = 7.7 Hz, 1 H), 7.12-7.04 (m, 1 H), 7.04-6.96 (m, 1 H), 6.90-6.80 (m, 1 H), 4.88 (s, 2 H), 4.81 (br s, 1 H), 3.90 (s, 3 H), 3.27-3.15 (m, 1 H), 2.80-2.55 (m, 5 H), 2.02-1.92 (m, 1 H), 1.71-1.58 (m, 1H), 1.58-1.46 (m, 1 H), 1.45-1.17 (m, 2 H). LCMS (Method 2): [MH+] = 431 at 3.73 min. |
| 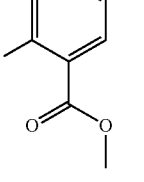 | Intermediate 76 | Intermediate 35 | $^1$H NMR (400 MHz, CDCl$_3$): δ 7.94 (d, J = 7.9 Hz, 1 H), 7.78 (d, J = 8.6 Hz, 1 H), 7.50-7.45 (m, 1 H), 7.39 (t, J = 7.7 Hz, 1 H), 7.12-7.00 (m, 1 H), 6.99-6.90 (m, 1 H), 6.81-6.74 (m, 1 H), 4.87 (s, 2 H), 4.84-4.77 (m, 1 H), 3.90 (s, 3 H), 3.29-3.16 (m, 1 H), 2.95-2.60 (m, 5 H), 2.00-1.91 (m, 1 H), 1.72-1.59 (m, 1 H), 1.59-1.49 (m, 1 H) 1.45-1.15 (m, 2 H). |

-continued

| Structure | Intermediate number | Precursor | Analytical Data |
|---|---|---|---|
| (structure) | Intermediate 77 | Intermediate 36 | ¹H NMR (400 MHz, CDCl$_3$): δ 7.94 (d, J = 5.8 Hz, 2 H), 7.47 (d, J = 7.7 Hz, 1 H), 7.39 (t, J = 7.8 Hz, 1 H), 7.18 (t, J = 7.7 Hz, 1 H), 7.05-6.89 (m, 3 H), 4.90 (d, J = 4.0 Hz, 2 H), 4.81-4.76 (m, 1 H), 3.90 (s, 3 H), 3.20 (dd, J = 14.8, 8.2 Hz, 1 H), 2.79-2.68 (m, 3 H), 2.68-2.54 (m, 2 H), 2.30 (s, 3 H), 2.00-1.94 (m, 1 H), 1.68-1.58 (m, 1 H), 1.57-1.46 (m, 1 H), 1.46-1.37 (m, 1 H), 1.29-1.21 (m, 1 H). |
| (structure) | Intermediate 78 | Intermediate 37 | ¹H NMR (400 MHz, CDCl$_3$): δ 7.96 (d, J = 7.4 Hz, 1 H), 7.92 (s, 1 H), 7.51-7.38 (m, 5 H), 7.38-7.28 (m, 1 H), 4.95 (d, J = 3.6 Hz, 2 H), 4.84-4.79 (m, 1 H), 3.90 (s, 3 H), 3.22 (ddd, J = 14.8, 8.2, 2.2 Hz, 1 H), 2.81-2.68 (m, 3 H), 2.68-2.53 (m, 2 H), 2.00-1.94 (m, 1 H), 1.70-1.60 (m, 1 H), 1.58-1.47 (m, 1 H), 1.44-1.33 (m, 1 H), 1.31-1.21 (m, 1 H). |
| (structure) | Intermediate 79 | Intermediate 38 | ¹H NMR (400 MHz, CDCl$_3$): δ 7.95 (d, J = 7.7 Hz, 1 H), 7.89 (s, 1 H), 7.51-7.45 (m, 1 H), 7.37 (t, J = 7.6 Hz, 1 H), 7.23-7.14 (m, 2 H), 7.09 (d, J = 8.0 Hz, 1 H), 6.83 (dd, J = 12.4, 7.8 Hz, 1 H), 5.02 (d, J = 14.6 Hz, 1 H), 4.80-4.70 (m, 1 H), 4.53 (d, J = 14.6 Hz, 1 H), 3.89 (s, 3 H), 3.22-3.12 (m, 1 H), 2.82-2.42 (m, 5 H), 2.13-2.02 (m, 3 H), 1.86 (br s, 1 H), 1.63-1.54 (m, 1 H), 1.54-1.45 (m, 1 H), 1.21-1.09 (m, 2 H). |
| (structure) | Intermediate 80 | Intermediate 39 | ¹H NMR (400 MHz, CDCl$_3$): δ 7.99-7.94 (m, 1 H), 7.90 (s, 1 H), 7.53-7.47 (m, 2 H), 7.45-7.40 (m, 4 H), 4.94 (d, J = 4.9 Hz, 2 H), 4.85-4.80 (m, 1 H), 3.91 (s, 3 H), 3.23 (ddd, J = 14.8, 8.2, 2.3 Hz, 1 H), 2.80-2.68 (m, 3 H), 2.68-2.52 (m, 2 H), 2.01-1.95 (m, 1 H), 1.70-1.59 (m, 1 H), 1.59-1.47 (m, 1 H), 1.45-1.33 (m, 1 H), 1.33-1.23 (m, 1 H). |

| Structure | Intermediate number | Precursor | Analytical Data |
|---|---|---|---|
| (structure with 2,3-difluorophenyl) | Intermediate 81 | Intermediate 40 | LCMS (Method 2): [MH+] = 431 at 3.35 min. |
| (structure with 2,4-difluorophenyl) | Intermediate 82 | Intermediate 41 | LCMS (Method 2): [MH+] = 431 at 3.34 min. |
| (structure with 2,5-difluorophenyl) | Intermediate 83 | Intermediate 43 | LCMS (Method 2): [MH+] = 431 at 3.34 min. |

| Structure | Intermediate number | Precursor | Analytical Data |
|---|---|---|---|
| 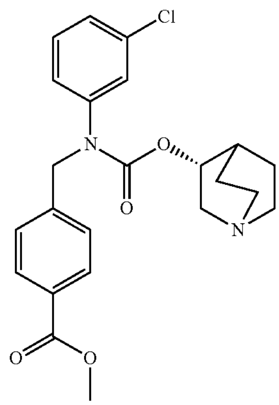 [SMILES: COC(=O)c1ccc(CN(C(=O)O[C@H]2CN3CCC2CC3)c2cccc(Cl)c2)cc1] | Intermediate 84 | Intermediate 44 | LCMS (Method 2): [MH+] = 429 at 3.49 min. |
| 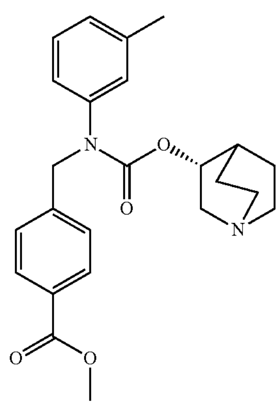 [SMILES: COC(=O)c1ccc(CN(C(=O)O[C@H]2CN3CCC2CC3)c2cccc(C)c2)cc1] | Intermediate 85 | Intermediate 45 | LCMS (Method 2): [MH+] = 409 at 3.38 min. |
| 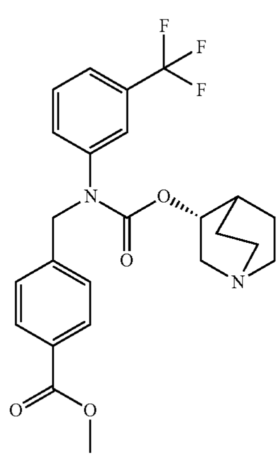 [SMILES: COC(=O)c1ccc(CN(C(=O)O[C@H]2CN3CCC2CC3)c2cccc(C(F)(F)F)c2)cc1] | Intermediate 86 | Intermediate 46 | LCMS (Method 2): [MH+] = 463 at 3.57 min. |

| Structure | Intermediate number | Precursor | Analytical Data |
|---|---|---|---|
| 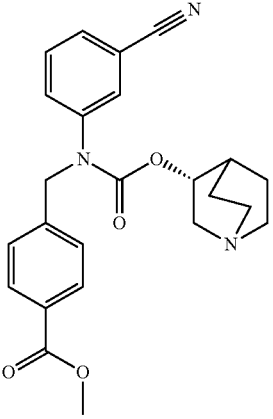 [SMILES: COC(=O)c1ccc(CN(C(=O)O[C@H]2CN3CCC2CC3)c2cccc(C#N)c2)cc1] | Intermediate 87 | Intermediate 47 | LCMS (Method 2): [MH+] = 420 at 3.08 min. |
| 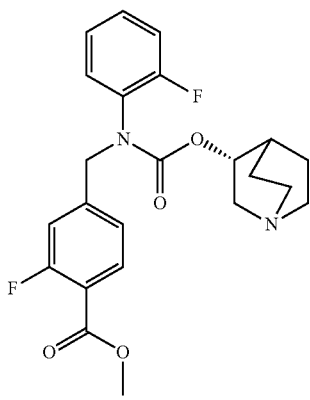 [SMILES: COC(=O)c1ccc(CN(C(=O)O[C@H]2CN3CCC2CC3)c2ccccc2F)cc1F] | Intermediate 88 | Intermediate 66 | LCMS (Method 2): [MH+] = 431 at 3.40 min. |
| 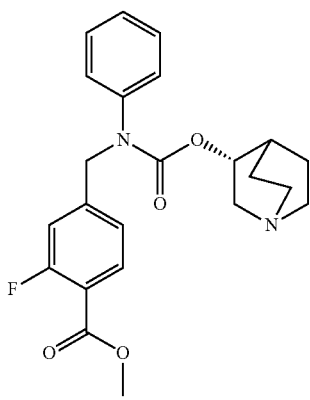 [SMILES: COC(=O)c1ccc(CN(C(=O)O[C@H]2CN3CCC2CC3)c2ccccc2)cc1F] | Intermediate 89 | Intermediate 67 | LCMS (Method 2): [MH+] = 413 at 3.38 min. |

-continued

| Structure | Intermediate number | Precursor | Analytical Data |
|---|---|---|---|
| 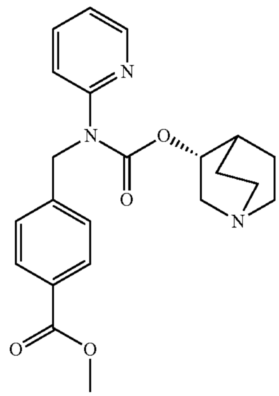 [SMILES: COC(=O)c1ccc(CN(C(=O)O[C@H]2CN3CCC2CC3)c2ccccn2)cc1] | Intermediate 90 | Intermediate 48 | ¹H NMR (400 MHz, CDCl₃): δ 8.41-8.40 (m, 1 H), 7.97 (d, J = 8.0 Hz, 2 H), 7.74-7.67 (m, 2 H), 7.28 (d, J = 8.0 Hz, 2 H), 7.12-7.10 (m, 1 H), 5.24-5.20 (m, 2 H), 5.05-5.04 (m, 1 H), 3.90 (s, 3 H), 3.58-3.47 (m, 1 H), 3.30-3.10 (m, 4 H), 2.82-2.77 (m, 1 H), 2.28-2.26 (m, 1 H), 2.01-1.76 (m, 4 H). LCMS (Method 1): [MH+] = 396 at 2.47 min. |
| 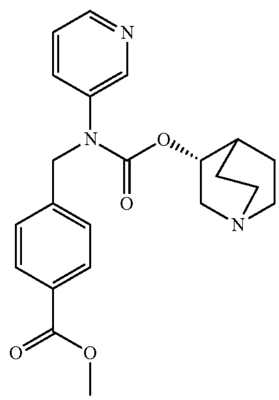 [SMILES: COC(=O)c1ccc(CN(C(=O)O[C@H]2CN3CCC2CC3)c2cccnc2)cc1] | Intermediate 91 | Intermediate 49 | LCMS (Method 2): [MH+] = 396 at 2.64 min. |
| 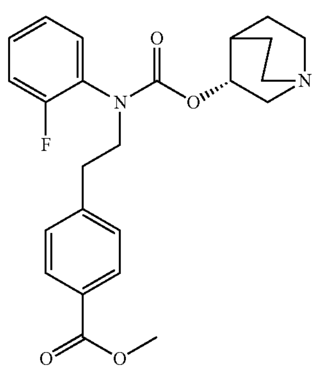 [SMILES: COC(=O)c1ccc(CCN(C(=O)O[C@H]2CN3CCC2CC3)c2ccccc2F)cc1] | Intermediate 92 | Intermediate 52 | ¹H NMR (400 MHz, CDCl₃): δ 7.94 (d, J = 8.4 Hz, 2 H), 7.32-7.23 (m, 3 H), 7.15-7.05 (m, 3 H), 4.79-4.78 (m, 1 H), 3.90 (s, 3 H), 3.86-3.84 (m, 2 H), 3.25-3.21 (m, 1 H), 2.97-2.93 (m, 2 H), 2.81-2.66 (m, 5 H), 2.04-1.98 (m, 1 H), 1.69-1.66 (m, 1 H), 1.59-1.55 (m, 1 H), 1.36-1.21 (m, 2 H). LCMS (Method 1): [MH+] = 427 at 2.69 min. |

Example 1

(1S)-2-(3,5-dichloro-1-oxido-pyridin-1-ium-4-yl)-1-(3,4-dimethoxylphenyl)-ethyl]3-[(4-fluoro-N-[(3R)-quinuclidin-3-yl]oxycarbonyl-anilino)methyl]benzoate

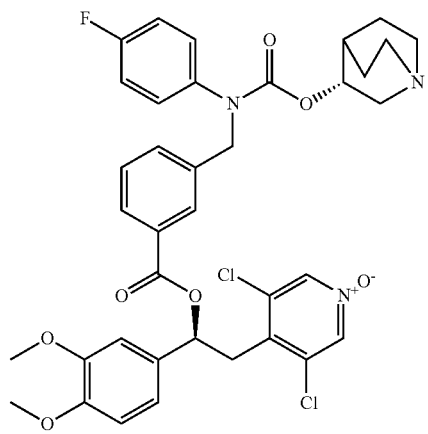

To a stirred solution of (R)-methyl 3-(((4-fluorophenyl)((quinuclidin-3-yloxy)carbonyl)amino)methyl)benzoate (0.471 g, 1.144 mmol) in tetrahydrofuran (5.8 mL) and methanol (5.8 mL) was added a solution of lithium hydroxide monohydrate (0.096 g, 2.29 mmol) in water (2.3 mL). The reaction was stirred rapidly at room temperature for 18 hours. The mixture was cooled using an ice bath and acidified by addition of concentrated hydrochloric acid (0.46 mL, 5.52 mmol) dropwise. The mixture was allowed to warm to room temperature, e and then the solvent was removed in vacuo (3× toluene azeotrope followed by 2× acetonitrile azeotrope) and dried in the vacuum oven at 40° C. to afford a pale yellow solid. This crude material was dissolved in dimethylformamide (5 mL) and added to a stirred suspension of (S)-3,5-dichloro-4-(2-(3,4-dimethoxylphenyl)-2-hydroxyethyl)pyridine 1-oxide (0.394 g, 1.144 mmol) in dimethylformamide (12 mL). To the resultant solution was added 4-(dimethylamino)-pyridine (0.0699 g, 0.572 mmol) followed by N-(3-dimethylaminopropyl)-N'-ethylcarbodiimide hydrochloride (0.439 g, 2.288 mmol), and the reaction was stirred at room temperature for 18 hours. The majority of the dimethylformamide was removed in vacuo and the residue was partitioned between ethyl acetate and saturated aqueous sodium bicarbonate solution. The organic layer was washed with brine (×2), and the solvent was removed in vacuo to afford an off white solid. The crude material was partially purified using an SCX-2 cartridge eluting sequentially with 1:1:1 methanol:acetonitrile:water, methanol and 2.3 M methanolic ammonia. Final purification was achieved by preparative HPLC to afford the title compound as a pale yellow solid (0.199 g, 24%).

$^1$H NMR (400 MHz, CDCl3): δ 8.42 (s, 1H), 8.13 (s, 2H), 7.97-7.91 (m, 1H), 7.87 (s, 1H), 7.46-7.35 (m, 2H), 7.03-6.95 (m, 6H), 6.86 (d, J=8.4 Hz, 1H), 6.27 (dd, J=9.9, 4.5 Hz, 1H), 4.94-4.78 (m, 3H), 3.90 (s, 3H), 3.88 (s, 3H), 3.69 (dd, J=14.0, 9.7 Hz, 1H), 3.38-3.26 (m, 2H), 2.93-2.61 (m, 5H), 2.12-2.06 (m, 1H), 1.82-1.72 (m, 1H), 1.71-1.59 (m, 1H), 1.58-1.31 (m, 2H). LCMS (Method 1): [MH+]=724 at 2.81 min.

The following compounds (Ex. 2 to 12) were synthesized via the same method as that used for compound of Ex. 1.

| Structure | Example number | Precursor | Analytical Data |
|---|---|---|---|
| [(1S)-2-(3,5-dichloro-1-oxido-pyridin-1-ium-4-yl)-1-(3,4-dimethoxyphenyl)ethyl] 3-[(2-fluoro-N-[(3R)-quinuclidin-3-yl]oxycarbonyl-anilino)methyl]benzoate | Example 2 | Intermediate 28 | $^1$H NMR (400 MHz, CDCl3): δ 8.42 (s, 1 H), 8.12 (s, 2 H), 7.96-7.87 (m, 2 H), 7.46 (d, J = 7.6 Hz, 1 H), 7.41-7.33 (m, 1 H), 7.32-7.23 (m, 1 H), 7.14-6.95 (m, 5 H), 6.85 (d, J = 8.1 Hz, 1 H), 6.29-6.23 (m, 1 H), 4.98-4.93 (m, 1 H), 4.91-4.77 (m, 2 H), 3.90 (s, 3 H), 3.88 (s, 3 H), 3.69 (dd, J = 14.0, 9.7 Hz, 1 H), 3.40-3.29 (m, 2 H), 3.01-2.61 (m, 5 H), 2.17 (s, 1 H), 1.85-1.75 (m, 1 H), 1.74-1.60 (m, 1 H), 1.59-1.47 (m, 1 H), 1.46-1.36 (m, 1 H). LCMS (Method 1): [MH+] = 724 at 2.77 min. |

-continued

| Structure | Example number | Precursor | Analytical Data |
|---|---|---|---|
| [(1S)-2-(3,5-dichloro-1-oxido-pyridin-1-ium-4-yl)-1-(3,4-dimethoxyphenyl)ethyl] 3-[(3-fluoro-N-[(3R)-quinuclidin-3-yl]oxycarbonyl-anilino)methyl]benzoate 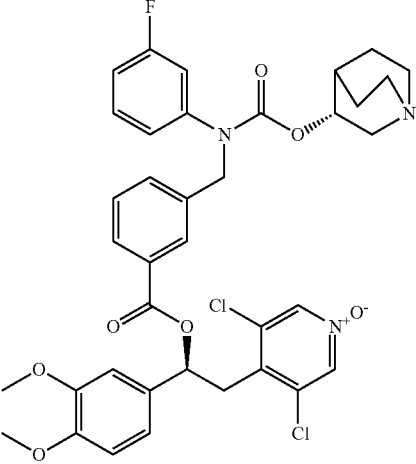 | Example 3 | Intermediate 19 | ¹H NMR (400 MHz, CDCl3): δ 8.12 (s, 2 H), 7.96-7.92 (m, 1 H), 7.88 (s, 1 H), 7.47-7.37 (m, 2 H), 7.32-7.24 (m, 1 H), 7.02-6.83 (m, 6 H), 6.27 (dd, J = 9.7, 4.5 Hz, 1 H), 4.96-4.84 (m, 3 H), 3.90 (s, 3 H), 3.88 (s, 3 H), 3.69 (dd, J = 14.0, 9.7 Hz, 1 H), 3.37-3.25 (m, 2 H), 2.90-2.61 (m, 5 H), 2.11-2.05 (m, 1 H), 1.79-1.69 (m, 1 H), 1.68-1.58 (m, 1 H), 1.53-1.43 (m, 1 H), 1.41-1.31 (m, 1 H).<br>LCMS (Method 1): [MH+] = 724 at 2.77 min. |
| [(1S)-2-(3,5-dichloro-1-oxido-pyridin-1-ium-4-yl)-1-(3,4-dimethoxyphenyl)ethyl] 3-[(2-methoxy-N-[(3R)-quinuclidin-3-yl]oxycarbonyl-anilino)methyl]benzoate 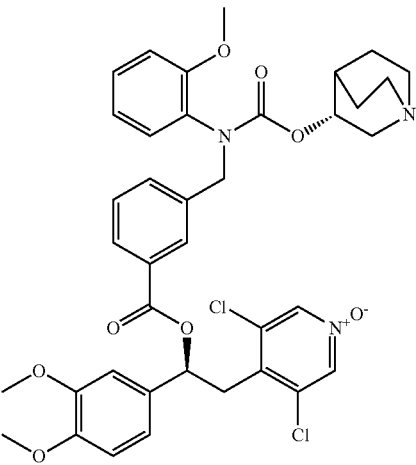 | Example 4 | Intermediate 29 | ¹H NMR (400 MHz, DMSO @ 85° C.): δ 8.39 (s, 2 H), 8.15 (s, 1 H), 7.90 (s, 1 H), 7.85 (d, J = 7.7 Hz, 1 H), 7.51 (d, J = 7.7 Hz, 1 H), 7.46-7.40 (m, 1 H), 7.28-7.21 (m, 1 H), 7.06-6.95 (m, 5 H), 6.90-6.83 (m, 1 H), 6.26 (dd, J = 9.2, 4.7 Hz, 1 H), 4.77 (s, 2 H), 4.67-4.62 (m, 1 H), 3.79 (s, 3 H), 3.79 (s, 3 H), 3.70 (s, 3 H), 3.63 (dd, J = 14.4, 9.1 Hz, 1 H), 3.38 (dd, J = 14.0, 4.7 Hz, 1 H), 3.13-3.03 (m, 1 H), 2.65-2.58 (m, 3 H), 2.51-2.39 (m, 2 H), 1.85-1.79 (m, 1 H), 1.61-1.52 (m, 1 H), 1.51-1.42 (m, 1 H), 1.35-1.21 (m, 1 H), 1.20-1.10 (m, 1 H).<br>LCMS (Method 1): [MH+] = 736 at 2.79 min. |

| Structure | Example number | Precursor | Analytical Data |
|---|---|---|---|
| [(1S)-2-(3,5-dichloro-1-oxido-pyridin-1-ium-4-yl)-1-(3,4-dimethoxyphenyl)ethyl] 3-[(3-methoxy-N-[(3R)-quinuclidin-3-yl]oxycarbonyl-anilino)methyl]benzoate 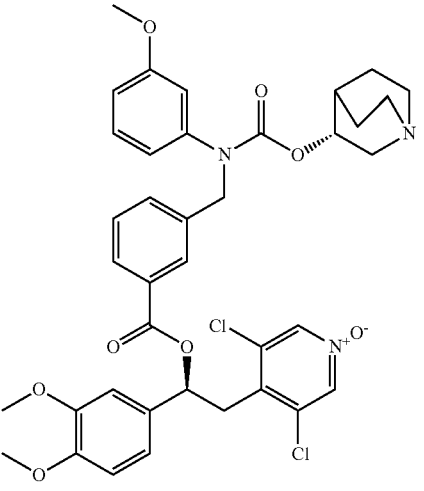 | Example 5 | Intermediate 20 | ¹H NMR (400 MHz, CDCl₃): δ 8.44 (s, 1 H), 8.12 (s, 2 H), 7.95-7.89 (m, 2 H), 7.46 (d, J = 7.7 Hz, 1 H), 7.39 (t, J = 7.6 Hz, 1 H), 7.21 (t, J = 8.1 Hz, 1 H), 7.01-6.96 (m, 2 H), 6.85 (d, J = 8.2 Hz, 1 H), 6.79 (dd, J = 8.3, 2.4 Hz, 1 H), 6.67 (s, 2 H), 6.27 (dd, J = 9.7, 4.5 Hz, 1 H), 4.93-4.84 (m, 3 H), 3.90 (s, 3 H), 3.88 (s, 3 H), 3.74 (s, 3 H), 3.69 (dd, J = 14.0, 9.7 Hz, 1 H), 3.36-3.24 (m, 2 H), 2.92-2.82 (m, 3 H), 2.77 (d, J = 14.8 Hz, 1 H), 2.71-2.60 (m, 1 H), 2.13-2.06 (m, 1 H), 1.79-1.69 (m, 1 H), 1.69-1.58 (m, 1 H), 1.56-1.46 (m, 1 H), 1.41-1.31 (m, 1 H). LCMS (Method 2): [MH+] = 736 at 3.65 min. |
| [(1S)-2-(3,5-dichloro-1-oxido-pyridin-1-ium-4-yl)-1-(3,4-dimethoxyphenyl)ethyl] 3-[(4-methoxy-N-[(3R)-quinuclidin-3-yl]oxycarbonyl-anilino)methyl]benzoate 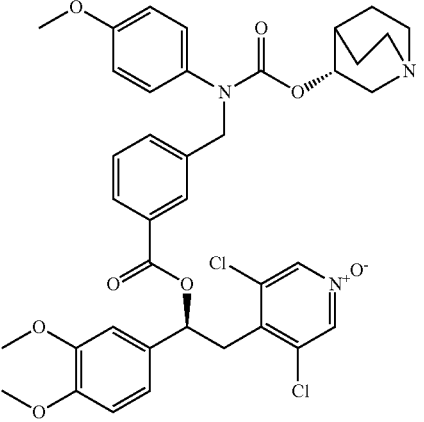 | Example 6 | Intermediate 21 | ¹H NMR (400 MHz, CDCl₃): δ 8.44 (s, 1 H), 8.13 (s, 2 H), 7.96-7.86 (m, 2 H), 7.46-7.33 (m, 2 H), 7.05-6.78 (m, 7 H), 6.27 (dd, J = 9.6, 4.4 Hz, 1 H), 4.95-4.90 (m, 1 H), 4.81 (s, 2 H), 3.90 (s, 3 H), 3.88 (s, 3 H), 3.79 (s, 3 H), 3.69 (dd, J = 14.1, 9.7 Hz, 1 H), 3.37-3.29 (m, 2 H), 3.00-2.61 (m, 5 H), 2.20-2.10 (m, 1 H), 1.84-1.74 (m, 1 H), 1.73-1.63 (m, 1 H), 1.62-1.47 (m, 1 H), 1.46-1.35 (m, 1 H). LCMS (Method 1): [MH+] = 736 at 2.80 min. |

-continued

| Structure | Example number | Precursor | Analytical Data |
|---|---|---|---|
| [(1S)-2-(3,5-dichloro-1-oxido-pyridin-1-ium-4-yl)-1-(3,4-dimethoxyphenyl)ethyl] 4-[N-[(3R)-quinuclidin-3-yl]oxycarbonyl-anilino)methyl]benzoate 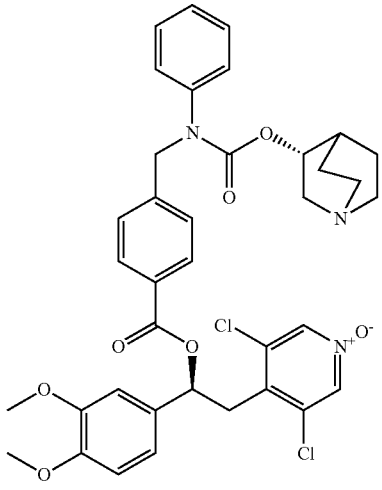 | Example 7 | Intermediate 22 | $^1$H NMR (400 MHz, CDCl3): δ 8.13 (s, 2 H), 7.97 (d, J = 8.0 Hz, 2 H), 7.35-7.21 (m, 5 H), 7.10 (br s, 2 H), 7.04-6.95 (m, 2 H), 6.85 (d, J = 8.2 Hz, 1 H), 6.30 (dd, J = 9.7, 4.6 Hz, 1 H), 4.95-4.89 (m, 1 H), 4.89 (s, 2 H), 3.90 (s, 3 H), 3.88 (s, 3 H), 3.71 (dd, J = 14.0, 9.7 Hz, 1 H), 3.40-3.28 (m, 2 H), 2.90 (t, J = 9.1 Hz, 2 H), 2.81 (d, J = 18.1 Hz, 2 H), 2.73-2.59 (m, 1 H), 2.16-2.10 (m, 1 H), 1.84-1.73 (m, 1 H), 1.72-1.60 (m, 1 H), 1.55-1.45 (m, 1 H), 1.44-1.33 (m, 1 H). LCMS (Method 1): [MH+] = 706 at 2.49 min. |
| [(1S)-2-(3,5-dichloro-1-oxido-pyridin-1-ium-4-yl)-1-(3,4-dimethoxyphenyl)ethyl] 4-[(2-fluoro-N-[(3R)-quinuclidin-3-yl]oxycarbonyl-anilino)methyl]benzoate 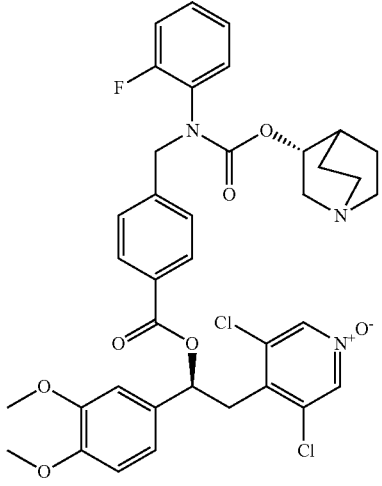 | Example 8 | Intermediate 23 | $^1$H NMR (400 MHz, CDCl3): S 8.44 (s, 1 H), 8.12 (s, 2 H), 7.95 (d, J = 7.8 Hz, 2 H), 7.32 (d, J = 7.9 Hz, 2 H), 7.25-7.22 (m, 1 H), 7.12-6.96 (m, 5 H), 6.85 (d, J = 8.2 Hz, 1 H), 6.29 (dd, J = 9.5, 4.1 Hz, 1 H), 4.95-4.79 (m, 3 H), 3.90 (s, 3 H), 3.88 (s, 3 H), 3.74-3.65 (m, 1 H), 3.38-3.27 (m, 2 H), 2.99-2.63 (m, 5 H), 2.11 (s, 1 H), 1.82-1.72 (m, 1 H), 1.70-1.58 (m, 1 H), 1.52-1.32 (m, 2 H). LCMS (Method 1): [MH+] = 724 at 2.81 min. |

| Structure | Example number | Precursor | Analytical Data |
|---|---|---|---|
| [(1S)-2-(3,5-dichloro-1-oxido-pyridin-1-ium-4-yl)-1-(3,4-dimethoxyphenyl)ethyl] 4-[(4-fluoro-N-[(3R)-quinuclidin-3-yl]oxycarbonyl-anilino)methyl]benzoate 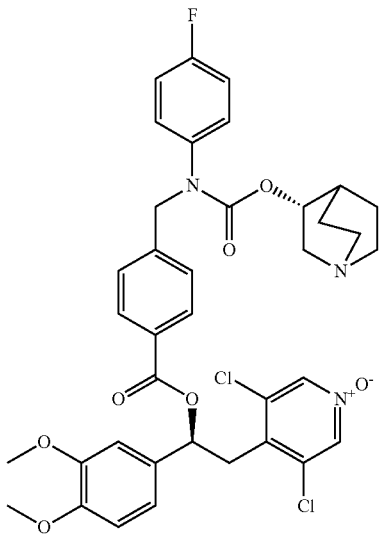 | Example 9 | Intermediate 25 | $^1$H NMR (400 MHz, CDCl3): δ 8.43 (s, 1 H), 8.13 (s, 2 H), 7.97 (d, J = 7.9 Hz, 2 H), 7.29 (d, J = 8.0 Hz, 2 H), 7.03-6.97 (m, 6 H), 6.86 (d, J = 8.2 Hz, 1 H), 6.30 (dd, J = 9.7, 4.6 Hz, 1 H), 4.94-4.84 (m, 3 H), 3.91 (s, 3 H), 3.88 (s, 3 H), 3.71 (dd, J = 14.0, 9.7 Hz, 1 H), 3.38-3.25 (m, 2 H), 2.90-2.60 (m, 5 H), 2.14-2.04 (m, 1 H), 1.82-1.72 (m, 1 H), 1.69-1.59 (m, 1 H), 1.54-1.34 (m, 2 H). LCMS (Method 1): [MH+] = 724 at 2.84 min. |
| [(1S)-2-(3,5-dichloro-1-oxido-pyridin-1-ium-4-yl)-1-(3,4-dimethoxyphenyl)ethyl] 4-[(2-methoxy-N-[(3R)-quinuclidin-3-yl]oxycarbonyl-anilino)methyl]benzoate 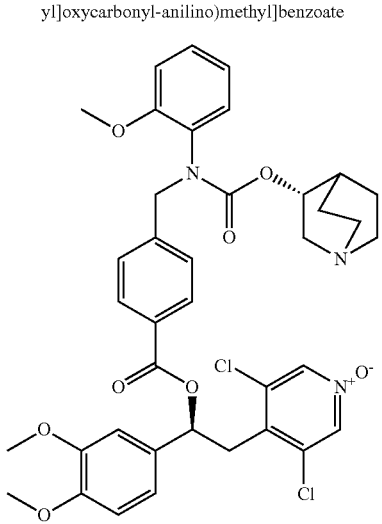 | Example 10 | Intermediate 30 | $^1$H NMR (400 MHz, DMSO @ 85° C.): δ 8.40 (s, 2 H), 7.91 (d, J = 8.1 Hz, 2 H), 7.40 (d, J = 8.1 Hz, 2 H), 7.29-7.23 (m, 1 H), 7.12-6.95 (m, 5 H), 6.90-6.85 (m, 1 H), 6.26 (dd, J = 9.2, 4.7 Hz, 1 H), 4.78 (s, 2 H), 4.73-4.68 (m, 1 H), 3.79 (s, 3 H), 3.78 (s, 3 H), 3.75 (s, 3 H), 3.64 (dd, J = 14.2, 9.2 Hz, 1 H), 3.38 (dd, J = 14.3, 5.4 Hz, 1 H), 3.23-3.15 (m, 1 H), 2.76-2.65 (m, 3 H), 2.59-2.46 (m, 2 H), 1.93-1.86 (m, 1 H), 1.69-1.49 (m, 2 H), 1.37-1.18 (m, 2 H). LCMS (Method 1): [MH+] = 736 at 2.84 min. |

-continued

| Structure | Example number | Precursor | Analytical Data |
|---|---|---|---|
| [(1S)-2-(3,5-dichloro-1-oxido-pyridin-1-ium-4-yl)-1-(3,4-dimethoxyphenyl)ethyl] 4-[(3-methoxy-N-[(3R)-quinuclidin-3-yl]oxycarbonyl-anilino)methyl]benzoate | Example 11 | Intermediate 26 | $^1$H NMR (400 MHz, CDCl$_3$): δ 8.13 (s, 2 H), 7.97 (d, J = 8.0 Hz, 2 H), 7.32 (d, J = 8.1 Hz, 2 H), 7.21 (t, J = 8.1 Hz, 1 H), 7.04-6.97 (m, 2 H), 6.86 (d, J = 8.2 Hz, 1 H), 6.78 (dd, J = 8.4, 2.4 Hz, 1 H), 6.68 (br s, 2 H), 6.30 (dd, J = 9.7, 4.6 Hz, 1 H), 4.96-4.90 (m, 1 H), 4.88 (s, 2 H), 3.91 (s, 3 H), 3.88 (s, 3 H), 3.75 (s, 3 H), 3.71 (dd, J = 14.0, 9.7 Hz, 1 H), 3.39-3.29 (m, 2 H), 2.91 (t, J = 9.2 Hz, 2 H), 2.83 (d, J = 15.0 Hz, 2 H), 2.75-2.64 (m, 1 H), 2.17-2.11 (m, 1 H), 1.84-1.74 (m, 1 H), 1.72-1.62 (m, 1 H), 1.59-1.49 (m, 1 H), 1.48-1.38 (m, 1 H). LCMS (Method 1): [MH+] = 736 at 2.50 min. |
| [(1S)-2-(3,5-dichloro-1-oxido-pyridin-1-ium-4-yl)-1-(3,4-dimethoxyphenyl)ethyl] 4-[(2-methyl-N-[(3R)-quinuclidin-3-yl]oxycarbonyl-anilino)methyl]benzoate | Example 12 | Intermediate 31 | $^1$H NMR (400 MHz, DMSO): δ 8.56 (s, 2 H), 7.97 (d, J = 8.1 Hz, 2 H), 7.50-7.37 (m, 2 H), 7.31-7.25 (m, 1 H), 7.25-7.12 (m, 2 H), 7.10-6.94 (m, 4 H), 6.24 (dd, J = 9.4, 4.4 Hz, 1 H), 5.05-4.95 (m, 1 H), 4.73-4.55 (m, 2 H), 3.81 (s, 3 H), 3.78 (s, 3 H), 3.66 (dd, J = 14.2, 9.6 Hz, 1 H), 3.40-3.32 (m, 1 H), 3.16-3.04 (m, 1 H), 2.67-2.55 (m, 3 H), 2.46-2.27 (m, 2 H), 2.14-2.02 (m, 3 H), 1.81-1.40 (m, 3 H), 1.35-1.00 (m, 2 H). LCMS (Method 2): [MH+] = 720 at 3.34 min. |

The following compounds were synthesized in a similar manner substituting (S)-3,5-dichloro-4-(2-(3,4-dimethoxylphenyl)-2-hydroxyethyl)pyridine 1-oxide with (R,S)-3,5-dichloro-4-(2-(3,4-dimethoxylphenyl)-2-hydroxyethyl)pyridine 1-oxide. Purification was achieved by preparative HPLC to afford a 1:1 mixture of diastereoisomers. Single diastereoisomers were obtained by SFC purification.

| Structure | Example number | Precursors | Analytical Data |
|---|---|---|---|
| [(1S)-2-(3,5-dichloro-1-oxido-pyridin-1-ium-4-yl)-1-(3,4-dimethoxyphenyl)ethyl] 4-[(2-methyl-N-[(3R)-quinuclidin-3-yl]oxycarbonyl-anilino)methyl]benzoate 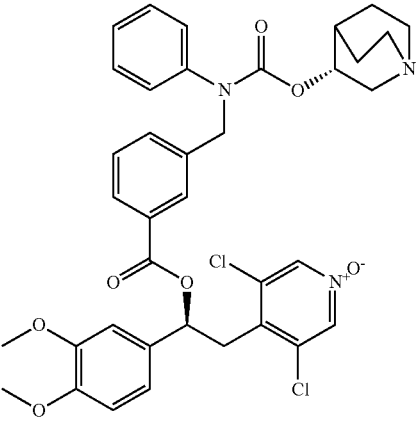 | Example 13 | Intermediate 18 | $^1$H NMR (400 MHz, CDCl3): δ 8.11 (s, 2H), 7.93-7.91 (m, 2H), 7.48-7.46 (m, 1H), 7.40-7.36 (m, 1H), 7.32-7.22 (m, 3H), 7.14-7.12 (m, 2H), 7.00-6.96 (m, 2H), 6.86-6.84 (m, 1H), 6.27 (dd, J = 9.6, 4.4 Hz, 1H), 4.89 (s, 2H), 4.82-4.81 (m, 1H), 3.89 (s, 3H), 3.87 (s, 3H), 3.68 (dd, J = 14.0, 9.6 Hz, 1H), 3.33 (dd, J = 14.0, 4.4 Hz, 1 H), 3.22-3.18 (m, 1H), 2.76-2.62 (m, 5H), 1.97-1.96 (m, 1H), 1.65-1.62 (m, 1H), 1.55-1.54 (m, 1H), 1.40-1.39 (m, 1H), 1.25-1.21 (m, 1H). LCMS (Method 1): [MH+] = 706 at 2.79 min. |
| [(1S)-2-(3,5-dichloro-1-oxido-pyridin-1-ium-4-yl)-1-(3,4-dimethoxyphenyl)ethyl] 3-[(N-[(3R)-quinuclidin-3-yl]oxycarbonyl-anilino)methyl]benzoate 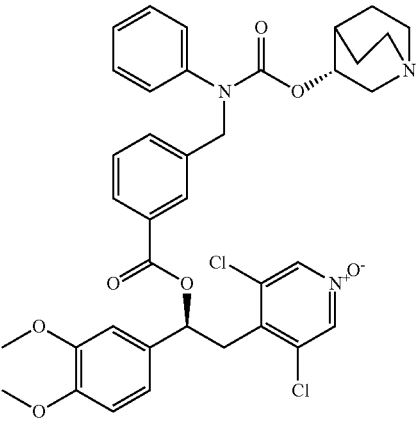 | Example 14 | Intermediate 18 | $^1$H NMR (400 MHz, CDCl3): δ 8.10 (s, 2H), 7.92-7.90 (m, 2H), 7.48-7.46 (m, 1H), 7.39-7.36 (m, 1H), 7.32-7.20 (m, 3H), 7.11-7.10 (m, 2H), 7.00-6.96 (m, 2H), 6.86-6.84 (m, 1H), 6.26 (dd, J = 9.6, 4.4 Hz, 1H), 4.95-4.78 (m, 3H), 3.89 (s, 3H), 3.87 (s, 3H), 3.68 (dd, J = 14.0, 10.0 Hz, 1H), 3.32 (dd, J = 14.0, 4.4 Hz, 1H), 3.22-3.16 (m, 1H), 2.72-2.55 (m, 5H), 1.95-1.94 (m, 1H), 1.64-1.61 (m, 1H), 1.53-1.51 (m, 1H), 1.39-1.37 (m, 1H), 1.25-1.21 (m, 1H). LCMS (Method 1): [MH+] = 706 at 2.79 min. |

-continued

| Structure | Example number | Precursors | Analytical Data |
|---|---|---|---|
| [(1S)-2-(3,5-dichloro-1-oxido-pyridin-1-ium-4-yl)-1-(3,4-dimethoxyphenyl)ethyl] 4-[(3-fluoro-N-[(3R)-quinuclidin-3-yl]oxycarbonyl-anilino)methyl]benzoate 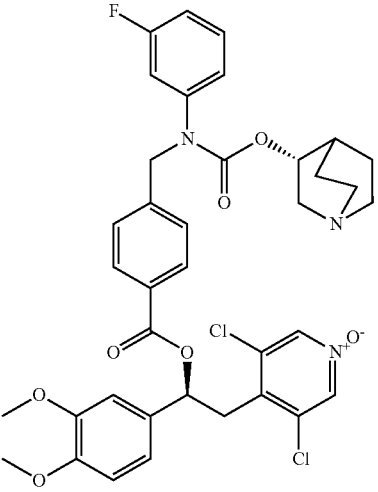 | Example 15 | Intermediate 24 | $^1$H NMR (400 MHz, CDCl3): δ 8.13 (s, 2H), 7.98 (d, J = 8.0 Hz, 2H), 7.32-7.23 (m, 3H), 7.02-6.90 (m, 4H), 6.85 (d, J = 8.0 Hz, 2H), 6.30 (dd, J = 9.6, 4.8 Hz, 1H), 4.92-4.79 (m, 3H), 3.90 (s, 3H), 3.87 (s, 3H), 3.70 (dd, J = 14.0, 9.6 Hz, 1H), 3.34 (dd, J = 14.0, 4.4 Hz, 1H), 3.23-3.19 (m, 1H), 2.76-2.60 (m, 5H), 2.00-1.97 (m, 1H), 1.66-1.62 (m, 1H), 1.54-1.52 (m, 1H), 1.41-1.39 (m, 114), 1.25-1.20 (m, 1H).<br>LCMS (Method 2): [MH+] = 724 at 3.20 min. |
| [(1R)-2-(3,5-dichloro-1-oxido-pyridin-1-ium-4-yl)-1-(3,4-dimethoxyphenyl)ethyl] 4-[(3-fluoro-N-[(3R)-quinuclidin-3-yl]oxycarbonyl-anilino)methyl]benzoate 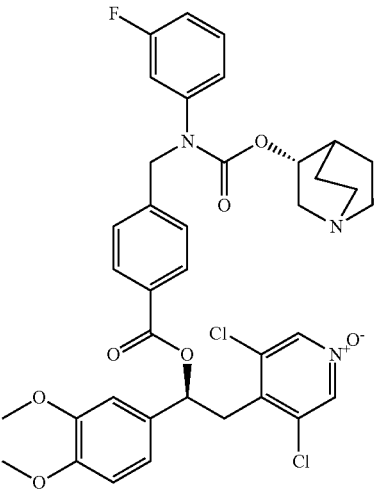 | Example 16 | Intermediate 24 | $^1$H NMR (400 MHz, CDCl3): δ 8.12 (s, 21-1), 7.97 (d, J = 8.0 Hz, 2H), 7.32-7.23 (m, 3H), 7.02-6.84 (m, 6H), 6.28 (dd, J = 9.6, 4.8 Hz, 1H), 4.90 (s, 2H), 4.83-4.82 (m, 1H), 3.90 (s, 3H), 3.88 (s, 3H), 3.71 (dd, J = 14.0, 9.6 Hz, 1H), 3.34 (dd, J = 14.0, 4.4 Hz, 1H), 3.24-3.23 (m, 1 H), 2.76-2.60 (m, 51-I), 2.02-1.99 (m, 1H), 1.68-1.65 (m, 1H), 1.58-1.57 (m, 1H), 1.41-1.39 (m, 1H), 1.29-1.20 (m, 1H).<br>LCMS (Method 2): [MH+] = 724 at 3.20 min. |

-continued

| Structure | Example number | Precursors | Analytical Data |
|---|---|---|---|
| [(1S)-2-(3,5-dichloro-1-oxido-pyridin-1-ium-4-yl)-1-(3,4-dimethoxyphenyl)ethyl] 4-[(4-methoxy-N-[(3R)-quinuclidin-3-yl]oxycarbonyl-anilino)methyl]benzoate 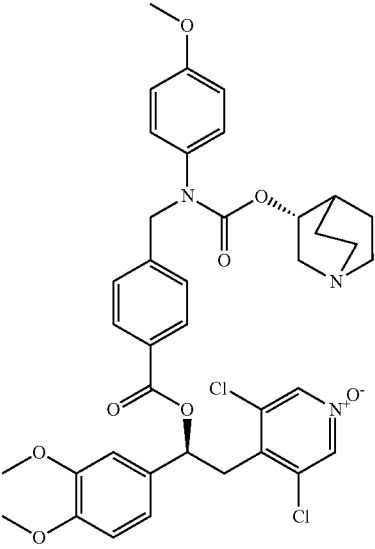 | Example 17 | Intermediate 27 | $^1$H NMR (400 MHz, CDCl3): δ 8.13 (s, 2 H), 7.96 (d, J = 7.9 Hz, 2 H), 7.31 (d, J = 8.0 Hz, 2 H), 7.03-6.89 (m, 4 H), 6.85 (d, J = 8.2 Hz, 1 H), 6.83-6.77 (m, 2 H), 6.30 (dd, J = 9.6, 4.5 Hz, 1 H), 4.84 (br s, 2 H), 4.81-4.75 (m, 1 H), 3.90 (s, 3 H), 3.88 (s, 3 H), 3.78 (s, 3 H), 3.70 (dd, J = 13.9, 9.7 Hz, 1 H), 3.35 (dd, J = 13.9, 4.6 Hz, 1 H), 3.25-3.15 (m, 1 H), 2.79-2.69 (m, 3 H), 2.67-2.52 (m, 2 H), 1.97 (br s, 1 H), 1.70-1.60 (m, 1 H), 1.60-1.50 (m, 1 H), 1.48-1.35 (m, 1 H), 1.33-1.24 (m, 1 H).<br>LCMS (Method 1): [MH+] = 736 at 2.76 min |
| [(1R)-2-(3,5-dichloro-1-oxido-pyridin-1-ium-4-yl)-1-(3,4-dimethoxyphenyl)ethyl] 4-[(4-methoxy-N-[(3R)-quinuclidin-3-yl]oxycarbonyl-anilino)methyl]benzoate 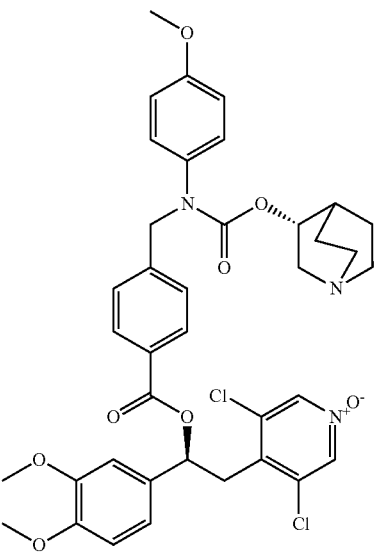 | Example 18 | Intermediate 27 | $^1$H NMR (400 MHz, CDCl3): δ 8.13 (s, 2 H), 7.96 (d, J = 7.8 Hz, 2 H), 7.31 (d, J = 7.9 Hz, 2 H), 7.03-6.89 (m, 4 H), 6.86 (d, J = 8.2 Hz, 1 H), 6.84-6.76 (m, 2 H), 6.29 (dd, J = 9.7, 4.6 Hz, 1 H), 4.87-4.77 (m, 3 H), 3.90 (s, 3 H), 3.88 (s, 3 H), 3.78 (s, 3 H), 3.71 (dd, J = 13.9, 9.7 Hz, 1 H), 3.35 (dd, J = 13.9, 4.6 Hz, 1 H), 3.22 (dd, J = 14.6, 8.2 Hz, 1 H), 2.78-2.71 (m, 3 H), 2.70-2.58 (m, 2 H), 1.99 (br s, 1 H), 1.70-1.60 (m, 1 H), 1.60-1.50 (m, 1 H), 1.48-1.35 (m, 1 H), 1.33-1.24 (m, 1 H).<br>LCMS (Method 1): [MH+] = 736 at 2.74 min |

The following compounds were synthesized via the same method as that used in Example 1.

| Structure | Example number | Precursors | Analytical Data |
|---|---|---|---|
| [2-(3,5-dichloro-1-oxido-pyridin-1-ium-4-yl)-1-(3,4-dimethoxyphenyl)ethyl] 3-[(N-[(3R)-quinuclidin-3-yl]oxycarbonylanilino)methyl]benzoate 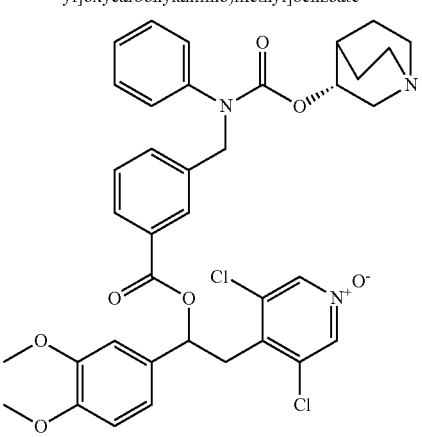 | Example 19 | Intermediate 18 | 1H NMR (300 MHz, DMSO-d6) δ ppm 8.50 and 8.51 (s, 2 H), 7.80-7.92 (m, 2 H), 7.51-7.59 (m, 1 H), 7.47 (t, 1 H), 7.30-7.40 (m, 2 H), 7.16-7.30 (m, 3 H), 6.88-7.06 (m, 3 H), 6.21 (dd, 1 H), 4.96 (s, 2 H), 4.71 (br. s., 1H), 3.77 (s, 3 H), 3.76 (s, 3 H), 3.60 (dd, 1 H), 3.32 (dd, 1 H), 2.96-3.22 (m, 1 H), 2.56-2.77 (m, 5 H), 1.87 (br. s., 1 H), 1.39-1.69 (m, 2 H), 1.02-1.39 (m, 2 H) LCMS (Method 1): [MH+] = 706 at 2.80 min. |
| [(1S)-2-(3,5-dichloro-1-oxido-pyridin-1-ium-4-yl)-1-(3,4-dimethoxyphenyl)ethyl] 3-bromo-5-[(2-fluoro-N-[(3R)-quinuclidin-3-yl]oxycarbonyl-anilino)methyl]benzoate formate salt 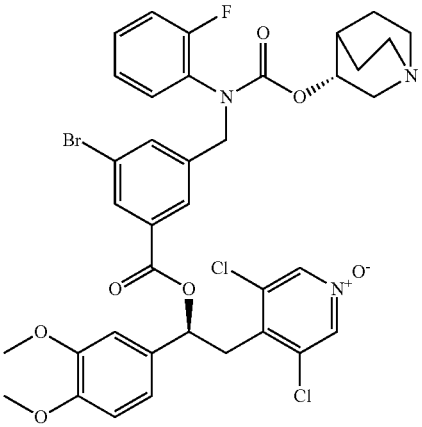 | Example 20 | Intermediate 70 | $^1$H NMR (400 MHz, CDCl3): δ 8.14 (s, 2 H), 8.06 (s, 1 H), 7.81 (s, 1 H), 7.59 (s, 1 H), 7.34-7.26 (m, 1 H), 7.16-7.07 (m, 2 H), 7.06-6.93 (m, 3 H), 6.86 (d, J = 8.2 Hz, 1 H), 6.22 (dd, J = 9.7, 4.4 Hz, 1 H), 5.03-4.98 (m, 1 H), 4.82-4.75 (m, 2 H), 3.91 (s, 3 H), 3.88 (s, 3 H), 3.70 (dd, J = 14.1, 9.8 Hz, 1 H), 3.45-3.35 (m, 1 H), 3.34 (dd, J = 14.0, 4.4 Hz, 1 H), 3.08-2.93 (m, 3 H), 2.86 (d, J = 14.9 Hz, 1 H), 2.80-2.65 (m, 1 H), 2.24 (bs, 1 H), 1.89-1.81 (m, 1 H), 1.80-1.70 (m, 1 H), 1.59-1.47 (m, 2 H). LCMS (Method 2): [MH+] = 802 at 3.27 min. |
| [(1S)-2-(3,5-dichloro-1-oxido-pyridin-1-ium-4-yl)-1-(3,4-dimethoxyphenyl)ethyl] 2-[4-[(N-[(3R)-quinuclidin-3-yl]oxycarbonylanilino)methyl]phenyl]acetate 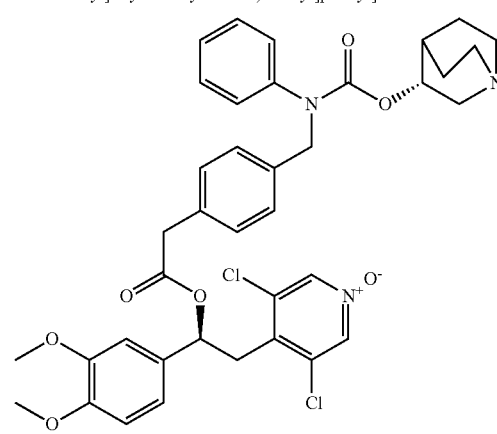 | Example 21 | Intermediate 71 | $^1$H NMR (400 MHz, DMSO): δ 8.54 (s, 2 H), 8.31 (s, 1 H), 7.34-7.30 (m, 2 H), 7.26-7.21 (m, 2 H), 7.20-7.12 (m, 4 H), 6.93-6.90 (m, 1 H), 6.83-6.81 (m, 2 H), 5.95 (dd, J = 9.6, 4.8 Hz, 1 H), 4.87 (s, 2 H), 4.67-4.64 (m, 1 H), 3.74 (s, 3 H), 3.70 (s, 3 H), 3.64-3.54 (m, 2 H), 3.49-3.35 (m, 2 H), 3.11-3.05 (m, 1 H), 2.67-2.47 (m, 5 H), 1.88-1.83 (m, 1 H), 1.58-1.52 (m, 1 H), 1.50-1.39 (m, 1 H), 1.37-1.22 (m, 1 H), 1.19-1.12 (m, 1 H). LCMS (Method 1): [MH+] = 720 at 2.73 min. |

-continued

| Structure | Example number | Precursors | Analytical Data |
|---|---|---|---|
| [(1S)-1-[3-(cyclopropylmethoxy)-4-(difluoromethoxy)phenyl]-2-(3,5-dichloro-1-oxido-pyridin-1-ium-4-yl)ethyl] 2-[4-[(N-[(3R)-quinuclidin-3-yl]oxycarbonylanilino)methyl]phenyl]acetate | Example 22 | Intermediate 71 | 1H NMR (400 MHz, DMSO): δ 8.47 (s, 2 H), 8.24 (s, 1 H), 7.34-7.19 (m, 4 H), 7.17-7.01 (m, 7 H), 6.91-6.87 (m, 1 H), 5.95 (dd, J = 4.4, 9.6 Hz, 1 H), 4.88 (brs, 2 H), 4.73-4.71 (m, 1 H), 3.85-3.83 (m, 2 H), 3.66-3.56 (m, 2 H), 3.38 (dd, J = 9.6, 14.0 Hz, 1 H), 3.21-3.16 (m, 2 H), 2.73-2.56 (m, 5 H), 1.91-1.89 (m, 1 H), 1.65-1.48 (m, 2 H), 1.28-1.14 (m, 3 H), 0.59-0.55 (m, 2 H), 0.36-0.34 (m, 2 H). LCMS (Method 1): [MH+] = 713 at 2.52 min. |
| [(1S)-2-(3,5-dichloro-1-oxido-pyridin-1-ium-4-yl)-1-(3,4-dimethoxyphenyl)ethyl] 2-[4-[(2-fluoro-N-[(3R)-quinuclidin-3-yl]oxycarbonyl-anilino)methyl]phenyl]acetate | Example 23 | Intermediate 72 | 1H NMR (400 MHz, CDCl3): δ 8.01 (s, 2 H), 7.28-7.18 (m, 3 H), 7.10-7.05 (m, 5 H), 6.84-6.78 (m, 3 H), 6.04 (dd, J = 9.6, 4.8 Hz, 1 H), 4.82-4.79 (m, 3 H), 3.86 (s, 3 H), 3.81 (s, 3 H), 3.59-3.47 (m, 3 H), 3.20-3.15 (m, 2 H), 2.71-2.62 (m, 5 H), 1.97-1.87 (m, 1 H), 1.68-1.56 (m, 1 H), 1.55-1.44 (m, 1 H), 1.38-1.24 (m, 1 H), 1.24-1.13 (m, 1 H). LCMS (Method 1): [MH+] = 738 at 2.73 min. |
| [(1S)-2-(3,5-dichloro-1-oxido-pyridin-1-ium-4-yl)-1-(3,4-dimethoxyphenyl)ethyl] 3-[(3-chloro-N-[(3R)-quinuclidin-3-yl]oxycarbonyl-anilino)methyl]benzoate | Example 24 | Intermediate 73 | ¹H NMR (400 MHz, CDCl3): δ 8.12 (s, 2 H), 7.97-7.92 (m, 1 H), 7.88 (s, 1 H), 7.46-7.38 (m, 2 H), 7.28-7.22 (m, 2 H), 7.17 (br s, 1 H), 7.02-6.96 (m, 3 H), 6.86 (d, J = 8.2 Hz, 1 H), 6.27 (dd, J = 9.7, 4.5 Hz, 1 H), 4.93-4.86 (m, 3 H), 3.90 (s, 3 H), 3.88 (s, 3 H), 3.70 (dd, J = 14.0, 9.8 Hz, 1 H), 3.37-3.27 (m, 2 H), 2.92-2.83 (m, 3 H), 2.76 (d, J = 15.0 Hz, 1 H), 2.72-2.60 (m, 1 H), 2.11-2.06 (s, 1 H), 1.81-1.70 (m, 1 H), 1.70-1.58 (m, 1 H), 1.54-1.43 (m, 1 H), 1.43-1.33 (m, 1 H). LCMS (Method 2): [MH+] = 742 at 3.45 min. |

-continued

| Structure | Example number | Precursors | Analytical Data |
|---|---|---|---|
| [(1S)-2-(3,5-dichloro-1-oxido-pyridin-1-ium-4-yl)-1-(3,4-dimethoxyphenyl)ethyl] 3-[(2,3-difluoro-N-[(3R)-quinuclidin-3-yl]oxycarbonyl-anilino)methyl]benzoate 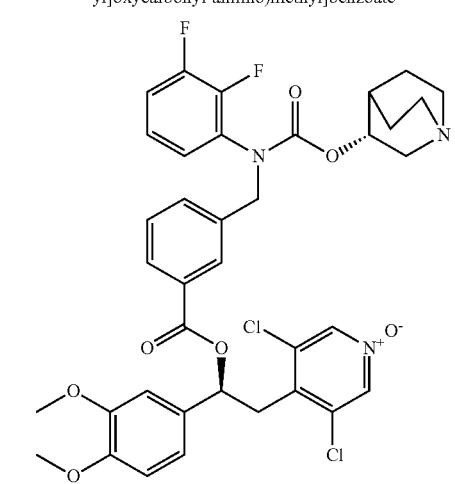 | Example 25 | Intermediate 75 | $^1$H NMR (400 MHz, CDCl3): δ 8.13 (s, 2 H), 7.96-7.88 (m, 2 H), 7.47 (d, J = 7.7 Hz, 1 H), 7.39 (t, J = 7.6 Hz, 1 H), 7.15-7.08 (m, 1 H), 7.06-6.96 (m, 3 H), 6.86 (d, J = 8.2 Hz, 2 H), 6.29-6.23 (m, 1 H), 4.93-4.88 (m, 1 H), 4.88-4.84 (m, 2 H), 3.91 (s, 3 H), 3.88 (s, 3 H), 3.70 (dd, J = 13.9, 9.8 Hz, 1 H), 3.37-3.27 (m, 2 H), 2.92-2.81 (m, 3 H), 2.81-2.65 (m, 2 H), 2.10 (br s, 1 H), 1.81-1.70 (m, 1 H), 1.69-1.58 (m, 1 H), 1.52-1.42 (m, 1 H), 1.42-1.32 (m, 1 H). LCMS (Method 2): [MH+] = 742 at 3.29 min. |
| [(1S)-2-(3,5-dichloro-1-oxido-pyridin-1-ium-4-yl)-1-(3,4-dimethoxyphenyl)ethyl] 3-[(2,5-difluoro-N-[(3R)-quinuclidin-3-yl]oxycarbonyl-anilino)methyl]benzoate 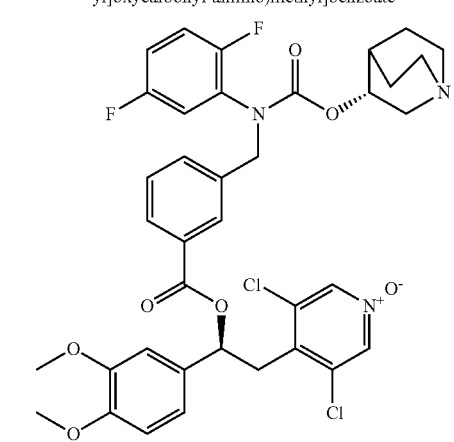 | Example 26 | Intermediate 76 | $^1$H NMR (400 MHz, CDCl3): δ 8.12 (s, 2 H), 7.95-7.89 (m, 2 H), 7.48 (d, J = 7.7 Hz, 1 H), 7.39 (t, J = 7.7 Hz, 1 H), 7.09-6.90 (m, 4 H), 6.86 (d, J = 8.2 Hz, 1 H), 6.84-6.75 (m, 1 H), 6.27 (dd, J = 9.7, 4.5 Hz, 1 H), 4.85 (s, 2 H), 4.82-4.76 (m, 1 H), 3.90 (s, 3 H), 3.88 (s, 3 H), 3.69 (dd, J = 14.0, 9.7 Hz, 1 H), 3.34 (dd, J = 14.0, 4.6 Hz, 1 H), 3.25-3.16 (m, 1 H), 2.78-2.68 (m, 3 H), 2.68-2.58 (m, 2 H), 1.95 (br s, 1 H), 1.67-1.57 (m, 1 H), 1.57-1.46 (m, 1 H), 1.40-1.29 (m, 1 H), 1.29-1.18 (m, 1 H). LCMS (Method 1): [MH+] = 742 at 2.75 min. |
| [(1S)-2-(3,5-dichloro-1-oxido-pyridin-1-ium-4-yl)-1-(3,4-dimethoxyphenyl)ethyl] 3-[(3-methyl-N-[(3R)-quinuclidin-3-yl]oxycarbonyl-anilino)methyl]benzoate 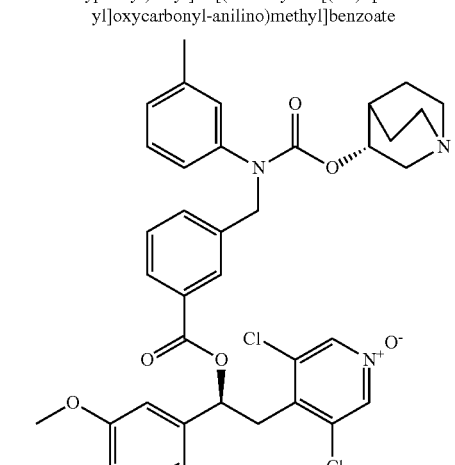 | Example 27 | Intermediate 77 | $^1$H NMR (400 MHz, CDCl3): δ 8.11 (s, 2 H), 7.94-7.89 (m, 2 H), 7.48 (d, J = 7.7 Hz, 1 H), 7.39 (t, J = 7.9 Hz, 1 H), 7.22-7.15 (m, 1 H), 7.05-6.87 (m, 5 H), 6.85 (d, J = 8.2 Hz, 1 H), 6.27 (dd, J = 9.7, 4.6 Hz, 1 H), 4.89 (s, 2 H), 4.80-4.75 (m, 1 H), 3.89 (s, 3 H), 3.88 (s, 3 H), 3.68 (dd, J = 14.0, 9.7 Hz, 1 H), 3.33 (dd, J = 14.0, 4.6 Hz, 1 H), 3.18 (dd, J = 14.8, 8.2 Hz, 1 H), 2.76-2.66 (m, 3 H), 2.65-2.55 (m, 2 H), 2.30 (s, 3 H), 1.96-1.91 (m, 1 H), 1.66-1.56 (m, 1 H), 1.55-1.45 (m, 1 H), 1.44-1.33 (m, 1 H), 1.26-1.15 (m, 1 H). LCMS (Method 1): [MH+] = 720 at 2.80 min. |

-continued

| Structure | Example number | Precursors | Analytical Data |
|---|---|---|---|
| [(1S)-2-(3,5-dichloro-1-oxido-pyridin-1-ium-4-yl)-1-(3,4-dimethoxyphenyl)ethyl] 3-[[N-[(3R)-quinuclidin-3-yl]oxycarbonyl-3-(trifluoromethyl)anilino]methyl]benzoate 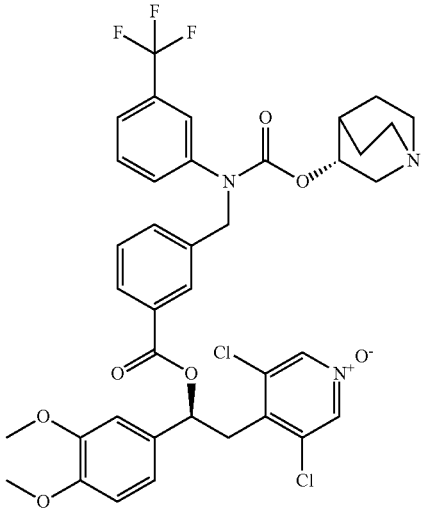 | Example 28 | Intermediate 78 | ¹H NMR (400 MHz, CDCl3): δ 8.11 (s, 2 H), 7.94 (d, J = 7.5 Hz, 1 H), 7.90 (s, 1 H), 7.50-7.38 (m, 6 H), 7.01-6.94 (m, 2 H), 6.85 (d, J = 8.1 Hz, 1 H), 6.30-6.24 (m, 1 H), 4.94 (s, 2 H), 4.83-4.77 (m, 1 H), 3.89 (s, 3 H), 3.88 (s, 3 H), 3.72-3.64 (m, 1 H), 3.37-3.30 (m, 1H), 3.24-3.15 (m, 1 H), 2.76-2.65 (m, 3 H), 2.63-2.50 (m, 2 H), 1.96-1.90 (m, 1 H), 1.65-1.50 (m, 2 H), 1.40-1.30 (m, 1 H), 1.27-1.18 (m, 1 H). LCMS (Method 1): [MH+] = 774 at 2.85 min. |
| [(1S)-2-(3,5-dichloro-1-oxido-pyridin-1-ium-4-yl)-1-(3,4-dimethoxyphenyl)ethyl] 3-[(2-methyl-N-[(3R)-quinuclidin-3-yl]oxycarbonyl-anilino)methyl]benzoate 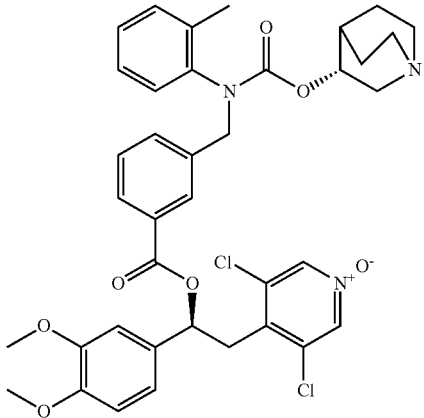 | Example 29 | Intermediate 79 | ¹H NMR (400 MHz, DMSO at 125° C.): δ 8.23 (s, 2 H), 7.83-7.76 (m, 2 H), 7.41 (d, J = 7.6 Hz, 1 H), 7.36 (t, J = 7.5 Hz, 1 H), 7.17-7.03 (m, 3 H), 6.97-6.88 (m, 4 H), 6.21 (dd, J = 9.0, 4.9 Hz, 1 H), 4.73 (br s, 2 H), 4.64-4.58 (m, 1 H), 3.72 (s, 6 H), 3.55 (dd, J = 14.2, 9.0 Hz, 1 H), 3.32 (dd, J = 14.2, 4.9 Hz, 1 H), 3.01 (ddd, J = 14.5, 8.1, 2.3 Hz, 1 H), 2.56-2.35 (m, 5 H), 1.99 (s, 3 H), 1.78-1.73 (m, 1 H), 1.55-1.45 (m, 1 H), 1.45-1.34 (m, 1 H), 1.27-1.17 (m, 1 H), 1.14-1.04 (m, 1 H). LCMS (Method 1): [MH+] = 720 at 2.76 min. |

-continued

| Structure | Example number | Precursors | Analytical Data |
|---|---|---|---|
| [(1S)-2-(3,5-dichloro-1-oxido-pyridin-1-ium-4-yl)-1-(3,4-dimethoxyphenyl)ethyl] 3-[(3-cyano-N-[(3R)-quinuclidin-3-yl]oxycarbonyl-anilino)methyl]benzoate 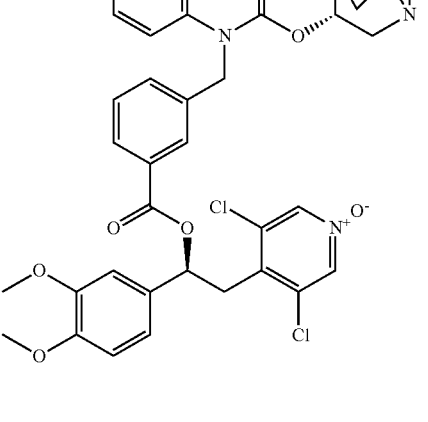 | Example 30 | Intermediate 80 | ¹H NMR (400 MHz, CDCl3): δ 8.12 (s, 2 H), 7.98-7.94 (m, 1 H), 7.87 (s, 1 H), 7.54-7.48 (m, 2 H), 7.46-7.39 (m, 4 H), 7.02-6.95 (m, 2 H), 6.86 (d, J = 8.2 Hz, 1 H), 6.28 (dd, J = 9.7, 4.6 Hz, 1 H), 4.93 (s, 2 H), 4.84-4.78 (m, 1 H), 3.90 (s, 3 H), 3.88 (s, 3 H), 3.70 (dd, J = 14.0, 9.8 Hz, 1 H), 3.35 (dd, J = 14.0, 4.6 Hz, 1 H), 3.21 (ddd, J = 14.8, 8.2, 2.2 Hz, 1 H), 2.78-2.67 (m, 3 H), 2.63-2.50 (m, 2 H), 1.98-1.92 (m, 1 H), 1.70-1.60 (m, 1 H), 1.57-1.46 (m, 1 H), 1.40-1.30 (m, 1 H), 1.30-1.20 (m, 1 H). LCMS (Method 1): [MH+] = 731 at 2.71 min. |
| [(1S)-2-(3,5-dichloro-1-oxido-pyridin-1-ium-4-yl)-1-[4-(difluoromethoxy)-3-methoxy-phenyl]ethyl] 3-[(2-fluoro-N-[(3R)-quinuclidin-3-yl]oxycarbonyl-anilino)methyl]benzoate 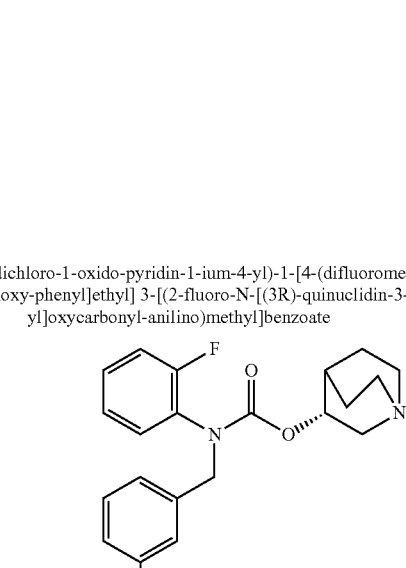 | Example 31 | Intermediate 28 | ¹H NMR (400 MHz, CDCl3): δ 8.14 (s, 2 H), 7.96-7.88 (m, 2 H), 7.47 (d, J = 7.6 Hz, 1 H), 7.38 (t, J = 7.7 Hz, 1 H), 7.30-7.23 (m, 1 H), 7.20-7.15 (m, 1 H), 7.13-6.98 (m, 5 H), 6.55 (t, J = 75.0 Hz, 1 H), 6.26 (dd, J = 9.8, 4.1 Hz, 1 H), 4.94-4.78 (m, 3 H), 3.90 (s, 3 H), 3.67 (dd, J = 14.1, 10.0 Hz, 1 H), 3.36-3.26 (m, 2 H), 2.94-2.61 (m, 5 H), 2.14-2.06 (m, 1 H), 1.81-1.56 (m, 2 H), 1.53-1.30 (m, 2 H). LCMS (Method 2): [MH+] = 760 at 3.56 min. |

-continued

| Structure | Example number | Precursors | Analytical Data |
|---|---|---|---|
| [(1S)-2-(3,5-dichloro-1-oxido-pyridin-1-ium-4-yl)-1-[4-(difluoromethoxy)-3-isopropoxy-phenyl]ethyl] 3-[(2-fluoro-N-[(3R)-quinuclidin-3-yl]oxycarbonyl-anilino)methyl]benzoate | Example 32 | Intermediate 28 | $^1$H NMR (400 MHz, CDCl3): δ 8.13 (s, 2 H), 7.94-7.88 (m, 2 H), 7.48 (d, J = 7.6 Hz, 1 H), 7.38 (t, J = 7.6 Hz, 1 H), 7.29-7.23 (m, 1 H), 7.19-7.14 (m, 1 H), 7.13-6.99 (m, 5 H), 6.55 (t, J = 75.3 Hz, 1 H), 6.23 (dd, J = 9.7, 4.2 Hz, 1 H), 4.92-4.78 (m, 3 H), 4.62-4.51 (m, 1 H), 3.65 (dd, J = 14.1, 9.9 Hz, 1 H), 3.35-3.24 (m, 2 H), 2.91-2.59 (m, 5 H), 2.11-2.05 (m, 1 H), 1.78-1.57 (m, 2 H), 1.50-1.26 (m, 8 H). LCMS (Method 2): [MH+] = 788 at 3.88 min. |
| [(1S)-2-(3,5-dichloro-1-oxido-pyridin-1-ium-4-yl)-1-[4-(difluoromethoxy)-3-ethoxy-phenyl]ethyl] 3-[(2-fluoro-N-[(3R)-quinuclidin-3-yl]oxycarbonyl-anilino)methyl]benzoate | Example 33 | Intermediate 28 | $^1$H NMR (400 MHz, CDCl3): δ 8.13 (s, 2 H), 7.94-7.88 (m, 2 H), 7.48 (d, J = 7.6 Hz, 1 H), 7.38 (t, J = 7.7 Hz, 1 H), 7.29-7.22 (m, 1 H), 7.19-7.14 (m, 1 H), 7.13-6.98 (m, 5 H), 6.56 (t, J = 75.2 Hz, 1 H), 6.24 (dd, J = 9.7, 4.2 Hz, 1 H), 4.91-4.79 (m, 3 H), 4.17-4.04 (m, 2 H), 3.66 (dd, J = 14.1, 9.9 Hz, 1 H), 3.35-3.23 (m, 2 H), 2.89-2.59 (m, 5 H), 2.10-2.03 (m, 1 H), 1.77-1.56 (m, 2 H), 1.49-1.26 (m, 5 H). LCMS (Method 2): [MH+] = 774 at 3.75 min. |
| [(1S)-2-(3,5-dichloro-1-oxido-pyridin-1-ium-4-yl)-1-[4-(difluoromethoxy)-3-methoxy-phenyl]ethyl] 3-[(3-fluoro-N-[(3R)-quinuclidin-3-yl]oxycarbonyl-anilino)methyl]benzoate | Example 34 | Intermediate 19 | $^1$H NMR (400 MHz, CDCl3): δ 8.14 (s, 2 H), 7.97-7.87 (m, 2 H), 7.48-7.38 (m, 2 H), 7.32-7.24 (m, 1 H), 7.20-7.15 (m, 1 H), 7.06-6.82 (m, 5 H), 6.54 (t, J = 74.9 Hz, 1 H), 6.27 (dd, J = 10.0, 4.2 Hz, 1 H), 4.95-4.83 (m, 3 H), 3.90 (s, 3 H), 3.68 (dd, J = 14.1, 10.1 Hz, 1 H), 3.36-3.24 (m, 2 H), 2.90-2.59 (m, 5 H), 2.10-2.04 (m, 1 H), 1.79-1.57 (m, 2 H), 1.52-1.30 (m, 2 H). LCMS (Method 2): [MH+] = 760 at 3.59 min. |

| Structure | Example number | Precursors | Analytical Data |
|---|---|---|---|
| [(1S)-2-(3,5-dichloro-1-oxido-pyridin-1-ium-4-yl)-1-[4-(difluoromethoxy)-3-isopropoxy-phenyl]ethyl] 3-[(3-fluoro-N-[(3R)-quinuclidin-3-yl]oxycarbonyl-anilino)methyl]benzoate 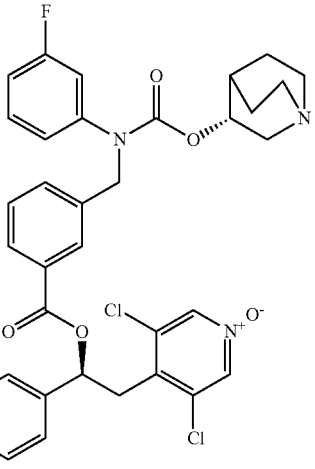 | Example 35 | Intermediate 19 | $^1$H NMR (400 MHz, CDCl$_3$): δ 8.13 (s, 2 H), 7.96-7.86 (m, 2 H), 7.49-7.38 (m, 2 H), 7.32-7.24 (m, 1 H), 7.19-7.15 (m, 1 H), 7.05-6.82 (m, 5 H), 6.55 (t, J = 75.3 Hz, 1 H), 6.24 (dd, J = 9.9, 4.3 Hz, 1 H), 4.94-4.84 (m, 3 H), 4.62-4.51 (m, 1 H), 3.66 (dd, J = 14.1, 9.9 Hz, 1 H), 3.35-3.23 (m, 2 H), 2.87-2.58 (m, 5 H), 2.08-2.03 (m, 1 H), 1.77-1.54 (m, 2 H), 1.51-1.40 (m, 1 H), 1.39-1.28 (m, 7 H). LCMS (Method 1): [MH+] = 788 at 3.13 min. |
| [(1S)-2-(3,5-dichloro-1-oxido-pyridin-1-ium-4-yl)-1-[4-(difluoromethoxy)-3-ethoxy-phenyl]ethyl] 3-[(3-fluoro-N-[(3R)-quinuclidin-3-yl]oxycarbonyl-anilino)methyl]benzoate 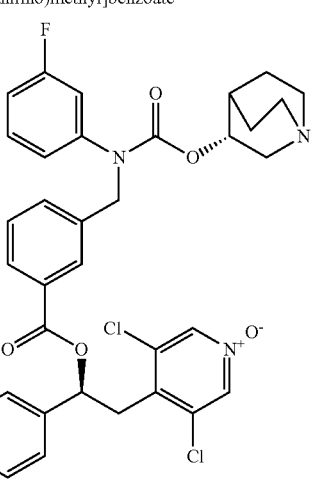 | Example 36 | Intermediate 19 | $^1$H NMR (400 MHz, CDCl3): δ 8.13 (s, 2 H), 7.96-7.87 (m, 2 H), 7.48-7.38 (m, 2 H), 7.32-7.24 (m, 1 H), 7.19-7.14 (m, 1 H), 7.05-6.83 (m, 5 H), 6.57 (t, J = 75.2 Hz, 1 H), 6.25 (dd, J = 9.9, 4.2 Hz, 1 H), 4.95-4.84 (m, 3 H), 4.17-4.04 (m, 2 H), 3.67 (dd, J = 14.1, 10.0 Hz, 1 H), 3.35-3.24 (m, 2 H), 2.90-2.59 (m, 5 H), 2.10-2.04 (m, 1 H), 1.79-1.57 (m, 2 H), 1.52-1.29 (m, 5 H). LCMS (Method 2): [MH+] = 774 at 3.77 min. |

-continued

| Structure | Example number | Precursors | Analytical Data |
|---|---|---|---|
| [(1S)-2-(3,5-dichloro-1-oxido-pyridin-1-ium-4-yl)-1-[4-(difluoromethoxy)-3-methoxy-phenyl]ethyl] 4-[(2-methoxy-N-[(3R)-quinuclidin-3-yl]oxycarbonyl-anilino)methyl]benzoate 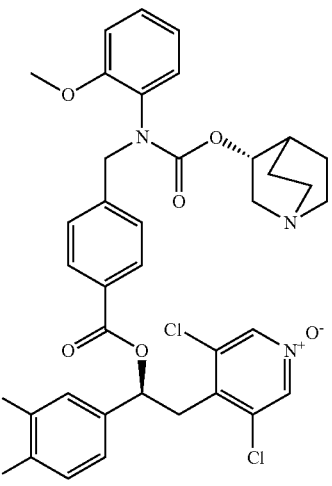 | Example 37 | Intermediate 30 | ¹H NMR (400 MHz, DMSO@85oC): δ 8.41 (s, 2 H), 7.95 (d, J = 8.1 Hz, 2 H), 7.44 (d, J = 8.0 Hz, 2 H), 7.31-7.20 (m, 3 H), 7.14-7.06 (m, 3 H), 7.00 (t, J = 74.8 Hz, 1 H), 6.93-6.88 (m, 1 H), 6.32 (dd, J = 9.1, 4.8 Hz, 1 H), 4.80 (s, 2 H), 4.69-4.64 (m, 1 H), 3.89 (s, 3 H), 3.78 (s, 3 H), 3.67 (dd, J = 14.2, 9.1 Hz, 1 H), 3.44 (dd, J = 14.3, 5.0 Hz, 1 H), 3.12-3.05 (m, 1 H), 2.71-2.55 (m, 3 H), 2.50-2.41 (m, 2 H), 1.87-1.81 (m, 1 H), 1.64-1.54 (m, 1 H), 1.54-1.43 (m, 1 H), 1.36-1.24 (m, 1 H), 1.23-1.13 (m, 1 H). LCMS (Method 2): [MH+] = 772 at 3.51 min. |
| [(1S)-2-(3,5-dichloro-1-oxido-pyridin-1-ium-4-yl)-1-[4-(difluoromethoxy)-3-isopropoxy-phenyl]ethyl] 4-[(2-methoxy-N-[(3R)-quinuclidin-3-yl]oxycarbonyl-anilino)methyl]benzoate 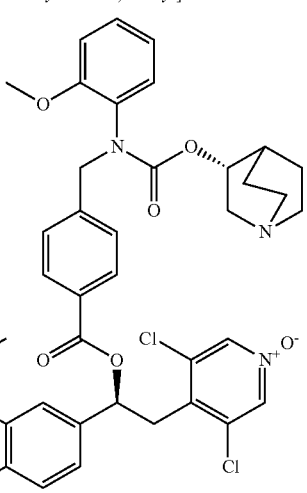 | Example 38 | Intermediate 30 | ¹H NMR (400 MHz, DMSO @85oC): δ 8.41 (s, 2 H), 7.94 (d, J = 8.1 Hz, 2 H), 7.44 (d, J = 8.1 Hz, 2 H), 7.31-7.19 (m, 3 H), 7.13-7.05 (m, 3 H), 6.97 (t, J = 74.9 Hz, 1 H), 6.93-6.87 (m, 1 H), 6.29 (dd, J = 8.9, 5.0 Hz, 1 H), 4.80 (s, 2 H), 4.70-4.60 (m, 2 H), 3.78 (s, 3 H), 3.66 (dd, J = 14.2, 8.9 Hz, 1 H), 3.44 (dd, J = 14.2, 5.1 Hz, 1 H), 3.12-3.04 (m, 1 H), 2.68-2.57 (m, 3 H), 2.50-2.40 (m, 2 H), 1.87-1.81 (m, 1 H), 1.64-1.55 (m, 1 H), 1.53-1.44 (m, 1 H), 1.36-1.25 (m, 7 H), 1.23-1.13 (m, 1 H). LCMS (Method 1): [MH+] = 800 at 3.04 min. |

-continued

| Structure | Example number | Precursors | Analytical Data |
|---|---|---|---|
| [(1S)-2-(3,5-dichloro-1-oxido-pyridin-1-ium-4-yl)-1-[4-(difluoromethoxy)-3-ethoxy-phenyl]ethyl] 4-[(2-methoxy-N-[(3R)-quinuclidin-3-yl]oxycarbonyl-anilino)methyl]benzoate 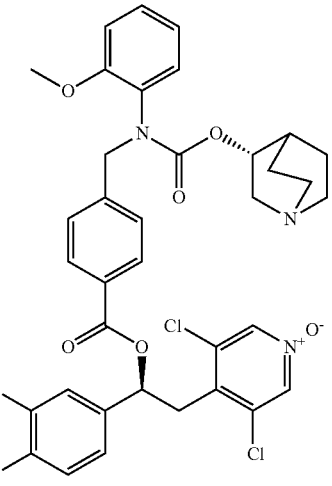 | Example 39 | Intermediate 30 | $^1$H NMR (400 MHz, DMSO@85oC): δ 8.41 (s, 2 H), 7.95 (d, J = 8.1 Hz, 2 H), 7.44 (d, J = 8.1 Hz, 2 H), 7.31-7.19 (m, 3 H), 7.14-7.05 (m, 3 H), 6.99 (t, J = 74.9 Hz, 1 H), 6.94-6.87 (m, 1 H), 6.30 (dd, J = 9.0, 4.9 Hz, 1 H), 4.80 (s, 2 H), 4.70-4.63 (m, 1 H), 4.23-4.11 (m, 2 H), 3.78 (s, 3 H), 3.66 (dd, J = 14.2, 9.1 Hz, 1 H), 3.43 (dd, J = 14.3, 5.0 Hz, 1 H), 3.12-3.04 (m, 1 H), 2.72-2.56 (m, 3 H), 2.50-2.39 (m, 2 H), 1.87-1.80 (m, 1 H), 1.65-1.54 (m, 1 H), 1.54-1.43 (m, 1 H), 1.37 (t, J = 6.9 Hz, 3 H), 1.34-1.24 (m, 1 H), 1.23-1.12 (m, 1 H). LCMS (Method 1): [MH+] = 786 at 2.98 min. |
| [(1S)-2-(3,5-dichloro-1-oxido-pyridin-1-ium-4-yl)-1-(3,4-dimethoxyphenyl)ethyl] 4-[(2,3-difluoro-N-[(3R)-quinuclidin-3-yl]oxycarbonyl-anilino)methyl]benzoate 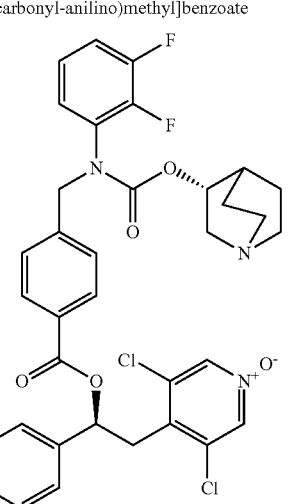 | Example 40 | Intermediate 81 | $^1$H NMR (400 MHz, CD3CN): δ 8.20 (s, 2 H), 8.00 (d, J = 7.9 Hz, 2 H), 7.41 (s, 2 H), 7.28-7.04 (m, 5 H), 6.94 (d, J = 8.2 Hz, 1 H), 6.23 (dd, J = 9.6, 4.5 Hz, 1 H), 4.98-4.79 (m, 3 H), 3.83 (s, 3 H), 3.81 (s, 3 H), 3.71 (dd, J = 14.1, 9.6 Hz, 1 H), 3.36 (dd, J = 14.1, 4.5 Hz, 1 H), 3.23 (ddd, J = 14.7, 8.2, 2.4 Hz, 1 H), 2.87-2.54 (m, 5 H), 2.00-1.80* (m, 1H), 1.76-1.64 (m, 1 H), 1.64-1.53 (m, 1 H), 1.41-1.28 (m, 2 H). LCMS (Method 1): [MH+] = 742 at 2.79 min. |

| Structure | Example number | Precursors | Analytical Data |
|---|---|---|---|
| [(1S)-2-(3,5-dichloro-1-oxido-pyridin-1-ium-4-yl)-1-(3,4-dimethoxyphenyl)ethyl] 4-[(2,4-difluoro-N-[(3R)-quinuclidin-3-yl]oxycarbonyl-anilino)methyl]benzoate formate salt 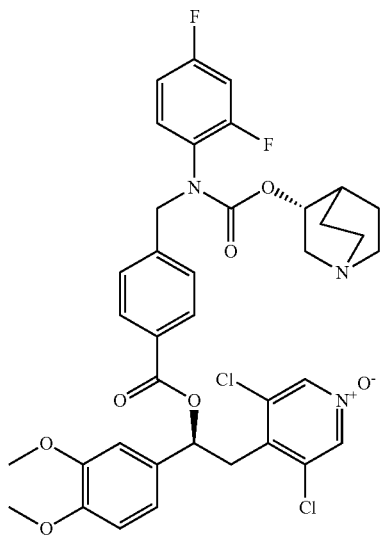 | Example 41 | Intermediate 82 | $^1$H NMR (400 MHz, CDCl3): δ 8.33 (s, 1 H), 8.13 (s, 2 H), 7.95 (d, J = 7.9 Hz, 2 H), 7.34-7.24 (m, 2 H), 7.04-6.95 (m, 3 H), 6.89-6.78 (m, 3 H), 6.30 (dd, J = 9.7, 4.6 Hz, 1 H), 5.01-4.93 (m, 1 H), 4.89-4.74 (m, 2 H), 3.91 (s, 3 H), 3.88 (s, 3 H), 3.71 (dd, J = 14.0, 9.7 Hz, 1 H), 3.44-3.31 (m, 2 H), 3.05-2.69 (m, 5 H), 2.25-2.13 (m, 1 H), 1.86-1.73 (m, 1 H), 1.83-1.63 (m, 1 H), 1.60-1.44 (m, 2 H). LCMS (Method 1): [MH+] = 742 at 2.78 min. |
| [(1S)-2-(3,5-dichloro-1-oxido-pyridin-1-ium-4-yl)-1-(3,4-dimethoxyphenyl)ethyl] 4-[(2,5-difluoro-N-[(3R)-quinuclidin-3-yl]oxycarbonyl-anilino)methyl]benzoate Formate salt 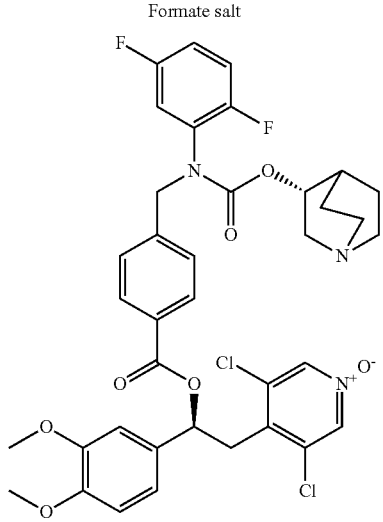 | Example 42 | Intermediate 83 | $^1$H NMR (400 MHz, CD3CN): δ 8.33 (s, 1 H), 8.17 (s, 2 H), 7.96 (d, J = 7.9 Hz, 2 H), 7.38 (d, J = 7.8 Hz, 2 H), 7.19-6.98 (m, 5 H), 6.91 (d, J = 8.2 Hz, 1 H), 6.20 (dd, J = 9.6, 4.5 Hz, 1 H), 4.95-4.80 (m, 3 H), 3.80 (s, 3 H), 3.78 (s, 3 H), 3.68 (dd, J = 14.1, 9.6 Hz, 1 H), 3.38-3.28 (m, 2 H), 2.95-2.77 (m, 4 H), 2.75-2.64 (m, 1 H), 2.12-1.99 (m, 1 H), 1.83-1.73 (m, 1 H), 1.72-1.60 (m, 1 H), 1.53-1.38 (m, 2 H). LCMS (Method 1): [MH+] = 742 at 2.77 min. |

-continued

| Structure | Example number | Precursors | Analytical Data |
|---|---|---|---|
| [(1S)-2-(3,5-dichloro-1-oxido-pyridin-1-ium-4-yl)-1-(3,4-dimethoxyphenyl)ethyl] 4-[(3-chloro-N-[(3R)-quinuclidin-3-yl]oxycarbonyl-anilino)methyl]benzoate Formate salt 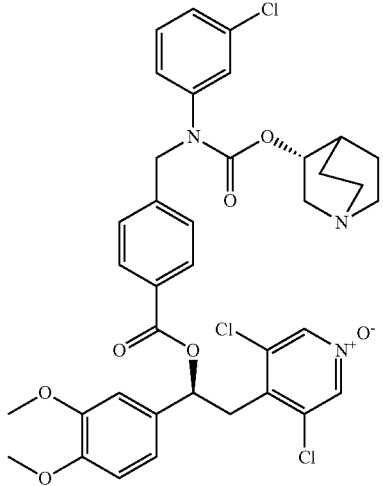 | Example 43 | Intermediate 84 | $^1$H NMR (400 MHz, CDCl3): δ 8.29 (s, 1 H), 8.14 (s, 2 H), 7.99 (d, J = 8.0 Hz, 2 H), 7.32-7.23 (m, 5 H), 7.04-6.96 (m, 3 H), 6.86 (d, J = 8.2 Hz, 1 H), 6.30 (dd, J = 9.7, 4.6 Hz, 1 H), 5.02-4.97 (m, 1 H), 4.88 (s, 2 H), 3.91 (s, 3 H), 3.88 (s, 3 H), 3.71 (dd, J = 13.9, 9.7 Hz, 1 H), 3.46-3.31 (m, 2 H), 3.08-2.90 (m, 4 H), 2.84-2.73 (m, 1 H), 2.23-2.16 (m, 1 H), 1.94-1.81 (m, 1 H), 1.80-1.68 (m, 1 H), 1.60-1.48 (m, 2 H). LCMS (Method 1): [MH+] = 740 at 2.82 min. |
| [(1S)-2-(3,5-dichloro-1-oxido-pyridin-1-ium-4-yl)-1-(3,4-dimethoxyphenyl)ethyl] 4-[(3-methyl-N-[(3R)-quinuclidin-3-yl]oxycarbonyl-anilino)methyl]benzoate Formate salt 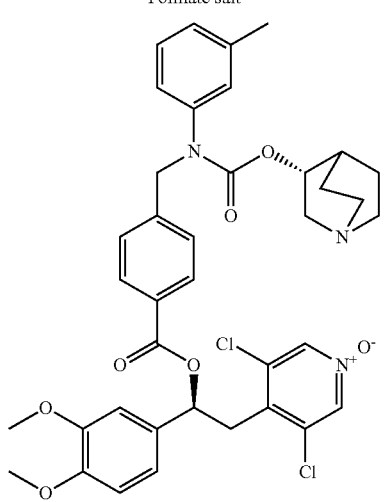 | Example 44 | Intermediate 85 | $^1$H NMR (400 MHz, CDCl3): δ 8.33 (s, 1 H), 8.14 (s, 2 H), 7.97 (d, J = 7.9 Hz, 2 H), 7.31 (d, J = 8.0 Hz, 2 H), 7.19 (t, J = 8.0 Hz, 1 H), 7.09-6.96 (m, 3 H), 6.95-6.76 (m, 2 H), 6.85 (d, J = 8.2 Hz, 1 H), 6.30 (dd, J = 9.6, 4.6 Hz, 1 H), 5.03-4.96 (m, 1 H), 4.86 (s, 2 H), 3.91 (s, 3 H), 3.88 (s, 3 H), 3.71 (dd, J = 13.9, 9.7 Hz, 1 H), 3.45-3.31 (m, 2 H), 3.10-2.90 (m, 4 H), 2.83-2.71 (m, 1 H), 2.31 (s, 3 H), 2.27-2.21 (m, 1 H), 1.93-1.82 (m, 1 H), 1.81-1.69 (m, 1 H), 1.62-1.46 (m, 2 H). LCMS (Method 1): [MH+] = 720 at 2.80 min. |

-continued

| Structure | Example number | Precursors | Analytical Data |
|---|---|---|---|
| [(1S)-2-(3,5-dichloro-1-oxido-pyridin-1-ium-4-yl)-1-(3,4-dimethoxyphenyl)ethyl] 4-[[N-[(3R)-quinuclidin-3-yl]oxycarbonyl-3-(trifluoromethyl)anilino]methyl]benzoate Formate salt 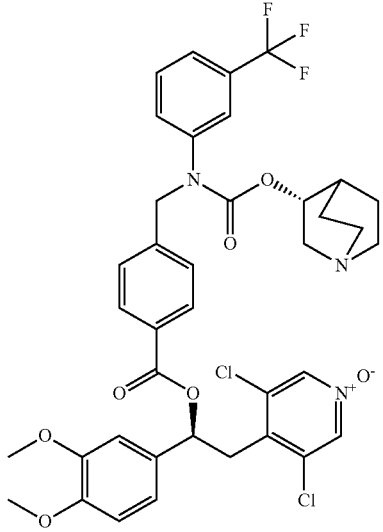 | Example 45 | Intermediate 86 | ¹H NMR (400 MHz, CDCl3): δ 8.33 (s, 1 H), 8.14 (s, 2 H), 7.99 (d, J = 8.0 Hz, 2 H), 7.55-7.34 (m, 4 H), 7.30 (d, J = 8.1 Hz, 2 H), 7.04-6.95 (m, 2 H), 6.86 (d, J = 8.2 Hz, 1 H), 6.30 (dd, J = 9.7, 4.6 Hz, 1 H), 5.05-4.96 (m, 1 H), 4.92 (s, 2 H), 3.91 (s, 3 H), 3.88 (s, 3 H), 3.71 (dd, J = 14.0, 9.8 Hz, 1 H), 3.47-3.31 (m, 2 H), 3.08-2.87 (m, 4 H), 2.84-2.70 (m, 1 H), 2.24-2.18 (m, 1 H), 1.93-1.82 (m, 1 H), 1.81-1.68 (m, 1 H), 1.58-1.46 (m, 2 H). LCMS (Method 1): [MH+] = 774 at 2.86 min. |
| [(1S)-2-(3,5-dichloro-1-oxido-pyridin-1-ium-4-yl)-1-(3,4-dimethoxyphenyl)ethyl] 4-[(3-cyano-N-[(3R)-quinuclidin-3-yl]oxycarbonyl-anilino)methyl]benzoate 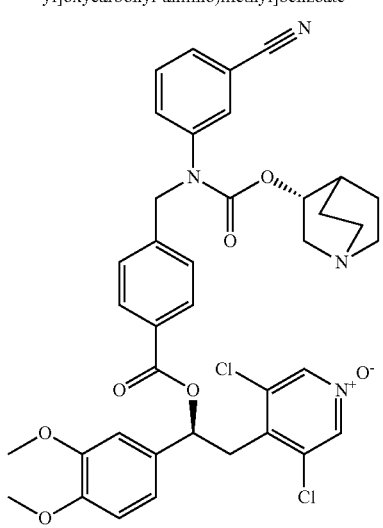 | Example 46 | Intermediate 87 | ¹H NMR (400 MHz, CDCl3): δ 8.14 (s, 2 H), 8.00 (d, J = 8.1 Hz, 2 H), 7.56-7.39 (m, 4 H), 7.30 (d, J = 8.2 Hz, 2 H), 7.04-6.96 (m, 2 H), 6.86 (d, J = 8.2 Hz, 1 H), 6.30 (dd, J = 9.7, 4.6 Hz, 1 H), 5.01-4.87 (m, 2 H), 4.84-4.78 (m, 1 H), 3.91 (s, 3 H), 3.88 (s, 3 H), 3.71 (dd, J = 14.0, 9.8 Hz, 1 H), 3.35 (dd, J = 14.0, 4.6 Hz, 1 H), 3.22 (ddd, J = 14.8, 8.2, 2.2 Hz, 1 H), 2.80-2.65 (m, 3 H), 2.59 (dt, J = 14.9, 2.6 Hz, 1 H), 2.55-2.45 (m, 1 H), 1.99-1.92 (m, 1 H), 1.71-1.58 (m, 1 H), 1.57-1.47 (m, 1 H), 1.40-1.21 (m, 2 H). LCMS (Method 1): [MH+] = 751 at 2.72 min. |

-continued

| Structure | Example number | Precursors | Analytical Data |
|---|---|---|---|
| [(1S)-2-(3,5-dichloro-1-oxido-pyridin-1-ium-4-yl)-1-(3,4-dimethoxyphenyl)ethyl] 2-fluoro-4-[(2-fluoro-N-[(3R)-quinuclidin-3-yl]oxycarbonyl-anilino)methyl]benzoate 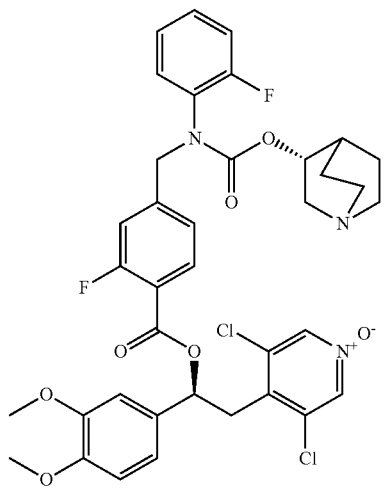 | Example 47 | Intermediate 88 | $^1$H NMR (400 MHz, CDCl3): δ 8.12 (s, 2 H), 7.83 (t, J = 7.3 Hz, 1 H), 7.16-6.90 (m, 8 H), 6.84 (d, J = 8.2 Hz, 1 H), 6.32 (dd, J = 9.1, 5.1 Hz, 1 H), 4.84 (s, 2 H), 4.82-4.74 (m, 1 H), 3.91 (s, 3 H), 3.88 (s, 3 H), 3.67 (dd, J = 14.0, 9.2 Hz, 1 H), 3.35 (dd, J = 13.9, 5.1 Hz, 1 H), 3.28-3.13 (m, 1 H), 2.83-2.53 (m, 5 H), 1.96-1.88 (m, 1 H), 1.68-1.45 (m, 2 H), 1.37-1.24 (m, 1 H), 1.24-1.13 (m, 1 H). LCMS (Method 1): [MH+] = 742 at 2.77 min. |
| [(1S)-2-(3,5-dichloro-1-oxido-pyridin-1-ium-4-yl)-1-(3,4-dimethoxyphenyl)ethyl] 2-fluoro-4-[(N-[(3R)-quinuclidin-3-yl]oxycarbonylanilino)methyl]benzoate 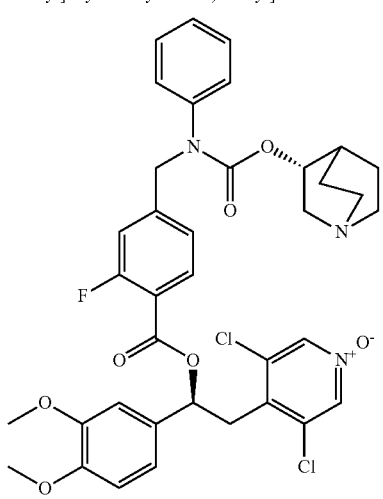 | Example 48 | Intermediate 89 | $^1$H NMR (400 MHz, CDCl3): δ 8.13 (s, 2 H), 7.85 (t, J = 7.7 Hz, 1 H), 7.33 (t, J = 7.6 Hz, 2 H), 7.28-6.93 (m, 6 H), 6.84 (d, J = 8.3 Hz, 1 H), 6.33 (dd, J = 9.1, 5.1 Hz, 1 H), 4.94-4.88 (m, 1 H), 4.86 (d, J = 6.8 Hz, 2 H), 3.91 (s, 3 H), 3.88 (s, 3 H), 3.67 (dd, J = 13.9, 9.1 Hz, 1 H), 3.35 (dd, J = 13.9, 5.0 Hz, 1 H), 3.30 (ddd, J = 14.8, 8.2, 2.2 Hz, 1 H), 2.87 (t, J = 7.8 Hz, 3 H), 2.78 (d, J = 14.8 Hz, 1 H), 2.71-2.62 (m, 1 H), 2.13-2.08 (m, 1 H), 2.05-1.71 (m, 2 H), 1.69-1.58 (m, 1 H), 1.54-1.44 (m, 1 H), 1.44-1.33 (m, 1 H). LCMS (Method 1): [MH+] = 724 at 2.78 min. |

-continued

| Structure | Example number | Precursors | Analytical Data |
|---|---|---|---|
| [(1S)-2-(3,5-dichloro-1-oxido-pyridin-1-ium-4-yl)-1-(3,4-dimethoxyphenyl)ethyl] 3-fluoro-5-[(2-fluoro-N-[(3R)-quinuclidin-3-yl]oxycarbonyl-anilino)methyl]benzoate | Example 49 | Intermediate 68 | $^1$H NMR (400 MHz, CDCl3): δ 8.11 (s, 2 H), 7.71 (s, 1 H), 7.59 (d, J = 8.0 Hz, 1 H), 7.26-7.22 (m, 2 H), 7.09-7.00 (m, 3 H), 6.98-6.95 (m, 2 H), 6.85 (d, J = 8.4 Hz, 1 H), 6.25 (dd, J = 4.4, 9.6 Hz, 1 H), 4.84 (s, 2 H), 4.83-4.81 (m, 1 H), 3.90 (s, 3 H), 3.88 (s, 3 H), 3.68 (dd, J = 9.6, 14.0 Hz, 1 H), 3.33 (dd, J = 4.4, 14.0 Hz, 1 H), 3.19-3.16 (m, 1 H), 2.71-2.61 (m, 5 H), 1.99-1.92 (m, 1 H), 1.62-1.59 (m, 1 H), 1.54-1.49 (m, 1 H), 1.36-1.24 (m, 1 H), 1.23-1.13 (m, 1 H). ). LCMS (Method 1): [MH+] = 742 at 2.77 min |
| [(1S)-2-(3,5-dichloro-1-oxido-pyridin-1-ium-4-yl)-1-(3,4-dimethoxyphenyl)ethyl] 3-fluoro-4-[(2-fluoro-N-[(3R)-quinuclidin-3-yl]oxycarbonyl-anilino)methyl]benzoate | Example 50 | Intermediate 69 | $^1$H NMR (400 MHz, CDCl3): δ 8.12 (s, 2 H), 7.76 (dd, J = 1.2, 8.0 Hz, 1 H), 7.62-7.60 (m, 1 H), 7.52-7.50 (m, 1 H), 7.25-7.22 (m, 1 H), 7.15-7.09 (m, 3 H), 7.06-6.95 (m, 2 H), 6.85 (d, J = 8.0 Hz, 1 H), 6.26 (dd, J = 4.4, 9.6 Hz, 1 H), 4.93-4.91 (m, 2 H), 4.85-4.83 (m, 1 H), 3.90 (s, 3 H), 3.87 (s, 3 H), 3.69 (dd, J = 9.6, 14.0 Hz, 1 H), 3.35 (dd, J = 4.4, 14.0 Hz, 1 H), 3.26-3.21 (m, 1 H), 2.80-2.55 (m, 5 H), 1.97-1.89 (m, 1 H), 1.67-1.57 (m, 1 H), 1.56-1.44 (m, 1 H), 1.37-1.25 (m, 1 H), 1.24-1.13 (m, 1 H). LCMS (Method 1): [MH+] = 742 at 2.80 min. |
| [(1S)-2-(3,5-dichloro-1-oxido-pyridin-1-ium-4-yl)-1-[4-(difluoromethoxy)-3-(trideuteriomethoxy)phenyl]ethyl] 3-[(2-fluoro-N-[(3R)-quinuclidin-3-yl]oxycarbonyl-anilino)methyl]benzoate | Example 51 | Intermediate 28 | $^1$H NMR (400 MHz, CDCl3): δ 8.13 (s, 2 H), 7.94-7.88 (m, 2 H), 7.48 (d, J = 7.6 Hz, 1 H), 7.38 (t, J = 7.7 Hz, 1 H), 7.30-7.23 (m, 1 H), 7.20-7.15 (m, 1 H), 7.13-6.99 (m, 5 H), 6.54 (t, J = 75.0 Hz, 1 H), 6.26 (dd, J = 9.8, 4.2 Hz, 1 H), 4.93-4.78 (m, 3 H), 3.67 (dd, J = 14.1, 10.0 Hz, 1 H), 3.36-3.25 (m, 2 H), 2.92-2.60 (m, 5 H), 2.12-2.05 (m, 1 H), 1.79-1.57 (m, 2 H), 1.50-1.28 (m, 2 H). LCMS (Method 1): [MH+] = 763 at 2.99 min. |

| Structure | Example number | Precursors | Analytical Data |
|---|---|---|---|
| [(1S)-2-(3,5-dichloro-1-oxido-pyridin-1-ium-4-yl)-1-[4-(difluoromethoxy)-3-(trideuteriomethoxy)phenyl]ethyl] 3-[(3-fluoro-N-[(3R)-quinuclidin-3-yl]oxycarbonyl-anilino)methyl]benzoate 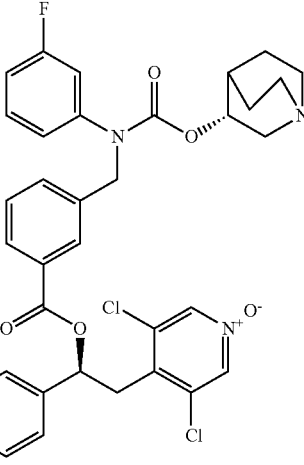 | Example 52 | Intermediate 19 | $^1$H NMR (400 MHz, CDCl3): δ 8.14 (s, 2 H), 7.97-7.88 (m, 2 H), 7.48-7.38 (m, 2 H), 7.32-7.25 (m, 1 H), 7.20-7.16 (m, 1 H), 7.06-6.83 (m, 5 H), 6.54 (t, J = 74.9 Hz, 1 H), 6.27 (dd, J = 10.0, 4.2 Hz, 1 H), 4.95-4.84 (m, 3 H), 3.68 (dd, J = 14.1, 10.1 Hz, 1 H), 3.35-3.24 (m, 2 H), 2.89-2.58 (m, 5 H), 2.09-2.03 (m, 1 H), 1.78-1.56 (m, 2 H), 1.51-1.29 (m, 2 H). LCMS (Method 2): [MH+] = 763 at 3.57 min. |
| [(1S)-2-(3,5-dichloro-1-oxido-pyridin-1-ium-4-yl)-1-[4-(difluoromethoxy)-3-(trideuteriomethoxy)phenyl]ethyl] 4-[(2-methoxy-N-[(3R)-quinuclidin-3-yl]oxycarbonyl-anilino)methyl]benzoate 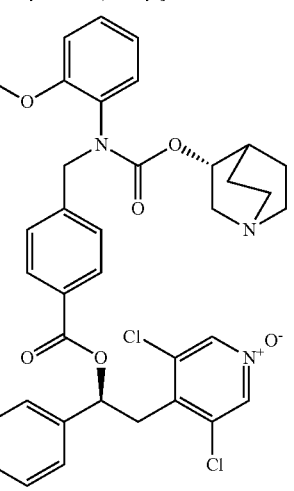 | Example 53 | Intermediate 30 | $^1$H NMR (400 MHz, DMSO@85oC): δ 8.41 (s, 2 H), 7.95 (d, J = 8.1 Hz, 2 H), 7.44 (d, J = 8.0 Hz, 2 H), 7.31-7.20 (m, 3 H), 7.14-7.05 (m, 3 H), 7.00 (t, J = 74.9 Hz, 1 H), 6.93-6.87 (m, 1 H), 6.32 (dd, J = 9.1, 4.8 Hz, 1 H), 4.80 (s, 2 H), 4.70-4.64 (m, 1 H), 3.78 (s, 3 H), 3.67 (dd, J = 14.2, 9.1 Hz, 1 H), 3.44 (dd, J = 14.2, 4.9 Hz, 1 H), 3.13-3.04 (m, 1 H), 2.71-2.55 (m, 3 H), 2.51-2.39 (m, 2 H), 1.87-1.81 (m, 1 H), 1.65-1.54 (m, 1 H), 1.54-1.43 (m, 1 H), 1.36-1.25 (m, 1 H), 1.23-1.12 (m, 1 H). LCMS (Method 2): [MH+] = 775 at 3.51 min. |

-continued

| Structure | Example number | Precursors | Analytical Data |
|---|---|---|---|
| [(1S)-2-(3,5-dichloro-1-oxido-pyridin-1-ium-4-yl)-1-(3,4-dimethoxyphenyl)ethyl] 4-[[2-pyridyl-[(3R)-quinuclidin-3-yl]oxycarbonyl-amino]methyl]benzoate 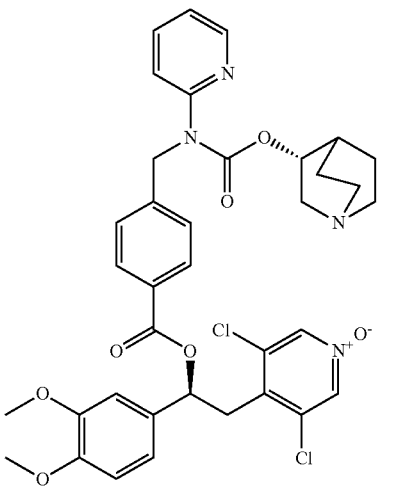 | Example 54 | Intermediate 90 | $^1$H NMR (400 MHz, CD3CN): δ 8.37 (dd, J = 4.9, 1.8 Hz, 1 H), 8.14 (s, 2 H), 7.95 (d, J = 8.1 Hz, 2 H), 7.79 (d, J = 8.4 Hz, 1 H), 7.69 (ddd, J = 8.4, 7.2, 2.0 Hz, 1 H), 7.36 (d, J = 8.1 Hz, 2 H), 7.06 (dd, J = 7.2, 4.9 Hz, 1 H), 7.02-6.96 (m, 2 H), 6.84 (d, J = 8.2 Hz, 1 H), 6.29 (dd, J = 9.7, 4.5 Hz, 1 H), 5.30 (dd, J = 37.3, 16.2 Hz, 2 H), 4.83-4.77 (m, 1 H), 3.90 (s, 3 H), 3.87 (s, 3 H), 3.69 (dd, J = 13.9, 9.7 Hz, 1 H), 3.33 (dd, J = 13.9, 4.5 Hz, 1 H), 3.19 (ddd, J = 14.8, 8.2, 2.2 Hz, 1 H), 2.79-2.62 (m, 3 H), 2.55 (dt, J = 14.7, 2.4 Hz, 1 H), 2.48-2.34 (m, 1 H), 1.97-1.91 (m, 1 H), 1.69-1.59 (m, 1 H), 1.56-1.46 (m, 1 H), 1.45-1.35 (m, 1 H), 1.30-1.20 (m, 1 H). LCMS (Method 1): [MH+] = 707 at 2.66 min. |
| [(1S)-1-[3-(cyclopropylmethoxy)-4-(difluoromethoxy)phenyl]-2-(3,5-dichloro-1-oxido-pyridin-1-ium-4-yl)ethyl] 4-[[2-pyridyl-[(3R)-quinuclidin-3-yl]oxycarbonyl-amino]methyl]benzoate 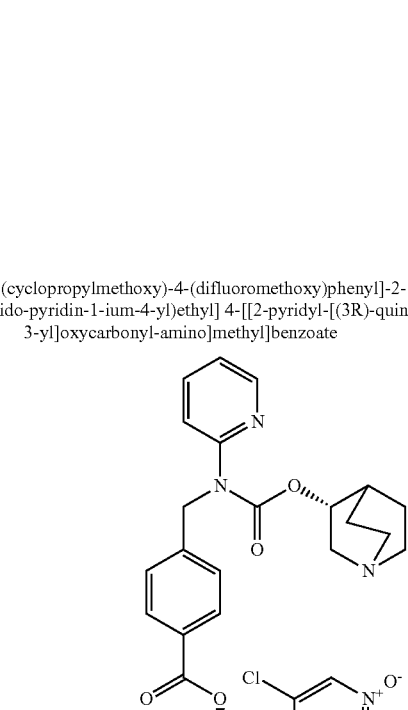 | Example 55 | Intermediate 90 | $^1$H NMR (400 MHz, CDCl3): δ 8.38 (d, J = 4.9 Hz, 1 H), 8.17-8.12 (m, 2 H), 7.95 (d, J = 8.1 Hz, 2 H), 7.76-7.63 (m, 2 H), 7.37 (d, J = 8.1 Hz, 2 H), 7.17 (d, J = 8.1 Hz, 1 H), 7.10-7.00 (m, 3 H), 6.61 (t, J = 75.3 Hz, 1 H), 6.26 (dd, J = 10.0, 4.2 Hz, 1 H), 5.29 (dd, J = 26.7, 16.3 Hz, 2 H), 4.88-4.83 (m, 1 H), 3.88 (d, J = 6.9 Hz, 2 H), 3.67 (dd, J = 14.1, 10.0 Hz, 1 H), 3.33-3.20 (m, 2 H), 2.84-2.71 (m, 3 H), 2.70-2.61 (m, 1 H), 2.61-2.37 (m, 1 H), 2.03-2.00 (m, 1 H), 1.74-1.66 (m, 1 H), 1.67-1.41 (m, 2 H), 1.35-1.22 (m, 2 H), 0.68-0.62 (m, 2 H), 0.38-0.33 (m, 2 H). LCMS (Method 1): [MH+] = 783 at 2.99 min. |

| Structure | Example number | Precursors | Analytical Data |
|---|---|---|---|
| [(1S)-2-(3,5-dichloro-1-oxido-pyridin-1-ium-4-yl)-1-(3,4-dimethoxyphenyl)ethyl] 4-[[3-pyridyl-[(3R)-quinuclidin-3-yl]oxycarbonyl-amino]methyl]benzoate Formate salt 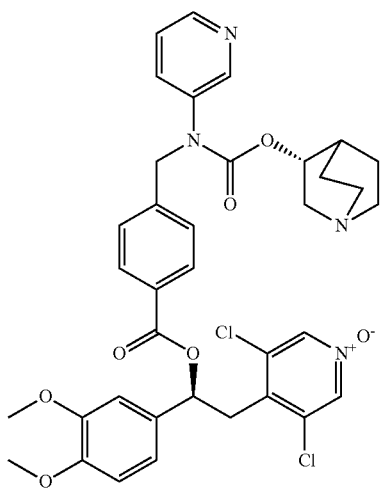 | Example 56 | Intermediate 91 | $^1$H NMR (400 MHz, CDCl3): δ 8.48 (d, J = 4.9 Hz, 1 H), 8.44 (s, 1 H), 8.35 (s, 1 H), 8.14 (s, 2 H), 7.98 (d, J = 8.0 Hz, 2 H), 7.33-7.23 (m, 4 H), 7.04-6.96 (m, 2 H), 6.86 (d, J = 8.2 Hz, 1 H), 6.30 (dd, J = 9.7, 4.6 Hz, 1 H), 4.96-4.90 (m, 1 H), 4.92 (s, 2 H), 3.91 (s, 3 H), 3.88 (s, 3 H), 3.71 (dd, J = 14.0, 9.7 Hz, 1 H), 3.38-3.29 (m, 2 H), 2.88 (t, J = 8.1 Hz, 3 H), 2.80 (d, J = 15.0 Hz, 1 H), 2.73-2.62 (m, 1 H), 2.14-2.09 (m, 1 H), 1.83-1.73 (m, 1 H), 1.72-1.60 (m, 1 H), 1.53-1.34 (m, 2 H). LCMS (Method 1): [MH+] = 707 at 2.57 min. |
| [(1S)-1-[3-(cyclopentoxy)-4-(difluoromethoxy)phenyl]-2-(3,5-dichloro-1-oxido-pyridin-1-ium-4-yl)ethyl] 3-[(2-fluoro-N-[(3R)-quinuclidin-3-yl]oxycarbonyl-anilino)methyl]benzoate formate salt 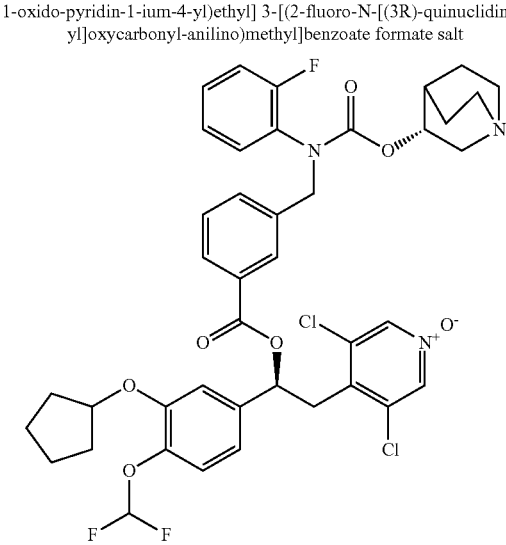 | Example 57 | Intermediate 28 | $^1$H NMR (400 MHz, CDCl3): δ 8.44 (s, 1 H), 8.13 (s, 2 H), 7.95-7.88 (m, 2 H), 7.49 (d, J = 7.6 Hz, 1 H), 7.38 (t, J = 7.7 Hz, 1 H), 7.32-7.19 (m, 2 H), 7.15 (d, J = 8.0 Hz, 1 H), 7.12-7.04 (m, 2 H), 7.02-6.95 (m, 2 H), 6.52 (t, J = 75.4 Hz, 1 H), 6.23 (dd, J = 9.5, 4.2 Hz, 1 H), 4.94-4.87 (m, 1 H), 4.89-4.77 (m, 3 H), 3.66 (dd, J = 14.0, 9.9 Hz, 1 H), 3.36-3.26 (m, 2 H), 3.01-2.70 (m, 3 H), 2.75 (d, J = 15.9 Hz, 1 H), 2.71-2.61 (m, 1 H), 2.14-2.05 (m, 1 H), 1.96-1.88 (m, 2 H), 1.87-1.70 (m, 5 H), 1.70-1.57 (m, 3 H), 1.50-1.40 (m, 1 H), 1.40-1.30 (m, 1 H). LCMS (Method 1): [MH+] = 814 at 3.11 min. |

| Structure | Example number | Precursors | Analytical Data |
|---|---|---|---|
| [(1S)-1-[3-(cyclopentoxy)-4-(difluoromethoxy)phenyl]-2-(3,5-dichloro-1-oxido-pyridin-1-ium-4-yl)ethyl] 4-[(2-fluoro-N-[(3R)-quinuclidin-3-yl]oxycarbonyl-anilino)methyl]benzoate 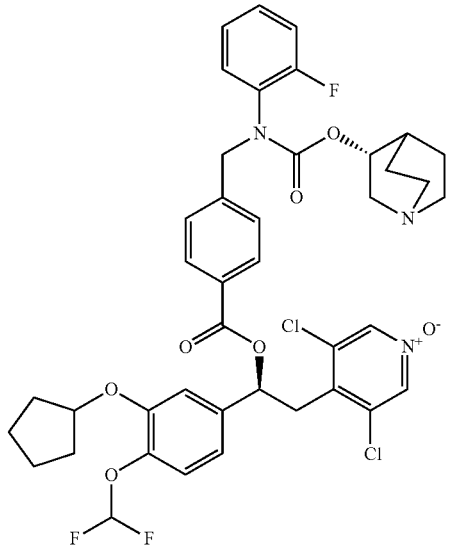 | Example 58 | Intermediate 23 | $^1$H NMR (400 MHz, CDCl3): δ 8.13 (s, 2 H), 7.95 (d, J = 7.8 Hz, 2 H), 7.34 (d, J = 8.0 Hz, 2 H), 7.25-7.20 (m, 1 H), 7.15 (d, J = 8.0 Hz, 1 H), 7.13-7.03 (m, 3 H), 7.04-6.95 (m, 2 H), 6.51 (t, J = 75.4 Hz, 1 H), 6.27 (dd, J = 9.6, 4.5 Hz, 1 H), 4.89-4.77 (m, 4 H), 3.67 (dd, J = 14.0, 9.7 Hz, 1 H), 3.33 (dd, J = 14.0, 4.6 Hz, 1 H), 3.25 (dd, J = 14.7, 8.3 Hz, 1 H), 2.82-2.73 (m, 3 H), 2.70 (d, J = 16.5 Hz, 1 H), 2.66-2.57 (m, 1 H), 2.05-1.97 (m, 1H), 1.92-1.88 (m, 2 H), 1.89-1.74 (m, 4 H), 1.73-1.51 (m, 4 H), 1.43-1.32 (m, 1 H), 1.32-1.22 (m, 1 H). LCMS (Method 1): [MH+] = 814 at 3.14 min. |
| [(1S)-2-(3,5-dichloro-1-oxido-pyridin-1-ium-4-yl)-1-(3,4-dimethoxyphenyl)ethyl] 3-[[3-[(N-[(3R)-quinuclidin-3-yl]oxycarbonylanilino)methyl]phenoxylmethyl]benzoate 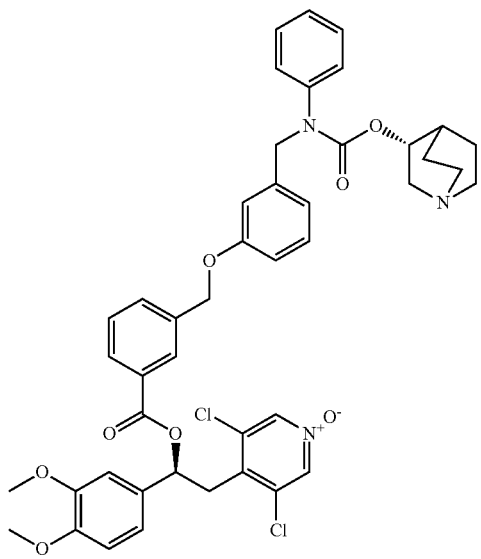 | Example 59 | Intermediate 63 | $^1$H NMR (400 MHz, CDCl3): δ 8.11 (s, 2 H), 8.08 (s, 1 H), 7.98 (d, J = 7.8 Hz, 1 H), 7.61 (d, J = 7.7 Hz, 1 H), 7.45 (t, J = 7.7 Hz, 1 H), 7.32-7.24 (m, 2 H), 7.24-7.10 (m, 4 H), 7.04-6.97 (m, 2 H), 6.90-6.83 (m, 4 H), 6.30 (dd, J = 9.7, 4.6 Hz, 1 H), 5.05 (s, 2 H), 4.86-4.82 (m, 2 H), 4.81-4.75 (m, 1 H), 3.89 (s, 3 H), 3.88 (s, 3 H), 3.71 (dd, J = 14.0, 9.7 Hz, 1 H), 3.35 (dd, J = 14.0, 4.6 Hz, 1 H), 3.21-3.14 (m, 1 H), 2.76-2.66 (m, 3 H), 2.65-2.51 (m, 2 H), 1.94 (br s, 1 H), 1.66-1.55 (m, 1 H), 1.55-1.45 (m, 1 H), 1.45-1.33 (m, 1 H), 1.27-1.15 (m, 1 H). LCMS (Method 1): [MH+] = 812 at 2.99 min. |

-continued

| Structure | Example number | Precursors | Analytical Data |
|---|---|---|---|
| [(1S)-2-(3,5-dichloro-1-oxido-pyridin-1-ium-4-yl)-1-(3,4-dimethoxyphenyl)ethyl] 4-[[3-[(N-[(3R)-quinuclidin-3-yl]oxycarbonylanilino)methyl]phenoxy]methyl]benzoate 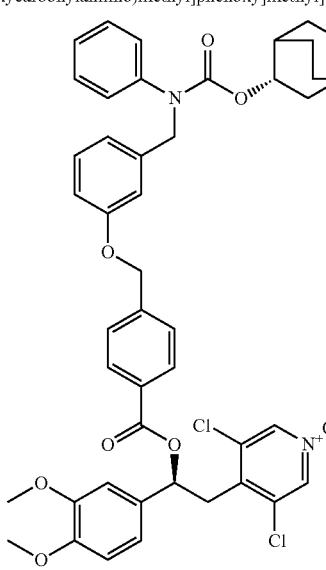 | Example 60 | Intermediate 62 | $^1$H NMR (400 MHz, CDCl3): δ 8.13 (s, 2 H), 8.03 (d, J = 8.2 Hz, 2 H), 7.47 (d, J = 8.1 Hz, 2 H), 7.31-7.25 (m, 2 H), 7.25-7.09 (m, 4 H), 7.04-6.98 (m, 2 H), 6.89-6.82 (m, 4 H), 6.31 (dd, J = 9.6, 4.6 Hz, 1 H), 5.07 (s, 2 H), 4.86-4.82 (m, 2 H), 4.80-4.75 (m, 1 H), 3.90 (s, 3 H), 3.88 (s, 3 H), 3.71 (dd, J = 14.0, 9.7 Hz, 1 H), 3.36 (dd, J = 13.9, 4.6 Hz, 1 H), 3.18 (ddd, J = 14.8, 8.2, 2.2 Hz, 1 H), 2.76-2.66 (m, 3 H), 2.65-2.50 (m, 2 H), 1.93 (br s, 1 H), 1.66-1.55 (m, 1H), 1.55-1.45 (m, 1 H), 1.45-1.34 (m, 1 H), 1.27-1.15 (m, 1 H). LCMS (Method 1): [MH+] = 812 at 2.98 min. |
| [(1S)-2-(3,5-dichloro-1-oxido-pyridin-1-ium-4-yl)-1-(3,4-dimethoxyphenyl)ethyl] 3-[[4-[(N-[(3R)-quinuclidin-3-yl]oxycarbonylanilino)methyl]phenoxy]methyl]benzoate 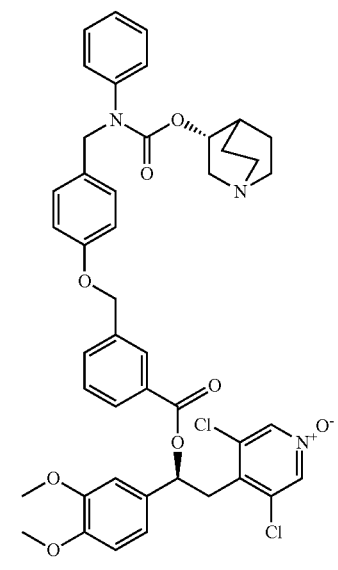 | Example 61 | Intermediate 61 | $^1$H NMR (400 MHz, CDCl3): δ 8.13-8.08 (m, 3 H), 7.98 (d, J = 7.8 Hz, 1 H), 7.63 (d, J = 7.7 Hz, 1 H), 7.46 (t, J = 7.7 Hz, 1 H), 7.34-7.20 (m, 3 H), 7.15 (d, J = 8.3 Hz, 2 H), 7.13-6.97 (m, 4 H), 6.92-6.84 (m, 3 H), 6.30 (dd, J = 9.7, 4.5 Hz, 1 H), 5.07 (s, 2 H), 4.96-4.90 (m, 1 H), 4.82-4.75 (m, 2 H), 3.90 (s, 3 H), 3.88 (s, 3 H), 3.72 (dd, J = 13.9, 9.8 Hz, 1 H), 3.39-3.28 (m, 2 H), 2.96-2.86 (m, 3 H), 2.86-2.78 (m, 1 H), 2.74-2.62 (m, 1 H), 2.14 (br s, 1 H), 1.83-1.73 (m, 1 H), 1.72-1.61 (m, 1 H), 1.60-1.46 (m, 1 H), 1.45-1.35 (m, 1 H). LCMS (Method 1): [MH+] = 812 at 3.01 min. |

-continued

| Structure | Example number | Precursors | Analytical Data |
|---|---|---|---|
| [(1S)-2-(3,5-dichloro-1-oxido-pyridin-1-ium-4-yl)-1-(3,4-dimethoxyphenyl)ethyl] 4-[[4-[(N-[(3R)-quinuclidin-3-yl]oxycarbonylanilino)methyl]phenoxy]methyl]benzoate formate salt 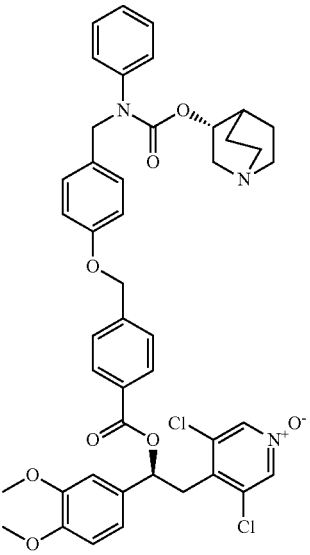 | Example 62 | Intermediate 60 | ¹H NMR (400 MHz, CDCl3): δ 8.49 (s, 1 H), 8.13 (s, 2 H), 8.04 (d, J = 8.1 Hz, 2 H), 7.49 (d, J = 8.1 Hz, 2 H), 7.34-7.28 (m, 2 H), 7.22 (t, J = 7.3 Hz, 1 H), 7.15 (d, J = 8.3 Hz, 2 H), 7.12-6.97 (m, 4 H), 6.91-6.84 (m, 3 H), 6.30 (dd, J = 9.7, 4.5 Hz, 1 H), 5.10 (s, 2 H), 4.91-4.85 (m, 1 H), 4.78 (s, 2 H), 3.91 (s, 3 H), 3.88 (s, 3 H), 3.72 (dd, J = 14.0, 9.8 Hz, 1 H), 3.35 (dd, J = 14.0, 4.6 Hz, 1 H), 3.32-3.24 (m, 1 H), 2.91-2.81 (m, 3 H), 2.76 (d, J = 14.9 Hz, 1 H), 2.70-2.59 (m, 1 H), 2.08 (br s, 1 H), 1.79-1.69 (m, 1 H), 1.67-1.57 (m, 1 H), 1.55-1.41 (m, 1 H), 1.41-1.30 (m, 1 H). LCMS (Method 1): [MH+] = 812 at 2.97 min. |
| [(1S)-1-[3-(cyclopropylmethoxy)-4-(difluoromethoxy)phenyl]-2-(3,5-dichloro-1-oxido-pyridin-1-ium-4-yl)ethyl] 4-[(2-fluoro-N-[(3R)-quinuclidin-3-yl]oxycarbonyl-anilino)methyl]benzoate formate salt 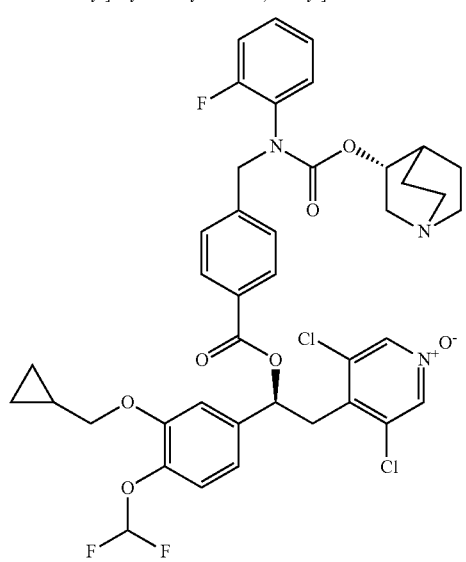 | Example 63 | Intermediate 23 | ¹H NMR (400 MHz, CDCl3): δ 8.37 (s, 1 H), 8.14 (s, 2 H), 7.94 (d, J = 7.9 Hz, 2 H), 7.36-7.23 (m, 3 H), 7.17 (d, J = 8.1 Hz, 1 H), 7.13-6.99 (m, 5 H), 6.61 (t, J = 75.3 Hz, 1 H), 6.26 (dd, J = 9.8, 4.3 Hz, 1 H), 5.04-4.97 (m, 1 H), 4.92-4.77 (m, 2 H), 3.88 (d, J = 6.9 Hz, 2 H), 3.68 (dd, J = 14.0, 9.9 Hz, 1 H), 3.47-3.37 (m, 1 H), 3.31 (dd, J = 14.0, 4.4 Hz, 1 H), 3.10-2.70 (m, 5 H), 2.28-2.20 (m, 1 H), 1.91-1.81 (m, 1 H), 1.80-1.69 (m, 1 H), 1.62-1.44 (m, 2 H), 1.33-1.21 (m, 1 H), 0.68-0.61 (m, 2 H), 0.40-0.33 (m, 2 H). LCMS (Method 1): [MH+] = 800 at 3.10 min. |

| Structure | Example number | Precursors | Analytical Data |
|---|---|---|---|
| [(1S)-2-(3,5-dichloro-1-oxido-pyridin-1-ium-4-yl)-1-[4-(difluoromethoxy)-3-isopropoxy-phenyl]ethyl] 4-[[2-pyridyl-[(3R)-quinuclidin-3-yl]oxycarbonyl-amino]methyl]benzoate 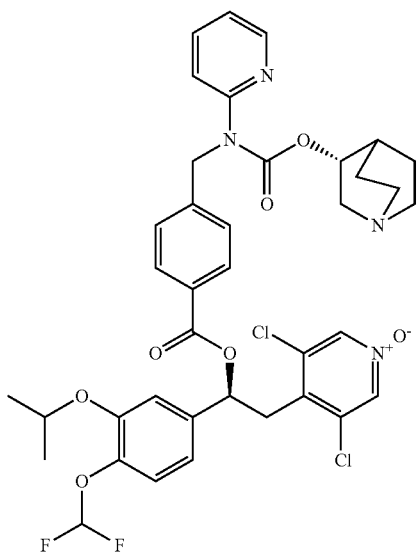 | Example 64 | Intermediate 90 | $^1$H NMR (400 MHz, CDCl3): δ 8.40-8.36 (m, 1 H), 8.17-8.12 (m, 2 H), 7.95 (d, J = 8.1 Hz, 2 H), 7.77-7.65 (m, 2 H), 7.37 (d, J = 8.0 Hz, 2 H), 7.16 (d, J = 8.0 Hz, 1 H), 7.10-7.00 (m, 3 H), 6.55 (t, J = 75.3 Hz, 1 H), 6.26 (dd, J = 9.9, 4.3 Hz, 1 H), 5.29 (dd, J = 12.5, 1.0 Hz, 2 H), 4.87-4.82 (m, 1 H), 4.60-4.53 (m, 1 H), 3.66 (dd, J = 14.0, 9.9 Hz, 1 H), 3.34-3.19 (m, 2 H), 2.82-2.71 (m, 3 H), 2.68-2.60 (m, 2 H), 2.53-2.41 (m, 1 H), 2.01 (s, 1 H), 1.76-1.49 (m, 2 H), 1.41-1.25 (m, 7 H). LCMS (Method 1): [MH+] = 771 at 2.97 min. |
| [(1S)-2-(3,5-dichloro-1-oxido-pyridin-1-ium-4-yl)-1-[4-(difluoromethoxy)-3-(trideuteriomethoxy)phenyl]ethyl] 4-[(2-fluoro-N-[(3R)-quinuclidin-3-yl]oxycarbonyl-anilino)methyl]benzoate 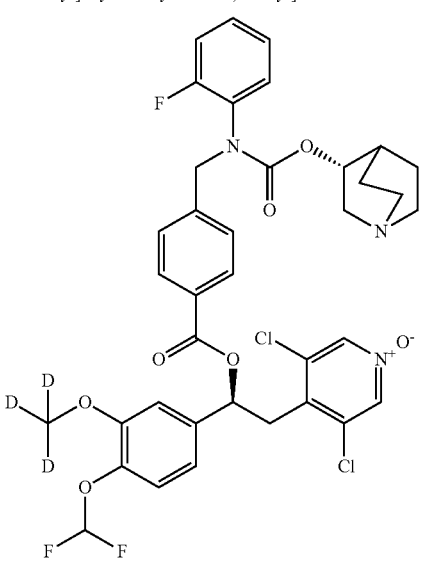 | Example 65 | Intermediate 23 | $^1$H NMR (400 MHz, CDCl3): δ 8.20 (s, 2 H), 7.95-7.93 (m, 2 H), 7.35-7.33 (m, 2 H), 7.25-6.99 (m, 7 H), 6.53 (t, J = 74.8 Hz, 1 H), 6.29 (dd, J = 4.4, 10.0 Hz, 1 H), 4.86-4.82 (m, 2 H), 4.79-4.78 (m, 1 H), 3.67 (dd, J = 10.0, 14.0 Hz, 1 H), 3.32 (dd, J = 4.4, 14.0 Hz, 1 H), 3.22-3.17 (m, 1 H), 2.78-2.56 (m, 4 H), 1.93-1.89 (m, 1 H), 1.53-1.44 (m, 3 H), 1.35-1.13 (m, 2 H). LCMS (Method 2): [MH+] = 763 at 3.44 min. |

| Structure | Example number | Precursors | Analytical Data |
|---|---|---|---|
| [(1S)-2-(3,5-dichloro-1-oxido-pyridin-1-ium-4-yl)-1-[4-(difluoromethoxy)-3-methoxy-phenyl]ethyl] 4-[(2-fluoro-N-[(3R)-quinuclidin-3-yl]oxycarbonyl-anilino)methyl]benzoate 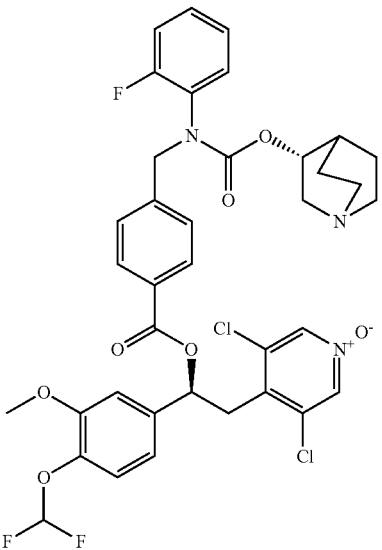 | Example 66 | Intermediate 23 | ¹H NMR (400 MHz, CDCl3): δ 8.16 (s, 2 H), 7.95-7.93 (m, 2 H), 7.33-7.31 (m, 2 H), 7.25-6.95 (m, 7 H), 6.53 (t, J = 74.8 Hz, 1 H), 6.28 (dd, J = 4.4, 10.0 Hz, 1 H), 4.86-4.76 (m, 3 H), 3.89 (s, 3 H), 3.37-3.65 (m, 1 H), 3.32 (dd, J = 4.4, 14.0 Hz, 1 H), 3.25-3.15 (m, 1 H), 2.75-2.50 (m, 4 H), 1.92-1.89 (m, 1 H), 1.51-1.45 (m, 3 H), 1.37-1.07 (m, 2 H). LCMS (Method 2): [MH+] = 760 at 3.44 min. |
| [(1S)-2-(3,5-dichloro-1-oxido-pyridin-1-ium-4-yl)-1-[4-(difluoromethoxy)-3-ethoxy-phenyl]ethyl] 4-[(2-fluoro-N-[(3R)-quinuclidin-3-yl]oxycarbonyl-anilino)methyl]benzoate 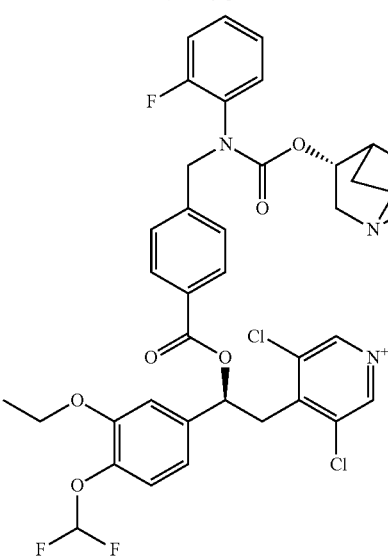 | Example 67 | Intermediate 23 | 1H N MR (400 MHz, CD3CN): δ 8.20 (s, 2 H), 7.99 (d, J = 7.9 Hz, 2 H), 7.49-7.25 (m, 4 H), 7.23-7.12 (m, 4 H), 7.11-7.04 (m, 1 H), 6.75 (t, J = 75.3 Hz, 1 H), 6.23-6.21 (m, 1 H), 5.10-4.81 (m, 3 H), 4.20-4.06 (m, 2 H), 3.75-3.53 (m, 2 H), 3.45-3.33 (m, 1 H), 3.27-3.03 (m, 4 H), 2.98-2.83 (m, 1 H), 2.24-2.13 (m, 1 H), 1.95-1.79 (m, 2 H), 1.72-1.47 (m, 2 H), 1.39 (t, J = 6.9 Hz, 3 H). LCMS (Method 1): [MH+] = 774 at 2.99 min. |

-continued

| Structure | Example number | Precursors | Analytical Data |
|---|---|---|---|
| [(1S)-2-(3,5-dichloro-1-oxido-pyridin-1-ium-4-yl)-1-[4-(difluoromethoxy)-3-isopropoxy-phenyl]ethyl] 4-[(2-fluoro-N-[(3R)-quinuclidin-3-yl]oxycarbonyl-anilino)methyl]benzoate formate salt 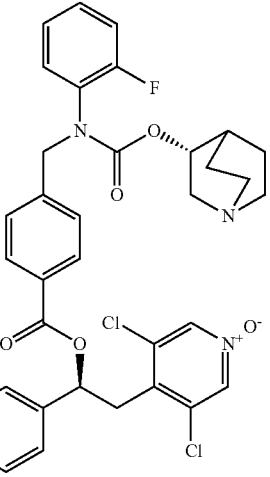 | Example 68 | Intermediate 23 | NMR (400 MHz, DMSO): δ 8.54 (s, 2 H), 8.29 (s, 1 H), 7.95 (d, J = 7.8 Hz, 2 H), 7.46-7.12 (m, 8 H), 7.07 (dd, J = 8.3, 1.9 Hz, 1 H), 7.02 (t, J = 74.6 Hz, 1 H), 6.19 (dd, J = 9.0, 4.7 Hz, 1 H), 4.90 (s, 2 H), 4.72-4.63 (m, 2 H), 3.60 (dd, J = 14.4, 9.1 Hz, 1 H), 3.35 (dd, J = 14.1, 4.8 Hz, 1 H), 3.07 (ddd, J = 14.7, 8.0, 2.2 Hz, 1 H), 2.65-2.34 (m, 5 H), 1.85-1.75 (m, 1 H), 1.61-1.49 (m, 1 H), 1.49-1.37 (m, 1 H), 1.29 (d, J = 6.0 Hz, 3 H), 1.22 (d, J = 6.0 Hz, 3 H), 1.19-1.09 (m, 2 H). LCMS (Method 1): [MH+] = 788 at 3.07 min. |
| [(1S)-2-(3,5-dichloro-1-oxido-pyridin-1-ium-4-yl)-1-(3,4-dimethoxyphenyl)ethyl] 2-fluoro-5-[(2-fluoro-N-[(3R)-quinuclidin-3-yl]oxycarbonyl-anilino)methyl]benzoate formate salt 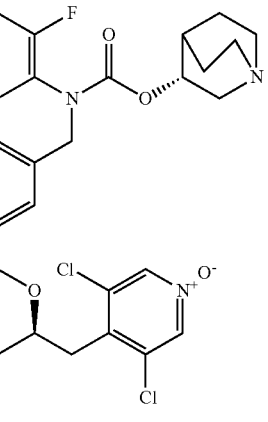 | Example 69 | Intermediate 74 | NMR (400 MHz, CDCl3): δ 8.28 (s, 1 H), 8.14 (s, 2 H), 7.73 (d, J = 6.6 Hz, 1 H), 7.46-7.39 (m, 1 H), 7.33-7.24 (m, 2 H), 7.15-6.99 (m, 4 H), 6.95 (dd, J = 8.2, 2.0 Hz, 1 H), 6.84 (d, J = 8.3 Hz, 1 H), 6.29 (dd, J = 9.2, 4.9 Hz, 1 H), 5.06-4.99 (m, 1 H), 4.78 (dd, J = 29.8, 15.0 Hz, 2 H), 3.91 (s, 3 H), 3.88 (s, 3 H), 3.66 (dd, J = 14.0, 9.2 Hz, 1 H), 3.50-3.39 (m, 1 H), 3.34 (dd, J = 14.1, 5.2 Hz, 1 H), 3.14-2.99 (m, 3 H), 2.92 (d, J = 14.3 Hz, 1 H), 2.83-2.72 (m, 1 H), 2.30-2.22 (m, 1 H), 1.94-1.84 (m, 1 H), 1.84-1.73 (m, 1 H), 1.64-1.48 (m, 2 H). LCMS (Method 2): [MH+] = 742 at 3.24 min. |

-continued

| Structure | Example number | Precursors | Analytical Data |
|---|---|---|---|
| [(1S)-2-(3,5-dichloro-1-oxido-pyridin-1-ium-4-yl)-1-(3,4-dimethoxyphenyl)ethyl] 4-[2-(2-fluoro-N-[(3R)-quinuclidin-3-yl]oxycarbonyl-anilino)ethyl]benzoate | Example 70 | Intermediate 92 | $^1$H NMR (400 MHz, CDCl3): δ 8.13 (s, 2 H), 7.92 (d, J = 7.9 Hz, 2 H), 7.38-7.16 (m, 3 H), 7.17-7.08 (m, 3 H), 7.03-6.97 (m, 2 H), 6.85 (d, J = 8.2 Hz, 1 H), 6.29 (dd, J = 9.6, 4.6 Hz, 1 H), 4.69 (s, 1 H), 3.92-3.79 (m, 7 H), 3.70 (dd, J = 14.0, 9.7 Hz, 1 H), 3.34 (dd, J = 14.0, 4.6 Hz, 1 H), 3.24-3.22 (m, 1 H), 2.96 (t, J = 7.8 Hz, 2 H), 2.73-2.65 (m, 6 H), 2.05-1.98 (m, 1 H), 1.78-1.52 (m, 2 H), 1.49-1.18 (m, 2 H). LCMS (Method 1): [MH+] = 738 at 2.81 min. |
| [2-(3,5-dichloro-4-pyridyl)-1-(3,4-dimethoxyphenyl)ethyl] 4-[(2-fluoro-N-[(3R)-quinuclidin-3-yl]oxycarbonyl-anilino)methyl]benzoate formate salt | Example 71 | Intermediate 23 | $^1$H NMR (400 MHz, CDCl$_3$): δ 8.43 (s, 2 H), 8.39 (s, 1 H), 7.96 (d, J = 7.9 Hz, 2 H), 7.32-7.23 (m, 2 H), 7.13-6.98 (m, 5 H), 6.97 (d, J = 2.0 Hz, 1 H), 6.85 (dd, J = 8.3, 2.2 Hz, 1 H), 6.36-6.30 (m, 1 H), 5.01-4.95 (m, 1 H), 4.92-4.75 (m, 2 H), 3.89 (s, 3 H), 3.87 (s, 3 H), 3.79 (ddd, J = 13.6, 9.8, 1.8 Hz, 1 H), 3.44-3.34 (m, 2 H), 3.07-2.91 (m, 3 H), 2.87 (d, J = 14.8 Hz, 1 H), 2.80-2.69 (m, 1 H), 2.26-2.16 (m, 1 H), 1.90-1.79 (m, 1 H), 1.78-1.66 (m, 1 H), 1.64-1.42 (m, 2 H). LCMS (Method 1): [MH+] = 708 at 3.01 min. |
| [2-(3,5-dichloro-4-pyridyl)-1-(3,4-dimethoxyphenyl)ethyl] 3-[(2-fluoro-N-[(3R)-quinuclidin-3-yl]oxycarbonyl-anilino)methyl]benzoate formate salt | Example 72 | Intermediate 28 | $^1$H NMR (400MHz, CDCl$_3$): δ 8.41 (s, 2 H), 8.39 (s, 1 H), 7.94 (d, J = 7.8 Hz, 1 H), 7.87 (s, 1 H), 7.47 (d, J = 7.7 Hz, 1 H), 7.37 (t, J = 7.5 Hz, 1 H), 7.13-6.92 (m, 6 H), 6.85 (d, J = 8.2 Hz, 1 H), 6.30 (dd, J = 9.7, 4.2 Hz, 1 H), 5.02-4.92 (m, 1 H), 4.84 (s, 2 H), 3.89 (s, 3 H), 3.88 (s, 3 H), 3.77 (ddd, J = 13.6, 10.0, 2.4 Hz, 1 H), 3.43-3.33 (m, 2 H), 3.04-2.90 (m, 3 H), 2.85 (d, J = 16.6 Hz, 1 H), 2.79-2.54 (m, 1 H), 2.24-2.17 (m, 1 H), 1.89-1.77 (m, 1 H), 1.77-1.64 (m, 1 H), 1.60-1.40 (m, 2 H). LCMS (Method 1): [MH+] = 708 at 2.98 min. |

Example 73

[(1S)-2-(3,5-dichloro-1-oxido-pyridin-1-ium-4-yl)-1-(3,4-dimethoxyphenyl)ethyl]3-[(2-fluoro-N-[(3R)-quinuclidin-3-yl]oxycarbonyl-anilino)methyl]-5-methyl-benzoate formate Salt

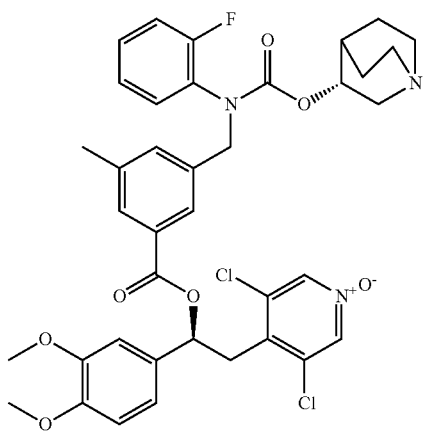

A mixture of [(1S)-2-(3,5-dichloro-1-oxido-pyridin-1-ium-4-yl)-1-(3,4-dimethoxyphenyl)ethyl]3-bromo-5-[(2-fluoro-N-[(3R)-quinuclidin-3-yl]oxycarbonyl-anilino)methyl]benzoate formate salt (98 mg, 0.20 mmol), methylboroxine (0.03 mL, 0.20 mmol) and Pd(PPh$_3$)$_4$ (23 mg, 0.02 mmol) in 10% dioxane in water (2.5 mL) was heated to 160° C. under microwave irradiation for 5 minutes. After cooling to room temperature, the reaction mixture was neutralized with 0.30 mL of 2 N HCl and filtered through celite, washed with EtOAc (50 mL) The solvent was removed in vacuo and the residue was azeotroped with toluene to yield a white foam that was redissolved in DMF (2 mL). (S)-3,5-dichloro-4-(2-(3,4-dimethoxyphenyl)-2-hydroxyethyl)pyridine 1-oxide (76 mg, 0.22 mmol) followed by 4-(dimethylamino)-pyridine (12 mg, 0.10 mmol) and N-(3-dimethylaminopropyl)-N'-ethylcarbodiimide hydrochloride (77 mg, 0.40 mmol) were then added, and the resulting mixture was stirred at room temperature for 18 hours. The reaction mixture was partitioned between ethyl acetate and saturated aqueous sodium bicarbonate solution. The organic layer was washed with brine, dried over Na$_2$SO$_4$, filtered and the solvent was removed in vacuo. The residue was purified by preparative HPLC to provide [(1S)-2-(3,5-dichloro-1-oxido-pyridin-1-ium-4-yl)-1-(3,4-dimethoxyphenyl)ethyl]3-[(2-fluoro-N-[(3R)-quinuclidin-3-yl]oxycarbonyl-anilino)methyl]-5-methyl-benzoate (19 mg) as white solid.

$^1$H NMR (400 MHz, CDCl$_3$): δ 8.42 (s, 1H), 8.11 (s, 2H), 7.71 (d, J=9.9 Hz, 2H), 7.32-7.20 (m, 3H), 7.13-7.03 (m, 2H), 7.01-6.95 (m, 2H), 6.85 (d, J=8.2 Hz, 1H), 6.24 (dd, J=9.6, 4.4 Hz, 1H), 4.92-4.86 (m, 1H), 4.81 (s, 2H), 3.90 (s, 3H), 3.88 (s, 3H), 3.68 (dd, J=13.9, 9.8 Hz, 1H), 3.33 (dd, J=13.4, 4.3 Hz, 1H), 3.28 (dt, J=8.5, 3.3 Hz, 1H), 2.88-2.80 (m, 3H), 2.75 (d, J=15.2 Hz, 1H), 2.70-2.63 (m, 1H), 2.35 (s, 3H), 2.08 (s, 1H), 1.80-1.68 (m, 1H), 1.68-1.56 (m, 1H), 1.49-1.38 (m, 1H), 1.38-1.28 (m, 1H). LCMS (Method 1): [MH+]=738 at 2.8 min.

Example 74

[(1S)-1-[3-(cyclopropylmethoxy)-4-(difluoromethoxy)phenyl]-2-(3,5-dichloro-1-oxido-pyridin-1-ium-4-yl)ethyl]2-[3-[(N-[(3R)-quinuclidin-3-yl]oxycarbonylanilino)methyl]phenyl]acetate formate salt Step1: Preparation of ethyl 2-[3-(bromomethyl)phenyl]acetate (E/74a)

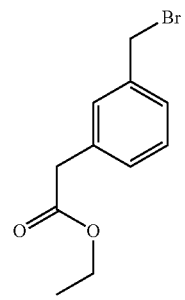

Acetonitrile (30 mL) was degased with nitrogen for 5 minutes, and then ethyl-m-tolylacetate (2 mL, 2 mmol), NBS (1.9 g, 10.7 mmol) and benzoyl peroxide (266 mg, 1.1 mmol) were added. The resulting mixture was heated to 70° C. for 18 hours. After cooling to room temperature, the solvent was removed in vacuo and the residue was partitioned between dichloromethane and saturated aqueous sodium bicarbonate solution. The organic layer was washed with brine, passed through a hydrophobic frit, and the solvent was removed in vacuo. The residue was purified by silica gel chromatography, eluting with 0-50% DCM in isohexane, to provide ethyl 2-[3-(bromomethyl)phenyl]-acetate (2.23 g, 77%).

$^1$H NMR (400 MHz, CDCl$_3$): δ 7.32-7.22 (m, 4H), 4.47 (s, 2H), 4.18-4.09 (m, 2H), 3.63 (s, 2H), 1.58-1.23 (m, 3H).

Step2: Preparation of ethyl 2-[3-[(N-[(3R)-quinuclidin-3-yl]oxycarbonyl-anilino)methyl]phenyl]acetate (E/74b)

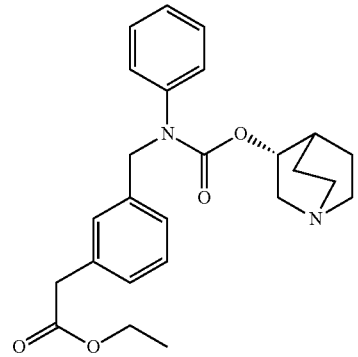 [SMILES: CCOC(=O)Cc1cccc(CN(C(=O)O[C@H]2CN3CCC2CC3)c2ccccc2)c1]

A mixture of ethyl 2-[3-(bromomethyl)phenyl]acetate (600 mg, 2.33 mmol), aniline (202 mg, 2.21 mmol) and potassium carbonate (420 mg, 3.04 mmol) in 1V, N-dimethylformamide (15 mL) was heated to 90° C. for 18 hours. After cooling to room temperature, the reaction was filtered and the solvent was removed in vacuo. The residue was taken up in ethyl acetate and washed with brine (3×20 mL). The organic phase was passed through a hydrophobic fit and the solvent was removed in vacuo. The crude material was dissolved in acetonitrile (5 mL), and (R)-quinuclidin-3-yl carbonochloridate hydrochloride (530 mg, 2.35 mmol) was added. The resulting mixture was heated to 100° C. for 30 minutes under microwave irradiation. The solvent was removed in vacuo, then the residue was partitioned between ethyl acetate and saturated aqueous sodium bicarbonate solution. The organic layer was washed with brine, passed through a hydrophobic fit and the solvent was removed in vacuo. The residue was purified by silica gel column chromatography eluting sequentially with ethyl acetate, 10% methanol in ethyl acetate and 10% 7N methanolic ammonia in ethyl acetate to afford the title compound as a yellow solid (331 mg, 35%).

$^1$H NMR (400 MHz, CDCl$_3$): δ 7.31-7.23 (m, 4H), 7.21-7.14 (m, 5H), 4.85 (s, 2H), 4.81-4.77 (m, 1H), 4.15-4.09 (m, 2H), 3.56 (s, 2H), 3.22-3.16 (m, 1H), 2.74-2.68 (m, 5H), 2.04-1.95 (m, 1H), 1.63-1.62 (m, 1H), 1.61-1.60 (m, 1H), 1.53-1.50 (m, 1H), 1.27-1.20 (m, 4H).

Step3: Preparation of [(1S)-1-[3-(cyclopropylmethoxy)-4-(difluoromethoxy)phenyl]-2-(3,5-dichloro-1-oxido-pyridin-1-ium-4-yl)ethyl]2-[3-[(N-[(3R)-quinuclidin-3-yl]oxycarbonylanilino)methyl]phenyl]acetate formate salt (Example 74)

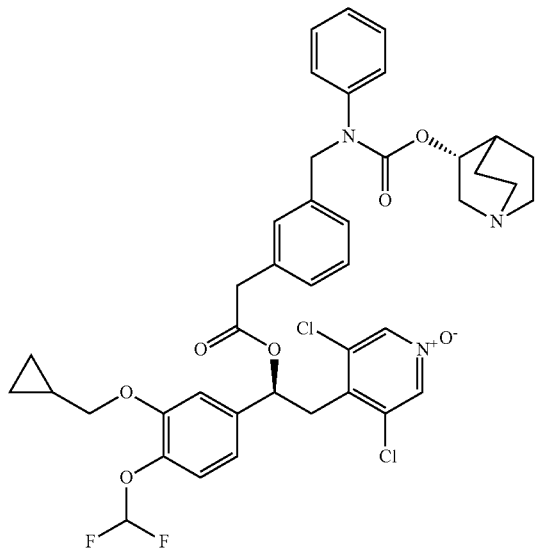

To a solution of ethyl 2-[3-[(N-[(3R)-quinuclidin-3-yl]oxycarbonylanilino)methyl]-phenyl]acetate (150 mg, 0.35 mmol) in THF (2.5 mL) and methanol (2.5 mL) was added 1M lithium hydroxide aqueous solution (0.8 mL) The mixture was stirred at room temperature for 18 hours then acidified with concentrated HCl until pH=2. The solvent was removed in vacuo and the residue was azeotroped with toluene and acetonitrile successively and then dried in a vacuum oven. The carboxylic acid previously obtained was then dissolved in N,N-dimethylformamide (3 mL) and (1S)-1-[3-(cyclopropylmethoxy)-4-(difluoromethoxy)phenyl]-2-(3,5-dichloro-1-oxido-pyridin-1-ium-4-yl)ethanol (148 mg, 0.35 mmol) followed by 4-(dimethylamino)-pyridine (21 mg, 0.175 mmol) and N-(3-dimethylaminopropyl)-N'-ethylcarbodiimide hydrochloride (136 mg, 0.70 mmol). The resulting mixture was stirred at room temperature for 18 hours. The solvent was removed in vacuo then the residue was partitioned between ethyl acetate and saturated aqueous sodium bicarbonate solution. The organic layer was washed with brine, passed through a hydrophobic fit and the solvent was removed in vacuo. The residue was dissolved in DMSO (1.5 mL) and purified by preparative HPLC to provide [(1S)-1-[3-(cyclopropylmethoxy)-4-(difluoromethoxy)phenyl]-2-(3,5-dichloro-1-oxido-pyridin-1-ium-4-yl)ethyl]2-[3-[(N-[(3R)-quinuclidin-3-yl]oxycarbonylanilino)methyl]-phenyl]acetate formic acid (10 mg) as white solid.

$^1$H NMR (400 MHz, CDCl$_3$): δ 8.38 (s, 1H), 8.04 (s, 2H), 7.31-7.21 (m, 5H), 7.15-7.05 (m, 5H), 6.89-6.86 (m, 2H), 6.61 (t, J=75.6 Hz, 1H), 6.02 (dd, J=4.4, 10.0 Hz, 1H), 5.00-4.98 (m, 1H), 4.85-4.80 (m, 2H), 3.82-3.74 (m, 2H), 3.59-3.50 (m, 2H), 3.48-3.38 (m, 2H), 3.15 (dd, J=4.4, 14.0 Hz, 1H), 3.08-2.93 (m, 4H), 2.71 (dd, J=10.0, 14.0 Hz, 1H), 2.23-2.21 (m, 1H), 1.90-1.83 (m, 1H), 1.82-1.73 (m, 1H), 1.58-1.46 (m, 2H), 1.28-1.21 (m, 1H), 0.68-0.63 (m, 2H), 0.37-0.33 (m, 2H). LCMS (Method 1): [MH+]=796 at 3.07 min.

Example 75

[(1S)-2-(3,5-dichloro-1-oxido-pyridin-1-ium-4-yl)-1-(3,4-dimethoxyphenyl)ethyl]2-[3-[(2-fluoro-N-[(3R)-quinuclidin-3-yl]oxycarbonyl-anilino)methyl]phenyl]acetate

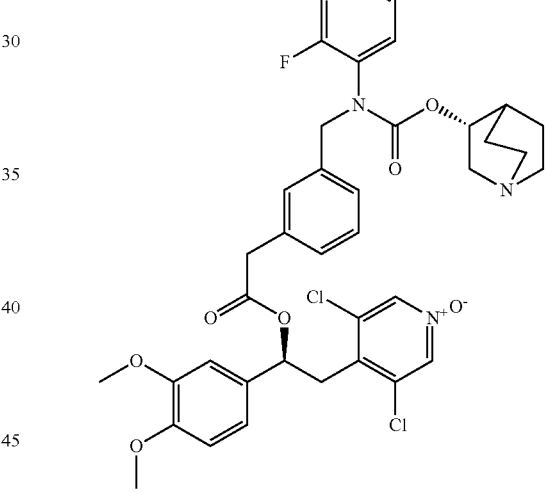

The compound was prepared similarly to Example 74, using as intermediates ethyl 2-[3-[(2-fluoro N-[(3R)-quinuclidin-3-yl]oxycarbonylanilino)methyl]phenyl]acetate and (S)-3,5-dichloro-4-(2-(3,4-dimethoxyphenyl)-2-hydroxyethyl)pyridine 1-oxide (S)-3,5-dichloro-4-(2-(3,4-dimethoxyphenyl)-2-hydroxyethyl)pyridine 1-oxide.

$^1$H NMR (400 MHz, CDCl$_3$): δ 8.03 (s, 2H), 7.25-6.99 (m, 8H), 6.83-6.78 (m, 3H), 6.03 (dd, J=9.6, 4.8 Hz, 1H), 4.82-4.79 (m, 3H), 3.86 (s, 3H), 3.80 (s, 3H), 3.57-3.49 (m, 2H), 3.48-3.44 (m, 1H), 3.20-3.16 (m, 2H), 2.72-2.61 (m, 5H), 1.98-1.86 (m, 1H), 1.68-1.53 (m, 1H), 1.57-1.44 (m, 1H), 1.37-1.22 (m, 1H), 1.21-1.13 (m, 1H). LCMS (Method 1): [MH+]=738 at 2.74 min.

The following compounds were synthesized in a similar manner by reacting the appropriate racemic alcoholic intermediate (intermediates 32/D, 32/E, and 32/F) with the suitable acid obtained in situ from the corresponding methyl ester (intermediates 23, 28, 90, and 1). The compounds were purified by HPLC and the single diastereoisomers were obtained by SFC purification.

| Structure | Example number | Precursors | Analytical Data |
|---|---|---|---|
| [(1R)-1-[3-(cyclopropylmethoxy)-4-methoxy-phenyl]-2-(3,5-dichloro-1-oxido-pyridin-1-ium-4-yl)ethyl] 4-[(2-fluoro-N-[(3R)-quinuclidin-3-yl]oxycarbonyl-anilino)methyl]benzoate 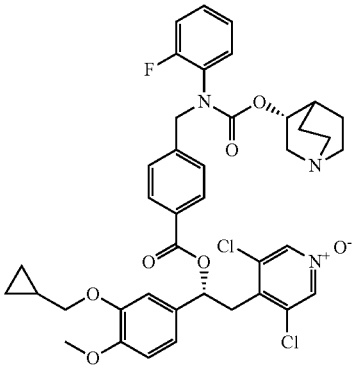 | Example 76 | Intermediate 23 and Intermediate 32/D | $^1$H NMR (400 MHz, CDCl3): δ 8.11 (s, 2 H), 7.94 (d, J = 7.9 Hz, 2 H), 7.33 (d, J = 8.0 Hz, 2 H), 7.28-7.19 (m, 1 H), 7.13-6.97 (m, 5 H), 6.85 (d, J = 8.2 Hz, 1 H), 6.26 (dd, J = 9.7, 4.6 Hz, 1 H), 4.86 (s, 2 H), 4.82-4.74 (m, 1 H), 3.89-3.84 (m, 5 H), 3.68 (dd, J = 13.9, 9.7 Hz, 1 H), 3.32 (dd, J = 13.9, 4.6 Hz, 1 H), 3.24-3.14 (m, 1 H), 2.79-2.53 (m, 5 H), 1.96-1.88 (m, 1 H), 1.70-1.44 (m, 2 H), 1.37-1.13 (m, 3 H), 0.67-0.60 (m, 2 H), 0.39-0.33 (m, 2 H). LCMS (Method 1): [MH+] = 764 at 2.92 min. |
| [(1S)-1-[3-(cyclopropylmethoxy)-4-methoxy-phenyl]-2-(3,5-dichloro-1-oxido-pyridin-1-ium-4-yl)ethyl] 4-[(2-fluoro-N-[(3R)-quinuclidin-3-yl]oxycarbonyl-anilino)methyl]benzoate 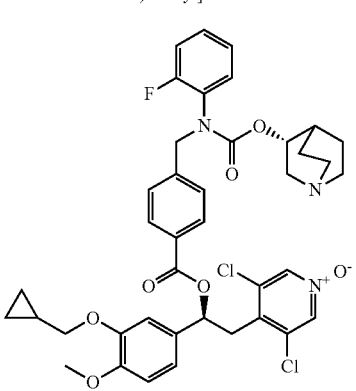 | Example 77 | Intermediate 23 and Intermediate 32/D | $^1$H NMR (400 MHz, CDCl3): δ 8.11 (s, 2 H), 7.94 (d, J = 7.8 Hz, 2 H), 7.32 (d, J = 7.8 Hz, 2 H), 7.29-7.22 (m, 1 H), 7.15-6.97 (m, 5 H), 6.86 (d, J = 8.1 Hz, 1 H), 6.27 (dd, J = 9.5, 4.7 Hz, 1 H), 4.92-4.82 (m, 3 H), 3.91-3.83 (m, 5 H), 3.68 (dd, J = 14.0, 9.6 Hz, 1 H), 3.37-3.23 (m, 2 H), 2.90-2.60 (m, 5 H), 2.11-2.03 (m, 1 H), 1.78-1.67 (m, 1 H), 1.66-1.54 (m, 1 H), 1.48-1.25 (m, 3 H), 0.68-0.60 (m, 2 H), 0.41-0.33 (m, 2 H). LCMS (Method 1): [MH+] = 764 at 2.92 min. |
| [(1R)-1-[3,4-bis(difluoromethoxy)phenyl]-2-(3,5-dichloro-1-oxido-pyridin-1-ium-4-yl)ethyl] 3-[(2-fluoro-N-[(3R)-quinuclidin-3-yl]oxycarbonyl-anilino)methyl]benzoate 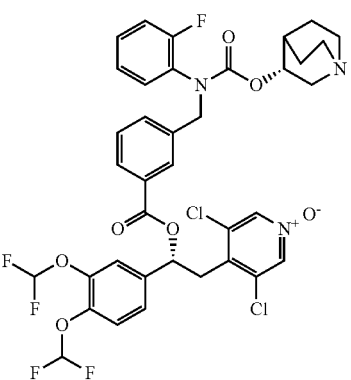 | Example 78 | Intermediate 28 and Intermediate 32/F | $^1$H NMR (400 MHz, CDCl3): δ 8.12 (s, 2 H), 7.95-7.88 (m, 2 H), 7.54-7.49 (m, 1 H), 7.42-7.21 (m, 5 H), 7.14-7.00 (m, 3 H), 6.55 (t, J = 73.4 Hz, 1 H), 6.53 (t, J = 73.2 Hz, 1 H), 6.27 (dd, J = 9.5, 4.6 Hz, 1 H), 4.87 (s, 2 H), 4.82-4.75 (m, 1 H), 3.64 (dd, J = 14.0, 9.6 Hz, 1 H), 3.32 (dd, J = 14.0, 4.7 Hz, 1 H), 3.23-3.14 (m, 1 H), 2.78-2.52 (m, 5 H), 1.98-1.89 (m, 1 H), 1.66-1.56 (m, 1 H), 1.56-1.45 (m, 1 H), 1.37-1.13 (m, 2 H). LCMS (Method 2): [MH+] = 796 at 3.73 min. |

| Structure | Example number | Precursors | Analytical Data |
|---|---|---|---|
| [(1S)-1-[3,4-bis(difluoromethoxy)phenyl]-2-(3,5-dichloro-1-oxido-pyridin-1-ium-4-yl)ethyl] 3-[(2-fluoro-N-[(3R)-quinuclidin-3-yl]oxycarbonyl-anilino)methyl]benzoate | Example 79 | Intermediate 28 and Intermediate 32/F | $^1$H NMR (400 MHz, CDCl3): δ 8.12 (s, 2 H), 7.96-7.88 (m, 2 H), 7.53-7.47 (m, 1 H), 7.41-7.21 (m, 5 H), 7.13-7.00 (m, 3 H), 6.56 (t, J = 73.39 Hz, 1 H), 6.53 (t, J = 73.2 Hz, 1 H), 6.26 (dd, J = 9.6, 4.5 Hz, 1 H), 4.94-4.76 (m, 3 H), 3.65 (dd, J = 14.0, 9.7 Hz, 1 H), 3.32 (dd, J = 14.0, 4.6 Hz, 1 H), 3.25-3.17 (m, 1 H), 2.78-2.54 (m, 5 H), 2.02-1.76 (m, 1 H), 1.69-1.57 (m, 1 H), 1.57-1.46 (m, 1 H), 1.36-1.14 (m, 2 H). LCMS (Method 1): [MH+] = 796 at 2.98 min. |
| [(1R)-1-[3,4-bis(difluoromethoxy)phenyl]-2-(3,5-dichloro-1-oxido-pyridin-1-ium-4-yl)ethyl] 4-[(2-fluoro-N-[(3R)-quinuclidin-3-yl]oxycarbonyl-anilino)methyl]benzoate | Example 80 | Intermediate 23 and Intermediate 32/F | $^1$H NMR (400 MHz, CDCl3): δ 8.13 (s, 2 H), 7.95 (d, J = 7.7 Hz, 2 H), 7.39-7.20 (m, 6 H), 7.13-7.00 (m, 3 H), 6.54 (t, J = 73.3 Hz, 1 H), 6.52 (t, J = 73.2 Hz, 1 H), 6.28 (dd, J = 9.4, 4.7 Hz, 1 H), 4.87 (s, 2 H), 4.82-4.74 (m, 1 H), 3.66 (dd, J = 14.0, 9.5 Hz, 1 H), 3.33 (dd, J = 14.0, 4.8 Hz, 1 H), 3.25-3.15 (m, 1 H), 2.79-2.53 (m, 5 H), 1.96-1.88 (m, 1 H), 1.78-1.44 (m, 2 H), 1.37-1.13 (m, 2 H). LCMS (Method 2): [MH+] = 796 at 4.08 min. |
| [(1S)-1-[3,4-bis(difluoromethoxy)phenyl]-2-(3,5-dichloro-1-oxido-pyridin-1-ium-4-yl)ethyl] 4-[(2-fluoro-N-[(3R)-quinuclidin-3-yl]oxycarbonyl-anilino)methyl]benzoate | Example 81 | Intermediate 23 and Intermediate 32/F | $^1$H NMR (400 MHz, CDCl3): δ 8.13 (s, 2 H), 7.96-7.94 (m, 2 H), 7.36-7.21 (m, 7 H), 7.11-7.06 (m, 2 H), 6.53 (t, J = 73.2 Hz, 1 H), 6.51 (t, J = 73.2 Hz, 1 H), 6.28 (dd, J = 4.4, 9.6 Hz, 1 H), 4.86 (brs, 2 H), 4.79 (brs, 1 H), 3.64 (dd, J = 9.6, 14.0 Hz, 1 H), 3.20 (dd, J = 4.4, 14.0 Hz, 1 H), 3.22-3.17 (m, 1 H), 2.73-2.59 (m, 5 H), 2.00-1.94 (m, 1 H), 1.64-1.61 (m, 1 H), 1.52-1.50 (m, 1 H), 1.32-1.30 (m, 1 H), 1.21-1.19 (m, 1 H). LCMS (Method 1): [MH+] = 796 at 2.99 min. |

| Structure | Example number | Precursors | Analytical Data |
|---|---|---|---|
| [(1R)-1-[3-(cyclopentoxy)-4-methoxy-phenyl]-2-(3,5-dichloro-1-oxido-pyridin-1-ium-4-yl)ethyl] 4-[(2-fluoro-N-[(3R)-quinuclidin-3-yl]oxycarbonyl-anilino)methyl]benzoate 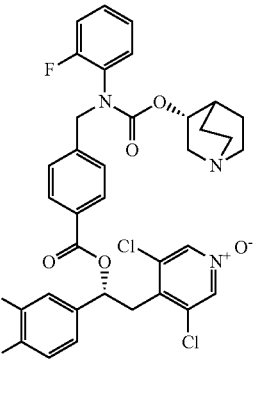 | Example 82 | Intermediate 23 and Intermediate 32/E | $^1$H NMR (400 MHz, CDCl3): δ 8.11 (s, 2 H), 7.95 (d, J = 7.9 Hz, 2 H), 7.33 (d, J = 8.0 Hz, 2 H), 7.27-7.20 (m, 1 H), 7.12-6.95 (m, 5 H), 6.85-6.82 (m, 1 H), 6.27 (dd, J = 9.4, 4.8 Hz, 1 H), 4.86 (s, 2 H), 4.81-4.74 (m, 2 H), 3.83 (s, 3 H), 3.67 (dd, J = 13.9, 9.5 Hz, 1 H), 3.34 (dd, J = 13.9, 4.8 Hz, 1 H), 3.24-3.14 (m, 1 H), 2.78-2.53 (m, 5 H), 1.97-1.76 (m, 7H), 1.69-1.45 (m, 4 H), 1.35-1.13 (m, 2 H). LCMS (Method 1): [MH+] = 778 at 3.04 min. |
| [(1S)-1-[3-(cyclopentoxy)-4-methoxy-phenyl]-2-(3,5-dichloro-1-oxido-pyridin-1-ium-4-yl)ethyl] 4-[(2-fluoro-N-[(3R)-quinuclidin-3-yl]oxycarbonyl-anilino)methyl]benzoate 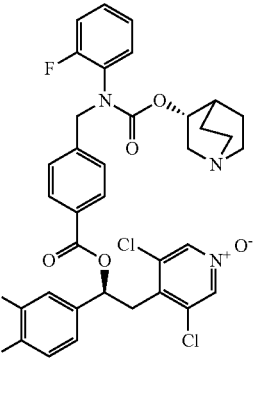 | Example 83 | Intermediate 23 and Intermediate 32/E | $^1$H NMR (400 MHz, CDCl3): δ 8.11 (s, 2 H), 7.95 (d, J = 7.8 Hz, 2 H), 7.33 (d, J = 7.9 Hz, 2 H), 7.28-7.20 (m, 1 H), 7.14-6.93 (m, 5 H), 6.83 (d, J = 8.5 Hz, 1 H), 6.27 (dd, J = 9.4, 4.8 Hz, 1 H), 4.86 (s, 2 H), 4.83-4.74 (m, 2 H), 3.83 (s, 3 H), 3.67 (dd, J = 13.9, 9.5 Hz, 1 H), 3.33 (dd, J = 13.9, 4.8 Hz, 1 H), 3.27-3.16 (m, 1 H), 2.82-2.55 (m, 5 H), 2.03-1.75 (m, 7 H), 1.70-1.47 (m, 4 H), 1.40-1.16 (m, 2 H). LCMS (Method 1): [MH+] = 778 at 3.03 min. |
| [(1R)-1-[3-(cyclopentoxy)-4-methoxy-phenyl]-2-(3,5-dichloro-1-oxido-pyridin-1-ium-4-yl)ethyl] 3-[(2-fluoro-N-[(3R)-quinuclidin-3-yl]oxycarbonyl-anilino)methyl]benzoate 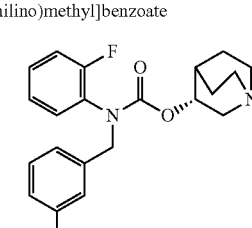 | Example 84 | Intermediate 28 and Intermediate 32/E | $^1$H NMR (400 MHz, CDCl3): δ 8.11 (s, 2 H), 7.94-7.88 (m, 2 H), 7.48 (d, J = 7.7 Hz, 1 H), 7.37 (t, J = 7.7 Hz, 1 H), 7.28-7.21 (m, 1 H), 7.13-6.94 (m, 5 H), 6.87-6.82 (m, 1 H), 6.24 (dd, J = 9.5, 4.5 Hz, 1 H), 4.91-4.82 (m, 3 H), 4.82-4.75 (m, 1 H), 3.84 (s, 3 H), 3.67 (dd, J = 13.9, 9.6 Hz, 1 H), 3.36-3.22 (m, 2 H), 2.85-2.58 (m, 5 H), 2.06-1.99 (m, 1 H), 1.97-1.76 (m, 6 H), 1.74-1.53 (m, 4 H), 1.44-1.23 (m, 2 H). LCMS (Method 2): [MH+] = 778 at 4.28 min. |

-continued

| Structure | Example number | Precursors | Analytical Data |
|---|---|---|---|
| [(1R)-1-[3-(cyclopropylmethoxy)-4-methoxy-phenyl]-2-(3,5-dichloro-1-oxido-pyridin-1-ium-4-yl)ethyl] 3-[(2-fluoro-N-[(3R)-quinuclidin-3-yl]oxycarbonyl-anilino)methyl]benzoate 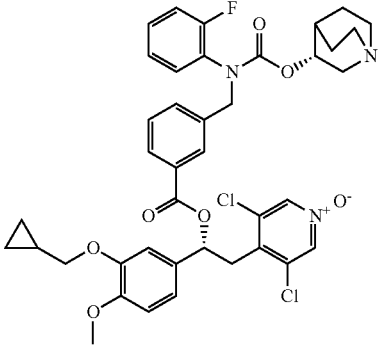 | Example 85 | Intermediate 28 and Intermediate 32/D | $^1$H NMR (400 MHz, CDCl3): δ 8.11 (s, 2 H), 7.93-7.88 (m, 2 H), 7.45 (d, J = 7.6 Hz, 1 H), 7.36 (t, J = 7.7 Hz, 1 H), 7.28-7.21 (m, 1 H), 7.12-6.96 (m, 5 H), 6.86 (d, J = 8.2 Hz, 1 H), 6.23 (dd, J = 9.7, 4.3 Hz, 1 H), 4.90-4.80 (m, 3 H), 3.89-3.84 (m, 5 H), 3.68 (dd, J = 14.0, 9.9 Hz, 1 H), 3.34-3.22 (m, 2 H), 2.85-2.58 (m, 5 H), 2.05-1.98 (m, 1 H), 1.74-1.64 (m, 1 H), 1.63-1.52 (m, 1 H), 1.44-1.22 (m, 3 H), 0.67-0.60 (m, 2 H), 0.39-0.33 (m, 2 H). LCMS (Method 2): [MH+] = 764 at 4.02 min. |
| [(1R)-1-[3-(cyclopentoxy)-4-methoxy-phenyl]-2-(3,5-dichloro-1-oxido-pyridin-1-ium-4-yl)ethyl] 4-[[2-pyridyl-[(3R)-quinuclidin-3-yl]oxycarbonyl-amino]methyl]benzoate 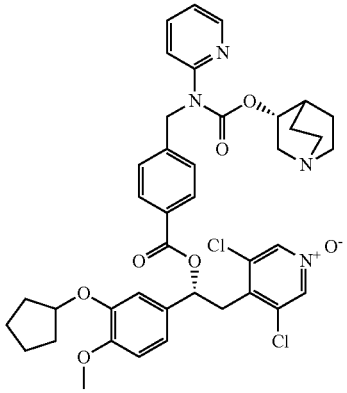 | Example 86 | Intermediate 90 and Intermediate 32/E | $^1$HNMR (400 MHz, CD$_3$CN): δ 8.35-8.33 (m, 1 H), 8.17 (s, 2 H), 7.99 (d, J = 8.3 Hz, 2 H), 7.84-7.75 (m, 2 H), 7.42 (d, J = 8.3 Hz, 2 H), 7.15-7.12 (m, 1 H), 7.02-7.00 (m, 2 H), 6.94-6.92 (m, 1 H), 6.22 (dd, J = 4.7, 9.3 Hz, 1 H), 5.36-5.20 (m, 2 H), 4.86-4.73 (m, 2 H), 3.79 (s, 3 H), 3.66 (dd, J = 9.3, 14.0 Hz, 1 H), 3.35 (dd, J = 4.7, 14.0 Hz, 1 H), 3.17-3.04 (m, 1 H), 2.75-2.59 (m, 3 H), 2.58-2.56 (m, 1 H), 2.49-2.35 (m, 1 H), 2.01-1.80 (m, 7 H), 1.78-1.44 (m, 4 H), 1.39-1.33 (m, 1 H), 1.31-1.18 (m, 1 H). LCMS (Method 1): [MH+] = 761 at 2.92 min. |
| [(1S)-1-[3-(cyclopentoxy)-4-methoxy-phenyl]-2-(3,5-dichloro-1-oxido-pyridin-1-ium-4-yl)ethyl] 4-[[2-pyridyl-[(3R)-quinuclidin-3-yl]oxycarbonyl-amino]methyl]benzoate 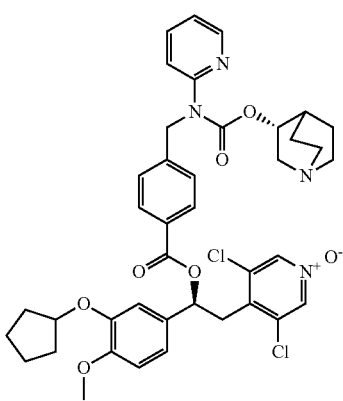 | Example 87 | Intermediate 90 and Intermediate 32/E | 1H NMR (400 MHz, CD$_3$CN): δ 8.36-8.34 (m, 1 H), 8.19 (s, 2 H), 7.99 (d, J = 8.3 Hz, 2 H), 7.86-7.75 (m, 2 H), 7.42 (d, J = 8.3 Hz, 2 H), 7.15-7.12 (m, 1 H), 7.03-7.01 (m, 2 H), 6.94-6.92 (m, 1 H), 6.22 (dd, J = 4.7, 9.3 Hz, 1 H), 5.36-5.23 (m, 2 H), 4.84-4.75 (m, 2 H), 3.79 (s, 3 H), 3.66 (dd, J = 9.3, 14.0 Hz, 1 H), 3.35 (dd, J = 4.7, 14.0 Hz, 1 H), 3.15-3.08 (m, 1 H), 2.75-2.58 (m, 3 H), 2.56-2.55 (m, 1 H), 2.35-2.26 (m, 1 H), 2.03-1.82 (m, 7 H), 1.79-1.47 (m, 4 H), 1.43-1.33 (m, 1 H), 1.31-1.14 (m, 1 H). LCMS (Method 1): [MH+] = 761 at 2.91 min. |

-continued

| Structure | Example number | Precursors | Analytical Data |
|---|---|---|---|
| [(1S)-1-[3-(cyclopentoxy)-4-methoxy-phenyl]-2-(3,5-dichloro-1-oxido-pyridin-1-ium-4-yl)ethyl] 4-[[3-pyridyl-[(3R)-quinuclidin-3-yl]oxycarbonyl-amino]methyl]benzoate | Example 88 | Intermediate 91 and Intermediate 32/E | $^1$H NMR (400 MHz, CDCl3): δ 8.46 (d, J = 5.0 Hz, 2 H), 8.14 (s, 2 H), 7.98 (d, J = 7.9 Hz, 2 H), 7.45 (brs, 1 H), 7.34-7.21 (m, 3 H), 6.99-6.96 (m, 2 H), 6.86-6.81 (m, 1 H), 6.27 (dd, J = 9.5, 4.7 Hz, 1 H), 4.94 (s, 2 H), 4.86-4.73 (m, 2 H), 3.84 (s, 3 H), 3.69 (dd, J = 13.9, 9.5 Hz, 1 H), 3.34 (dd, J = 13.9, 4.8 Hz, 1 H), 3.25-3.18 (m, 1 H), 2.66-2.58 (m, 2 H), 2.01-1.81 (m, 9 H), 1.72-1.58 (m, 4 H), 1.39-1.21 (m, 3 H). LCMS (Method 2): [MH+] = 761 at 9.72 min. |
| [(1R)-1-[3-(cyclopentoxy)-4-methoxy-phenyl]-2-(3,5-dichloro-1-oxido-pyridin-1-ium-4-yl)ethyl] 4-[[3-pyridyl-[(3R)-quinuclidin-3-yl]oxycarbonyl-amino]methyl]benzoate | Example 89 | Intermediate 91 and Intermediate 32/E | $^1$H NMR (400 MHz, CDCl3): δ 8.47-8.44 (m, 2 H), 8.13 (s, 2 H), 7.98 (d, J = 8.0 Hz, 2 H), 7.54-7.35 (brs, 1 H), 7.01-6.95 (m, 2 H), 6.84 (d, J = 8.4 Hz, 1 H), 6.29-6.24 (m, 1 H), 4.93 (s, 2 H), 4.85-4.73 (m, 2 H), 3.84 (s, 3 H), 3.69 (dd, J = 13.9, 9.6 Hz, 1 H), 3.34 (dd, J = 14.0, 4.7 Hz, 1 H), 3.26-3.18 (m, 1 H), 2.77-2.68 (m, 4 H), 2.67-2.57 (m, 2 H), 2.00-1.79 (m, 7 H), 1.72-1.50 (m, 5 H), 1.32-1.21 (m, 3 H). LCMS (Method 1): [MH+] = 761 at 2.77 min. |
| [(1S)-1-[3-(cyclopropylmethoxy)-4-methoxy-phenyl]-2-(3,5-dichloro-1-oxido-pyridin-1-ium-4-yl)ethyl] 4-[[3-pyridyl-[(3R)-quinuclidin-3-yl]oxycarbonyl-amino]methyl]benzoate | Example 90 | Intermediate 91 and Intermediate 32/D | $^1$H NMR (400 MHz, CDCl3): δ 8.49-8.45 (m, 2 H), 8.14 (s, 2 H), 7.97 (d, J = 7.9 Hz, 2 H), 7.57-7.34 (brs, 1 H) 7.29 (m, 3 H), 7.05-6.96 (m, 2 H), 6.86 (d, J = 8.4 Hz, 1 H), 6.27 (dd, J = 9.6, 4.3 Hz, 1 H), 4.96-4.85 (m, 3 H), 3.87 (m, 5 H), 3.70 (dd, J = 14.0, 9.8 Hz, 1 H), 3.33 (m, 2 H), 2.86 (m, 3 H), 2.77 (m, 1 H), 2.65 (s, 1 H) 2.08 (s, 1 H), 1.75-1.49 (m, 1 H), 1.57-1.23 (m, 2 H), 1.39-1.25 (m, 2 H), 0.67-0.61 (m, 2 H), 0.38-0.33 (m, 2 H). LCMS (Method 2): [MH+] = 747 at 3.48 min. |

| Structure | Example number | Precursors | Analytical Data |
| --- | --- | --- | --- |
| [(1R)-1-[3-(cyclopropylmethoxy)-4-methoxy-phenyl]-2-(3,5-dichloro-1-oxido-pyridin-1-ium-4-yl)ethyl] 4-[[3-pyridyl-[(3R)-quinuclidin-3-yl]oxycarbonyl-amino]methyl]benzoate | Example 91 | Intermediate 91 and Intermediate 32/D | $^1$H NMR (400 MHz, CDCl$_3$): δ 8.48-8.44 (m, 2 H), 8.13 (s, 2 H), 7.97 (d, J = 8.0 Hz, 2 H), 7.57-7.35 (brs, 1 H), 7.31 (d, J = 7.9 Hz, 2 H), 7.28-7.23 (m, 1 H), 7.03-6.96 (m, 2 H), 6.86 (d, J = 8.3 Hz, 1 H), 6.26 (dd, J = 9.8, 4.5 Hz, 1 H), 4.93 (s, 2 H), 4.84-4.78 (m, 1 H), 3.91-3.85 (m, 5 H), 3.70 (dd, J = 14.0, 9.8 Hz, 1 H), 3.33 (dd, J = 14.0, 4.6 Hz, 1 H), 3.21 (m, 1 H), 2.76-2.68 (m, 4 H), 2.65-2.55 (m, 2 H), 1.97 (s, 1 H), 1.39-1.21 (m, 4 H), 0.67-0.61 (m, 2 H), 0.38-0.33 (m, 2 H). LCMS (Method 2): [MH+] = 747 at 3.25 min. |
| [(1S)-1-[3-(cyclopropylmethoxy)-4-methoxy-phenyl]-2-(3,5-dichloro-1-oxido-pyridin-1-ium-4-yl)ethyl] 4-[[2-pyridyl-[(3R)-quinuclidin-3-yl]oxycarbonyl-amino]methyl]benzoate | Example 92 | Intermediate 90 and Intermediate 32/D | $^1$H NMR (400 MHz, CD$_3$CN): δ 8.25-8.23 (m, 1 H), 8.07 (s, 2 H), 7.87 (d, J = 8.2 Hz, 2 H), 7.73-7.67 (m, 2 H), 7.31 (d, J = 8.2 Hz, 2 H), 7.04-7.01 (m, 1 H), 6.94-6.92 (m, 2 H), 6.84-6.82 (m, 1 H), 6.11 (dd, J = 4.4, 9.6 Hz, 1 H), 5.22-5.13 (m, 2 H), 4.68-4.66 (m, 1 H), 3.73-3.62 (m, 5 H), 3.55 (dd, J = 9.6, 14.0 Hz, 1 H), 3.21 (dd, J = 4.4, 14.0 Hz, 1 H), 3.05-2.98 (m, 1 H), 2.64-2.25 (m, 5 H), 1.86-1.78 (m, 1 H), 1.61-1.47 (m, 1 H), 1.46-1.37 (m, 1 H), 1.35-1.34 (m, 1 H), 1.23-1.21 (m, 2 H), 0.51-0.47 (m, 2 H), 0.23-0.19 (m, 2 H). LCMS (Method 1): [MH+] = 747 at 2.82 min. |
| [(1R)-1-[3-(cyclopropylmethoxy)-4-methoxy-phenyl]-2-(3,5-dichloro-1-oxido-pyridin-1-ium-4-yl)ethyl] 4-[[2-pyridyl-[(3R)-quinuclidin-3-yl]oxycarbonyl-amino]methyl]benzoate | Example 93 | Intermediate 90 and Intermediate 32/D | $^1$H NMR (400 MHz, CD$_3$CN): δ 8.24-8.23 (m, 1 H), 8.05 (s, 2 H), 7.87 (d, J = 8.2 Hz, 2 H), 7.73-7.64 (m, 2 H), 7.30 (d, J = 8.2 Hz, 2 H), 7.04-7.01 (m, 1 H), 6.93-6.91 (m, 2 H), 6.83-6.81 (m, 1 H), 6.09 (dd, J = 4.4, 9.6 Hz, 1 H), 5.24-5.11 (m, 2 H), 4.68-4.66 (m, 1 H), 3.75-3.67 (m, 5 H), 3.55 (dd, J = 9.6, 14.0 Hz, 1 H), 3.22 (dd, J = 4.4, 14.0 Hz, 1 H), 3.05-2.98 (m, 1 H), 2.63-2.26 (m, 5 H), 1.84-1.76 (m, 1 H), 1.60-1.48 (m, 1 H), 1.47-1.36 (m, 1 H), 1.35-1.34 (m, 1 H), 1.23-1.21 (m, 2 H), 0.52-0.45 (m, 2 H), 0.25-0.17 (m, 2 H). LCMS (Method 1): [MH+] = 747 at 2.81 min. |

Intermediate 93. [(1S)-2-(3,5-Dichloro-1-oxido-pyridin-1-ium-4-yl)-1-(3,4-dimethoxyphenyl)ethyl]3-formylbenzoate

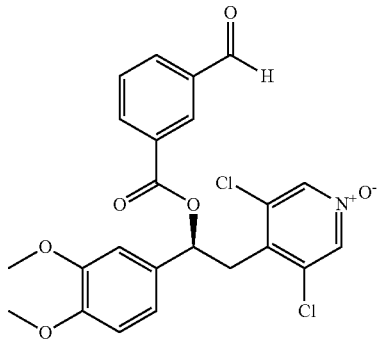

A solution of (S)-3,5-dichloro-4-(2-(3,4-dimethoxyphenyl)-2-hydroxyethyl)pyridine 1-oxide (0.688 g, 2 mmol), 3-formylbenzoic acid (0.300 g, 2 mmol), N-(3-dimethylaminopropyl)-N'-ethylcarbodiimide hydrochloride (0.767 g, 4 mmol), and 4-(dimethylamino)pyridine (0.122 g, 1 mmol) in anhydrous DCM (30 mL) was stirred at RT for 21 hours. The reaction mixture was partitioned between saturated aqueous $NaHCO_3$ (20 mL) and DCM (10 mL) and filtered through a phase separator. The solvent was removed in vacuo and the crude material was purified by silica gel column chromatography eluting with 1:1 DCM:EtOAc to afford the title compound as an off-white solid (0.863 g, 91%).

$^1$H NMR (400 MHz, $CDCl_3$): δ 10.08 (s, 1H), 8.54 (t, J=1.7 Hz, 1H), 8.27 (dt, J=7.8, 1.5 Hz, 1H), 8.14 (s, 2H), 8.09 (dt, J=7.7, 1.5 Hz, 1H), 7.63 (t, J=7.7 Hz, 1H), 7.05 (dd, J=8.2, 2.1 Hz, 1H), 7.00 (d, J=2.1 Hz, 1H), 6.87 (d, J=8.3 Hz, 1H), 6.33 (dd, J=9.7, 4.6 Hz, 1H), 3.92 (s, 3H), 3.88 (s, 3H), 3.76 (dd, J=14.0, 9.8 Hz, 1H), 3.39 (dd, J=14.0, 4.6 Hz, 1H). LCMS (Method 1): [MH+]=476 at 3.55 min.

The following intermediates were synthesized similarly to the method of the intermediate 93 by reacting the suitable alcoholic intermediate I-32 (I-32/A to I-32/N) with the suitable formylbenzoic acid.

| Structure | Intermediate number | Analytical Data |
|---|---|---|
| 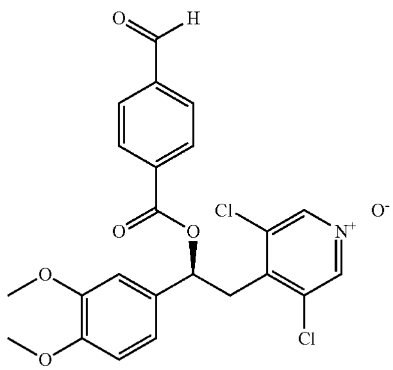 | Intermediate 94 | $^1$H NMR (400 MHz, $CDCl_3$): δ 10.10 (s, 1 H), 8.18 (d, J = 8.0 Hz, 2 H), 8.13 (s, 2 H), 7.95 (d, J = 8.0 Hz, 2 H), 7.05-6.99 (m, 2 H), 6.87 (d, J = 8.4 Hz, 1 H), 6.33 (dd, J = 4.4, 9.6 Hz, 1 H), 3.91 (s, 3 H), 3.88 (s, 3 H), 3.75 (dd, J = 9.6, 14.0 Hz, 1 H), 3.38 (dd, J = 4.4, 14.0 Hz, 1 H). LCMS (method 1): [MH+] = 476 at 3.65 min. |
| 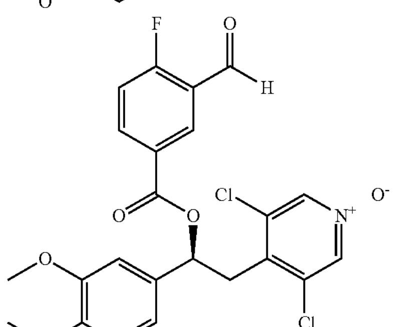 | Intermediate 95 | $^1$H NMR (400 MHz, $CDCl_3$): δ 10.37 (s, 1 H), 8.59 (dd, J = 6.7, 2.3 Hz, 1 H), 8.25 (ddd, J = 8.7, 5.0, 2.4 Hz, 1 H), 8.15 (s, 2 H), 7.06-6.99 (m, 2 H), 6.88 (d, J = 8.3 Hz, 1 H), 6.29 (dd, J = 9.1, 4.5 Hz, 1 H), 3.92 (s, 3 H), 3.88 (s, 3 H), 3.75 (dd, J = 14.1, 9.8 Hz, 1 H), 3.38 (dd, J = 14.4, 4.4 Hz, 1 H). LCMS (Method 1): [MH+] = 494 at 3.64 min. |
| 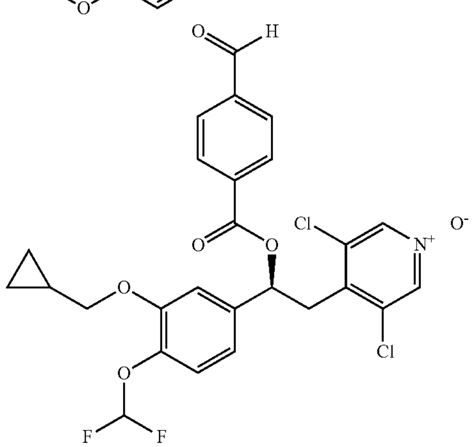 | Intermediate 96 | $^1$H NMR (400 MHz, $CDCl_3$): δ 10.10 (s, 1 H), 8.18-8.13 (m, 2 H), 8.12 (s, 2 H), 7.96-7.94 (m, 2 H), 7.20-7.18 (m, 1 H), 7.08-7.03 (m, 2 H), 6.43 (t, J = 75.2 Hz, 1 H), 6.29 (dd, J = 4.4, 9.6 Hz, 1 H), 3.90-3.88 (m, 2 H), 3.72 (dd, J = 9.6, 14.0 Hz, 1 H), 3.33 (dd, J = 4.4, 14.0 Hz, 1 H), 1.30-1.24 (m, 1 H), 0.67-0.64 (m, 2 H), 0.38-0.35 (m, 2 H). LCMS (Method 2): [MH+] = 552 at 3.97 min. |

-continued

| Structure | Intermediate number | Analytical Data |
|---|---|---|
| 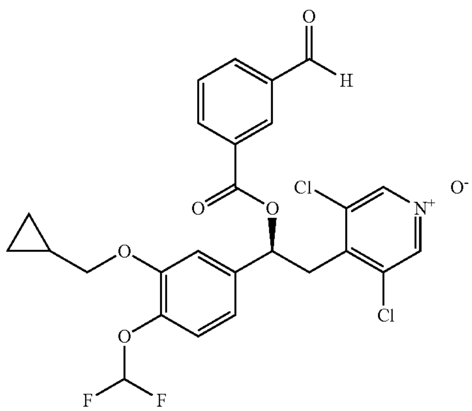 | Intermediate 97 | $^1$H NMR (400 MHz, CDCl$_3$): δ 10.08 (s, 1 H), 8.53 (s, 1 H), 8.26 (d, J = 7.8 Hz, 1 H), 8.15 (s, 2 H), 8.10 (d, J = 7.6 Hz, 1 H), 7.64 (t, J = 7.7 Hz, 1 H), 7.19 (d, J = 8.1 Hz, 1 H), 7.10-7.03 (m, 2 H), 6.62 (t, J = 75.3 Hz, 1 H), 6.30 (dd, J = 10.0, 4.3 Hz, 1 H), 3.91 (d, J = 6.9 Hz, 2 H), 3.73 (dd, J = 14.1, 10.0 Hz, 1 H), 3.35 (dd, J = 14.1, 4.3 Hz, 1 H), 1.32-1.23 (m, 1 H), 0.69-0.63 (m, 2 H), 0.40-0.35 (m, 2 H). LCMS (Method 2): [MH+] = 552 at 4.00 min. |
| 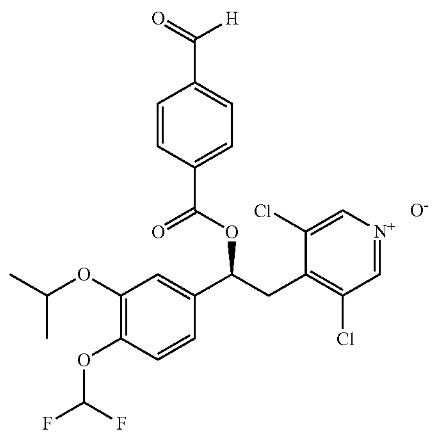 | Intermediate 98 | $^1$H NMR (400 MHz, CDCl$_3$): δ 10.10 (s, 1 H), 8.18-8.14 (m, 2 H), 8.12 (s, 2 H), 7.97-7.95 (m, 2 H), 7.19-7.17 (m, 1 H), 7.07-7.04 (m, 2 H), 6.55 (t, J = 75.2 Hz, 1 H), 6.29 (dd, J = 4.4, 9.6 Hz, 1 H), 4.60-4.54 (m, 1 H), 3.70 (dd, J = 9.6, 14.0 Hz, 1 H), 3.34 (dd, J = 4.4, 14.0 Hz, 1 H), 1.38-1.27 (m, 6 H). LCMS (Method 2): [MH+] = 540 at 4.02 min. |
| 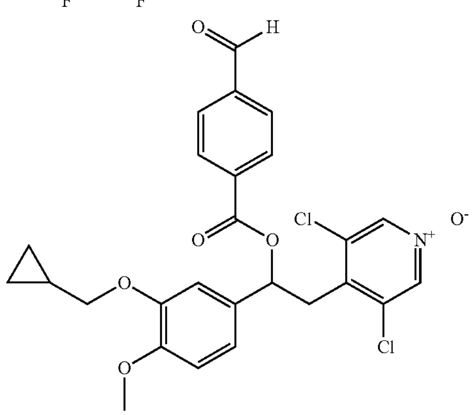 | Intermediate 99 | $^1$H NMR (400 MHz, CDCl$_3$): δ 10.10 (s, 1 H), 8.15 (d, J = 8.0 Hz, 2 H), 8.12 (s, 2 H), 7.94 (d, J = 8.0 Hz, 2 H), 7.04-6.99 (m, 2 H), 6.88-6.86 (m, 1 H), 6.29 (dd, J = 4.4, 9.6 Hz, 1 H), 3.88 (s, 2 H), 3.87 (s, 3 H), 3.69 (dd, J = 9.6, 14.0 Hz, 1 H), 3.35 (dd, J = 4.4, 14.0 Hz, 1 H), 1.33-1.30 9m, 1 H), 0.66-0.62 (m, 2 H), 0.38-0.35 (m, 2 H). LCMS (Method 1): [MH+] = 516 at 3.97 min. |
| 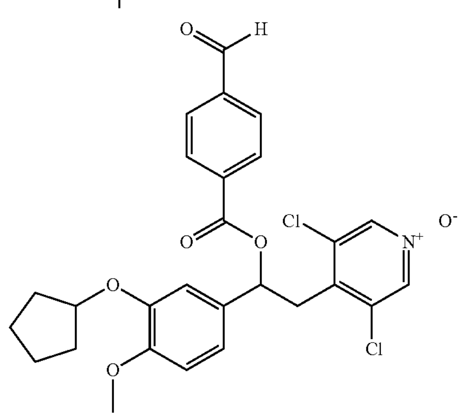 | Intermediate 100 | $^1$H NMR (400 MHz, CDCl$_3$): δ 10.10 (s, 1 H), 8.18 (d, J = 8.4 Hz, 2 H), 8.12 (s, 2 H), 7.95 (d, J = 8.4 Hz, 2 H), 7.00-6.98 (m, 2 H), 6.86-6.84 (m, 1 H), 6.30 (dd, J = 4.4, 9.6 Hz, 1 H), 4.79-4.77 (m, 1 H), 3.84 (s, 3 H), 3.71 (dd, J = 9.6, 14.0 Hz, 1 H), 3.35 (dd, J = 4.4, 14.0 Hz, 1 H), 2.04-1.83 (m, 6 H), 1.61-1.56 (m, 2 H). LCMS (Method 1): [MH+] = 530 at 4.21 min. |

-continued
| Structure | Intermediate number | Analytical Data |
|---|---|---|
| 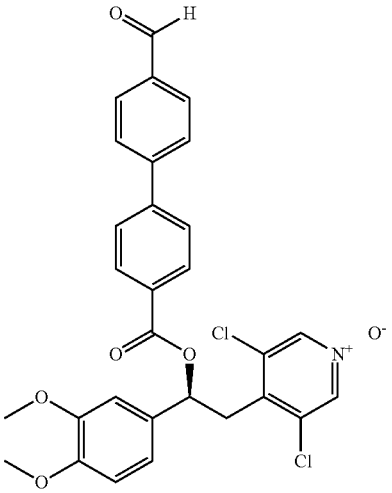 | Intermediate 101 | $^1$H NMR (400 MHz, CDCl$_3$): δ 10.1 (s, 1 H), 8.14-8.11 (m, 4 H), 7.99-7.97 (m, 2 H), 7.78-7.70 (m, 2 H), 7.69-7.68 (m, 2 H), 7.06-6.99 (m, 2 H), 6.88-6.85 (m, 1 H), 6.33 (dd, J = 4.4, 9.6 Hz, 1 H), 3.90 (s, 3 H), 3.87 (s, 3 H), 3.74 (dd, J = 9.6, 14.0 Hz, 1 H), 3.37 (dd, J = 4.4, 14.0 Hz, 1 H). LCMS (Method 2): [MH+] = 552 at 3.51 min. |
| 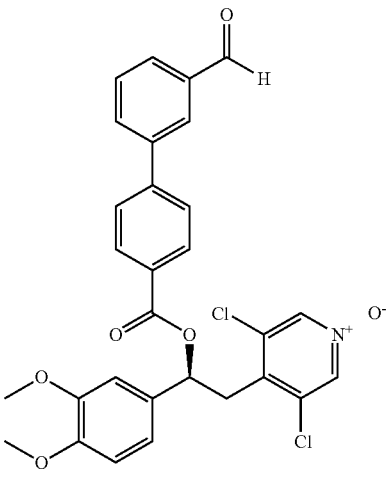 | Intermediate 102 | LCMS (Method 2): [MH+] = 552 at 3.54 min. |
| 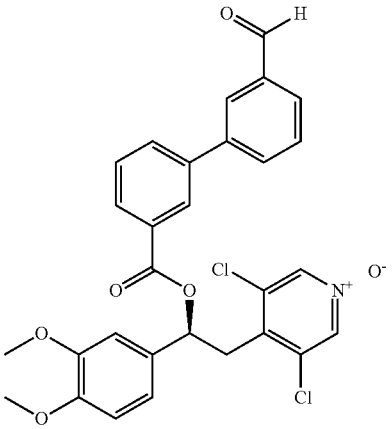 | Intermediate 103 | $^1$H NMR (400 MHz, CDCl$_3$): δ 10.10 (s, 1 H), 8.29-8.28 (m, 1 H), 8.17 (s, 1 H), 8.13-8.12 (m, 1 H), 8.06-8.04 (m, 1 H), 7.90-7.81 (m, 3 H), 7.67-7.63 (m, 1 H), 7.57-7.53 (m, 1 H), 7.06-7.02 (m, 2 H), 6.88-6.86 (m, 1 H), 6.33 (dd, J = 4.4, 9.6 Hz, 1 H), 3.91 (s, 3 H), 3.87 (s, 3 H), 3.75 (dd, J = 9.6, 14.0 Hz, 1 H), 3.37 (dd, J = 4.4, 14.0 Hz, 1 H). LCMS (Method 2): : [MH+] = 552 at 3.54 min. |

| Structure | Intermediate number | Analytical Data |
|---|---|---|
| 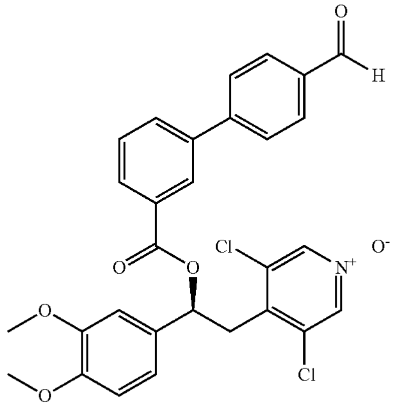 | Intermediate 104 | ¹H NMR (400 MHz, CDCl₃): δ 10.07 (s, 1 H), 8.29-8.28 (m, 1 H), 8.14 (s, 2 H), 8.08-8.06 (m, 1 H), 7.99-7.97 (m, 2 H), 7.84-7.82 (m, 1 H), 7.75 (d, J = 8.2 Hz, 2 H), 7.58-7.54 (m, 1 H), 7.07-7.01 (m, 2 H), 6.88-6.86 (m, 1 H), 6.34 (dd, J = 4.4, 9.6 Hz, 1 H), 3.91 (s, 3 H), 3.88 (s, 3 H), 3.74 (dd, J = 9.6, 14.0 Hz, 1 H), 3.37 (dd, J = 4.4, 14.0 Hz, 1 H). LCMS (Method 2): : [MH+] = 552 at 3.49 min |

Intermediate 105. [(1S)-2-(3,5-dichloro-1-oxido-pyridin-1-ium-4-yl)-1-(3,4-dimethoxyphenyl)ethyl] 3-[(2-chloroanilino)methyl]benzoate

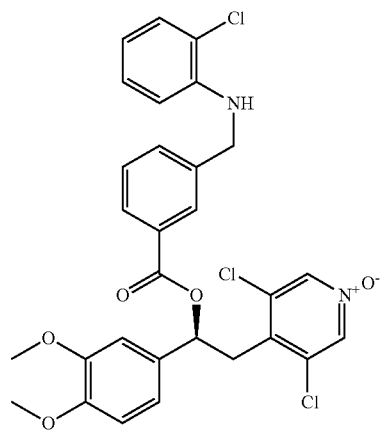

To a solution of [(1S)-2-(3,5-dichloro-1-oxido-pyridin-1-ium-4-yl)-1-(3,4-dimethoxyphenyl)ethyl]3-formylbenzoate (332 mg, 0.697 mmol) and 2-chloroaniline (0.077 mL, 0.732 mmol) in anhydrous DCM (3.5 mL) was added acetic acid (0.042 mL, 0.732 mmol). The mixture was stirred at room temperature for 24 hours. NaBH(OAc)₃ (369 mg, 1.74 mmol) was added, and the mixture was stirred at room temperature for 24 hours. After addition of water (2.5 mL), the mixture was stirred at room temperature for 1 hour. The reaction mixture was filtered through a phase separator, and the solvent was removed in vacuo. The crude material was purified by silica gel column chromatography eluting with 1:1 DCM: EtOAc to afford the title compound as a white solid (274 mg, 67%).

¹H NMR (400 MHz, CDCl₃): δ 8.08 (s, 2H), 8.04 (s, 1H), 7.93 (d, J=7.8 Hz, 1H), 7.56 (d, J=7.7 Hz, 1H), 7.42 (t, J=7.7 Hz, 1H), 7.29 (dd, J=7.9, 1.5 Hz, 1H), 7.11-7.05 (m, 1H), 7.01 (dd, J=8.2, 1.9 Hz, 1H), 6.97 (d, J=2.0 Hz, 1H), 6.85 (d, J=8.2 Hz, 1H), 6.67 (td, J=7.6, 1.4 Hz, 1H), 6.54 (dd, J=8.2, 1.4 Hz, 1H), 6.29 (dd, J=10.0, 4.4 Hz, 1H), 4.86-4.81 (m, 1H), 4.47 (d, J=5.6 Hz, 2H), 3.89 (s, 3H), 3.88 (s, 3H), 3.70 (dd, J=13.9, 10.0 Hz, 1H), 3.32 (dd, J=14.0, 4.4 Hz, 1H).

The following intermediates were synthesized similarly to the method of the intermediate 105 by using the suitable amine.

| Structure | Intermediate number | Precursor | Analytical Data |
|---|---|---|---|
| 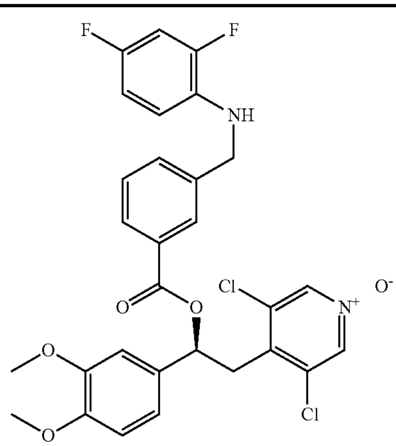 | Intermediate 106 | Intermediate 93 | ¹H NMR (400 MHz, CDCl₃): δ 8.14 (s, 2 H), 8.02 (s, 1 H), 7.94 (d, J = 7.8 Hz, 1 H), 7.56 (d, J = 7.7 Hz, 1 H), 7.42 (t, J = 7.7 Hz, 1 H), 7.02-6.96 (m, 2 H), 6.88-6.76 (m, 2 H), 6.74-6.66 (m, 1 H), 6.50 (td, J = 9.3, 5.4 Hz, 1 H), 6.29 (dd, J = 9.9, 4.5 Hz, 1 H), 4.40 (s, 2 H), 3.89 (s, 3 H), 3.88 (s, 3 H), 3.71 (dd, J = 14.0, 9.9 Hz, 1 H), 3.34 (dd, J = 14.0, 4.5 Hz, 1 H). |

-continued

| Structure | Intermediate number | Precursor | Analytical Data |
|---|---|---|---|
| 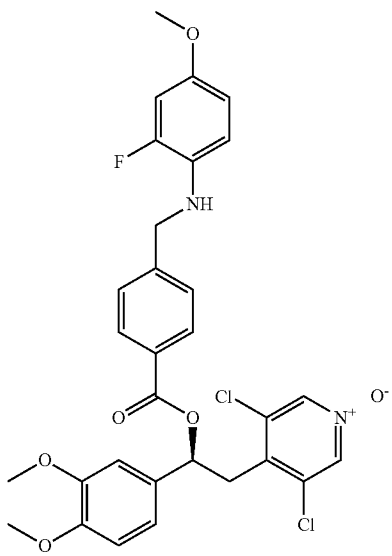 | Intermediate 107 | Intermediate 94 | $^1$H NMR (400 MHz, DMSO): δ 8.54 (s, 2 H), 7.93 (d, J = 7.8 Hz, 2 H), 7.48 (d, J = 7.8 Hz, 2 H), 7.05-6.95 (m, 3 H), 6.76-6.72 (m, 1 H), 6.49-6.45 (m, 2 H), 6.20 (dd, J = 9.6, 4.4 Hz, 1 H), 5.82-5.81 (m, 1 H), 4.37-4.35 (m, 2 H), 3.77 (s, 3 H), 3.75 (s, 3 H), 3.65-3.61 (m, 4 H), 3.35-3.29 (m, 1 H). LCMS (Method 2): [MH+] = 601 at 3.22 min. |
| 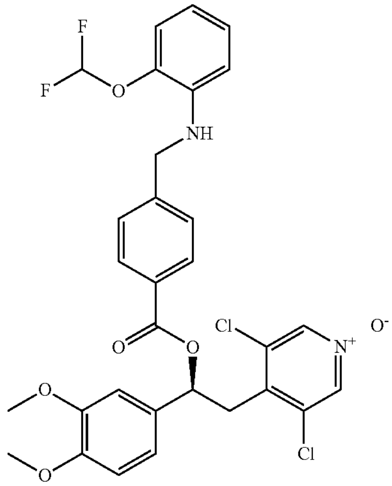 | Intermediate 108 | Intermediate 94 | $^1$H NMR (400 MHz, CDCl$_3$): δ 8.12 (s, 2 H), 7.99 (d, J = 8.4 Hz, 2 H), 7.41 (d, J = 8.4 Hz, 2 H), 7.04-6.98 (m, 4 H), 6.86-6.83 (m, 1 H), 6.68-6.66 (m, 1 H), 6.55-6.53 (m, 1 H), 6.50 (d, J = 74.4 Hz, 1 H), 6.28 (dd, J = 4.8, 9.6 Hz, 1 H), 4.74-4.72 (m, 1 H), 4.45-4.44 (m, 2 H), 3.89 (s, 3 H), 3.87 (s, 3 H), 3.70 (dd, J = 9.6, 14.0 Hz, 1 H), 3.33 (dd, J = 4.8, 14.0 Hz, 1 H). LCMS (Method 1): [MH+] = 619 at 4.22 min. |
| 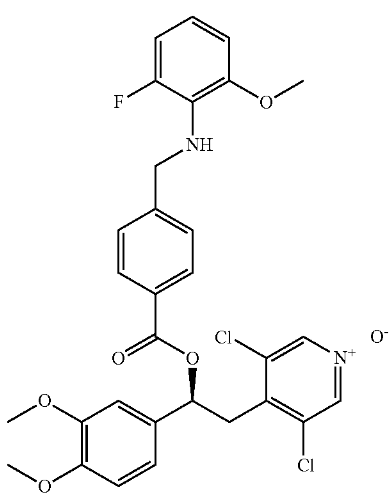 | Intermediate 109 | Intermediate 94 | $^1$H NMR (400 MHz, CDCl$_3$): δ 8.11 (s, 2 H), 7.97 (d, J = 8.0 Hz, 2 H), 7.39 (d, J = 8.0 Hz, 2 H), 7.01-6.97 (m, 2 H), 6.71-6.69 (m, 1 H), 6.67-6.58 (m, 3 H), 6.28 (dd, J = 4.4, 9.6 Hz, 1 H), 4.52 (s, 2 H), 4.29 (brs, 1 H), 3.91 (s, 3 H), 3.89 (s, 3 H), 3.86 (s, 3 H), 3.72 (dd, J = 9.6, 14.0 Hz, 1 H), 3.32 (dd, J = 4.4, 14.0 Hz, 1 H). LCMS (Method 2): [MH+] = 601 at 3.41 min. |

| Structure | Intermediate number | Precursor | Analytical Data |
|---|---|---|---|
| 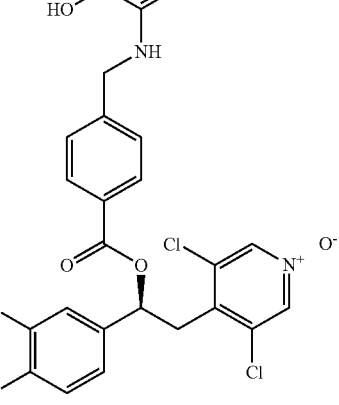 | Intermediate 110 | Intermediate 94 | $^1$H NMR (400 MHz, DMSO): δ 9.63 (brs, 1 H), 8.54 (s, 2 H), 7.92 (d, J = 8.0 Hz, 2 H), 7.47 (d, J = 8.0 Hz, 2 H), 7.04-6.94 (m, 3 H), 6.65-6.64 (m, 1 H), 6.51-6.49 (m, 1 H), 6.40-6.36 (m, 1 H), 6.29-6.27 (m, 1 H), 6.19 (dd, J = 4.4, 9.6 Hz, 1 H), 5.43 (t, J = 6.2 Hz, 1 H), 4.38 (d, J = 6.2 Hz, 2 H), 3.77 (s, 3 H), 3.74 (s, 3 H), 3.61 (dd, J = 9.6, 14.0 Hz, 1 H), 3.34-3.31 (m, 1 H). LCMS (Method 1): [MH+] = 569 at 3.64 min. |
| 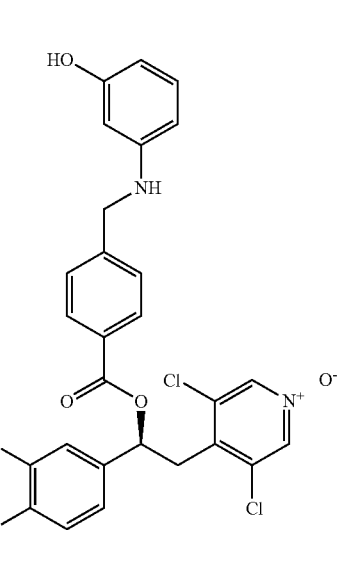 | Intermediate 111 | Intermediate 94 | $^1$H NMR (400 MHz, CDCl$_3$): δ 8.09 (s, 2 H), 7.94 (d, J = 8.4 Hz, 2 H), 7.40 (d, J = 8.4 Hz, 2 H), 7.05-6.97 (m, 3 H), 6.86-6.82 (m, 2 H), 6.34-6.29 (m, 1 H), 6.28-6.16 (m, 1 H), 6.15-6.03 (m, 1 H), 4.39 (s, 2 H), 3.94 (s, 3 H), 3.89 (s, 3 H), 3.71 (dd, J = 9.6, 14.0 Hz, 1 H), 3.32 (dd, J = 4.8, 14.0 Hz, 1 H). NH and OH not observed. LCMS (Method 1): [MH+] = 569 at 3.58 min. |
| 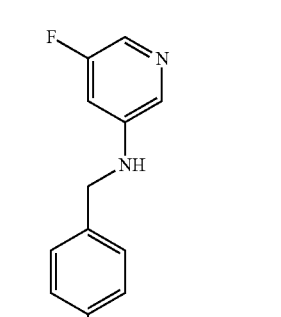 | Intermediate 112 | Intermediate 94 | $^1$H NMR (400 MHz, DMSO): δ 8.55 (s, 2 H), 7.96-7.94 (m, 2 H), 7.50-7.45 (m, 3 H), 7.15-7.11 (m, 1 H), 7.05-6.95 (m, 3 H), 6.87-6.84 (m, 1 H), 6.54 (t, J = 6.4 Hz, 1 H), 6.20 (dd, J = 4.4, 9.6 Hz, 1 H), 4.36 (d, J = 6.4 Hz, 2 H), 3.77 (s, 3 H), 3.74 (s, 3 H), 3.61 (dd, J = 9.6, 14.0, 1 H), 3.32 (dd, J = 4.4, 14.0 Hz, 1 H). LCMS (Method 1): [MH+] = 572 at 3.75 min |

-continued

| Structure | Intermediate number | Precursor | Analytical Data |
|---|---|---|---|
| 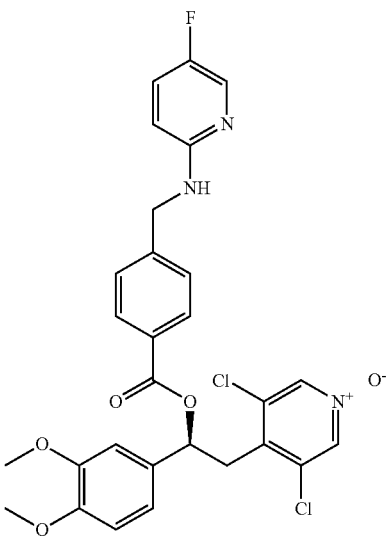 | Intermediate 113 | Intermediate 94 | 1H NMR (400 MHz, DMSO): δ 8.55 (s, 2 H), 7.99-7.94 (m, 4 H), 7.62-7.58 (m, 1 H), 7.48-7.45 (m, 2 H), 7.06-6.95 (m, 3 H), 6.78-6.75 (m, 1 H), 6.20 (dd, J = 4.4, 9.6 Hz, 1 H), 4.58 (brs, 2 H), 3.78 (s, 3 H), 3.77 (s, 3 H), 3.62 (dd, J = 9.6, 14.0 Hz, 1 H), 3.33 (dd, J = 4.4, 14.0 Hz, 1 H). LCMS (Method 1): [MH+] = 572 at 3.48 min |
| 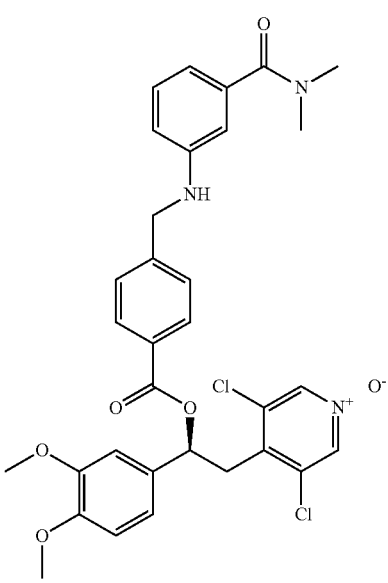 | Intermediate 114 | Intermediate 94 | $^1$H NMR (400 MHz, CDCl$_3$): δ 8.12 (s, 2 H), 7.98 (d, J = 8.4 Hz, 2 H), 7.41 (d, J = 8.4 Hz, 2 H), 7.15 (t, J = 8.0 Hz, 1 H), 7.02-6.98 (m, 2 H), 6.85 (d, J = 8.0 Hz, 1 H), 6.72-6.71 (m, 1 H), 6.63-6.58 (m, 2 H), 6.29 (dd, J = 4.4, 9.6 Hz, 1 H), 4.42-4.41 (brs, 2 H), 4.25-4.24 (brs, 1 H), 3.90 (s, 3 H), 3.87 (s, 3 H), 3.70 (dd, J = 9.6, 14.0 Hz, 1 H), 3.34 (dd, J = 4.4, 14.0 Hz, 1 H), 3.10-3.06 (brs, 3 H), 2.99-2.92 (brs, 3 H). LCMS (Method 1): [MH+] = 624 at 2.98 min. |
| 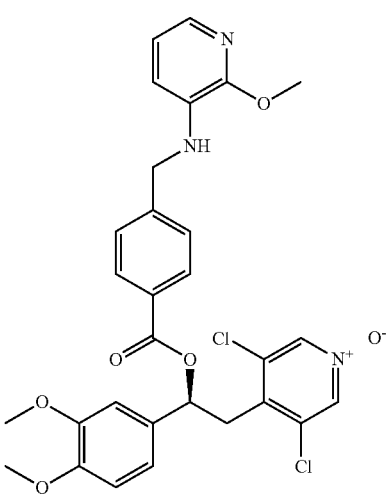 | Intermediate 115 | Intermediate 94 | $^1$H NMR (400 MHz, CDCl$_3$): δ 8.12 (s, 2 H), 7.99 (d, J = 8.4 Hz, 2 H), 7.50-7.49 (m, 1 H), 7.41 (d, J = 8.4 Hz, 2 H), 7.02-6.99 (m, 2 H), 6.86-6.84 (m, 1 H), 6.71-6.68 (m, 1 H), 6.57-6.55 (m, 1 H), 6.29 (dd, J = 4.4, 9.6 Hz, 1 H), 4.71-4.68 (m, 1 H), 4.42-4.41 (m, 2 H), 4.00 (s, 3 H), 3.90 (s, 3 H), 3.87 (s, 3 H), 3.70 (dd, J = 9.6, 14.0 Hz, 1 H), 3.32 (dd, J = 4.4, 14.0 Hz, 1 H). LCMS (Method 1): [MH+] = 584 at 3.92 min. |

| Structure | Intermediate number | Precursor | Analytical Data |
|---|---|---|---|
| (structure) | Intermediate 116 | Intermediate 94 | $^1$H NMR (400 MHz, CDCl$_3$): δ 8.19 (d, J = 2.0 Hz, 1 H), 8.12 (s, 2 H), 7.99 (d, J = 8.4 Hz, 2 H), 7.55 (d, J = 2.0 Hz, 1 H), 7.43 (d, J = 8.4 Hz, 2 H), 7.02-6.97 (m, 2 H), 6.86-6.84 (m, 1 H), 6.51-6.50 (m, 1 H), 6.31-6.27 (m, 2 H), 4.47-4.45 (m, 2 H), 3.91 (s, 3 H), 3.88 (s, 3 H), 3.79 (s, 3 H), 3.70 (dd, J = 9.6, 14.0 Hz, 1 H), 3.32 (dd, J = 4.4, 14.0 Hz, 1 H). LCMS (Method 1): [MH+] = 584 at 2.67 min. |
| (structure) | Intermediate 117 | Intermediate 94 | LCMS (Method 2): [MH+] = 584 at 2.67 min. |
| (structure) | Intermediate 118 | Intermediate 94 | LCMS (Method 1): [MH+] = 578 at 4.04 min. |

| Structure | Intermediate number | Precursor | Analytical Data |
|---|---|---|---|
| 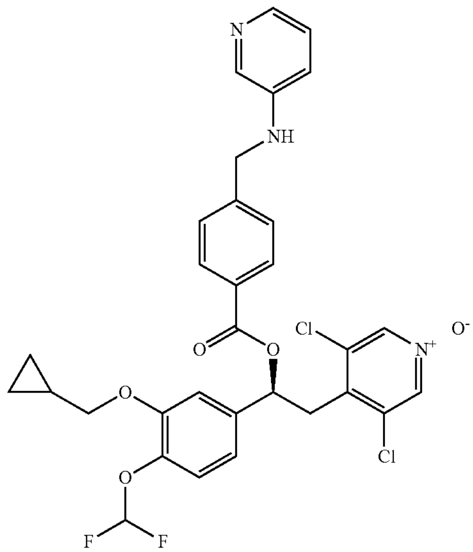 | Intermediate 119 | Intermediate 96 | ¹H NMR (400 MHz, CDCl₃): δ 8.13 (s, 2 H), 8.06-8.00 (m, 1 H), 7.98-7.97 (m, 3 H), 7.43 (d, J = 8.0 Hz, 2 H), 7.18-7.16 (m, 1 H), 7.07-7.02 (m, 3 H), 6.83-6.81 (m, 1 H), 6.42 (t, J = 75.2 Hz, 1 H), 6.26 (dd, J = 4.4, 9.6 Hz, 1 H), 4.43-4.42 (m, 2 H), 4.32-4.31 (m, 1 H), 4.03-4.00 (m, 2 H), 3.68 (dd, J = 9.6, 14.0 Hz, 1 H), 3.31 (dd, J = 4.4, 14.0 Hz, 1 H), 1.28-1.25 (m, 1 H), 0.66-0.62 (m, 2 H), 0.37-0.34 (m, 2 H). |
| 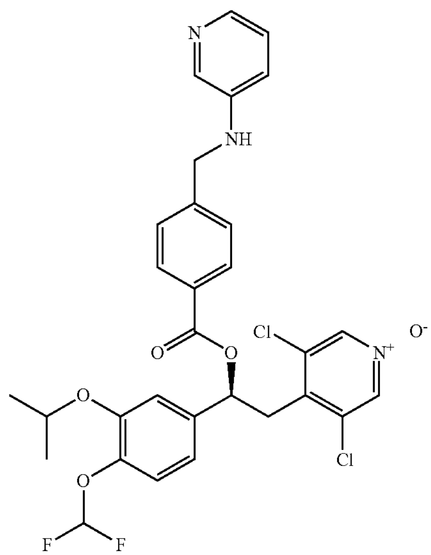 | Intermediate 120 | Intermediate 98 | ¹H NMR (400 MHz, CDCl₃): δ 8.13-8.10 (m, 3 H), 8.00-7.97 (m, 3 H), 7.43 (d, J = 8.0 Hz, 2 H), 7.17-7.15 (m, 1 H), 7.10-7.02 (m, 3 H), 6.86-6.83 (m, 1 H), 6.54 (t, J = 75.2 Hz, 1 H), 6.27 (dd, J = 4.4, 9.6 Hz, 1 H), 4.59-4.53 (m, 1 H), 4.43-4.41 (m, 3 H), 3.67 (dd, J = 9.6, 14.0 Hz, 1 H), 3.31 (dd, J = 4.4, 14.0 Hz, 1 H), 1.37-1.32 (m, 6 H). |
| 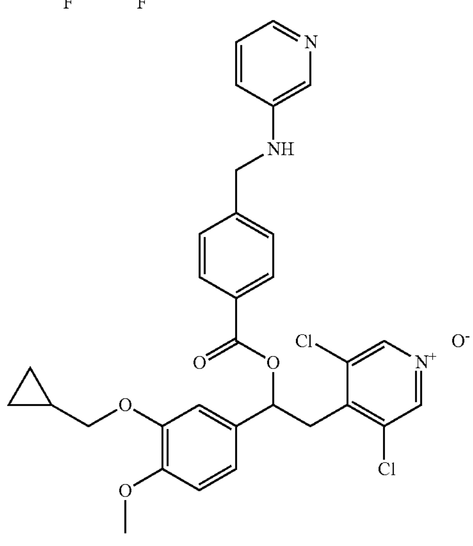 | Intermediate 121 | Intermediate 99 | ¹H NMR (400 MHz, CDCl₃): δ 8.35-8.31 (m, 1 H), 8.11 (s, 2 H), 8.00 (d, J = 8.0 Hz, 2 H), 7.98-7.93 (m, 1 H), 7.42 (d, J = 8.0 Hz, 2 H), 7.19-7.16 (m, 1 H), 7.02-6.91 (m, 3 H), 6.86-6.84 (m, 1 H), 6.28 (dd, J = 4.4, 9.6 Hz, 1 H), 5.34 (brs, 1 H), 4.47-4.45 (m, 2 H), 3.87 (s, 2 H), 3.86 (s, 3 H), 3.66 (dd, J = 9.6, 14.0 Hz, 1 H), 3.33 (dd, J = 4.4, 14.0 Hz, 1 H), 1.32-1.24 (m, 1 H), 0.64-0.61 (m, 2 H), 0.37-0.34 (m, 2 H). LCMS (Method 1): [MH+] = 594 at 2.73 min. |

-continued

| Structure | Intermediate number | Precursor | Analytical Data |
|---|---|---|---|
| 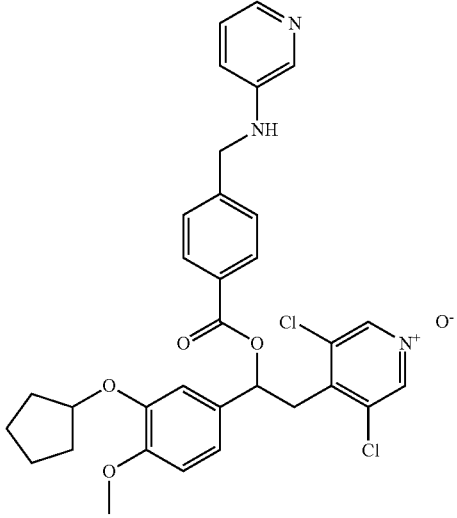 | Intermediate 122 | Intermediate 100 | ¹H NMR (400 MHz, CDCl₃): δ 8.16 (s, 2 H), 8.11-8.06 (m, 1 H), 8.01-7.98 (m, 3 H), 7.43-7.41 (m, 2 H), 7.21-7.19 (m, 1 H), 7.07-6.96 (m, 2 H), 6.85-6.81 (m, 2 H), 6.28 (dd, J = 4.4, 9.6 Hz, 1 H), 4.78-4.76 (m, 1 H), 4.43-4.42 (m, 2 H), 4.13-4.11 (m, 1 H), 3.83 (s, 3 H), 3.69 (dd, J = 9.6, 14.0 Hz, 1 H), 3.33 (dd, J = 4.4, 14.0 Hz, 1 H), 1.92-1.82 (m, 6 H), 1.27-1.24 (m, 2 H). LCMS (Method 1): [MH+] = 6.08 at 2.81 min. |
| 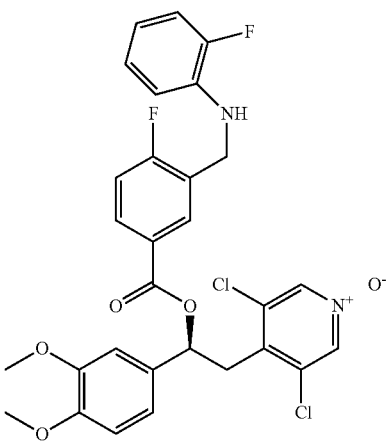 | Intermediate 123 | Intermediate 95 | ¹H NMR (400 MHz, CDCl₃): δ 8.10 (dd, J = 7.2, 2.2 Hz, 1 H), 8.05 (s, 2 H), 7.95-7.90 (m, 1 H), 7.12 (t, J = 9.0 Hz, 1 H), 7.02 (ddd, J = 11.9, 8.0, 1.4 Hz, 1 H), 6.98-6.92 (m, 3 H), 6.84 (d, J = 8.2 Hz, 1 H), 6.71-6.64 (m, 1 H), 6.63-6.55 (m, 1 H), 6.24 (dd, J = 10.1, 4.3 Hz, 1 H), 4.52-4.39 (m, 3 H), 3.87 (s, 3 H), 3.86 (s, 3 H), 3.65 (dd, J = 14.0, 10.1 Hz, 1 H), 3.28 (dd, J = 14.0, 4.3 Hz, 1 H). HPLC (Method 1): [MH+] = 589 at 4.24 min |
| 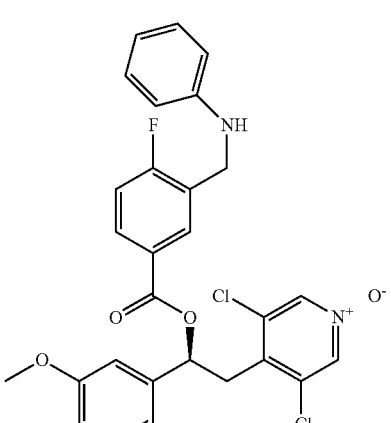 | Intermediate 124 | Intermediate 95 | ¹H NMR (400 MHz, CDCl₃): δ 8.10 (dd, J = 7.2, 2.0 Hz, 1 H), 8.06 (s, 2 H), 7.93 (ddd, J = 8.6, 5.1, 2.3 Hz, 1 H), 7.49 (d, J = 8.0 Hz, 1 H), 7.35-7.28 (m, 1 H), 7.18 (dd, J = 8.4, 7.2 Hz, 2 H), 7.11 (t, J = 8.9 Hz, 2 H), 6.95 (dd, J = 7.9, 1.8 Hz, 1 H), 6.93 (dd, J = 10.0, 2.0 Hz, 1 H), 6.83 (d, J = 8.2 Hz, 1 H), 6.24 (dd, J = 10.0, 4.3 Hz, 1 H), 4.44 (d, J = 5.3 Hz, 2 H), 4.13 (d, J = 6.7 Hz, 1 H), 3.87 (s, 3 H), 3.86 (s, 3 H), 3.65 (dd, J = 14.0, 10.0 Hz, 1 H), 3.29 (dd, J = 14.0, 4.3 Hz, 1 H). LCMS (Method 1) [MH+] = 571 at 4.23 min |

-continued

| Structure | Intermediate number | Precursor | Analytical Data |
|---|---|---|---|
| 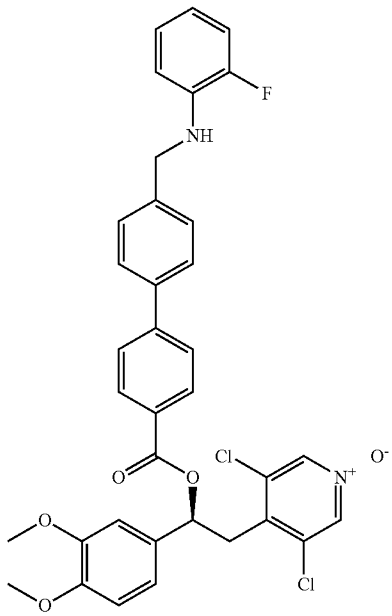 | Intermediate 125 | Intermediate 101 | ¹H NMR (400 MHz, CDCl$_3$): δ 8.13 (s, 2 H), 8.06 (d, J = 8.4 Hz, 2 H), 7.64 (d, J = 8.4 Hz, 2 H), 7.60 (d, J = 8.4 Hz, 2 H), 7.47 (d, J = 8.4 Hz, 2 H), 7.05-6.94 (m, 4 H), 6.87-6.85 (m, 1 H), 6.69-6.63 (m, 2 H), 6.32 (dd, J = 4.4, 9.6 Hz, 1 H), 4.45-4.43 (m, 3 H), 3.90 (s, 3 H), 3.88 (s, 3 H), 3.73 (dd, J = 9.6, 14.0 Hz, 1 H), 3.38 (dd, J = 4.4, 14.0 Hz, 1 H). LCMS (Method 1): [MH+] = 647 at 4.58 min. |
| 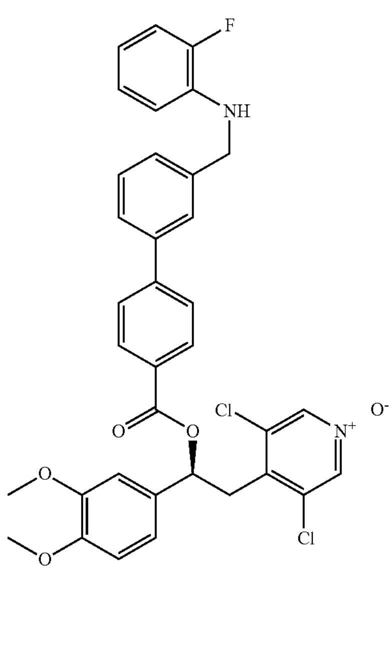 | Intermediate 126 | Intermediate 102 | ¹H NMR (400 MHz, CDCl$_3$): δ 8.13 (s, 2 H), 8.09-8.07 (m, 2 H), 7.65-7.62 (m, 3 H), 7.54-7.51 (m, 1 H), 7.46-7.39 (m, 2 H), 7.05-6.93 (m, 4 H), 6.86 (d, J = 8.4 Hz, 1 H), 6.70-6.61 (m, 2 H), 6.32 (dd, J = 4.4, 9.6 Hz, 1 H), 4.43-4.40 (m, 3 H), 3.89 (s, 3 H), 3.87 (s, 3 H), 3.73 (dd, J = 9.6, 14.0 Hz, 1 H), 3.35 (dd, J = 4.4, 14.0 Hz, 1 H). LCMS (Method 1): [MH+] = 647 at 4.59 min. |

-continued

| Structure | Intermediate number | Precursor | Analytical Data |
|---|---|---|---|
| 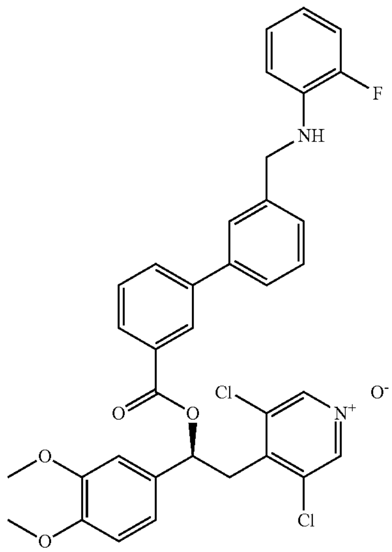 | Intermediate 127 | Intermediate 103 | $^1$H NMR (400 MHz, CDCl$_3$): δ 8.25 (s, 1 H), 8.12 (s, 2 H), 8.00-7.99 (m, 1 H), 7.78-7.76 (m, 1 H), 7.61 (s, 1 H), 7.52-7.39 (m, 4 H), 7.06-6.94 (m, 4 H), 6.85 (d, J = 8.4 Hz, 1 H), 6.71-6.60 (m, 2 H), 6.31 (dd, J = 4.4, 9.6 Hz, 1 H), 4.45-4.44 (m, 3 H), 3.89 (s, 3 H), 3.87 (s, 3 H), 3.37 (dd, J = 9.6, 14.0 Hz, 1 H), 3.35 (dd, J = 4.4, 14.0 Hz, 1 H). LCMS (Method 1): [MH+] = 647 at 4.60 min. |
| 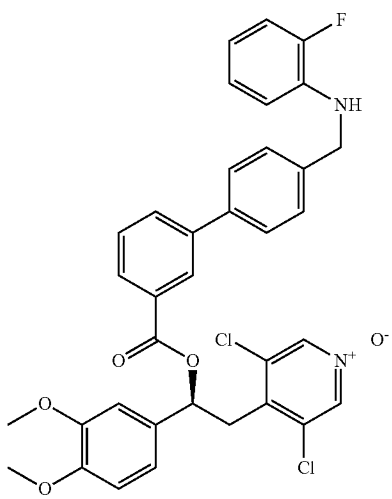 | Intermediate 128 | Intermediate 104 | $^1$H NMR (400 MHz, CDCl$_3$): δ 8.26 (s, 1 H), 8.12 (s, 2 H), 8.00-7.98 (m, 1 H), 7.77-7.75 (m, 1 H), 7.58-7.56 (m, 2 H), 7.51-7.45 (m, 3 H), 7.05-6.93 (m, 4 H), 6.85 (d, J = 8.4 Hz, 1 H), 6.69-6.60 (m, 2 H), 6.32 (dd, J = 4.4, 9.6 Hz, 1 H), 4.44-4.42 (m, 3 H), 3.89 (s, 3 H), 3.86 (s, 3 H), 3.72 (dd, J = 9.6, 14.0 Hz, 1 H), 3.36 (dd, J = 4.4, 14.0 Hz, 1 H). LCMS (Method 1): [MH+] = 647 at 4.61 min. |
| 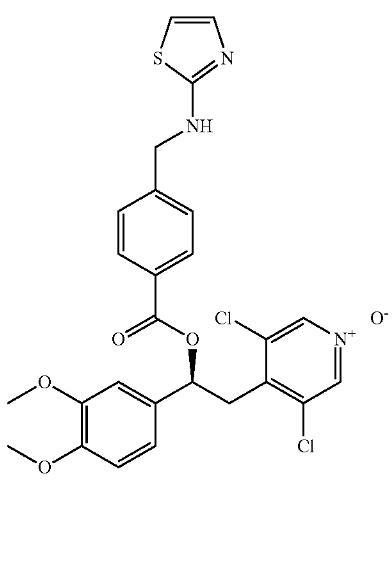 | Intermediate 129 | Intermediate 94 | $^1$H NMR (400 MHz, CDCl$_3$): δ 8.12 (s, 2 H), 8.00 (d, J = 8.1 Hz, 2 H), 7.44 (d, J = 8.1 Hz, 2 H), 7.08 (d, J = 3.6 Hz, 1 H), 7.04 (d, J = 3.6 Hz, 1 H), 7.02 (dd, J = 8.3, 2.5 Hz, 1 H), 6.98 (d, J = 2.1 Hz, 1 H), 6.85 (d, J = 8.2 Hz, 1 H), 6.30 (dd, J = 9.6, 4.5 Hz, 1 H), 5.12-5.01 (bs, 1H), 4.56 (s, 2 H), 3.90 (s, 3 H), 3.87 (s, 3 H), 3.70 (dd, J = 14.7, 9.7 Hz, 1 H), 3.35 (dd, J = 14.7, 4.3 Hz, 1 H). LCMS (Method 1) [MH+] = 560 at 2.74 min |

-continued

| Structure | Intermediate number | Precursor | Analytical Data |
|---|---|---|---|
| 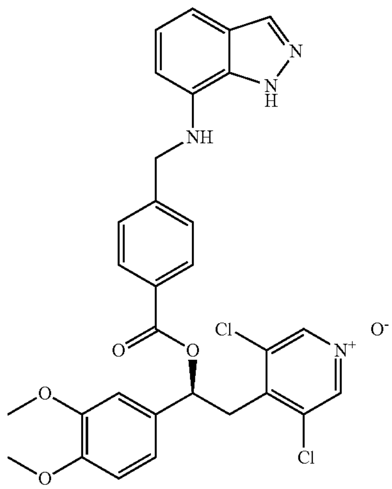 | Intermediate 130 | Intermediate 94 | ¹H NMR (400 MHz, CDCl₃): δ 8.07 (s, 2 H), 8.02 (s, 1 H), 7.96 (d, J = 8.03 Hz, 2 H), 7.46 (d, J = 8.01 Hz, 2 H), 7.16 (d, J = 8.12 Hz, 1 H), 7.03-6.96 (m, 3 H), 6.85 (d, J = 8.16 Hz, 1 H), 6.44 (d, J = 7.34 Hz, 1 H), 6.31 (dd, J = 9.73, 4.62 Hz, 1 H), 4.52 (s, 2 H), 3.88 (d, J = 9.08 Hz, 6 H), 3.71 (dd, J = 13.97, 9.70 Hz, 1 H), 3.34 (dd, J = 14.00, 4.70 Hz, 1 H). LCMS (Method 1): [MH+] = 593 at 3.83 min |
| 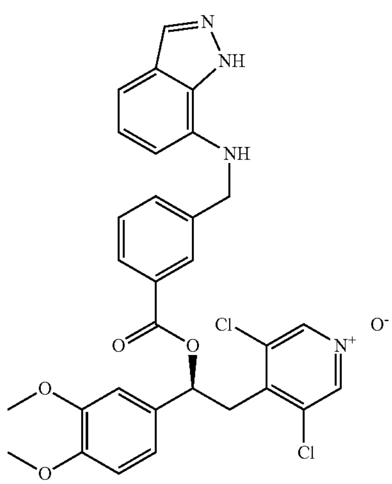 | Intermediate 131 | Intermediate 93 | ¹H NMR (400 MHz, CDCl₃): δ 8.07-8.00 (m, 3 H), 7.93 (s, 1 H), 7.88 (d, J = 7.84 Hz, 1 H), 7.60 (d, J = 7.74 Hz, 1 H), 7.40 (t, J = 7.79 Hz, 1 H), 7.17 (d, J = 8.09 Hz, 1 H), 7.04-6.95 (m, 3 H), 6.86 (d, J = 8.24 Hz, 1 H), 6.47 (d, J = 7.38 Hz, 1 H), 6.35 (dd, J = 9.99, 4.77 Hz, 1 H), 5.10 (s, 1 H), 4.49 (d, J = 5.85 Hz, 2 H), 3.88 (t, J = 10.44 Hz, 7 H), 3.66 (dd, J = 13.94, 9.98 Hz, 1 H), 3.36 (dd, J = 13.95, 4.75 Hz, 1 H). LCMS (Method 1): [MH+] = 593 at 3.84 min |
| 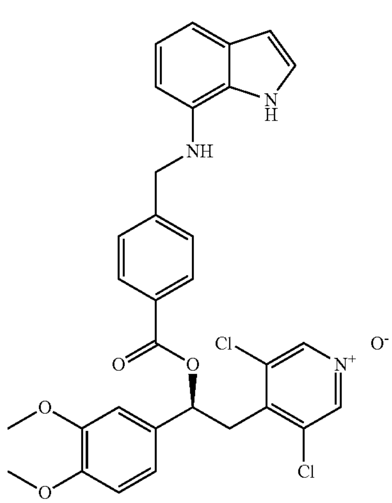 | Intermediate 132 | Intermediate 94 | ¹H NMR (400 MHz, CDCl₃): δ 8.42 (s, 1 H), 8.08 (t, J = 9.97 Hz, 2 H), 7.96 (t, J = 8.10 Hz, 2 H), 7.45 (dd, J = 16.60, 8.05 Hz, 2 H), 7.18-7.13 (m, 2 H), 7.03-6.95 (m, 3 H), 6.85 (d, J = 8.21 Hz, 1 H), 6.54 (dd, J = 3.18, 1.96 Hz, 1 H), 6.45 (d, J = 7.50 Hz, 1 H), 6.30 (dd, J = 9.81, 4.62 Hz, 1 H), 4.50 (s, 2 H), 4.13 (s, 1 H), 3.88 (d, J = 8.13 Hz, 6 H), 3.75-3.65 (m, 1 H), 3.34 (dd, J = 13.98, 4.65 Hz, 1 H), LCMS (Method 1): [MH+] = 592 at 4.05 min. |

-continued

| Structure | Intermediate number | Precursor | Analytical Data |
|---|---|---|---|
| 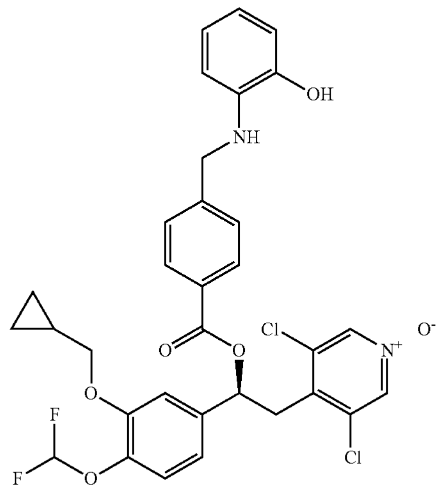 | Intermediate 133 | Intermediate 96 | ¹H NMR (400 MHz, CDCl₃): δ 8.14 (s, 2 H), 7.97 (d, J = 8.09 Hz, 2 H), 7.44 (d, J = 8.06 Hz, 2 H), 7.17 (d, J = 8.12 Hz, 1 H), 7.07-6.97 (m, 3 H), 6.81-6.72 (m, 2 H), 6.65-6.59 (m, 1 H), 6.55-6.52 (m, 1 H), 6.27 (dd, J = 10.06, 4.19 Hz, 1 H), 5.17 (s, 1 H), 4.43 (s, 2 H), 3.88 (d, J = 6.89 Hz, 2 H), 3.68 (dd, J = 14.06, 10.09 Hz, 1 H), 3.31 (dd, J = 14.07, 4.23 Hz, 1 H), 2.28 (s, 1 H), 1.30-1.24 (m, 1 H), 0.67-0.61 (m, 2 H), 0.38-0.33 (m, 2 H). LCMS (Method 2): [MH+] = 645 at 3.66 min. |
| 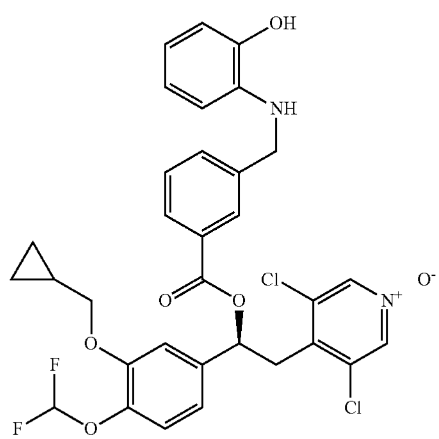 | Intermediate 134 | Intermediate 97 | LCMS (Method 2): [MH+] = 645 at 3.71 min. |
| 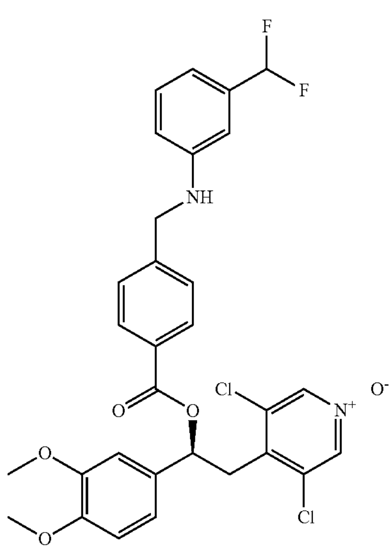 | Intermediate 135 | Intermediate 94 | ¹H NMR (400 MHz, CDCl₃): δ 8.12 (s, 2 H), 8.00 (d, J = 8.1 Hz, 2 H), 7.42 (d, J = 8.1 Hz, 2 H), 7.22 (t, J = 7.9 Hz, 1 H), 7.04-6.98 (m, 2 H), 6.88-6.81 (m, 2 H), 6.73 (s, 1 H), 6.71-6.40 (m, 2 H), 6.30 (dd, J = 9.8, 4.5 Hz, 1 H), 4.43 (d, J = 5.7 Hz, 2 H), 4.30 (t, J = 5.7 Hz, 1 H), 3.90 (s, 3 H), 3.87 (s, 3 H), 3.71 (dd, J = 14.0, 9.8 Hz, 1 H), 3.35 (dd, J = 14.0, 4.6 Hz, 1 H). LCMS (Method 1): [MH+] = 603 at 4.17 min. |

-continued

| Structure | Intermediate number | Precursor | Analytical Data |
|---|---|---|---|
| 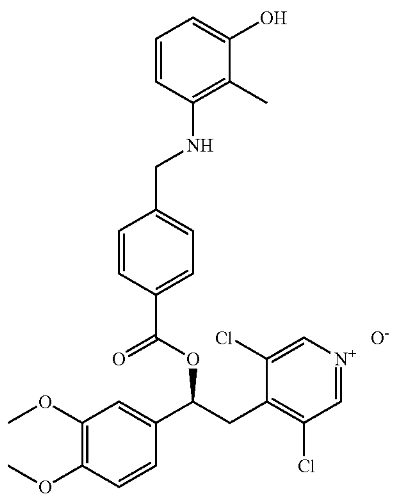 | Intermediate 136 | Intermediate 94 | LCMS (Method 1): [MH+] = 583 at 3.70 min. |
| 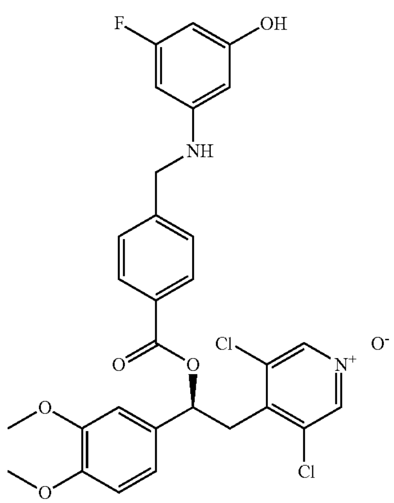 | Intermediate 137 | Intermediate 94 | LCMS (Method 1): [MH+] = 587 at 3.56 min. |
| 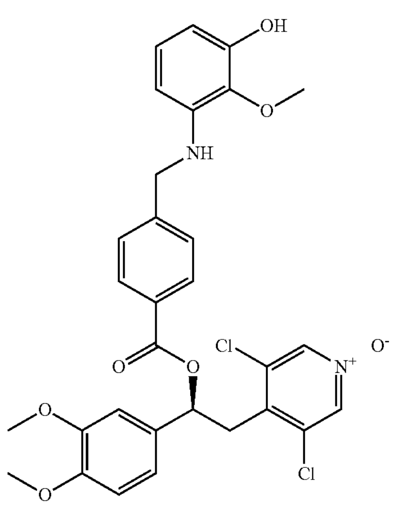 | Intermediate 138 | Intermediate 94 | LCMS (Method 1): [MH+] = 599 at 3.69 min. |

| Structure | Intermediate number | Precursor | Analytical Data |
|---|---|---|---|
| 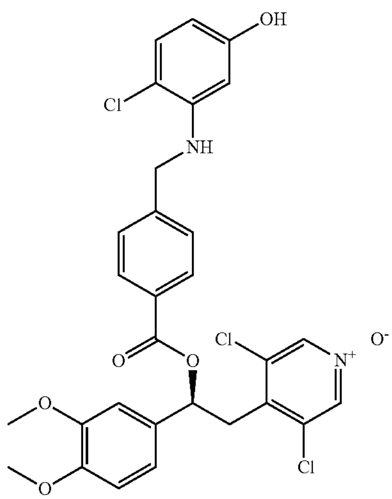 | Intermediate 139 | Intermediate 94 | LCMS (Method 2): [MH+] = 603 at 3.71 min. |
| 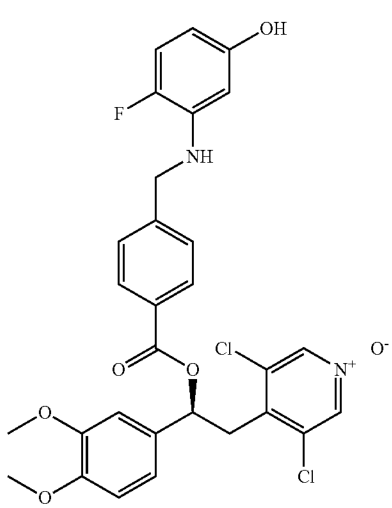 | Intermediate 140 | Intermediate 94 | LCMS (Method 1): [MH+] = 587 at 3.70 min. |

-continued

| Structure | Intermediate number | Precursor | Analytical Data |
|---|---|---|---|
| 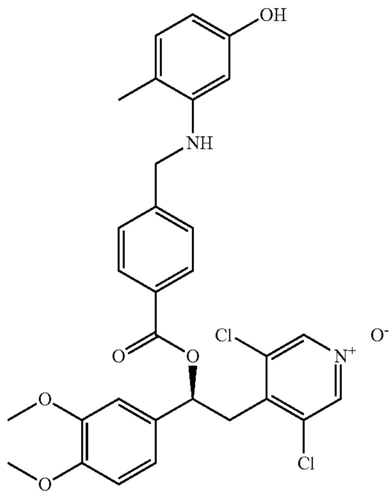 | Intermediate 141 | Intermediate 94 | LCMS (Method 2): [MH+] = 583 at 3.58 min. |
| 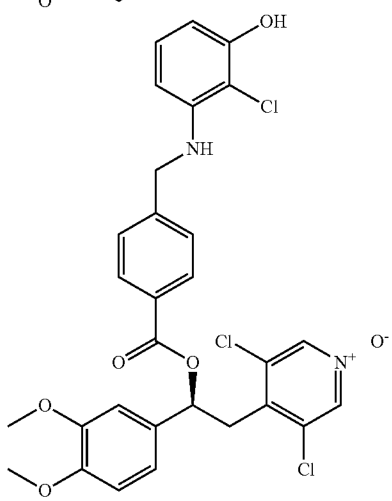 | Intermediate 142 | Intermediate 94 | LCMS (Method 2): [MH+] = 603 at 3.63 min |

Example 94

[(1S)-2-(3,5-dichloro-1-oxido-pyridin-1-ium-4-yl)-1-(3,4-dimethoxyphenyl)ethyl]3-[(2-chloro-N-[(3R)-quinuclidin-3-yl]oxycarbonyl-anilino)methyl]benzoate

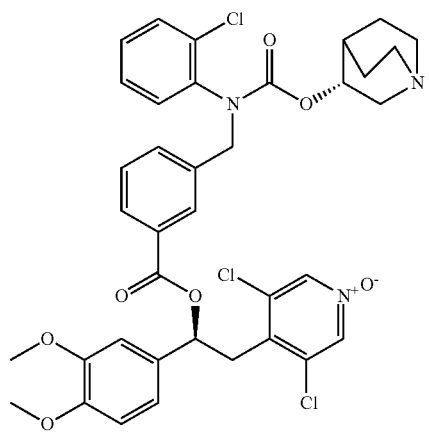

A suspension of [(1S)-2-(3,5-dichloro-1-oxido-pyridin-1-ium-4-yl)-1-(3,4-dimethoxyphenyl)ethyl]3-[(2-chloroanilino)methyl]benzoate (72 mg, 0.123 mmol) and (R)-quinuclidin-3-yl carbonochloridate hydrochloride (138 mg, 0.612 mmol) in anhydrous $CH_3CN$ (1 mL) was heated at 80° C. for 3 minutes under microwave irradiation. After cooling to room temperature, the solvent was removed in vacuo. Purification of the crude material by preparative HPLC afforded the title compound as a yellow solid (47.8 mg, 53%).

$^1$H NMR (400 MHz, DMSO at 125° C.): δ 8.23 (s, 2H), 7.84 (br s, 1H), 7.78 (d, J=7.8 Hz, 1H), 7.46-7.39 (m, 2H), 7.36 (t, J=7.6 Hz, 1H), 7.26-7.17 (m, 2H), 7.10-7.06 (m, 1H), 6.96 (d, J=2.0 Hz, 1H), 6.95-6.88 (m, 2H), 6.21 (dd, J=8.9, 4.8 Hz, 1H), 4.76 (br s, 2H), 4.65-4.60 (m, 1H), 3.72 (s, 6H), 3.56 (dd, J=14.2, 9.1 Hz, 1H), 3.32 (dd, J=14.2, 4.9 Hz, 1H), 3.05-2.97 (m, 1H), 2.61-2.45 (m, 5H), 1.80-1.74 (m, 1H), 1.55-1.45 (m, 1H), 1.45-1.35 (m, 1H), 1.28-1.17 (m, 1H), 1.15-1.04 (m, 1H). LCMS (Method 1): [MH+]=742 at 2.77 min.

The following compounds were synthesized similarly to the method of the example 94.

| Structure | Example number | Precursor | Analytical Data |
|---|---|---|---|
| [(1S)-2-(3,5-dichloro-1-oxido-pyridin-1-ium-4-yl)-1-(3,4-dimethoxyphenyl)ethyl] 3-[(2,4-difluoro-N-[(3R)-quinuclidin-3-yl]oxycarbonyl-anilino)methyl]benzoate 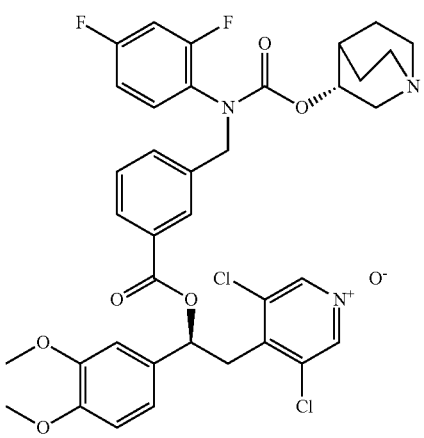 | Example 95 | Intermediate 106 | $^1$H NMR (400 MHz, CDCl$_3$): δ 8.13 (s, 2 H), 7.93 (d, J = 7.7 Hz, 1 H), 7.88 (s, 1 H), 7.45 (d, J = 7.6 Hz, 1 H), 7.38 (t, J = 7.7 Hz, 1 H), 7.02-6.94 (m, 3 H), 6.89-6.77 (m, 3 H), 6.30-6.24 (m, 1 H), 4.91-4.74 (m, 3 H), 3.90 (s, 3 H), 3.88 (s, 3 H), 3.69 (dd, J = 14.0, 9.7 Hz, 1 H), 3.38-3.24 (m, 2 H), 2.90-2.80 (m, 3 H), 2.76-2.60 (m, 2 H), 2.08-2.02 (m, 1H), 1.78-1.68 (m, 1 H), 1.67-1.56 (m, 1 H), 1.46-1.29 (s, 2 H). LCMS (Method 1): [MH+] = 742 at 2.85 min. |
| [(1S)-2-(3,5-dichloro-1-oxido-pyridin-1-ium-4-yl)-1-(3,4-dimethoxyphenyl)ethyl] 4-fluoro-3-[(2-fluoro-N-[(3R)-quinuclidin-3-yl]oxycarbonyl-anilino)methyl]benzoate 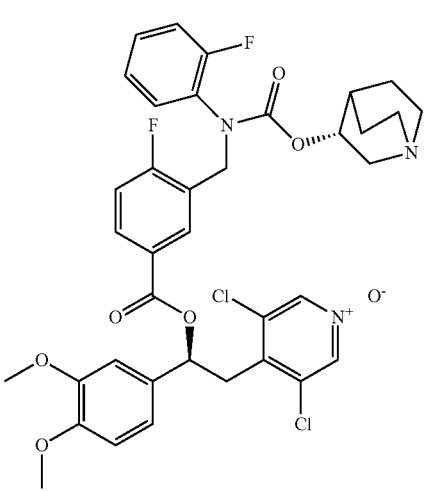 | Example 96 | Intermediate 123 | $^1$H NMR (400 MHz, CDCl$_3$): δ 8.13-8.11 (m, 3 H), 7.93-7.90 (m, 1 H), 7.24-7.22 (m, 1 H), 7.18-6.98 (m, 6 H), 6.86 (d, J = 8.0 Hz, 1 H), 6.25 (dd, J = 4.4, 9.6 Hz, 1 H), 4.92 (s, 2 H), 4.81-4.78 (m, 1 H), 3.90 (s, 3 H), 3.88 (s, 3 H), 3.68 (dd, J = 9.6, 14.0 Hz, 1 H), 3.33 (dd, J = 4.4, 14.0 Hz, 1 H), 3.20-3.15 (m, 1 H), 2.70-2.59 (m, 5 H), 1.99-1.93 (m, 1 H), 1.62-1.57 (m, 1 H), 1.53-1.47 (m, 1 H), 1.36-1.24 (m, 1 H), 1.22-1.14 (m, 1 H). LCMS (Method 1): [MH+] = 742 at 2.75 min. |

-continued

| Structure | Example number | Precursor | Analytical Data |
|---|---|---|---|
| [(1S)-2-(3,5-dichloro-1-oxido-pyridin-1-ium-4-yl)-1-(3,4-dimethoxyphenyl)ethyl] 4-fluoro-3-[(N-[(3R)-quinuclidin-3-yl]oxycarbonylanilino)methyl]benzoate 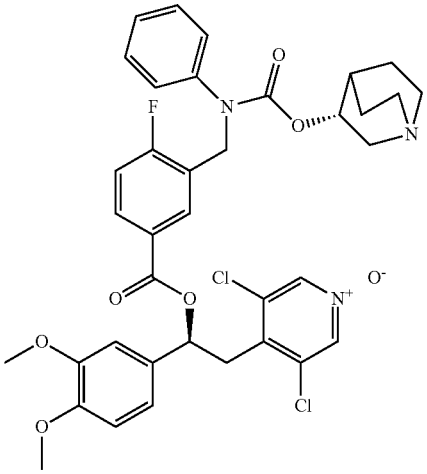 | Example 97 | Intermediate 124 | $^1$H NMR (400 MHz, CDCl$_3$): δ 8.10-8.06 (m, 3 H), 7.95-7.91 (m, 1 H), 7.33-7.29 (m, 2 H), 7.24-7.18 (m, 3 H), 7.05 (t, J = 8.9 Hz, 1 H), 6.99-6.95 (m, 2 H), 6.85 (d, J = 8.0 Hz, 1 H), 6.25 (dd, J = 4.4, 9.6 Hz, 1 H), 4.97 (s, 2 H), 4.79-4.77 (m, 1 H), 3.88 (s, 3 H), 3.87 (s, 3 H), 3.66 (dd, J = 9.6, 14.0 Hz, 1 H), 3.33 (dd, J = 4.4, 14.0 Hz, 1 H), 3.17-3.15 (m, 1 H), 2.72-2.59 (m, 5 H), 2.00-1.92 (m, 1 H), 1.60-1.57 (m, 1 H), 1.52-1.47 (m, 1 H), 1.42-1.31 (m, 1 H), 1.24-1.17 (m, 1 H). LCMS (Method 2): [MH+] = 724 at 3.48 min |
| [(1S)-2-(3,5-dichloro-1-oxido-pyridin-1-ium-4-yl)-1-(3,4-dimethoxyphenyl)ethyl] 4-[(2-fluoro-4-methoxy-N-[(3R)-quinuclidin-3-yl]oxycarbonyl-anilino)methyl]benzoate 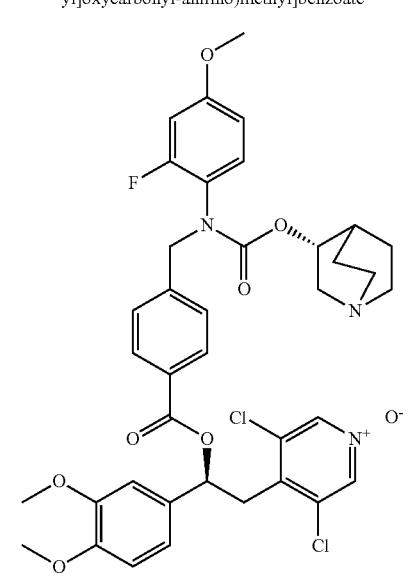 | Example 98 | Intermediate 107 | $^1$H NMR (400 MHz, DMSO): δ 8.53 (s, 2 H), 7.99-7.88 (m, 2 H), 7.48-7.32 (m, 2 H), 7.29-7.14 (m, 1 H), 7.07-6.93 (m, 3 H), 6.91-6.81 (m, 1 H), 6.78-6.65 (m, 1 H), 6.21 (dd, J = 9.6, 4.4 Hz, 1 H), 4.91-4.69 (m, 2 H), 4.69-4.58 (m, 1 H), 3.77 (s, 3 H), 3.74 (s, 3 H), 3.73 (s, 3 H), 3.61 (dd, J = 14.0, 4.4 Hz, 1 H), 3.47-3.45 (m, 1 H), 3.11-3.01 (m, 1 H), 2.67-2.53 (m, 3 H), 2.46-2.33 (m, 2 H), 1.94-1.73 (m, 1 H), 1.59-1.36 (m, 2 H), 1.28-1.09 (m, 2 H). LCMS (Method 1): [MH+] = 754 at 2.78 min. |

-continued

| Structure | Example number | Precursor | Analytical Data |
|---|---|---|---|
| [(1S)-2-(3,5-dichloro-1-oxido-pyridin-1-ium-4-yl)-1-(3,4-dimethoxyphenyl)ethyl] 4-[[2-(difluoromethoxy)-N-[(3R)-quinuclidin-3-yl]oxycarbonyl-anilino]methyl]benzoate 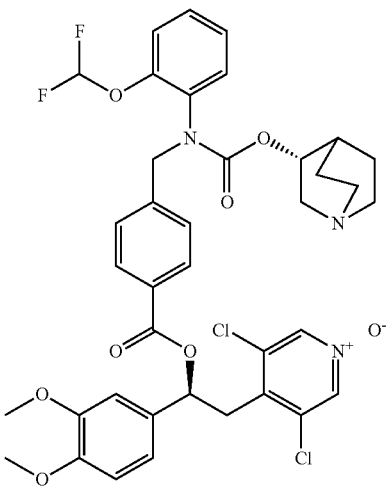 | Example 99 | Intermediate 108 | $^1$H NMR (400 MHz, DMSO @ 110° C.): δ 8.32 (s, 2 H), 7.91-7.88 (m, 2 H), 7.40-7.30 (m, 3 H), 7.25-7.14 (m, 3 H), 7.04-6.94 (m, 4 H), 6.26 (dd, J = 4.8, 9.1 Hz, 1 H), 4.81-4.80 (m, 2 H), 4.67-4.63 (m, 1 H), 3.78 (s, 3 H), 3.77 (s, 3 H), 3.62 (dd, J = 9.1, 14.1 Hz, 1 H), 3.37 (dd, J = 4.8, 14.1 Hz, 1 H), 3.08-3.04 (m, 1 H), 2.65-2.50 (m, 5 H), 1.82-1.80 (m, 1 H), 1.58-1.52 (m, 1 H), 1.49-1.41 (m, 1 H), 1.34-1.27 (m, 1 H), 1.20-1.17 (m, 1 H). LCMS (Method 2): [MH+] = 772 at 3.58 min. |
| [(1S)-2-(3,5-dichloro-1-oxido-pyridin-1-ium-4-yl)-1-(3,4-dimethoxyphenyl)ethyl] 4-[(2-fluoro-6-methoxy-N-[(3R)-quinuclidin-3-yl]oxycarbonyl-anilino)methyl]benzoate formate salt 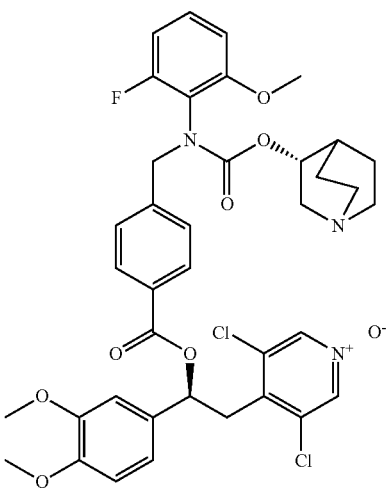 | Example 100 | Intermediate 109 | $^1$H NMR (400 MHz, DMSO @ 125° C.): δ 8.31 (s, 2 H), 8.20 (s, 1 H), 7.89 (d, J = 8.4 Hz, 2 H), 7.39 (d, J = 8.4 Hz, 2 H), 7.30-7.24 (m, 1 H), 7.06-6.97 (m, 3 H), 7.06-7.04 (m, 1 H), 6.89-6.74 (m, 1 H), 6.28 (dd, J = 4.8, 9.2 Hz, 1 H), 4.81-4.66 (m, 3 H), 3.80 (s, 3 H), 3.79 (s, 3 H), 3.77 (s, 3 H), 3.64 (dd, J = 9.2, 14.0 Hz, 1 H), 3.40 (dd, J = 4.8, 14.0 Hz, 1 H), 3.10-3.04 (m, 1 H), 2.66-2.54 (m, 5 H), 1.84-1.81 (m, 1 H), 1.58-1.56 (m, 1 H), 1.55-1.47 (m, 1 H), 1.43-1.31 (m, 1 H), 1.30-1.18 (m, 1 H). LCMS (Method 1): [MH+] = 754 at 2.76 min. |

-continued

| Structure | Example number | Precursor | Analytical Data |
|---|---|---|---|
| [(1S)-2-(3,5-dichloro-1-oxido-pyridin-1-ium-4-yl)-1-(3,4-dimethoxyphenyl)ethyl] 4-[(2-hydroxy-N-[(3R)-quinuclidin-3-yl]oxycarbonyl-anilino)methyl]benzoate<br>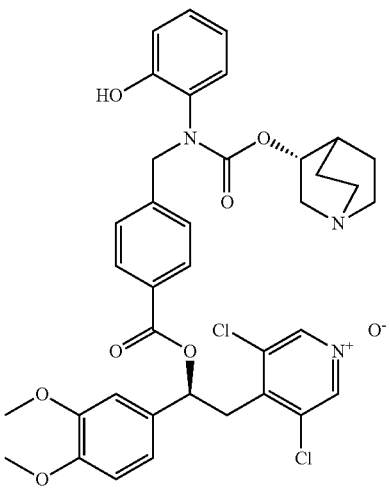 | Example 101 | Intermediate 110 | 1H NMR (400 MHz, CD$_3$CN): δ 8.22 (brs, 1 H), 8.09 (s, 2 H), 7.85 (d, J = 7.8 Hz, 2 H), 7.32-7.30 (m, 2 H), 7.02-6.92 (m, 3 H), 6.86-6.78 (m, 3 H), 6.69-6.59 (m, 1 H), 6.13 (dd. J = 4.6, 9.6 Hz, 1 H), 4.93-4.70 (m, 2 H), 4.63-4.50 (m, 1 H), 3.78 (s, 3 H), 3.75 (s, 3 H), 3.59 (dd, J = 9.6, 14.0 Hz, 1 H), 3.25 (dd, J = 4.6, 14.0 Hz, 1 H), 3.22-3.13 (m, 1 H), 2.92-2.72 (m, 5 H), 2.02-1.92 (m, 1 H), 1.66-1.53 (m, 1 H), 1.52-1.39 (m, 1 H), 1.28-1.13 (m, 2 H). LCMS (Method 1): [MH+] = 722 at 2.68 min. |
| [(1S)-2-(3,5-dichloro-1-oxido-pyridin-1-ium-4-yl)-1-(3,4-dimethoxyphenyl)ethyl] 4-[(3-hydroxy-N-[(3R)-quinuclidin-3-yl]oxycarbonyl-anilino)methyl]benzoate trifluoroacetic acid salt<br>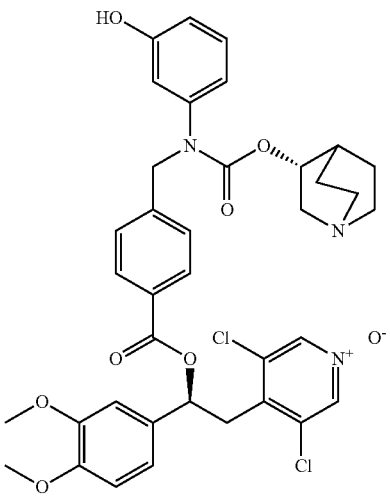 | Example 102 | Intermediate 111 | $^1$H NMR (400 MHz, CD$_3$CD): δ 8.21 (s, 2 H), 7.99 (d, J = 8.4 Hz, 2 H), 7.40 (d, J = 8.4 Hz, 2 H), 7.19-7.15 (m, 1 H), 7.09-7.05 (m, 2 H), 6.95-6.93 (m, 1 H), 6.77-6.70 (m, 3 H), 6.24 (dd, J = 4.4, 9.6 Hz, 1 H), 5.02-5.01 (m, 1 H), 4.94-4.92 (m, 2 H), 3.83 (s, 3 H), 3.81 (s, 3 H), 3.73 (dd, J = 9.6, 14.0 Hz, 1 H), 3.59-3.55 (m, 1 H), 3.39 (dd, J = 4.4, 14.0 Hz, 1 H), 3.22-3.13 (m, 4 H), 2.99-2.94 (m, 1 H), 2.24-2.21 (m, 1 H), 1.89-1.74 (m, 2 H), 1.70-1.69 (m, 2 H). OH not observed. LCMS (Method 1): [MH+] = 722 at 2.64 min. |

| Structure | Example number | Precursor | Analytical Data |
|---|---|---|---|
| [(1S)-2-(3,5-dichloro-1-oxido-pyridin-1-ium-4-yl)-1-(3,4-dimethoxyphenyl)ethyl] 4-[[(5-fluoro-3-pyridyl)-[(3R)-quinuclidin-3-yl]oxycarbonyl-amino]methyl]benzoate formate salt 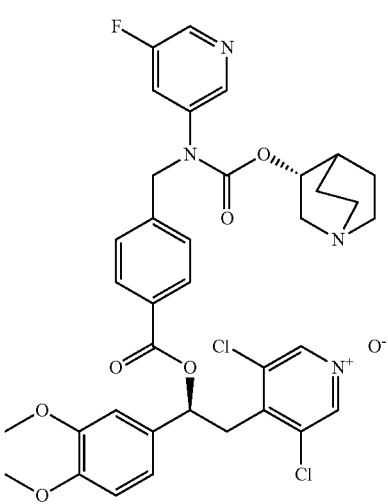 | Example 103 | Intermediate 112 | $^1$H NMR (400 MHz, CDCl$_3$): δ 8.38 (s, 1 H), 8.14 (s, 2 H), 7.99-7.97 (m, 3 H), 7.49 (brs, 1 H), 7.29-7.26 (m, 2 H), 7.03-6.97 (m, 2 H), 6.92-6.89 (m, 1 H), 6.86 (d, J = 8.4 Hz, 1 H), 6.30 (dd, J = 4.8, 10.0 Hz, 1 H), 4.99-4.96 (m, 1 H), 4.91-4.88 (m, 2 H), 3.93 (s, 3 H), 3.90 (s, 3 H), 3.71 (dd, J = 10.0, 14.0 Hz, 1 H), 3.42-3.36 (m, 2 H), 3.01-2.89 (m, 4 H), 2.80-2.77 (m, 1 H), 2.19-2.17 (m, 1 H), 1.87-1.86 (m, 1 H), 1.84-1.82 (m, 1 H), 1.61-1.49 (m, 2 H). LCMS (Method 1): [MH+] = 725 at 2.72 min |
| [(1S)-2-(3,5-dichloro-1-oxido-pyridin-1-ium-4-yl)-1-(3,4-dimethoxyphenyl)ethyl] 4-[[(4-fluoro-2-pyridyl)-[(3R)-quinuclidin-3-yl]oxycarbonyl-amino]methyl]benzoate formate salt 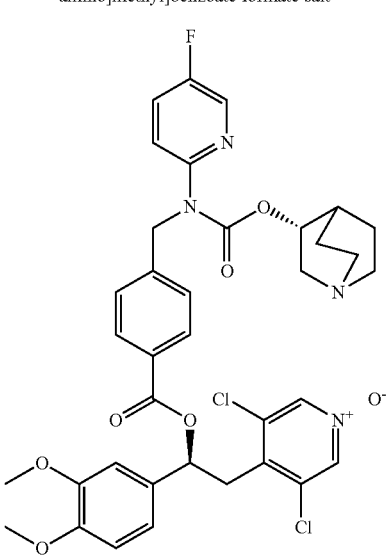 | Example 104 | Intermediate 113 | 1H NMR (400 MHz, DMSO): δ 8.55 (s, 2 H), 8.40 (s, 1 H), 8.38-8.37 (m, 1 H), 7.94-7.92 (m, 2 H), 7.85-7.77 (m, 2 H), 7.45-7.40 (m, 2 H), 7.05-6.95 (m, 3 H), 6.21 (dd, J = 9.6, 4.4 Hz, 1 H), 5.24-5.13 (m, 2 H), 4.76-4.73 (m, 1 H), 3.78 (s, 3 H), 3.74 (s, 3 H), 3.59 (dd, J = 9.6, 14.0 Hz, 1 H), 3.30 (dd, J = 4.4, 14.0 Hz, 1 H), 3.16-3.10 (m, 1 H), 2.70-2.51 (m, 4 H), 2.33-2.32 (m, 1 H), 1.89-1.88 (m, 1 H), 1.58-1.55 (m, 1 H), 1.53-1.47 (m, 1 H), 1.32-1.19 (m, 2 H). LCMS (Method 2): [MH+] = 725 at 3.63 min |

| Structure | Example number | Precursor | Analytical Data |
|---|---|---|---|
| [(1S)-2-(3,5-dichloro-1-oxido-pyridin-1-ium-4-yl)-1-(3,4-dimethoxyphenyl)ethyl] 4-[[3-(dimethylcarbamoyl)-N-[(3R)-quinuclidin-3-yl]oxycarbonyl-anilino]methyl]benzoate formate salt 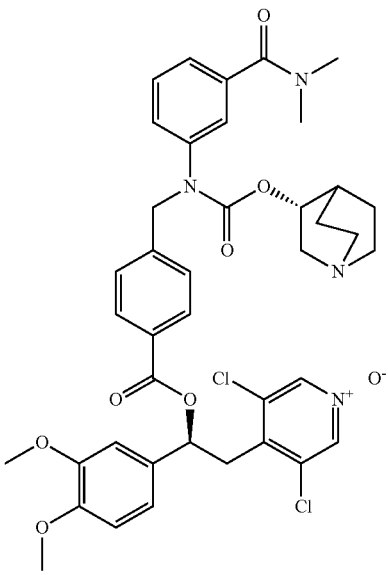 | Example 105 | Intermediate 114 | $^1$H NMR (400 MHz, DMSO): δ 8.53 (s, 2 H), 8.21 (s, 1 H), 7.94 (d, J = 8.4 Hz, 2 H), 7.42-7.35 (m, 4 H), 7.31-7.29 (m, 1 H), 7.22-7.20 (m, 1 H), 7.04-6.95 (m, 3 H), 6.20 (dd, J = 4.4, 9.6 Hz, 1 H), 4.99 (brs, 2H), 4.70-4.68 (m, 1 H), 3.77 (s, 3 H), 3.75 (s, 3 H), 3.66-3.57 (m, 1 H), 3.36-3.29 (m, 1 H), 3.16-3.06 (m, 1 H), 2.98 (brs, 3 H), 2.77 (brs, 3 H), 2.69-2.54 (m, 3 H), 2.47-2.30 (m, 2 H), 1.89-1.82 (m, 1 H), 1.63-1.52 (m, 1 H), 1.51-1.41 (m, 1 H), 1.33-1.24 (m, 1 H), 1.23-1.13 (m, 1 H). LCMS (Method 1): [MH+] = 777 at 2.65 min. |
| [(1S)-2-(3,5-dichloro-1-oxido-pyridin-1-ium-4-yl)-1-(3,4-dimethoxyphenyl)ethyl] 4-[[[(2-methoxy-3-pyridyl)-[(3R)-quinuclidin-3-yl]oxycarbonyl-amino]methyl]benzoate formate salt 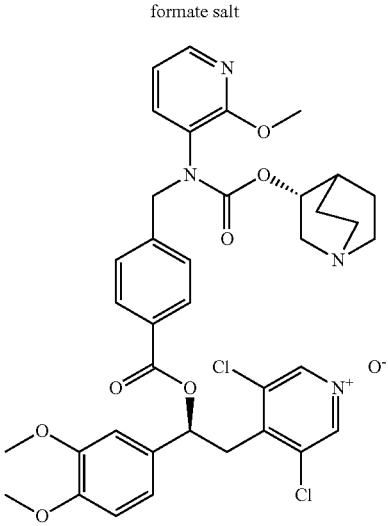 | Example 106 | Intermediate 115 | $^1$H NMR (400 MHz, CDCl$_3$): δ 8.40 (s, 1 H), 8.13 (s, 2 H), 8.10-8.06 (m, 1 H), 7.94 (d, J = 7.8 Hz, 2 H), 7.31 (d, J = 7.9 Hz, 2 H), 7.14 (d, J = 7.5 Hz, 1 H), 7.03-6.96 (m, 2 H), 6.85 (d, J = 8.2 Hz, 1 H), 6.83-6.76 (m, 1 H), 6.29 (dd, J = 9.6, 4.5 Hz, 1 H), 4.88 (br s, 2 H), 4.85-4.75 (m, 1 H), 3.92 (s, 3 H), 3.90 (s, 3 H), 3.88 (s, 3 H), 3.71 (dd, J = 14.0, 9.7 Hz, 1 H), 3.38-3.27 (m, 2 H), 2.94-2.84 (m, 3 H), 2.83-2.73 (m, 1 H), 2.70-2.59 (m, 1 H), 2.10-2.02 (m, 1 H), 1.82-1.71 (m, 1 H), 1.70-1.58 (m, 1 H), 1.45-1.28 (m, 2 H). LCMS (Method 1): [MH+] = 737 at 2.71 min. |

| Structure | Example number | Precursor | Analytical Data |
|---|---|---|---|
| [(1S)-2-(3,5-dichloro-1-oxido-pyridin-1-ium-4-yl)-1-(3,4-dimethoxyphenyl)ethyl] 4-[[(5-methoxy-3-pyridyl)-[(3R)-quinuclidin-3-yl]oxycarbonyl-amino]methyl]benzoate 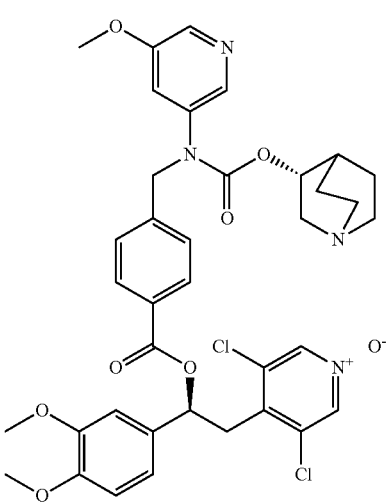 | Example 107 | Intermediate 116 | ¹H NMR (400 MHz, CDCl₃): δ 8.24-8.19 (m, 4 H), 8.01 (d, J = 8.0 Hz, 2 H), 7.34-7.28 (m, 3 H), 7.04-6.97 (m, 2 H), 6.86 (d, J = 8.3 Hz, 1 H), 6.31 (dd, J = 9.7, 4.5 Hz, 1 H), 5.13-5.07 (m, 1 H), 4.95 (s, 2 H), 3.91 (s, 3 H), 3.88 (s, 6 H), 3.74 (dd, J = 13.9, 9.7 Hz, 1 H), 3.60 (dd, J = 14.8, 8.6 Hz, 1 H), 3.38 (dd, J = 14.0, 4.7 Hz, 1 H), 3.34-3.15 (m, 4 H), 3.08-2.96 (m, 1 H), 2.39 (br s, 1 H), 2.09-1.98 (m, 1 H), 1.94-1.83 (m, 1 H), 1.73-1.65 (m, 2 H). LCMS (Method 2): [MH+] = 737 at 3.25 min. |
| [(1S)-2-(3,5-dichloro-1-oxido-pyridin-1-ium-4-yl)-1-(3,4-dimethoxyphenyl)ethyl] 4-[[(6-hydroxy-3-pyridyl)-[(3R)-quinuclidin-3-yl]oxycarbonyl-amino]methyl]benzoate 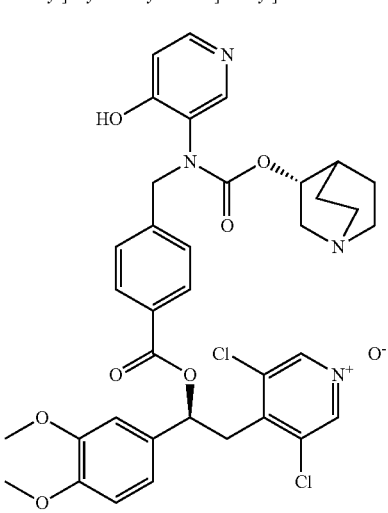 | Example 108 | Intermediate 117 | ¹H NMR (400 MHz, DMSO): δ 11.40 (br s, 1 H), 8.55 (s, 2 H), 7.92 (d, J = 8.0 Hz, 2 H), 7.60 (br s, 2 H), 7.50-7.42 (m, 2 H), 7.07-6.95 (m, 3 H), 6.27-6.18 (m, 2 H), 4.85-4.62 (m, 2 H), 4.58 (br s, 1 H), 3.78 (s, 3 H), 3.75 (s, 3 H), 3.63 (dd, J = 14.1, 9.6 Hz, 1 H), 3.40-3.30 (m, 1 H), 3.06-2.97 (m, 1 H), 2.66-2.48 (m, 5 H), 1.81 (br s, 1 H), 1.59-1.50 (m, 1 H), 1.50-1.38 (m, 1 H), 1.38-1.28 (m, 1 H), 1.22-1.10 (m, 1 H). LCMS (Method 1): [MH+] = 723 at 2.44 min. |

| Structure | Example number | Precursor | Analytical Data |
|---|---|---|---|
| [(1S)-2-(3,5-dichloro-1-oxido-pyridin-1-ium-4-yl)-1-(3,4-dimethoxyphenyl)ethyl] 4-[(2-cyano-N-[(3R)-quinuclidin-3-yl]oxycarbonyl-anilino)methyl]benzoate formate salt 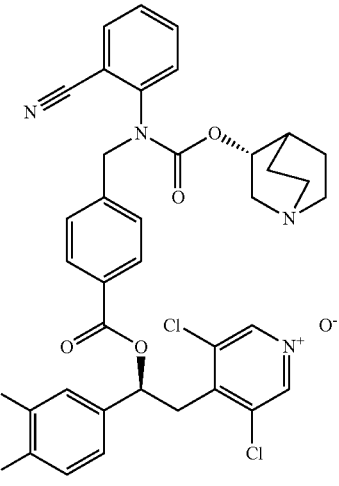 | Example 109 | Intermediate 118 | $^1$H NMR (400 MHz, CDCl$_3$): δ 8.41 (s, 1 H), 8.13 (s, 2 H), 7.96 (d, J = 7.8 Hz, 2 H), 7.66 (d, J = 7.6 Hz, 1 H), 7.57 (t, J = 7.9 Hz, 1 H), 7.39 (t, J = 7.7 Hz, 1 H), 7.33 (d, J = 8.0 Hz, 2 H), 7.17-7.10 (m, 1 H), 7.04-6.96 (m, 2 H), 6.86 (d, J = 8.2 Hz, 1 H), 6.29 (dd, J = 9.2, 4.3 Hz, 1 H), 5.04-4.85 (m, 3 H), 3.91 (s, 3 H), 3.88 (s, 3 H), 3.71 (dd, J = 13.8, 9.8 Hz, 1 H), 3.42-3.31 (m, 2 H), 2.98-2.87 (m, 3 H), 2.87-2.68 (m, 2 H), 2.20-2.10 (m, 1 H), 1.86-1.75 (m, 1 H), 1.75-1.64 (m, 1 H), 1.57-1.37 (m, 1 H). LCMS (Method 1): [MH+] = 731 at 2.71 min. |
| [(1S)-1-[3-(cyclopropylmethoxy)-4-(difluoromethoxy)phenyl]-2-(3,5-dichloro-1-oxido-pyridin-1-ium-4-yl)ethyl] 4-[[3-pyridyl-[(3R)-quinuclidin-3-yl]oxycarbonyl-amino]methyl]benzoate 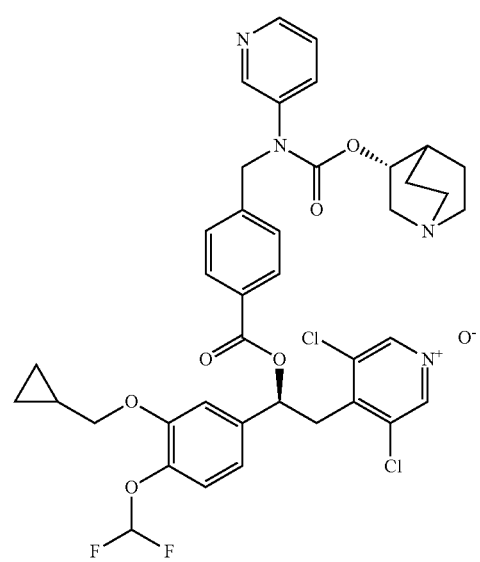 | Example 110 | Intermediate 119 | $^1$H NMR (400 MHz, CDCl$_3$): δ 8.46 (dd, J = 4.7, 1.6 Hz, 2 H), 8.14 (s, 2 H), 8.00-7.93 (m, 2 H), 7.47 (s, 1 H), 7.35-7.29 (m, 2 H), 7.26 (m, 1 H), 7.18 (d, J = 8.1 Hz, 1 H), 7.06-7.01 (m, 2 H), 6.61 (t, J = 75.3 Hz, 1 H), 6.27 (dd, J = 9.9, 4.2 Hz, 1 H), 4.97-4.89 (m, 2 H), 4.84-4.79 (m, 1 H), 3.89 (d, J = 6.9 Hz, 2 H), 3.68 (dd, J = 14.1, 10.0 Hz, 1 H), 3.31 (dd, J = 14.1, 4.3 Hz, 1 H), 3.26-3.18 (m, 1 H), 2.78-2.68 (m, 3 H), 2.66-2.50 (m, 2 H), 1.97-1.94 (m, 1 H), 1.70-1.60 (m, 1 H), 1.56-1.47 (m, 1 H), 1.30-1.31 (m, 3 H), 0.68-0.62 (m, 2 H), 0.39-0.34 (m, 2 H). LCMS (Method 1): [MH+] = 783 at 2.86 min. |

| Structure | Example number | Precursor | Analytical Data |
|---|---|---|---|
| [(1S)-2-(3,5-dichloro-1-oxido-pyridin-1-ium-4-yl)-1-[4-(difluoromethoxy)-3-isopropoxy-phenyl]ethyl] 4-[[3-pyridyl-[(3R)-quinuclidin-3-yl]oxycarbonyl-amino]methyl]benzoate 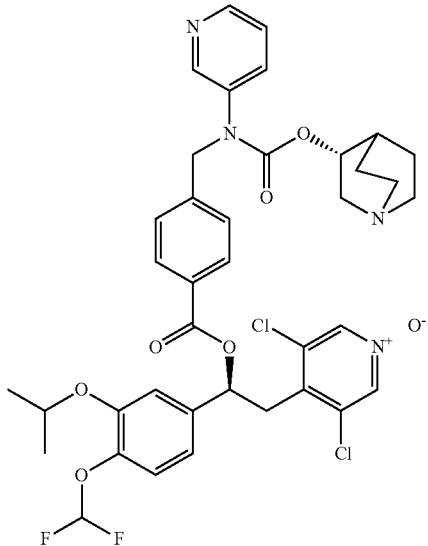 | Example 111 | Intermediate 120 | $^1$H NMR (400 MHz, CDCl$_3$): δ 8.48-8.44 (m, 2 H), 8.15 (s, 2 H), 7.98 (d, J = 8.0 Hz, 2 H), 7.53-7.45 (m, 1 H), 7.32 (d, J = 8.0 Hz, 2 H), 7.17 (d, J = 8.2 Hz, 1 H), 7.05-7.00 (m, 2 H), 6.55 (t, J = 75.3 Hz, 1 H), 6.27 (dd, J = 9.8, 4.4 Hz, 1 H), 4.96-4.88 (m, 2 H), 4.83-4.78 (m, 1 H), 4.60-4.53 (m, 1 H), 3.68 (dd, J = 14.0, 9.8 Hz, 1 H), 3.33 (dd, J = 14.1, 4.4 Hz, 1 H), 3.24-3.16 (m, 1 H), 2.79-2.51 (m, 6 H), 2.01-1.91 (m, 1 H), 1.68-1.60 (m, 1 H), 1.52 (m, 1 H), 1.39-1.30 (m, 8 H). LCMS (Method 1): [MH+] = 771 at 2.85 min. |
| [1-[3-(cyclopropylmethoxy)-4-methoxy-phenyl]-2-(3,5-dichloro-1-oxido-pyridin-1-ium-4-yl)ethyl] 4-[[3-pyridyl-[(3R)-quinuclidin-3-yl]oxycarbonyl-amino]methyl]benzoate 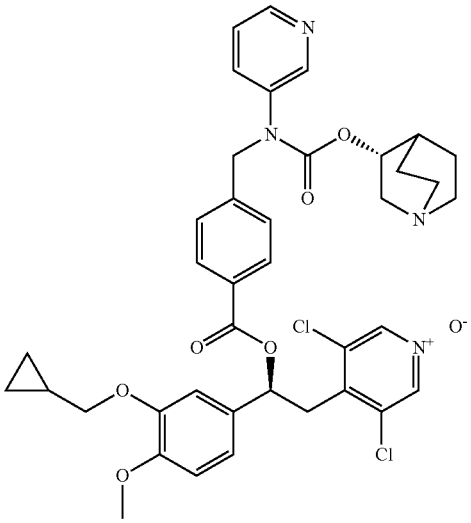 | Example 112 | Intermediatie 121 | $^1$H NMR (400 MHz, CDCl$_3$): δ 8.47-8.44 (m, 2 H), 8.14 (d, J = 3.0 Hz, 2 H), 8.00-7.94 (m, 2 H), 7.46 (s, 1 H), 7.34-7.27 (m, 3 H), 7.04-6.97 (m, 2 H), 6.86 (d, J = 8.2 Hz, 1 H), 6.28-6.23 (m, 1 H), 4.93 (s, 2 H), 4.83-4.78 (m, 1 H), 3.89-3.85 (m, 5 H), 3.70 (dd, J = 14.0, 9.8 Hz, 1 H), 3.33 (dd, J = 14.0, 4.6 Hz, 1 H), 3.25-3.17 (m, 1 H), 2.76-2.68 (m, 3 H), 2.64-2.56 (m, 2 H), 1.96 (m, 1 H), 1.68-1.60 (m, 1 H), 1.56-1.48 (m, 1 H), 1.38-1.21 (m, 3 H), 0.67-0.61 (m, 2 H), 0.39-0.34 (m, 2 H). LCMS (Method 1): [MH+] = 747 at 2.73 min. |

| Structure | Example number | Precursor | Analytical Data |
|---|---|---|---|
| [1-[3-(cyclopentoxy)-4-methoxy-phenyl]-2-(3,5-dichloro-1-oxido-pyridin-1-ium-4-yl)ethyl] 4-[[3-pyridyl-[(3R)-quinuclidin-3-yl]oxycarbonyl-amino]methyl]benzoate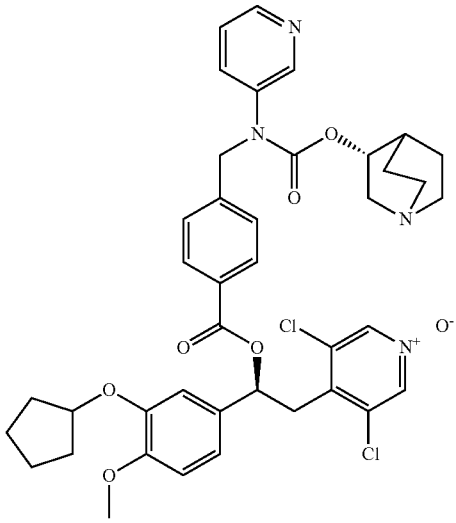 | Example 113 | Intermediate 122 | $^1$H NMR (400 MHz, CDCl$_3$): δ 8.55-8.50 (m, 2 H), 8.20 (d, J = 5.1 Hz, 2 H), 8.00 (d, J = 7.9 Hz, 2 H), 7.58-7.41 (m, 2 H), 7.29 (d, J = 8.1 Hz, 2 H), 7.02-6.95 (m, 2 H), 6.88-6.81 (m, 1 H), 6.33-6.24 (m, 1 H), 5.23-5.01 (m, 1 H), 4.97 (s, 2 H), 4.85-4.73 (m, 1 H), 3.84 (s, 3 H), 3.76-3.67 (m, 1 H), 3.74-3.47 (m, 1 H), 3.43-3.10 (m, 5 H), 3.15-2.90 (m, 1 H), 2.44-2.33 (m, 1 H), 2.08-1.83 (m, 9 H), 1.70-1.57 (m, 3 H). LCMS (Method 1): [MH+] = 761 at 2.81 min. |
| [(1S)-2-(3,5-dichloro-1-oxido-pyridin-1-ium-4-yl)-1-(3,4-dimethoxyphenyl)ethyl] 4-[3-[(2-fluoro-N-[(3R)-quinuclidin-3-yl]oxycarbonyl-anilino)methyl]phenyl]benzoate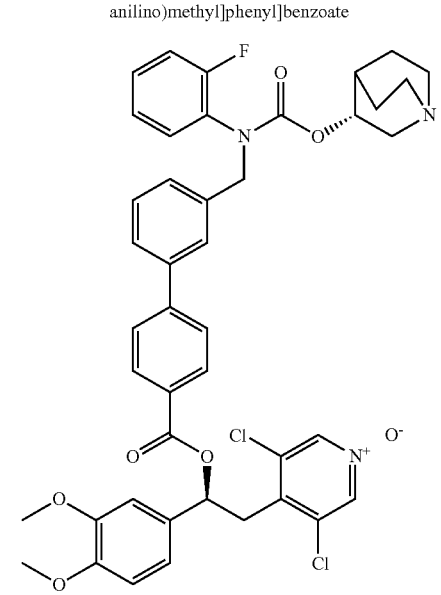 | Example 114 | Intermediatie 126 | $^1$H NMR (400 MHz, CDCl$_3$): δ 8.14 (s, 2 H), 8.07 (d, J = 8.4 Hz, 2 H), 7.59-7.57 (d, J = 8.4 Hz, 2 H), 7.51-7.48 (m, 2 H), 7.40-7.36 (m, 1 H), 7.28-7.22 (m, 2 H), 7.11-7.00 (m, 5 H), 6.88 (d, J = 8.4 Hz, 1 H), 6.32 (dd, J = 4.4, 9.6 Hz, 1 H), 4.89-4.85 (m, 3 H), 3.91 (s, 3 H), 3.88 (s, 3 H), 3.73 (dd, J = 9.6, 14.0 Hz, 1 H), 3.36 (dd, J = 4.4, 14.0 Hz, 1 H), 3.31-3.25 (m, 1 H), 2.85-2.61 (m, 5 H), 2.10-2.05 (m,1 H), 1.78-1.68 (m, 1 H), 1.65-1.54 (m, 1 H), 1.50-1.38 (m, 1 H), 1.37-1.26 (m, 1 H). LCMS (Method 1): [MH+] = 800 at 2.98 min. |

| Structure | Example number | Precursor | Analytical Data |
|---|---|---|---|
| [(1S)-2-(3,5-dichloro-1-oxido-pyridin-1-ium-4-yl)-1-(3,4-dimethoxyphenyl)ethyl] 3-[3-[(2-fluoro-N-[(3R)-quinuclidin-3-yl]oxycarbonyl-anilino)methyl]phenyl]benzoate 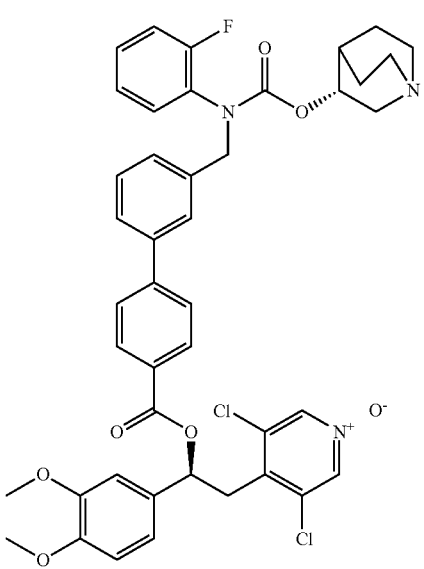 | Example 115 | Intermediate 127 | $^1$H NMR (400 MHz, CDCl$_3$): δ 8.19 (s, 1 H), 8.16 (s, 2 H), 7.99 (d, J = 7.6 Hz, 1 H), 7.72-7.70 (m, 1 H), 7.51-7.47 (m, 3 H), 7.38 (t, J = 7.6 Hz, 1 H), 7.26-7.21 (m, 2 H), 7.11-6.99 (m, 5 H), 6.86 (d, J = 8.4 Hz, 1 H), 6.32 (dd, J = 4.4, 9.6 Hz, 1 H), 4.93-4.87 (m, 3 H), 3.90 (s, 3 H), 3.87 (s, 3 H), 3.74 (dd, J = 9.6, 14.0 Hz, 1 H), 3.36 (dd, J = 4.4, 14.0 Hz, 1 H), 3.29-3.24 (m, 1 H), 2.82-2.63 (m, 5 H), 2.06-2.00 (m, 1 H), 1.72-1.68 (m, 1 H), 1.65-1.52 (m, 1 H), 1.50-1.37 (m,1 H), 1.36-1.25 (m, 1 H). LCMS (Method 1): [MH+] = 800 at 2.97 min. |
| [(1S)-2-(3,5-dichloro-1-oxido-pyridin-1-ium-4-yl)-1-(3,4-dimethoxyphenyl)ethyl] 4-[4-[(2-fluoro-N-[(3R)-quinuclidin-3-yl]oxycarbonyl-anilino)methyl]phenyl]benzoate 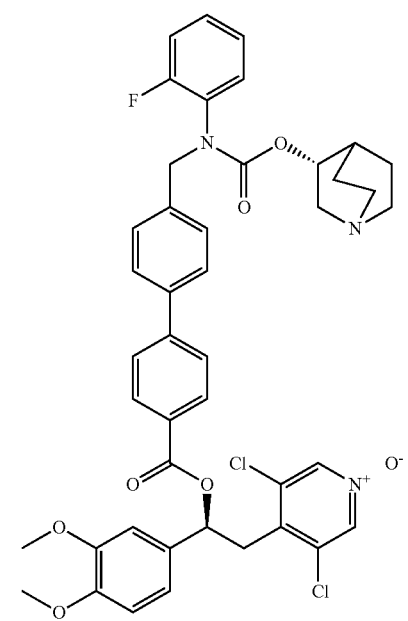 | Example 116 | Intermediate 125 | $^1$H NMR (400 MHz, CDCl$_3$): δ 8.13 (s, 2 H), 8.08-8.06 (m, 2 H), 7.64-7.61 (m, 2 H), 7.55-7.53 (m, 2 H), 7.35-7.33 (m, 2 H), 7.26-7.23 (m, 1 H), 7.07-7.00 (m, 5 H), 6.86 (d, J = 8.4 Hz, 1 H), 6.32 (dd, J = 4.4, 9.6 Hz, 1 H), 4.92-4.86 (m, 3 H), 3.91 (s, 3 H), 3.88 (s, 3 H), 3.72 (dd, J = 9.6, 14.0 Hz, 1 H), 3.36 (dd, J = 4.4, 14.0 Hz, 1 H), 3.28-3.25 (m, 1 H), 2.84-2.72 (m, 5 H), 2.05-2.00 (m, 1 H), 1.72-1.69 (m, 1 H), 1.61-1.57 (m, 1 H), 1.49-1.37 (m, 1 H), 1.36-1.22 (m, 1 H). LCMS (Method 1): [MH+] = 800 at 2.95 min. |

| Structure | Example number | Precursor | Analytical Data |
|---|---|---|---|
| [(1S)-2-(3,5-dichloro-1-oxido-pyridin-1-ium-4-yl)-1-(3,4-dimethoxyphenyl)ethyl] 3-[4-[(2-fluoro-N-[(3R)-quinuclidin-3-yl]oxycarbonyl-anilino)methyl]phenyl]benzoate 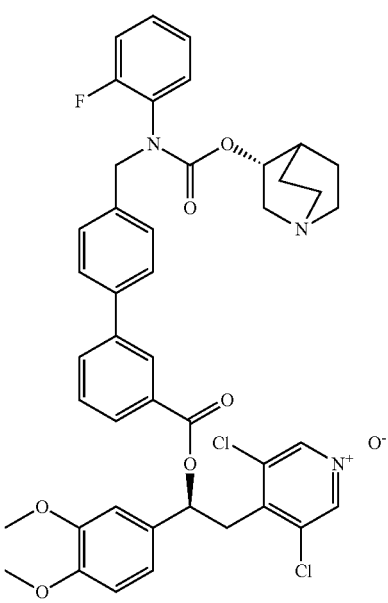 | Example 117 | Intermediate 128 | $^1$H NMR (400 MHz, CDCl$_3$): δ 8.22 (s, 1 H), 8.13 (s, 2 H), 7.98 (d, J = 8.0 Hz, 1 H), 7.77-7.75 (m, 1 H), 7.53-7.47 (m, 3 H), 7.35-7.33 (m, 2 H), 7.26-7.22 (m, 1 H), 7.12-6.99 (m, 5 H), 6.86 (d, J = 8.4 Hz, 1 H), 6.31 (dd, J = 4.4, 9.6 Hz, 1 H), 4.91-4.87 (m, 3 H), 3.90 (s, 3 H), 3.87 (s, 3 H), 3.73 (dd, J = 9.6, 14.0 Hz, 1 H), 3.36 (dd, J = 4.4, 14.0 Hz, 1 H), 3.29-3.26 (m, 1 H), 2.86-2.78 (m, 5 H), 2.08-2.00 (m, 1 H), 1.74-1.71 (m, 1 H), 1.63-1.60 (m, 1 H), 1.51-1.38 (m, 1 H), 1.37-1.28 (m, 1 H). LCMS (Method 1): [MH+] = 800 at 2.97 min. |
| [(1S)-2-(3,5-dichloro-1-oxido-pyridin-1-ium-4-yl)-1-(3,4-dimethoxyphenyl)ethyl] 4-[[[(3R)-quinuclidin-3-yl]oxycarbonyl-thiazol-2-yl-amino]methyl]benzoate formate salt 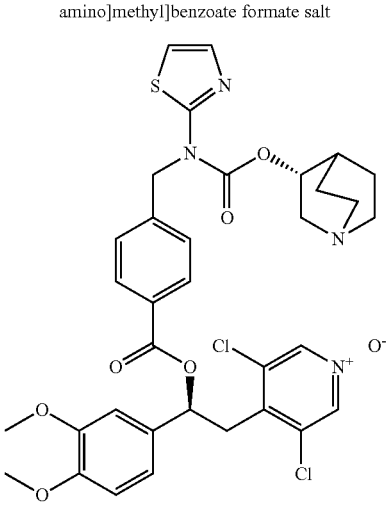 | Example 118 | Intermediate 129 | $^1$H NMR (400 MHz, CDCl$_3$): δ 8.36 (s, 1 H), 8.14 (s, 2 H), 7.97 (d, J = 8.2 Hz, 2 H), 7.43 (d, J = 3.6 Hz, 1 H), 7.35 (d, J = 7.9 Hz, 2 H), 7.02-6.95 (m, 3 H), 6.84 (d, J = 8.2 Hz, 1 H), 6.29 (dd, J = 9.7, 4.6 Hz, 1 H), 5.50 (d, J = 16.5 Hz, 1 H), 5.43 (d, J = 17.0 Hz, 1 H), 4.99 (s, 1 H), 3.89 (s, 3 H), 3.87 (s, 3 H), 3.69 (dd, J = 13.9, 9.8 Hz, 1 H), 3.34 (dd, J = 13.9, 4.5 Hz, 1 H), 3.34-3.29 (m, 1 H), 2.92-2.75 (m, 4 H), 2.13-2.03 (m, 1 H), 1.83-1.71 (m, 2 H), 1.68-1.57 (m, 1 H), 1.54-1.31 (m, 2 H). LCMS (Method 2): [MH+] = 713 at 3.59 min. |

| Structure | Example number | Precursor | Analytical Data |
|---|---|---|---|
| [(1S)-2-(3,5-dichloro-1-oxido-pyridin-1-ium-4-yl)-1-(3,4-dimethoxyphenyl)ethyl] 4-[[1H-indazol-7-yl-[(3R)-quinuclidin-3-yl]oxycarbonyl-amino]methyl]benzoate formate salt 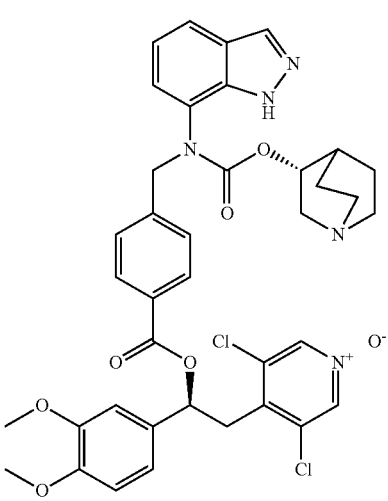 | Example 119 | Intermediate 130 | ¹H NMR (400 MHz, DMSO at 105° C.): δ 8.35 (s, 2 H), 8.17 (s, 1 H), 8.06 (s, 1 H), 7.90-7.85 (m, 2 H), 7.64 (dd, J = 7.90, 1.05 Hz, 1 H), 7.45 (d, J = 8.07 Hz, 2 H), 7.10-6.96 (m, 5 H), 6.26 (dd, J = 9.04, 4.84 Hz, 1 H), 5.01 (s, 2 H), 4.74-4.70 (m, 1 H), 3.81-3.76 (m, 7 H), 3.63 (dd, J = 14.15, 9.12 Hz, 1 H), 3.38 (dd, J = 14.18, 4.95 Hz, 2 H), 3.10-3.00 (m, 2 H), 2.32 (d, J = 11.73 Hz, 1 H), 2.04 (s, 1 H), 1.81 (s, 1 H), 1.57-1.46 (m, 2 H), 1.04 (s, 2 H). LCMS (Method 1): [MH+] = 746 at 2.74 min |
| [(1S)-2-(3,5-dichloro-1-oxido-pyridin-1-ium-4-yl)-1-(3,4-dimethoxyphenyl)ethyl] 3-[[1H-indazol-7-yl-[(3R)-quinuclidin-3-yl]oxycarbonyl-amino]methyl]benzoate formate salt 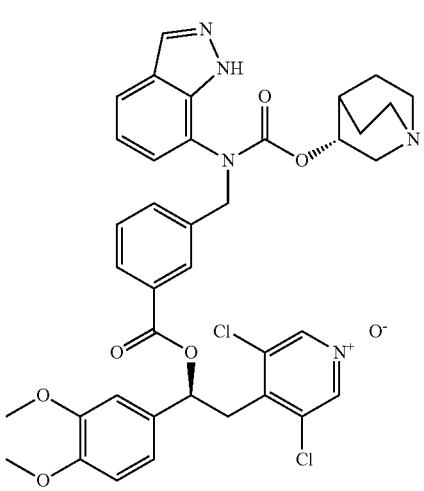 | Example 120 | Intermediate 131 | ¹H NMR (400 MHz, DMSO- at 105° C.): δ 8.34 (t, J = 2.51 Hz, 2 H), 8.20 (s, 1 H), 8.07 (s, 1 H), 7.89 (s, 1 H), 7.84 (d, J = 7.76 Hz, 1 H), 7.67-7.62 (m, 1 H), 7.57 (d, J = 7.69 Hz, 1 H), 7.42 (t, J = 7.68 Hz, 1 H), 7.03-6.94 (m, 5 H), 6.25 (dd, J = 9.10, 4.86 Hz, 1 H), 5.00 (s, 2 H), 4.74-4.69 (m, 1 H), 3.79 (s, 6 H), 3.65-3.57 (m, 1 H), 3.38 (dd, J = 14.19, 5.07 Hz, 2 H), 2.60-2.52 (m, 3 H), 2.36-2.28 (m, 1 H), 1.80 (d, J = 4.36 Hz, 1 H), 1.58-1.43 (m, 3 H), 1.04 (s, 2 H). LCMS (Method 1): [MH+] = 746 at 2.74 min |

| Structure | Example number | Precursor | Analytical Data |
|---|---|---|---|
| [(1S)-2-(3,5-dichloro-1-oxido-pyridin-1-ium-4-yl)-1-(3,4-dimethoxyphenyl)ethyl] 4-[[1H-indol-7-yl-[(3R)-quinuclidin-3-yl]oxycarbonyl-amino]methyl]benzoate 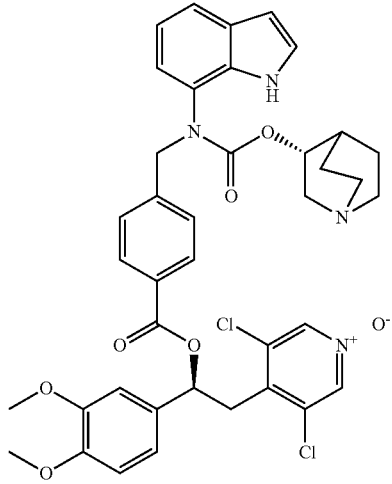 | Example 121 | Intermediate 132 | ¹H NMR (400 MHz, DMSO @ 110° C.): δ 10.85 (s, 1 H), 8.35 (s, 2 H), 7.89 (d, J = 8.13 Hz, 2 H), 7.46 (dd, J = 13.89, 7.99 Hz, 3 H), 7.30 (t, J = 2.81 Hz, 1 H), 7.07-6.91 (m, 4 H), 6.85 (d, J = 7.45 Hz, 1 H), 6.49 (dd, J = 3.09, 1.89 Hz, 1 H), 6.27 (dd, J = 9.12, 4.88 Hz, 1 H), 5.00 (br s, 3 H), 3.84-3.77 (m, 6 H), 3.69-3.59 (m, 2 H), 3.39 (dd, J = 14.33, 5.45 Hz, 2 H), 2.68 (dd, J = 5.34, 3.35 Hz, 1 H), 2.11 (s, 1 H), 1.88-1.78 (m, 3 H), 1.49 (br s, 1 H), 1.20 (br s, 1 H). LCMS (Method 1): [MH+] = 745 at 2.83 min. |
| [(1S)-1-[3-(cyclopropylmethoxy)-4-(difluoromethoxy)phenyl]-2-(3,5-dichloro-1-oxido-pyridin-1-ium-4-yl)ethyl] 4-[(2-hydroxy-N-[(3R)-quinuclidin-3-yl]oxycarbonyl-anilino)methyl]benzoate formate salt 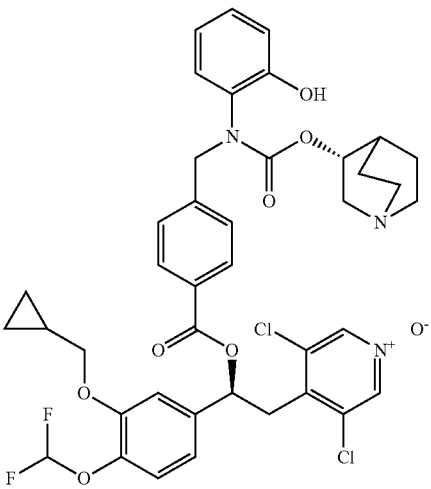 | Example 122 | Intermediate 133 | ¹H NMR (400 MHz, DMSO D₂O): δ 8.22 (s, 2 H), 8.08 (s, 1 H), 7.99 (s, 1 H), 7.64 (d, J = 8.21 Hz, 2 H), 7.19 (dd, J = 24.61, 7.95 Hz, 2 H), 6.95-6.39 (m, 8 H), 5.92 (dd, J = 9.16, 4.53 Hz, 1 H), 4.85-4.20 (br m, 4 H), 3.63 (d, 2 H), 3.36 (dd, J = 14.17, 9.58 Hz, 1 H), 3.13-3.05 (m, 2 H), 2.61 (s, 4 H), 2.45-2.35 (m, 1 H), 1.69 (s, 1 H), 1.56-0.85 (m, 5 H), 0.32-0.24 (m, 2 H), 0.07-0.02 (m, 2 H). LCMS (Method 1): [MH+] = 798 at 2.98 min. |

| Structure | Example number | Precursor | Analytical Data |
|---|---|---|---|
| [(1S)-1-[3-(cyclopropylmethoxy)-4-(difluoromethoxy)phenyl]-2-(3,5-dichloro-1-oxido-pyridin-1-ium-4-yl)ethyl] 3-[(2-hydroxy-N-[(3R)-quinuclidin-3-yl]oxycarbonyl-anilino)methyl]benzoate formate salt 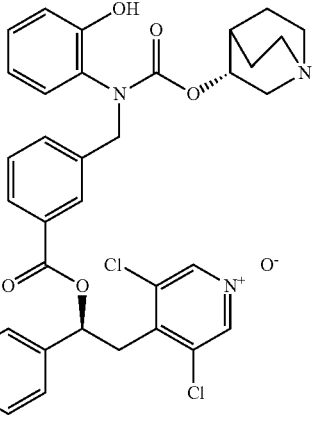 | Example 123 | Intermediate 134 | $^1$H NMR (400 MHz, DMSOD2O): δ 8.41 (s, 2 H), 8.33 (s, 1 H), 8.22 (s, 1 H), 7.90-7.76 (t, 2 H), 7.52-7.38 (m, 2 H), 7.19-6.64 (m, 6 H), 6.15 (s, 1 H), 5.10 (br m, 3 H), 3.85 (d, J = 6.78 Hz, 2 H), 3.60 (t, J = 10.46 Hz, 1 H), 3.33 (d, J = 13.75 Hz, 2 H), 2.88-2.53 (m, 4 H), 1.99 (s, 1 H), 1.65 (d, J = 35.98 Hz, 2 H), 1.40-1.10 (m, 3 H), 0.50 (d, J = 7.43 Hz, 2 H), 0.26 (s, 2 H).<br>LCMS (Method 1): [MH+] = 798 at 2.98 min. |
| [(1S)-2-(3,5-dichloro-1-oxido-pyridin-1-ium-4-yl)-1-(3,4-dimethoxyphenyl)ethyl] 4-[[3-(difluoromethyl)-N-[(3R)-quinuclidin-3-yl]oxycarbonyl-anilino]methyl]benzoate formate salt 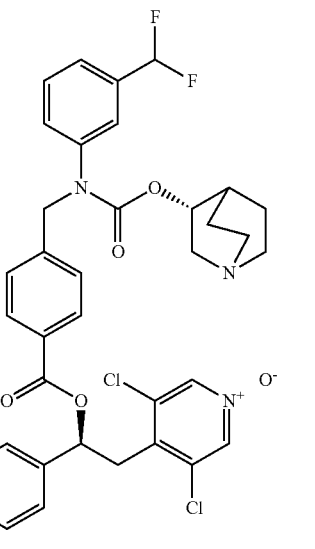 | Example 124 | Intermediate 135 | $^1$H NMR (400 MHz, CDCl$_3$): δ 8.42 (s, 1 H), 8.13 (s, 2 H), 7.98 (d, J = 8.0 Hz, 2 H), 7.48-7.26 (m, 5 H), 7.23 (s, 1 H), 7.03-6.97 (m, 2 H), 6.86 (d, J = 8.2 Hz, 1 H), 6.60 (t, J = 56.3 Hz, 1 H), 6.30 (dd, J = 9.7, 4.5 Hz, 1 H), 4.98-4.86 (m, 3 H), 3.90 (s, 3 H), 3.88 (s, 3 H), 3.71 (dd, J = 14.0, 9.7 Hz, 1 H), 3.39-3.28 (m, 2 H), 2.93-2.77 (m, 4 H), 2.73-2.60 (m, 1 H), 2.11 (s, 1 H), 1.83-1.73 (m, 1 H), 1.70-1.59 (m, 1 H), 1.50-1.36 (m, 2 H). LCMS (Method 1): [MH+] = 756 at 2.82 min |

| Structure | Example number | Precursor | Analytical Data |
|---|---|---|---|
| [(1S)-2-(3,5-dichloro-1-oxido-pyridin-1-ium-4-yl)-1-(3,4-dimethoxyphenyl)ethyl] 4-[(3-fluoro-5-hydroxy-N-[(3R)-quinuclidin-3-yl]oxycarbonyl-anilino)methyl]benzoate trifluoroacetic acid salt 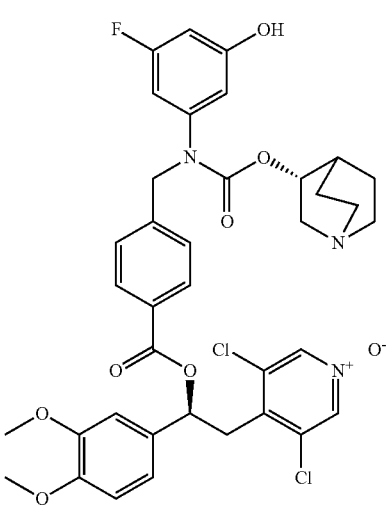 | Example 125 | Intermediate 137 | $^1$H NMR (400 MHz, DMSO): δ 10.05 (brs, 1 H), 9.52 (brs, 1 H), 8.55 (s, 2 H), 7.95 (d, J = 8.0 Hz, 2 H), 7.42 (d, J = 8.0 Hz, 2 H), 7.04-6.95 (m, 3 H), 6.72-6.70 (m, 1 H), 6.56 (s, 1 H), 6.44-6.42 (m, 1 H), 6.22 (dd, J = 4.4, 9.6 Hz, 1 H), 5.00-4.91 (m, 3 H), 3.77 (s, 3 H), 3.75 (s, 3 H), 3.67-3.51 (m, 1 H), 3.35-3.31 (m, 3 H), 3.28-3.20 (m, 3 H), 3.17-3.01 (m, 1 H), 2.08-2.07 (m, 1 H), 1.87-1.80 (m, 2 H), 1.63-1.55 (m, 2 H). LCMS (Method 1): [MH+] = 740 at 2.74 min |
| [(1S)-2-(3,5-dichloro-1-oxido-pyridin-1-ium-4-yl)-1-(3,4-dimethoxyphenyl)ethyl] 4-[(2-methoxy-3-hydroxy-N-[(3R)-quinuclidin-3-yl]oxycarbonyl-anilino)methyl]benzoate formate salt 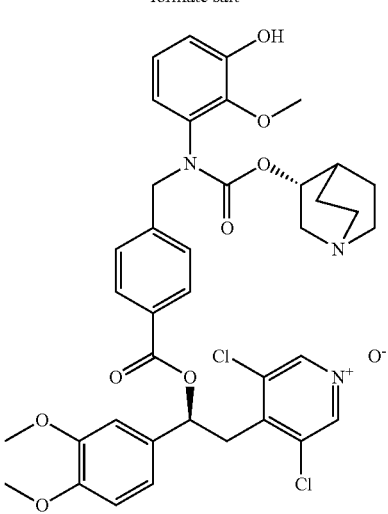 | Example 126 | Intermediate 138 | $^1$H NMR (400 MHz, DMSO): δ 9.60 (brs, 1 H), 8.53 (s, 2 H), 8.21 (s, 1 H), 7.94-7.92 (m, 2 H), 7.49-7.42 (m, 2 H), 7.04-6.92 (m, 3 H), 6.78-6.68 (m, 2 H), 6.61-6.51 (m, 1 H), 6.22 (dd, J = 4.4, 9.6 Hz, 1 H), 4.97-4.91 (m, 1 H), 4.64-4.62 (m, 2 H), 3.83 (s, 3 H), 3.82 (s, 3 H), 3.77 (s, 3 H), 3.73-3.16 (m, 4 H), 3.10-3.04 (m, 2 H), 2.67-2.60 (m, 2 H), 1.91-1.90 (m, 1 H), 1.62-1.49 (m, 2 H), 1.31-1.13 (m, 2 H). LCMS (Method 1): [MH+] = 752 at 2.70 min |

-continued

| Structure | Example number | Precursor | Analytical Data |
|---|---|---|---|
| [(1S)-2-(3,5-dichloro-1-oxido-pyridin-1-ium-4-yl)-1-(3,4-dimethoxyphenyl)ethyl] 4-[(2-methyl-3-hydroxy-N-[(3R)-quinuclidin-3-yl]oxycarbonyl-anilino)methyl]benzoate trifluoroacetic acid salt 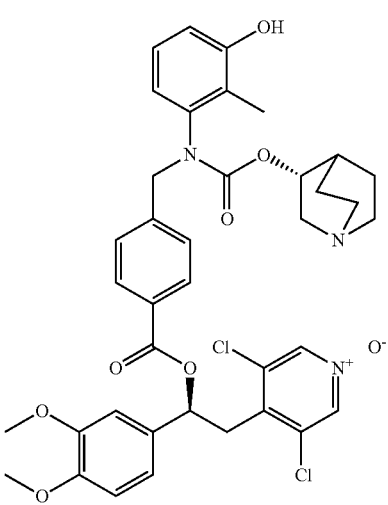 | Example 127 | Intermediate 136 | $^1$H NMR (400 MHz, DMSO @ 90° C.): δ 9.14 (brs, 1 H), 8.42 (s, 2 H), 7.92 (d, J = 8.4 Hz, 2 H), 7.39 (d, J = 8.4 Hz, 2 H), 7.06-6.92 (m, 4 H), 6.77-6.76 (m, 1 H), 6.55-6.52 (m, 1 H), 6.25 (dd, J = 4.4, 9.6 Hz, 1 H), 5.00-4.98 (m, 2 H), 4.62-4.61 (m, 1 H), 3.79 (s, 3 H), 3.78 (s, 3 H), 3.70-3.60 (m, 2 H), 3.57-3.51 (m, 1 H), 3.48-3.10 (m, 5 H), 2.18-2.09 (m, 1 H), 1.92-1.73 (m, 5 H), 1.63-1.53 (m, 2 H). LCMS (Method 1): [MH+] = 736 at 2.66 min |
| [(1S)-2-(3,5-dichloro-1-oxido-pyridin-1-ium-4-yl)-1-(3,4-dimethoxyphenyl)ethyl] 4-[(2-chloro-5-hydroxy-N-[(3R)-quinuclidin-3-yl]oxycarbonyl-anilino)methyl]benzoate formate salt 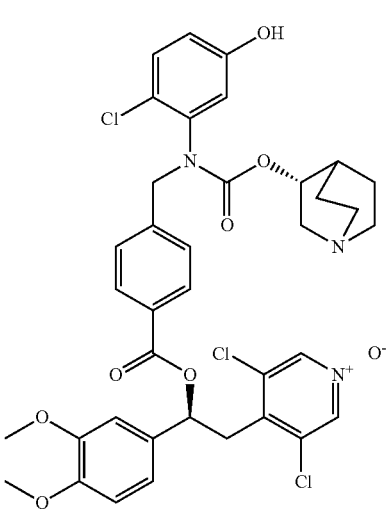 | Example 128 | Intermediate 139 | $^1$H NMR (400 MHz, DMSO @ 90° C.): δ 8.38 (s, 2 H), 8.31 (s, 1 H), 7.95-7.93 (m, 2 H), 7.43-7.41 (m, 2 H), 7.27 (d, J = 8.8 Hz, 1 H), 7.06-6.95 (m, 3 H), 6.74-6.72 (m, 1 H), 6.60-6.59 (m, 1 H), 6.27 (dd, J = 4.4, 9.6 Hz, 1 H), 4.69-4.66 (m, 3 H), 3.79 (s, 3 H), 3.78 (s, 3 H), 3.63 (dd, J = 9.6, 14.0 Hz, 1 H), 3.37 (dd, J = 4.4, 14.0 Hz, 1 H), 3.11-3.05 (m, 5 H), 2.61-2.59 (m, 1 H), 1.84-1.83 (m, 1 H), 1.60-1.58 (m, 1 H), 1.57-1.53 (m, 1 H), 1.49-1.44 (m, 1 H), 1.31-1.17 (m, 1 H). OH not observed. LCMS (Method 1): [MH+] = 756 at 2.75 min |

-continued

| Structure | Example number | Precursor | Analytical Data |
|---|---|---|---|
| [(1S)-2-(3,5-dichloro-1-oxido-pyridin-1-ium-4-yl)-1-(3,4-dimethoxyphenyl)ethyl] 4-[(2-fluoro-5-hydroxy-N-[(3R)-quinuclidin-3-yl]oxycarbonyl-anilino)methyl]benzoate formate salt 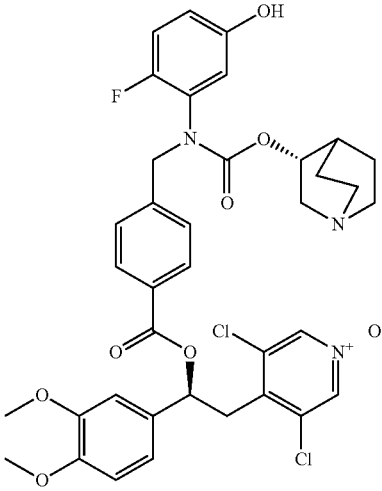 | Example 129 | Intermediate 140 | $^1$H NMR (400 MHz, CDCl$_3$): δ 8.48 (s, 1 H), 8.12 (s, 2 H), 7.89 (d, J = 8.4 Hz, 2 H), 7.29-7.26 (m, 3 H), 7.08-6.87 (m, 4 H), 6.73-6.72 (m, 1 H), 6.37-6.34 (m, 2 H), 5.07 (brs, 1 H), 4.91-4.62 (m, 2 H), 3.91 (s, 3 H), 3.88 (s, 3 H), 3.75 (dd, J = 9.6, 14.0 Hz, 1 H), 3.38 (dd, J = 4.4, 14.0 Hz, 1 H), 3.27-3.21 (m, 1 H), 2.98-2.91 (m, 5 H), 2.22-2.21 (m, 1 H), 1.86-1.47 (m, 4 H). LCMS (Method 1): [MH+] = 740 at 2.705 min |
| [(1S)-2-(3,5-dichloro-1-oxido-pyridin-1-ium-4-yl)-1-(3,4-dimethoxyphenyl)ethyl] 4-[(5-hydroxy-2-methyl-N-[(3R)-quinuclidin-3-yl]oxycarbonyl-anilino)methyl]benzoate trifluoroacetic acid salt 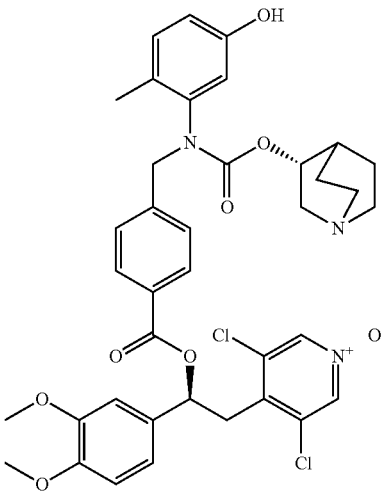 | Example 130 | Intermediate 141 | $^1$H NMR (400 MHz, DMSO @ 90° C.): δ 9.71 (br s, 1 H), 8.66-8.63 (m, 2 H), 8.23-8.18 (m, 2 H), 7.70-7.65 (m, 2 H), 7.34-7.23 (m, 4 H), 6.95-6.90 (m, 1 H), 6.76-6.73 (m, 1 H), 6.54-6.53 (m, 1 H), 5.27 (br s, 1 H), 5.07-5.04 (m, 2 H), 4.08 (s, 3 H), 4.07 (s, 3 H), 4.05-3.19 (m, 8 H), 2.47-2.44 (m, 1 H), 2.25-2.11 (m, 5 H), 1.89-1.85 (m, 2 H). LCMS (Method 1): [MH+] = 736 at 2.70 min |

| Structure | Example number | Precursor | Analytical Data |
|---|---|---|---|
| [(1S)-2-(3,5-dichloro-1-oxido-pyridin-1-ium-4-yl)-1-(3,4-dimethoxyphenyl)ethyl] 4-[(2-chloro-3-hydroxy-N-[(3R)-quinuclidin-3-yl]oxycarbonyl-anilino)methyl]benzoate trifluoroacetic acid salt 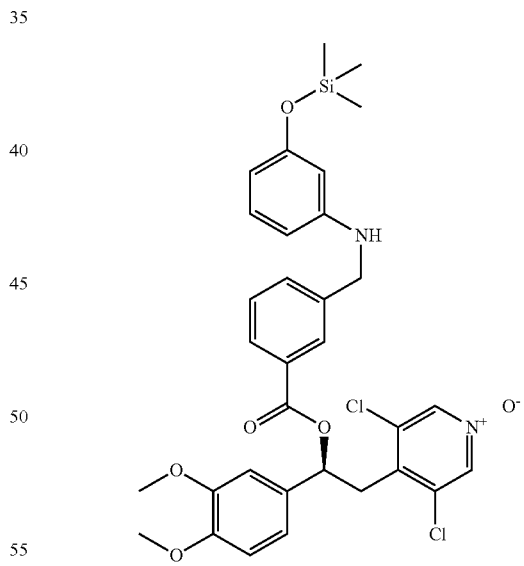 | Example 131 | Intermediate 142 | $^1$H NMR (400 MHz, DMSO): δ 10.45 (br s, 1 H), 9.58-9.53 (m, 1 H), 8.55 (s, 2 H), 7.96-7.91 (m, 2 H), 7.48-7.40 (m, 2 H), 7.12-6.92 (m, 4 H), 6.75-6.62 (m, 1 H), 6.21 (dd, J = 4.4, 9.6 Hz, 1 H), 5.10-4.95 (m, 2 H), 4.54-4.48 (m, 1 H), 3.78 (s, 3 H), 3.75 (s, 3 H), 3.72-2.85 (m, 8 H), 2.09-2.07 (m, 1 H), 1.82-1.81 (m, 2 H), 1.57-1.55 (m, 1 H), 1.32-1.30 (m, 1 H). LCMS (Method 1): [MH+] = 758 at 2.72 min |

Example 132

[(1S)-2-(3,5-Dichloro-1-oxido-pyridin-1-ium-4-yl)-1-(3,4-dimethoxyphenyl)ethyl]3-[(3-hydroxy-N-[(3R)-quinuclidin-3-yl]oxycarbonyl-anilino)methyl]benzoate formate Salt Step 1: Preparation of 3-((trimethylsilyl)oxy)aniline

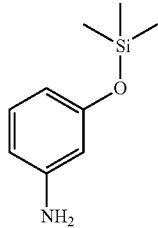

To a mixture of 3-aminophenol (0.67 g, 6.15 mmol) and hexamethyldisilazane (10 mL) was added a catalytic amount of concentrated sulfuric acid (0.05 mL), and the mixture was heated at reflux for 18 hours. The mixture was cooled and excess solvent was removed in vacuo. Trituration with diethyl ether gave a precipitate which was filtered and the filtrate was evaporated in vacuo. The crude material was purified by silica gel column, eluting with 0-100% EtOAc in isohexane, to give the title product as a red-brown mobile oil (0.782 g, 70%).

$^1$H NMR (400 MHz, CDCl$_3$): δ 7.26 (s, 1H), 7.00 (t, J=7.99 Hz, 1H), 6.34-6.20 (m, 3H), 3.60 (s, 2H), 0.28-0.21 (m, 9H). LCMS (Method 2): [MH+]=182 at 3.28 min.

Step 2: Preparation of [(1S)-2-(3,5-dichloro-1-oxido-pyridin-1-ium-4-yl)-1-(3,4-dimethoxyphenyl)ethyl] 3-[(3-trimethylsilyloxyanilino)methyl]benzoate A mixture of [(1S)-2-(3,5-Dichloro-1-oxido-pyridin-1-ium-4-yl)-1-(3,4-dimethoxyphenyl)ethyl]3-formylbenzoate (0.34 g, 0.71 mmol) and 3-((trimethylsilyl)-oxy)aniline (0.136 g, 0.75 mmol) in DCM (5 mL) was stirred at RT for 20 hours. NaBH(OAc)$_3$ (0.38 g, 1.79 mmol) followed by acetic acid (0.043 mL), 0.75 mmol) was added, and the reaction mixture was stirred at room temperature for a further 4 hours. The reaction mixture was diluted with DCM (10 mL) and washed with saturated aqueous NaHCO$_3$ solution (20 mL). The aqueous phase was further extracted with DCM (10 mL), combined the organic phases and filtered through a phase separator cartridge and the solvent was removed in vacuo to give a mixture of [(1S)-2-(3,5-dichloro-1-oxido-pyridin-1-ium-4-yl)-1-(3,4-dimethoxyphenyl)ethyl]3-[(3-trimethylsilyloxyanilino)methyl]-benzoate and [(1S)-2-(3,5-dichloro-1-oxido-pyridin-1-ium-4-yl)-1-(3,4-dimethoxy-phenyl)ethyl]3-[(3-hydroxyanilino)methyl]benzoate white solid (457 mg, quant).

¹H NMR (400 MHz, CDCl₃): δ 8.10 (t, J=7.61 Hz, 2H), 8.03 (s, 1H), 7.92 (d, J=7.97 Hz, 1H), 7.57 (d, J=7.54 Hz, 1H), 7.44-7.38 (m, 1H), 7.04-6.95 (m, 3H), 6.86 (dd, J=8.20, 4.03 Hz, 1H), 6.32-6.19 (m, 3H), 6.10 (t, J=2.27 Hz, 1H), 4.35 (s, 2H), 4.07 (s, 1H), 3.91-3.86 (m, 6H), 3.70 (dd, J=13.97, 9.67 Hz, 1H), 3.34 (dd, J=13.97, 4.56 Hz, 1H), 0.20 (s, 9H). LCMS (Method 1): [MH+]=569 at 3.59 min.

Step 3: Preparation of [(1S)-2-(3,5-dichloro-1-oxido-pyridin-1-ium-4-yl)-1-(3,4-dimethoxyphenyl)ethyl] 3-[(3-hydroxy-N-[(3R)-quinuclidin-3-yl]oxycarbonyl-anilino)methyl]benzoate formate salt

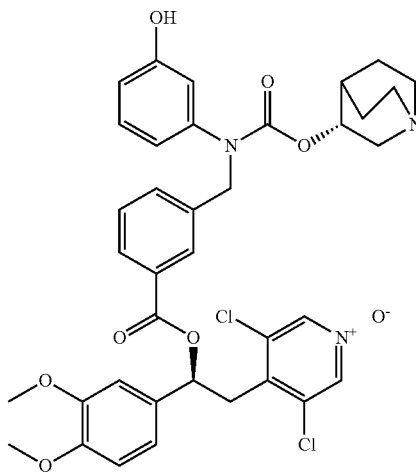

Part of the mixture previously obtained (0.29 g, 0.45 mmol) and (R)-quinuclidin-3-yl carbonochloridate hydrochloride (0.112 g, 0.50 mmol) in CH₃CN (5 mL) was heated at 80° C. in the microwave for 6 minutes. The mixture was diluted with EtOAc (20 mL) and extracted with water (10 mL). The aqueous phase was basified by addition of saturated aqueous NaHCO₃ solution (10 mL) and extracted with EtOAc (3×20 mL), the organic extracts were combined and filtered through a phase separator and the solvent was removed in vacuo. Purification by preparative HPLC gave the formate salt of the title compound as a light brown solid (0.135 g, 47%).

¹H NMR (400 MHz, DMSO): δ 8.52 (s, 2H), 8.20 (s, 1H), 7.91-7.82 (m, 2H), 7.54-7.45 (m, 2H), 7.12 (t, J=7.96 Hz, 1H), 7.04-6.91 (m, 3H), 6.71-6.58 (m, 3H), 6.21 (dd, J=9.60, 4.32 Hz, 1H), 4.96-4.85 (m, 2H), 4.70-4.65 (m, 1H), 3.78-3.72 (m, 7H), 3.68-3.54 (m, 1H), 3.32 (dd, J=16.44, −0.02 Hz, 1H), 3.24-3.05 (m, 1H), 2.61 (d, J=9.20 Hz, 4H), 1.85 (s, 1H), 1.60-1.42 (m, 2H), 1.31 (s, 1H), 1.17 (s, 1H). LCMS (Method 1): [MH+]=722 at 2.63 min.

Example 133

[(1S)-2-(3,5-dichloro-1-oxido-pyridin-1-ium-4-yl)-1-(3,4-dimethoxyphenyl)ethyl]3-[(2,6-difluoro-N-[(3R)-quinuclidin-3-yl]oxycarbonyl-anilino)methyl] benzoate

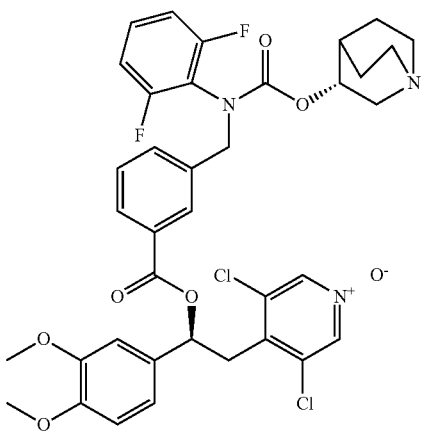

To a solution of [(1S)-2-(3,5-dichloro-1-oxido-pyridin-1-ium-4-yl)-1-(3,4-dimethoxyphenyl)ethyl]3-formylbenzoate (167 mg, 0.35 mmol) and 2,4-difluoroaniline (47.4 mg, 0.367 mmol) in anhydrous DCM (1.5 mL) was added acetic acid (0.021 mL, 0.367 mmol). The mixture was stirred at room temperature for 72 hours. NaBH(OAc)₃ (185 mg, 0.875 mmol) was added, and the mixture was stirred at room temperature for 24 hours. After addition of water (1.25 mL) the mixture was stirred at room temperature for 10 minutes. The reaction mixture was filtered through a phase separator and the solvent was removed in vacuo. The crude material (82 mg, 0.139 mmol) and (R)-quinuclidin-3-yl carbonochloridate hydrochloride (157 mg, 0.696 mmol) in anhydrous CH₃CN (1.1 mL) was heated at 80° C. for 3 minutes under microwave irradiation. After cooling to room temperature, the solvent was removed in vacuo. Purification of the crude material by preparative HPLC afforded the title compound as a pale yellow solid (56.5 mg, 55%). ¹H NMR (400 MHz, CDCl₃): δ 8.12 (s, 2H), 7.95-7.87 (m, 2H), 7.48 (d, J=7.9 Hz, 1H), 7.34 (t, J=7.9 Hz, 1H), 7.26-7.17 (m, 1H), 7.02-6.95 (m, 2H), 6.94-6.83 (m, 3H), 6.26 (dd, J=9.8, 4.5 Hz, 1H), 4.93-4.76 (m, 3H), 3.90 (s, 3H), 3.88 (s, 3H), 3.69 (dd, J=14.0, 9.8 Hz, 1H), 3.33 (dd, J=14.2, 4.4 Hz, 1H), 3.30-3.24 (m, 1H), 2.90-2.77 (m, 3H), 2.71 (d, J=15.7 Hz, 1H), 2.67-2.59 (m, 1H), 2.11-2.04 (m, 1H), 1.77-1.67 (m, 1H), 1.67-1.55 (m, 1H), 1.47-1.37 (m, 1H), 1.37-1.27 (m, 1H). LCMS (Method 2): [MH+]= 742 at 3.22 min.

The following compounds could also be synthesized using the above procedures.

| Name/Structure | Example number | Analytical Data |
|---|---|---|
| [(1S)-1-[3-(cyclopropylmethoxy)-4-(difluoromethoxy)phenyl]-2-(3,5-dichloro-1-oxido-pyridin-1-ium-4-yl)ethyl] 3-[(3-fluoro-N-[(3R)-quinuclidin-3-yl]oxycarbonyl-anilino)methyl]benzoate 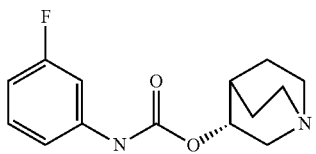 | Example 134 | $^1$H NMR (300 MHz, DMSO) δ 8.51 (s, 2 H), 7.81-7.95 (m, 2 H), 7.56 (dt, 1 H), 7.49 (t, 1 H), 7.38 (td, 1 H), 7.16-7.27 (m, 2 H), 7.07-7.15 (m, 1 H), 7.05 (dd, 1 H), 6.97-7.27 (m, 2 H), 7.06 (t, 1 H), 6.20 (dd, 1 H), 5.02 (d, 1 H), 4.96 (m, 1 H), 4.66-4.79 (m, 1 H), 3.92 (d, 2 H), 3.59 (dd, 1 H), 3.33 (dd, 1 H), 3.06-3.22 (m, 1 H), 2.56-2.80 (m, 5 H), 1.81-1.99 (m, 1 H), 1.41-1.71 (m, 2 H), 1.04-1.40 (m, 3 H), 0.44-0.69 (m, 2 H), 0.20-0.44 (m, 2 H). LCMS (Method 1): [MH+] = 800 at 3.12 min. |
| [(1S)-2-(3,5-dichloro-1-oxido-pyridin-1-ium-4-yl)-1-(3,4-dimethoxyphenyl)ethyl] 3-[[2-pyridyl-[(3R)-quinuclidin-3-yl]oxycarbonyl-amino]methyl]benzoate 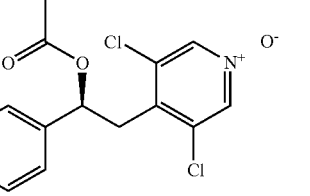 | Example 135 | $^1$H NMR (400 MHz, CDCl$_3$) δ 8.39 (d, J = 4.9 Hz, 1 H), 8.11 (s, 2 H), 7.98 (s, 1 H), 7.89 (d, J = 7.8 Hz, 1 H), 7.75 (d, J = 8.5 Hz, 1 H), 7.71-7.65 (m, 1 H), 7.52 (d, J = 7.6 Hz, 1 H), 7.36 (t, J = 7.7 Hz, 1 H), 7.09-7.05 (m, 1 H), 7.00-6.94 (m, 2 H), 6.84 (d, J = 8.2 Hz, 1 H), 6.26 (dd, J = 9.7, 4.6 Hz, 1 H), 5.28 (d, J = 6.0 Hz, 2 H), 4.86-4.80 (m, 1 H), 3.88 (s, 6 H), 3.67 (dd, J = 14.0, 9.7 Hz, 1 H), 3.32 (dd, J = 14.0, 4.6 Hz, 1 H), 3.25-3.16 (m, 1 H), 2.80-2.66 (m, 3 H), 2.64-2.47 (m, 2 H), 2.00-1.92 (m, 1 H), 1.70-1.59 (m, 1 H), 1.58-1.48 (m, 1 H), 1.48-1.38 (m, 1 H), 1.30-1.19 (m, 1 H). LCMS (Method 1): [MH+] = 707 at 2.67 min. |

| Name/Structure | Example number | Analytical Data |
|---|---|---|
| [(1S)-2-(3,5-dichloro-1-oxido-pyridin-1-ium-4-yl)-1-(3,4-dimethoxyphenyl)ethyl] 4-[(2-chloro-N-[(3R)-quinuclidin-3-yl]oxycarbonyl-anilino)methyl]benzoate 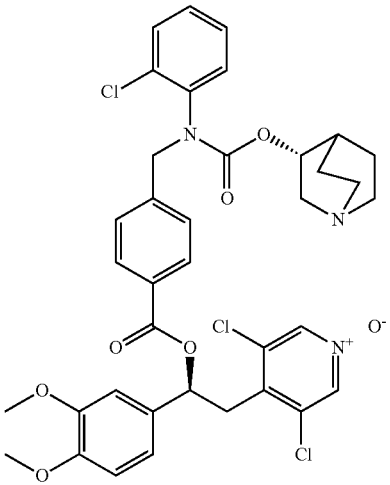 | Example 136 | $^1$H NMR (400 MHz, DMSO): δ 8.54 (s, 2 H), 7.93 (d, J = 8.0 Hz, 2 H), 7.58-7.45 (m, 1 H), 7.42 (d, J = 8.0 Hz, 2 H), 7.37-7.27 (m, 2 H), 7.26-7.14 (m, 1 H), 7.07-6.94 (m, 3 H), 6.25-6.18 (m, 1 H), 5.12-5.02 (m, 1 H), 4.68-4.50 (m, 2 H), 3.78 (s, 3 H), 3.75 (s, 3 H), 3.63 (dd, J = 13.9, 9.4 Hz, 1 H), 3.36-3.30 (m, 1 H), 3.10-3.00 (m, 1 H), 2.60-2.30 (m, 5 H), 1.80-1.69 (m, 1 H), 1.60-1.37 (m, 2 H), 1.15-1.00 (m, 2 H). LCMS (Method 1): [MH+] = 742 at 2.83 min. |
| [(1S)-2-(3,5-dichloro-1-oxido-pyridin-1-ium-4-yl)-1-(3,4-dimethoxyphenyl)ethyl] 4-[(2,6-difluoro-N-[(3R)-quinuclidin-3-yl]oxycarbonyl-anilino)methyl]benzoate 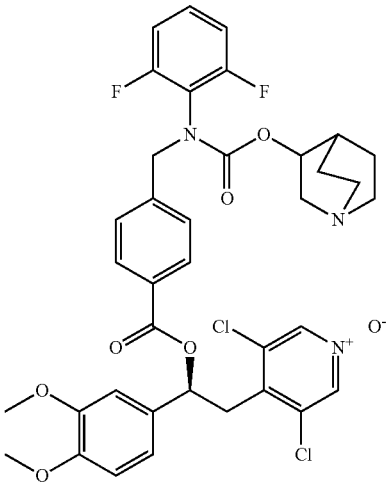 | Example 137 | $^1$H NMR (400 MHz, DMSO at 125° C.) δ 8.29 (s, 2 H), 8.20 (s, 1 H), 7.87 (d, J = 7.9 Hz, 2 H), 7.40-7.31 (m, 3 H), 7.10-6.93 (m, 5 H), 6.26 (dd, J = 8.9, 4.9 Hz, 1 H), 4.81 (d, J = 6.3 Hz, 2 H), 4.72-4.67 (m, 1 H), 3.79-3.75 (m, 6 H), 3.62 (dd, J = 14.3, 9.1 Hz, 1 H), 3.38 (dd, J = 14.2, 4.9 Hz, 1 H), 3.08 (dd, J = 15.2, 8.2 Hz, 1 H), 2.67-2.55 (m, 5 H), 1.84 (br s, 1 H), 1.62-1.51 (m, 1 H), 1.51-1.40 (m, 1 H), 1.35-1.24 (m, 1 H) 1.24-1.13 (m, 1 H). LCMS (Method 1): [MH+] = 742 at 2.82 min. |

| Name/Structure | Example number | Analytical Data |
|---|---|---|
| [(1S)-2-(3,5-dichloro-1-oxido-pyridin-1-ium-4-yl)-1-(3,4-dimethoxyphenyl)ethyl] 3-[[3-pyridyl-[(3R)-quinuclidin-3-yl]oxycarbonyl-amino]methyl]benzoate formate salt | Example 138 | ¹H NMR (400 MHz, CDCl₃): δ 8.49 (d, J = 4.8 Hz, 1 H), 8.43-8.35 (m, 2 H), 8.14 (s, 2 H), 7.95 (d, J = 7.1 Hz, 1 H), 7.87 (s, 1 H), 7.46-7.38 (m, 3 H), 7.30-7.25 (m, 1 H), 7.02-6.96 (m, 2 H), 6.86 (d, J = 8.2 Hz, 1 H), 6.27 (dd, J = 9.7, 4.5 Hz, 1 H), 4.98-4.93 (m, 1 H), 4.90 (s, 2 H), 3.90 (s, 3 H), 3.88 (s, 3 H), 3.70 (dd, J = 13.9, 9.8 Hz, 1 H), 3.39-3.30 (m, 2 H), 2.95-2.85 (m, 3 H), 2.81 (d, J = 15.2 Hz, 1 H), 2.74-2.61 (m, 1 H), 2.16-2.10 (m, 1 H), 1.84-1.74 (m, 1 H), 1.73-1.62 (m, 1 H), 1.54-1.36 (m, 2 H).<br>LCMS (Method 1): [MH+] = 707 at 2.56 min. |
| [(1S)-2-(3,5-dichloro-1-oxido-pyridin-1-ium-4-yl)-1-(3,4-dimethoxyphenyl)ethyl] 3-[(2-fluoro-4-hydroxy-N-[(3R)-quinuclidin-3-yl]oxycarbonyl-anilino)methyl]benzoate | Example 139 | 1H NMR (400 MHz, DMSO) δ 8.52 (s, 2 H), 8.18 (s, 1 H), 7.72-7.99 (m, 2 H), 7.46 (d, J = 12.13 Hz, 2 H), 6.87-7.18 (m, 4 H), 6.42-6.67 (m, 2 H), 6.19 (d, J = 4.85 Hz, 1 H), 4.70-4.93 (m, 2 H), 4.56-4.70 (m, 1 H), 3.51 and 3.85 (2s, 6 H, 3H each), 3.25-3.40 (m, 6 H), 2.96-3.14 (m, 2 H), 1.82 (m, 1 H), 1.18-1.61 (m, 4 H)<br>MS/ESI + [MH+] = 370.4, 739.8 |
| [(1S)-2-(3,5-dichloro-1-oxido-pyridin-1-ium-4-yl)-1-(3,4-dimethoxyphenyl)ethyl] 3-[(4-hydroxy-N-[(3R)-quinuclidin-3-yl]oxycarbonyl-anilino)methyl]benzoate | Example 140 | 1H NMR (400 MHz, DMSO) δ 9.46 (br. s., 1 H), 7.95 (s, 2 H), 7.70-7.80 (m, 2 H), 7.32-7.62 (m, 2 H), 6.87-7.16 (m, 5 H), 6.68 (d, J = 8.60 Hz, 2 H), 6.21 (dd, J = 9.48, 4.41 Hz, 1 H), 4.84 (d, J = 4.63 Hz, 2 H), 4.48-4.71 (m, 1 H), 3.76 and 3.79 (2 s, 6 H, 3H each), 3.60 (dd, J = 14.11, 9.70 Hz, 1 H), 3.34 (d, J = 4.63 Hz, 2 H), 2.94-3.11 (m, 1 H), 2.55 (d, J = 6.62 Hz, 2 H), 2.42 (d, J = 14.55 Hz, 2 H), 1.81 (d, J = 2.65 Hz, 1 H), 1.22-1.60 (m, 4 H).<br>MS/ESI + [MH+] = 722.1 |

| Name/Structure | Example number | Analytical Data |
|---|---|---|
| [(1S)-2-(3,5-dichloro-1-oxido-pyridin-1-ium-4-yl)-1-(3,4-dimethoxyphenyl)ethyl] 3-[[4-(methanesulfonamido)-N-[(3R)-quinuclidin-3-yl]oxycarbonyl-anilino]methyl]benzoate 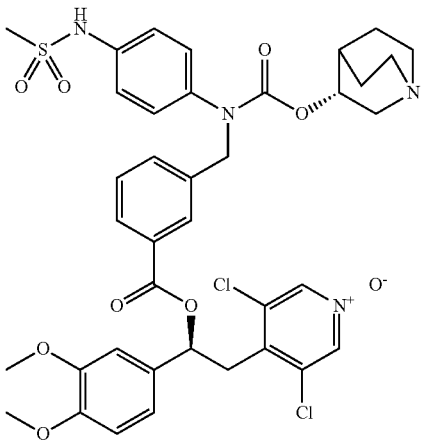 | Example 141 | 1H NMR (400 MHz, DMSO) δ 9.46-9.98 (s, 1 H), 8.51 (s, 2 H), 7.87 (m, 2 H), 7.49 (d, J = 15.22 Hz, 2 H), 7.10-7.31 (m, 4 H), 6.89-7.07 (m, 3 H), 6.12-6.28 (m, 1 H), 4.91 (s, 2 H), 4.57-4.71 (m, 1 H), 3.75 and 3.76 (2s, 6 H, 3 H each), 3.51-3.63 (m, 1 H), 2.98-3.13 (m, 1 H), 2.95 (s, 3 H), 2.56 (m, 4 H), 2.30-2.47 (m, 2 H), 1.76-1.86 (m, 1 H), 1.38-1.57 (m, 2 H), 1.15-1.28 (m, 2 H). MS/ESI + [MH+] = 799.1 |
| [(1S)-2-(3,5-dichloro-1-oxido-pyridin-1-ium-4-yl)-1-(3,4-dimethoxyphenyl)ethyl] 3-[[3-tert-butyl-N-[(3R)-quinuclidin-3-yl]oxycarbonyl-anilino)methyl]benzoate 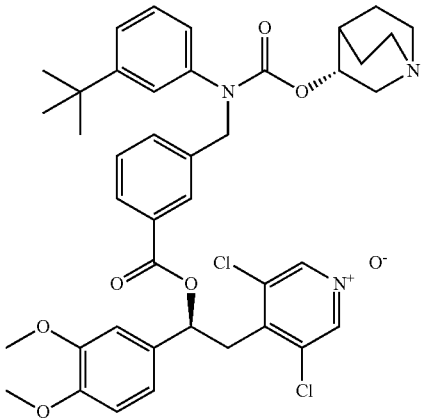 | Example 142 | 1H NMR (400 MHz, DMSO) δ 8.51 (s, 2 H), 7.80-7.90 (m, 2 H), 7.41-7.58 (m, 2 H), 7.19-7.34 (m, 2 H), 7.12 (m, 1 H), 6.87-7.07 (m, 4 H), 6.20 (dd, J = 9.59, 4.30 Hz, 1 H), 4.92 (s, 2 H), 4.62-4.73 (m, 1 H), 3.75 (s, 6 H), 3.59 (dd, J = 14.11, 9.70 Hz, 1 H), 3.32 (dd, J = 14.11, 4.41 Hz, 1 H), 3.08 (dd, J = 13.45, 8.16 Hz, 1 H), 2.53-2.64 (m, 3 H), 2.43 (m, 2 H), 1.83 (d, J = 2.43 Hz, 1 H), 1.39-1.60 (m, 2 H), 1.21-1.30 (m, 2 H), 1.19 (s, 9 H). MS/ESI + [MH+] = 762.3 |

-continued

| Name/Structure | Example number | Analytical Data |
|---|---|---|
| [(1S)-2-(3,5-dichloro-1-oxido-pyridin-1-ium-4-yl)-1-[4-(difluoromethoxy)-3-propoxy-phenyl]ethyl] 4-[(2-fluoro-N-[(3R)-quinuclidin-3-yl]oxycarbonyl-anilino)methyl]benzoate | Example 143 | 1H NMR (400 MHz, DMSO) δ 10.28 (br. s., 1 H), 8.54 (s, 2 H), 7.93 (d, J = 7.94 Hz, 2 H), 7.13-7.50 (m, 8 H), 6.98-7.10 (m, 2 H), 6.20 (dd, J = 9.26, 4.41 Hz, 1 H), 4.67-5.06 (m, 3 H), 3.91-4.10 (m, 2 H), 3.49-3.67 (m, 2 H), 3.34 (dd, J = 14.11, 4.41 Hz, 1 H), 3.15-3.30 (m, 5 H), 2.10-2.20 (m, 2 H), 1.49-1.94 (m, 5 H), 0.97 (t, J = 7.50 Hz, 3 H).<br>MS/ESI + [MH+] = 788.2, 394.7 |
| [(1S)-2-(3,5-dichloro-1-oxido-pyridin-1-ium-4-yl)-1-[4-(difluoromethoxy)-3-propoxy-phenyl]ethyl] 4-[(3-pyridyl-N-[(3R)-quinuclidin-3-yl]oxycarbonyl-anilino)methyl]benzoate | Example 144 | 1H NMR (400 MHz, DMSO) δ 9.80-9.91 (bs, 1 H), 8.61 (d, J = 2.21 Hz, 1 H), 8.55 (s, 2 H), 8.37-8.44 (m, 1 H), 7.94 (d, J = 8.38 Hz, 2 H), 7.82 (d, J = 8.38 Hz, 1 H), 7.45 (d, J = 8.38 Hz, 3 H), 7.15-7.27 (m, 2 H), 7.07 (dd, J = 8.16, 1.54 Hz, 1 H), 7.03 (t, J = 75.00 Hz, 1 H), 6.20 (dd, J = 9.26, 4.41 Hz, 1 H), 4.92-5.14 (m, 3 H), 4.01 (d, J = 7.94 Hz, 2 H), 3.39-3.59 (m, 1 H), 3.33 (m, 3 H), 3.13 (m, 3 H), 2.92-3.05 (m, 1 H), 2.16 (m, 1 H), 1.72 (m, 6 H), 0.97 (t, J = 7.28 Hz, 3 H).<br>MS/ESI + [MH+] = 771.2, 386.2 |

| Name/Structure | Example number | Analytical Data |
|---|---|---|
| [(1S)-2-(3,5-dichloro-1-oxido-pyridin-1-ium-4-yl)-1-(3,4-dimethoxyphenyl)ethyl] 3-[[3-(methanesulfonamido)-N-[(3R)-quinuclidin-3-yl]oxycarbonyl-anilino]methyl]benzoate | Example 145 | 1H NMR (400 MHz, DMSO) δ 8.51 (s, 2 H), 8.19 (s, 1 H), 7.78-8.01 (m, 2 H), 7.41-7.57 (m, 2 H), 7.22-7.38 (m, 1 H), 6.71-7.18 (m, 6 H), 6.19 (dd, J = 9.70, 4.41 Hz, 1 H), 4.93 (d, J = 3.97 Hz, 2 H), 4.61-4.78 (m, 1 H), 3.67 and 3.81 (2 s, 6 H), 3.49-3.62 (m, 1 H), 3.32 (dd, J = 14.11, 4.41 Hz, 1 H), 3.07-3.21 (m, 1 H), 2.55-2.67 (m, 5 H), 1.88 (d, J = 2.65 Hz, 1 H), 1.02-1.62 (m, 4 H).<br>MS/ESI + [MH+] = 799.1 |
| [(1S)-2-(3,5-dichloro-1-oxido-pyridin-1-ium-4-yl)-1-(3,4-dimethoxyphenyl)ethyl] 4-[[4-(methanesulfonamido)-N-[(3R)-quinuclidin-3-yl]oxycarbonyl-anilino]methyl]benzoate | Example 146 | 1H NMR (400 MHz, DMSO) δ 9.71 (s, 1 H), 8.61 (s, 2 H), 7.89-8.01 (m, 2 H), 7.38-7.52 (m, 2 H), 7.25-7.34 (m, 1 H), 6.94-7.16 (m, 6 H), 6.41 (s, 1 H), 6.13-6.28 (m, 1 H), 4.52-5.00 (m, 3 H), 3.72 and 3.84 (2 s, 6 H, 3 H each), 3.38-3.65 (m, 5 H), 3.15-2.95 (m, 3 H), 2.94 (s, 3 H), 1.59-1.93 (m, 2 H), 1.40-1.60 (m, 3 H)<br>MS/ESI + [MH+] = 799.1, 401.1 |

| Name/Structure | Example number | Analytical Data |
|---|---|---|
| [(1S)-2-(3,5-dichloro-1-oxido-pyridin-1-ium-4-yl)-1-(3,4-dimethoxyphenyl)ethyl] 4-[[2-(cyclopropylmethoxy)-N-[(3R)-quinuclidin-3-yl]oxycarbonyl-anilino]methyl]benzoate<br />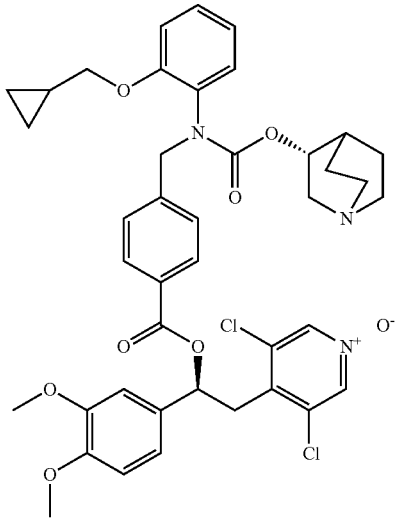 | Example 147 | 1H NMR (400 MHz, DMSO) δ 8.39 (s, 2 H), 8.04 (s, 2 H), 7.77 (d, J = 7.94 Hz, 2 H), 7.28 (d, J = 7.50 Hz, 2 H), 6.59-7.14 (m, 7 H), 5.94-6.19 (m, 1 H), 4.51 (m, 4 H), 2.96-3.76 (m, 9 H), 2.20-2.60 (m, 6 H), 1.54-1.79 (m, 1 H), 1.24-1.47 (m, 2 H), 1.01 (m, 3 H), 0.41 (d, J = 6.62 Hz, 2 H), 0.14 (m, 2 H).<br />MS/ESI + [MH+] = 776.22 |
| [(1S)-2-(3,5-dichloro-1-oxido-pyridin-1-ium-4-yl)-1-(3,4-dimethoxyphenyl)ethyl] 3-[(2-hydroxy-N-[(3R)-quinuclidin-3-yl]oxycarbonyl-anilino)methyl]benzoate<br />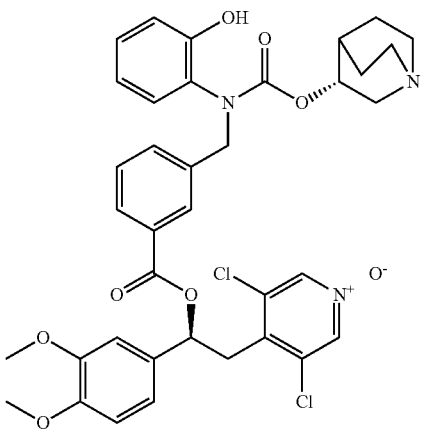 | Example 148 | 1H NMR (400 MHz, DMSO) δ 8.52 (s, 2 H), 8.21 (s, 1 H), 7.79-8.01 (m, 2 H), 7.44 (m, 2 H), 6.79-7.13 (m, 6 H), 6.58-6.79 (m, 1 H), 6.06-6.30 (m, 1 H), 4.69-5.20 (m, 3 H), 3.70-3.76 (m, 7 H), 3.51-3.67 (m, 1 H), 3.26-3.39 (m, 1 H), 3.01-3.21 (m, 1 H), 2.66 (m, 4 H), 1.74-1.87 (m, 1 H), 1.40-1.67 (m, 2 H), 1.12-1.34 (m, 2 H)<br />MS/ESI + [MH+] = 722.1 |

| Name/Structure | Example number | Analytical Data |
|---|---|---|
| [(1S)-2-(3,5-dichloro-1-oxido-pyridin-1-ium-4-yl)-1-(3,4-dimethoxyphenyl)ethyl] 4-[(2-fluoro-6-hydroxy-N-[(3R)-quinuclidin-3-yl]oxycarbonyl-anilino)methyl]benzoate 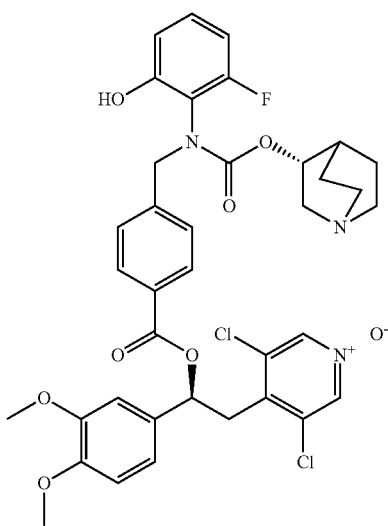 | Example 149 | 1H NMR (400 MHz, DMSO) δ 9.80-10.80 (m, 1 H), 8.54 (s, 2 H), 8.21 (s, 1 H), 7.81-7.99 (m, 2 H), 7.39 (t, J = 7.94 Hz, 2 H), 6.91-7.18 (m, 4 H), 6.71 (d, J = 7.94 Hz, 2 H), 6.10-6.26 (m, 1 H), 4.84-5.09 (m, 1 H), 4.62 (m, 1 H), 4.56 (m, 1 H), 3.75 and 3.77 (2 s, 3 H each, 6 H), 3.56-3.66 (m, 2 H), 3.25-3.36 (m, 4 H), 3.06 (d, J = 7.50 Hz, 2 H), 2.53-2.70 (m, 4 H), 2.44 (m, 2 H), 1.69-1.83 (m, 1 H), 1.38-1.66 (m, 2 H), 1.14-1.27 (m, 2 H). MS/ESI + [MH+] = 740.1 |
| [(1S)-2-(3,5-dichloro-1-oxido-pyridin-1-ium-4-yl)-1-(3,4-dimethoxyphenyl)ethyl] 4-[[3-(hydroxymethyl)-N-[(3R)-quinuclidin-3-yl]oxycarbonyl-anilino]methyl]benzoate 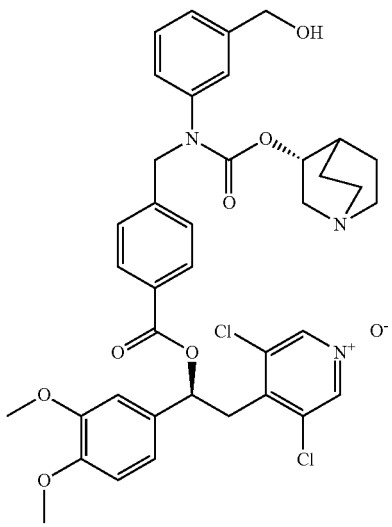 | Example 150 | 1H NMR (400 MHz, DMSO) δ 8.53 (s, 2 H), 8.19 (s, 2 H), 7.95 (d, J = 8.38 Hz, 2 H), 7.41 (d, J = 8.38 Hz, 2 H), 7.22-7.33 (m, 2 H), 7.14 (d, J = 7.50 Hz, 2 H), 6.88-7.06 (m, 3 H), 6.21 (dd, J = 9.70, 4.41 Hz, 1 H), 4.96 (s, 2 H), 4.64-4.74 (m, 1 H), 4.45 (s, 2 H), 3.77 and 3.84 (2 s, 3 H each, 6 H), 3.61 (dd, J = 13.89, 9.48 Hz, 1 H), 3.32 (dd, J = 13.89, 4.63 Hz, 1 H), 3.05-3.18 (m, 2 H), 2.55-2.69 (m, 4 H), 1.87 (d, J = 2.65 Hz, 1 H), 1.41-1.67 (m, 2 H), 1.17-1.37 (m, 2 H). MS/ESI + [MH+] = 736.2 |

| Name/Structure | Example number | Analytical Data |
|---|---|---|
| [(1S)-2-(3,5-dichloro-1-oxido-pyridin-1-ium-4-yl)-1-(3,4-dimethoxyphenyl)ethyl] 4-[(2-carbamoyl-N-[(3R)-quinuclidin-3-yl]oxycarbonyl-anilino)methyl]benzoate | Example 151 | 1H NMR (400 MHz, DMSO) δ 8.54 (s, 2 H), 7.86-8.01 (m, 2 H), 7.23-7.81 (m, 7 H), 6.91-7.10 (m, 4 H), 6.10-6.30 (m, 1 H), 5.12-5.30 (m, 1 H), 4.47-4.67 (m, 2 H), 3.76 and 3.77 (2 s, 6 H), 3.55-3.67 (m, 1 H), 2.89-3.13 (m, 1 H), 2.52-2.57 (m, 2 H), 2.22-2.44 (m, 4 H), 1.59-1.90 (m, 1 H), 0.92-1.54 (m, 4 H).<br>MS/ESI + [MH+] = 749.2 |
| [(1S)-2-(3,5-dichloro-1-oxido-pyridin-1-ium-4-yl)-1-(3,4-dimethoxyphenyl)ethyl] 4-[(2,3-dihydroxy-N-[(3R)-quinuclidin-3-yl]oxycarbonyl-anilino)methyl]benzoate | Example 152 | 1H NMR (400 MHz, DMSO) δ 8.53 (s, 2 H), 8.25 (s, 1 H), 7.91 (d, J = 7.06 Hz, 2 H), 7.41 (d, J = 7.50 Hz, 2 H), 6.93-7.08 (m, 3 H), 6.31-6.73 (m, 3 H), 6.20 (d, J = 4.41 Hz, 1 H), 4.60 (m, 3 H), 3.74 and 3.77 (2 s, 3 H each, 6 H), 3.55-3.64 (m, 1 H), 3.32 (dd, J = 14.11, 4.41 Hz, 1 H), 3.06 (m, 2 H), 2.59 (m, 4 H), 1.78 (m, 1 H), 0.99-1.61 (m, 4 H). |

-continued

| Name/Structure | Example number | Analytical Data |
|---|---|---|
| [(1S)-2-(3,5-dichloro-1-oxido-pyridin-1-ium-4-yl)-1-(3,4-dimethoxyphenyl)ethyl] 4-[(2-hydroxy-5-methoxy-N-[(3R)-quinuclidin-3-yl]oxycarbonyl-anilino)methyl]benzoate | Example 153 | 1H NMR (400 MHz, DMSO) δ 9.87-10.25 (bs, 1 H), 9.24-9.58 (bs, 1 H), 8.54 (s, 2 H), 8.13 (s, 1 H), 7.91 (d, J = 7.94 Hz, 2 H), 7.45 (d, J = 7.94 Hz, 2 H), 6.93-7.14 (m, 3 H), 6.50-6.90 (m, 3 H), 6.20 (dd, J = 9.26, 3.97 Hz, 1 H), 4.89 (m, 3 H), 3.77 and 3.83 (2 s, 6 H, 3 H each), 3.55-3.63 (m, 4 H), 2.87-3.48 (m, 7 H), 1.80 (m, 5 H). MS/ESI + [MH+] = 752.64 |
| [(1S)-2-(3,5-dichloro-1-oxido-pyridin-1-ium-4-yl)-1-(3,4-dimethoxyphenyl)ethyl] 4-[[[(3R)-quinuclidin-3-yl]oxycarbonyl-(1H-tetrazol-5-yl)amino]methyl]benzoate | Example 154 | 1H NMR (400 MHz, DMSO) δ 10.48-10.75 (bs, 1 H), 8.54 (s, 2 H), 7.99 (d, J = 8.38 Hz, 2 H), 7.37 (d, J = 7.94 Hz, 2 H), 6.76-7.14 (m, 3 H), 6.10-6.30 (m, 1 H), 5.69 (s, 2 H), 4.89-5.07 (m, 1 H), 3.76 (m, 7 H), 2.95-3.31 (m, 7 H), 2.12-2.27 (m, 1 H), 1.60-1.99 (m, 4 H). MS/ESI + [MH+] = 698.55 |

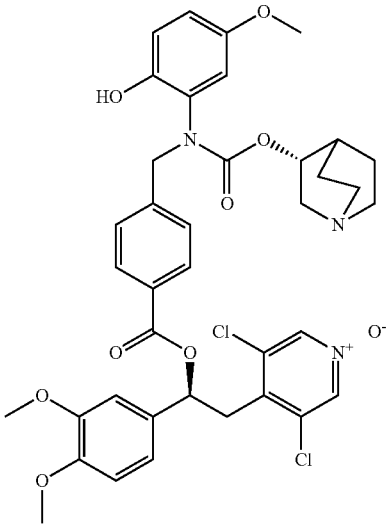

| Name/Structure | Example number | Analytical Data |
|---|---|---|
| [(1S)-1-[3-(cyclopropylmethoxy)-4-(difluoromethoxy)phenyl]-2-(3,5-dichloro-1-oxido-pyridin-1-ium-4-yl)ethyl] 3-[(2-fluoro-N-[(3R)-quinuclidin-3-yl]oxycarbonyl-anilino)methyl]benzoate 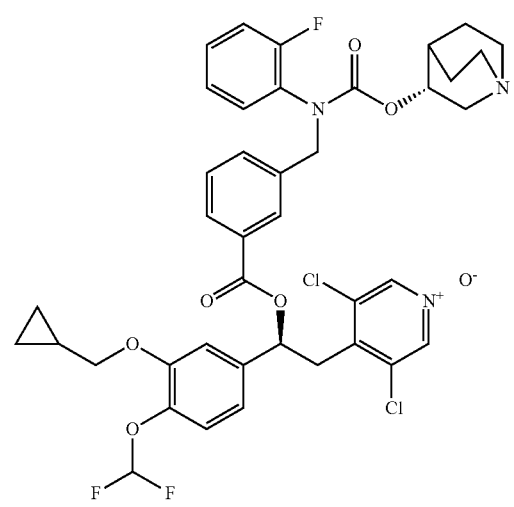 | Example 155 | 1H NMR (400 MHz, DMSO) δ 8.52 (s, 2 H), 8.18 (s, 1 H), 7.81-7.94 (m, 2 H), 7.37-7.56 (m, 2 H), 7.13-7.35 (m, 6 H), 7.02-7.10 (m, 2 H), 6.19 (d, J = 5.09 Hz, 1 H), 4.76-5.03 (m, 2 H), 4.61-4.72 (m, 1 H), 3.92 (d, J = 7.04 Hz, 2 H), 3.58 (dd, J = 14.09, 9.59 Hz, 1 H), 3.09 (dd, J = 14.48, 8.22 Hz, 1 H), 2.58 (t, J = 7.34 Hz, 4 H), 2.44 (m, 2 H), 1.81 (m, 1 H), 1.38-1.62 (m, 2 H), 1.00-1.32 (m, 3 H), 0.49-0.62 (m, 2 H), 0.22-0.40 (m, 2 H).<br>MS/ESI + [MH+] = 800.6 |
| [(1S)-1-[3-(cyclopropylmethoxy)-4-(difluoromethoxy)phenyl]-2-(3,5-dichloro-1-oxido-pyridin-1-ium-4-yl)ethyl] 3-[(N-[(3R)-quinuclidin-3-yl]oxycarbonyl-anilino)methyl]benzoate 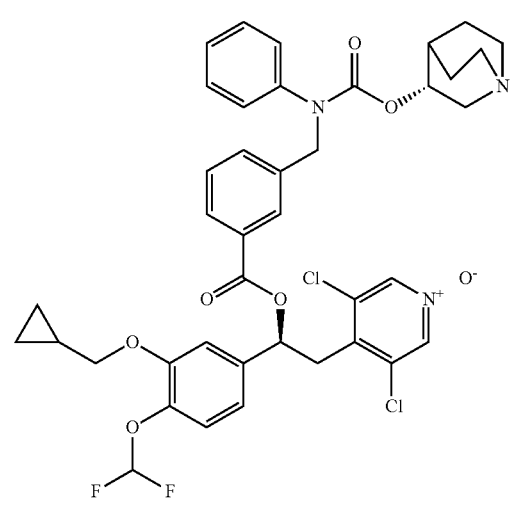 | Example 156 | 1H NMR (400 MHz, DMSO) δ 8.51 (s, 2 H), 7.81-7.94 (m, 2 H), 7.54 (dt, 1 H), 7.48 (t, 1 H), 7.30-7.44 (m, 2 H), 7.17-7.30 (m, 5 H), 7.05 (dd, 1 H), 7.06 (t, 1 H), 6.21 (dd, 1 H), 4.88-5.04 (m, 2 H), 4.63-4.82 (m, 1 H), 3.92 (d, 2 H), 3.59 (dd, 1 H), 3.31-3.40 (m, 1 H), 3.08-3.26 (m, 1 H), 2.56-2.85 (m, 5 H), 1.77-1.99 (m, 1 H), 1.42-1.75 (m, 2 H), 1.10-1.42 (m, 3 H), 0.44-0.68 (m, 2 H), 0.22-0.44 (m, 2 H).<br>MS/ESI + [MH+] = 782 |

Example 157

[(1S)-1-[3-(cyclopropylmethoxy)-4-(difluoromethoxy)phenyl]-2-(3,5-dichloro-1-oxido-pyridin-1-ium-4-yl)ethyl]2-hydroxy-3-[[(2-hydroxy-N-[(3R)-quinuclidin-3-yl]oxycarbonyl-anilino)methyl] benzoate formate Salt

Step 1: Preparation of methyl 2-(benzyloxy)-3-formylbenzoate

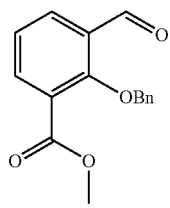 [SMILES: COC(=O)c1cccc(C=O)c1OCc1ccccc1]

A slurry of methyl 3-formyl-2-hydroxybenzoate (640 mg, 3.56 mmol), $K_2CO_3$ (982 mg, 7.12 mmol), and benzyl bromide (0.63 mL, 5.34 mmol) in DMF (3 mL) was stirred at room temperature for 16 hours and diluted with EtOAc (100 mL) and water (40 mL). The layers were separated and the organic phase dried over $MgSO_4$. After filtration and concentration in vacuo, the residue was purified via silica gel chromatography, eluting with 0-15% EtOAc in isohexane, to give the title compound as a white solid (598 mg, 62%).

$^1$H NMR (400 MHz, $CDCl_3$): δ 10.22 (s, 1H), 8.11 (dd, J=7.7, 1.9 Hz, 1H), 7.98 (dd, J=7.7, 1.9 Hz, 1H), 7.41-7.30 (m, 5H), 7.29-7.22 (m, 1H), 5.11 (s, 2H), 3.90 (s, 3H).

LCMS (Method 1): [MH+]=271 at 4.19 min.

Step 2: Preparation of [(1S)-1-[3-(cyclopropylmethoxy)-4-(difluoromethoxy)phenyl]-2-(3,5-dichloro-1-oxido-pyridin-1-ium-4-yl)ethyl]2-benzyloxy-3-formyl-benzoate

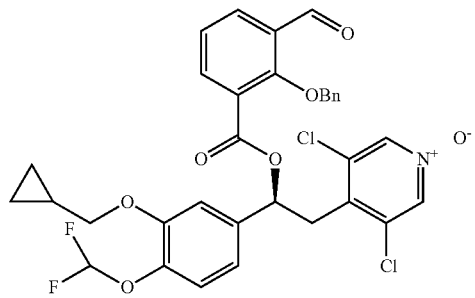

A solution of methyl 2-(benzyloxy)-3-formylbenzoate (598 mg, 2.21 mmol) in THF (4 mL) and MeOH (2 mL) and a solution of 4 N NaOH (1.10 mL, 4.43 mmol) was added at 0° C., and the reaction mixture stirred for 30 minutes. 2N HCl was then added at 0° C. to adjust the pH to ~2. After concentration in vacuo, the residue was azeotroped with toluene to dryness. The crude solid was dissolved in DMF (4.4 mL). To half of this solution (2.2 mL, 1.1 mmol) was added (S)-3,5-dichloro-4-(2-(3-(cyclopropylmethoxy)-4-(difluoromethoxy)phenyl)-2-hydroxyethyl)pyridine 1-oxide (553 mg, 1.32 mmol), 4-(dimethylamino)-pyridine (67 mg, 0.55 mmol), and N-(3-dimethylaminopropyl)-N'-ethylcarbodiimide hydrochloride (422 mg, 2.2 mmol), and the resulting mixture was stirred at room temperature for 4 hours. The reaction mixture was diluted with DCM (100 mL), the organic phase washed with sat. $NaHCO_3$ (2×50 mL). The phases were separated over a hydrophobic fit and concentrated in vacuo. The residue was purified via silica gel chromatography, eluting with 0-100% EtOAc in isohexane to give the title compound as a white solid (784 mg, 54% over two steps).

$^1$H NMR (400 MHz, $CDCl_3$): δ 10.16 (s, 1H), 8.13 (s, 2H), 8.07 (dd, J=7.9, 1.6 Hz, 1H), 8.02-7.99 (m, 2H), 7.35-7.28 (m, 3H), 7.26-7.21 (m, 2H), 7.15 (d, J=8.4 Hz, 1H), 7.05-6.99 (m, 2H), 6.60 (t, J=75.3 Hz, 1H), 6.31 (dd, J=9.2, 5.0 Hz, 1H), 4.98-4.90 (m, 2H), 3.89-3.80 (m, 2H), 3.66 (dd, J=14.1, 9.2 Hz, 1H), 3.35 (dd, J=13.9, 5.1 Hz, 1H), 0.92-0.82 (m, 1H), 0.66-0.58 (m, 2H), 0.37-0.30 (m, 2H).

LCMS (Method 2): [MH+]=657 at 4.33 min.

Step 3: Preparation of [(1S)-1-[3-(cyclopropylmethoxy)-4-(difluoromethoxy)phenyl]-2-(3,5-dichloro-1-oxido-pyridin-1-ium-4-yl)ethyl]3-formyl-2-hydroxy-benzoate

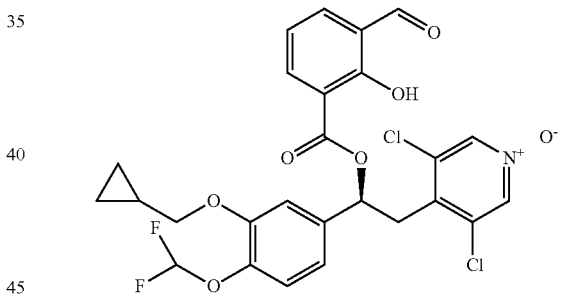

TFA (0.4 mL) was carefully added to a solution of [(1S)-1-[3-(cyclopropylmethoxy)-4-(difluoromethoxy)phenyl]-2-(3,5-dichloro-1-oxido-pyridin-1-ium-4-yl)ethyl]2-benzyloxy-3-formyl-benzoate (116 mg, 0.18 mmol) in toluene (0.8 mL) at 0° C. The resulting mixture was stirred at 0° C. for 50 minutes. The solution was diluted with DCM (20 mL) and sat. $NaHCO_3$ (20 mL). The layers were separated over a hydrophobit frit and the organic phase concentrated in vacuo, the residue azeotroped with toluene to dryness. The yellow gum (120 mg) was used in the next step without further purification.

$^1$H NMR (400 MHz, $CDCl_3$): δ 11.20 (s, 1H), 10.38 (s, 1H), 8.15 (s, 2H), 8.00 (d, J=7.4 Hz, 1H), 7.29-7.22 (m, 2H), 7.24-6.98 (m, 3H), 6.60 (t, J=75.3 Hz, 1H), 6.30 (dd, J=9.8, 4.3 Hz, 1H), 3.90 (d, J=7.0 Hz, 2H), 3.72 (dd, J=14.2, 9.9 Hz, 1H), 3.35 (dd, J=14.2, 4.3 Hz, 1H), 1.35-1.23 (m, 1H), 0.69-0.62 (m, 2H), 0.40-0.34 (m, 2H). LCMS (Method 2): [MH+]=568 at 4.08 min.

Step 4: Preparation of [(1S)-1-[3-(cyclopropyl-methoxy)-4-(difluoromethoxy)phenyl]-2-(3,5-dichloro-1-oxido-pyridin-1-ium-4-yl)ethyl]2-hydroxy-3-[(2-hydroxyanilino)methyl]benzoate

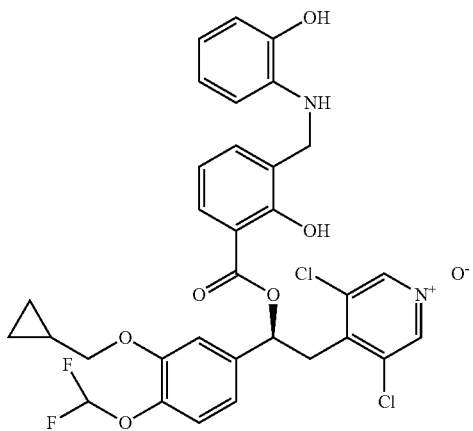

A solution of [(1S)-1-[3-(cyclopropylmethoxy)-4-(difluoromethoxy)phenyl]-2-(3,5-dichloro-1-oxido-pyridin-1-ium-4-yl)ethyl]3-formyl-2-hydroxy-benzoate (800 mg, 1.41 mmol), MeOH (5 mL) AcOH (0.5 mL) and 2-aminophenol (184 mg, 1.69 mmol) was stirred at room temperature for 16 hours before adding NaBH$_3$(CN) (444 mg, 7.05 mmol) in one portion. The resulting mixture was stirred at room temperature for 3 h, concentrated in vacuo to a sticky pink oil. The residue was used in the next step without further purification. LCMS (Method 2): [MH+]=661 at 3.68 min.

Step 5: Preparation of [(1S)-1-[3-(cyclopropyl-methoxy)-4-(difluoromethoxy)phenyl]-2-(3,5-dichloro-1-oxido-pyridin-1-ium-4-yl)ethyl]2-hydroxy-3-[(2-hydroxy-N-[(3R)-quinuclidin-3-yl]oxycarbonyl-anilino)methyl]benzoate formate Salt

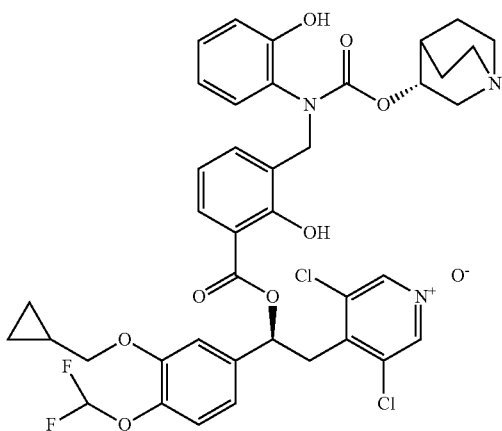

A solution of [(1S)-1-[3-(cyclopropylmethoxy)-4-(difluoromethoxy)phenyl]-2-(3,5-dichloro-1-oxido-pyridin-1-ium-4-yl)ethyl]2-hydroxy-3-[(2-hydroxyanilino)-methyl]benzoate (250 mg, 0.38 mmol) in CH$_3$CN (6 mL) was added (R)-quinuclidin-3-yl carbonochloridate hydrochloride (150 mg, 0.66 mmol) in one portion. The resulting slurry was stirred at room temperature for 1 hour and concentrated in vacuo. The residue was purified by preparative HPLC to provide the title compound as a pale yellow solid (130 mg, 42%).

$^1$H NMR (400 MHz, DMSO): δ 10.74-9.51 (m, 2H), 8.42 (s, 2H), 7.76 (d, J=8.0 Hz, 1H), 7.51 (d, J=7.6 Hz, 1H), 7.13-7.04 (m, 3H), 6.99-6.86 (m, 3H), 6.93 (t, J=75 Hz, 1H), 6.84 (t, J=7.6 Hz, 1H), 6.73 (d, J=7.6 Hz, 1H), 6.52 (t, J=7.9 Hz, 1H), 6.11-6.04 (m, 1H), 4.92-4.53* (m, 1H), 4.52-4.44 t (m, 1H), 3.79 (d, J=6.9 Hz, 2H), 3.50 (dd, J=14.5, 9.4 Hz, 1H), 3.22 (dd, J=14.7, 4.8 Hz, 1H), 3.00-2.91 (m, 1H), 2.59-2.39 (m, 3H), 2.39-2.24 (m, 2H), 1.77-1.70* (m, 1H), 1.70-1.62† (m, 1H), 1.49-1.38 (m, 1H), 1.37-1.29 (m, 1H), 1.11-0.98 (m, 3H), 0.45-0.39 (m, 2H), 0.23-0.18 (m, 2H), † and * refer to different rotamers (arbitrarily assigned). LCMS (Method 1): [MH+]=814 at 3.04 mM.

Pharmacological Activity of the Compounds of the Invention:

In Vitro Determination of PDE4 Inhibitory Activity:

In vitro determination of PDE4 inhibitory activity for compounds of the invention may be determined according to one of the protocols herebelow reported.

PDE4B2 HTRF Assay:

PDE4B2 activity is detected using the LANCE Ultra cAMP homogeneous time resolved fluorescence resonance energy transfer (TR-FRET) assay from Perkin Elmer. The assay is based on the competition between the europium (Eu) chelate-labeled cAMP tracer and sample cAMP for binding sites on cAMP-specific monoclonal antibodies (mAb) labelled with the ULight™ dye. The assay is carried out in 384-well low volume plates in a volume of 10 μl. Human recombinant PDE4B2 (80 pM) is incubated for 2 hours with 3 nM cAMP in buffer containing 1×HBSS, 5 mM HEPES, 3 mM MgCl$_2$, 0.1% BSA, pH 7.4 with or without test compounds. The enzymatic reactions are efficiently stopped by the addition of 500 μM IBMX present in the combined Stop/Detection buffer containing europium (Eu) chelate-labeled cAMP tracer and cAMP-specific monoclonal antibodies (mAb) labelled with the ULight™ dye. Samples are then further incubated for 1 hour before plates are read at ex 340 nm and em at 665 nm and 615 nm on an EnVision reader. IC$_{50}$ values are determined from competition curves using a non-linear curve fitting program.

PDE4 Cell Free Assay Protocol:

PDE4 activity is determined in U937 human monocytic supernatants cells lysate. Cells are cultured, harvested and supernatant fraction prepared essentially as described in Torphy T J et al., J. Pharmacol. Exp. Ther., 1992; 263:1195-1205, which is incorporated herein by reference in its entirety. U937 cells are grown at 37° C., 5% CO$_2$ in RPMI 1640 with GlutaMAX™-I medium supplemented with 10% fetal bovine serum and 100 μg/mL Pen-strep (Gibco). Cells are harvested and washed twice by centrifugation (150×g, 8 min) in cold PBS. Washed cells are re-suspended in cold Krebs-Ringer-Henseleit buffer at a final concentration 20×10$^6$ cells/mL and sonicated. After centrifugation at 15000× g for 20 minutes, the supernatants are pooled, divided in aliquots and stored at −80° C. PDE4 activity is determined in cells supernatants by assaying cAMP disappearance from the incubation mixtures. The concentration of the test compounds ranges between 10$^{-12}$ M and 10$^{-6}$ M. Reactions are stopped by enzyme heat inactivation (2.5 minutes at 100° C.) and residual cAMP content is determined using the 'LANCE cAMP Assay' from PerkinElmer following the provider instructions.

The results, expressed as mean±standard deviation of the molar concentration of the test compound producing 50% inhibition of cAMP disappearance (IC$_{50}$). Percentage of inhibition of PDE4 activity is calculated, assuming cAMP disappearance in the absence of inhibitors as 100% and cAMP disappearance in heat inactivated samples as 0%.

Representative compounds of the invention, when tested in one of the above reported protocols, displayed an IC$_{50}$ lower than 100 nM.

In vitro Determination of M3 Antagonism:

In vitro determination of M3 antagonism for compounds of the invention may be determined according to one of the protocols herebelow reported.

M3 Receptor Radioligand Binding Assay:

Human M$_3$ receptor membranes (15 μg/well) from Perkin Elmer are incubated with 0.52 nM Scopolamine Methyl Chloride, [N-methyl-3H] with or without test compounds, or a saturating concentration of Atropine (5 μM) for the determination of non-specific binding. The assay is carried out in 96-well polypropylene plates in a volume of 250 μl. The assay buffer used is 50 mM Tris-HCl, 154 mM NaCl (pH 7.4). The final assay concentration of DMSO is 0.5% (v/v). The plates are sealed and incubated for 2 hours at room temperature on an orbital shaker (slow speed). Membranes are harvested onto 96-well unifilter GF/C filter plates pre-treated with 0.5% polyethyleneimine (v/v), using a filter manifold, washed four times with 200 μl of assay buffer. The plates are dried before addition of 50 μl of microscint-0, sealed then read in a Trilux Microbeta scintillation counter. IC$_{50}$ values are determined from competition curves using a non-linear curve fitting program. K$_i$ values are calculated from IC$_{50}$ values by the Cheng and Prusoff equation.

M3 Binding Assay:

CHO-K 1 clone cells expressing the human M3-receptor (Swissprot P20309) were harvested in Ca$^{++}$/Mg$^{++}$ free phosphate-buffered saline and collected by centrifugation at 1500 rpm for 3 minutes. The pellets were resuspended in ice cold buffer A (15 mM Tris-HCl pH 7.4, 2 mM MgCl$_2$, 0.3 mM EDTA, 1 mM EGTA) and homogenized by a PBI politron (setting 5 for 15 s). The crude membrane fraction was collected by two consecutive centrifugation steps at 40000 g for 20 minutes at 4° C., separated by a washing step in buffer A. The pellets obtained were finally resuspended in buffer B (75 mM Tris HCl pH 7.4, 12.5 mM MgCl$_2$, 0.3 mM EDTA, 1 mM EGTA, 250 mM sucrose), and aliquots were stored at –80° C.

The day of experiment, frozen membranes were resuspended in buffer C (50 mM Tris-HCl pH 7.4, 2.5 mM MgCl$_2$, 1 mM EDTA). The non selective muscarinic radioligand [$^3$H]-N-methyl scopolamine (see Mol. Pharmacol. 45:899-907, which is incorporated herein by reference in its entirety) was used to label the M3 binding sites. Binding experiments were performed in duplicate (ten point concentrations curves) in 96 well plates at radioligand concentration of 0.1-0.3 nM. The non specific binding was determined in the presence of cold N-methyl scopolamine 10 μM. Samples (final volume 0.75 mL) were incubated at room temperature for 90 minutes. The reaction was terminated by rapid filtration through GF/B Unifilter plates and two washes (0.75 mL) with cold buffer C using a Packard Filtermate Harvester. Radioactivity on the filters was measured by a microplate scintillation counter TriCarb 2500 (PerkinElmer).

Representative compounds of the invention, when tested in one of the above reported protocols, displayed an IC$_{50}$ lower than 100 nM.

Representative compounds of the invention displayed an IC$_{50}$ lower than 100 nM in both PDE4 cell free and M3 binding assays.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A compound represented by formula (I):

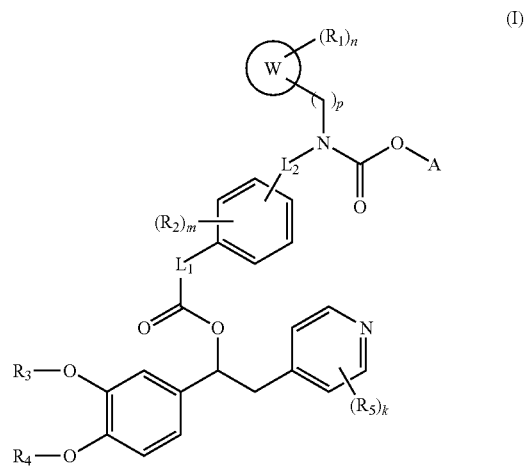

wherein
W is aryl or heteroaryl;
each R$_1$ is independently hydrogen, halogen, (C$_1$-C$_4$) alkyl, (C$_1$-C$_4$) alkoxy, (C$_1$-C$_4$) haloalkyl, hydroxy, —SO$_2$NR$_6$R$_7$, —CN, —NR$_8$SO$_2$R$_9$, —NR$_6$R$_7$, —CONR$_6$R$_7$, or —NR$_8$COR$_9$, and wherein said (C$_1$-C$_4$) alkyl is optionally substituted by one or more groups selected from the group consisting of (C$_3$-C$_7$) cycloalkyl, hydroxyl, and —NR$_6$R$_7$ and said (C$_1$-C$_4$) alkoxy is optionally substituted by one or more halogen atoms or (C$_3$-C$_7$) cycloalkyl groups, and
wherein,
R$_6$ is hydrogen or (C$_1$-C$_6$) alkyl;
R$_7$ is hydrogen or (C$_1$-C$_6$) alkyl;
R$_8$ is hydrogen or (C$_1$-C$_6$) alkyl;
R$_9$ is hydrogen or (C$_1$-C$_6$) alkyl;
n is an integer ranging from 1 to 3;
each R$_2$ is independently hydrogen, halogen, (C$_1$-C$_4$) alkyl, (C$_1$-C$_4$) alkoxy, (C$_1$-C$_4$)haloalkyl, hydroxy, —SO$_2$NR$_{10}$R$_{11}$, —CN, or —NR$_{12}$SO$_2$R$_{13}$, and wherein said (C$_1$-C$_4$) alkyl and (C$_1$-C$_4$) alkoxy are optionally substituted by one (C$_3$-C$_7$) cycloalkyl group,
R$_{10}$ is hydrogen or (C$_1$-C$_6$) alkyl;
R$_{11}$ is hydrogen or (C$_1$-C$_6$) alkyl;
R$_{12}$ is hydrogen or (C$_1$-C$_6$) alkyl;
R$_{13}$ is hydrogen or (C$_1$-C$_6$) alkyl;
m is an integer ranging from 1 to 3;
p is zero or 1;
L$_1$ is a group (CH$_2$)$_t$ wherein t is 0 or an integer ranging from 1 to 3;
L$_2$ is:
(CH$_2$)$_q$ wherein q is an integer ranging from 1 to 3,
divalent ortho-benzyl (o-C$_6$H$_4$—CH$_2$—),
divalent meta-benzyl (m-C$_6$H$_4$—CH$_2$—),
divalent para-benzyl (p-C$_6$H$_4$—CH$_2$—),
divalent ortho-methyleneoxy-benzyl (o-CH$_2$—O—C$_6$H$_4$—CH$_2$—),
divalent meta-methyleneoxy-benzyl (m-CH$_2$—O—C$_6$H$_4$—CH$_2$—), or
divalent para-methylenoxy-benzyl (p-CH$_2$—O—C$_6$H$_4$—CH$_2$—), wherein the carbon chain atom of the benzyl group is linked to the nitrogen atom and the respective aromatic carbon atom or the methylene carbon atom of the methylene oxy group is linked to the phenyl group;

$R_3$ and $R_4$ are different or the same and are each independently:

H;

($C_3$-$C_7$) cycloalkylcarbonyl;

($C_1$-$C_6$) alkyl, optionally substituted by one or more substituents selected from ($C_3$-$C_7$) cycloalkyl or ($C_5$-$C_7$) cycloalkenyl;

($C_1$-$C_6$) haloalkyl;

($C_3$-$C_7$) cycloalkyl;

($C_5$-$C_7$) cycloalkenyl;

($C_2$-$C_6$) alkenyl; or ($C_2$-$C_6$) alkynyl;

or $R_3$ and $R_4$, together with the interconnecting atoms, form a 2,2-difluoro-1,3-dioxolane ring of formula (r) fused to the phenyl moiety which bears groups —$OR_3$ and —$OR_4$, wherein asterisks indicate carbon atoms shared with the phenyl ring:

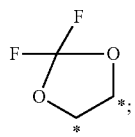

(r)

each $R_5$ is independently CN, $NO_2$, $CF_3$ or a halogen atom;

k is an integer ranging from 1 to 3; and

A is a nitrogen containing group which may be:

a group (a) which is —$(CH_2)_s$—$NR_{14}R_{15}$ wherein s is an integer ranging from 1 to 4 and $R_{14}$ and $R_{15}$ are independently hydrogen or ($C_1$-$C_4$) alkyl; or a group (b) which is a saturated monocyclic, bicyclic, or tricyclic heterocyclic ring system optionally substituted by one or two groups $R_{16}$ which are at each occurrence independently ($C_1$-$C_4$) alkyl or benzyl;

an N-oxide on the pyridine ring, deuterated derivative, or a pharmaceutically acceptable salt thereof.

2. A compound, N-oxide, deuterated derivative, or a pharmaceutically acceptable salt according to claim 1, which is represented by formula (IB):

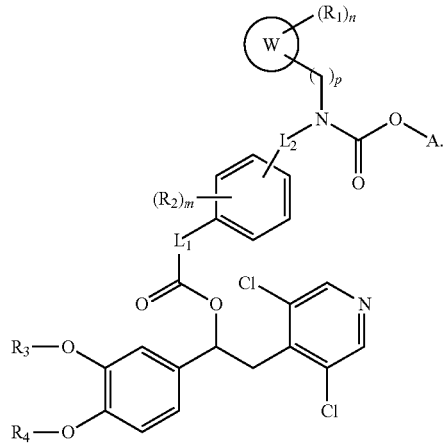

(IB)

3. A compound, N-oxide, deuterated derivative, or a pharmaceutically acceptable salt according to claim 1, which is represented by the formula (ID):

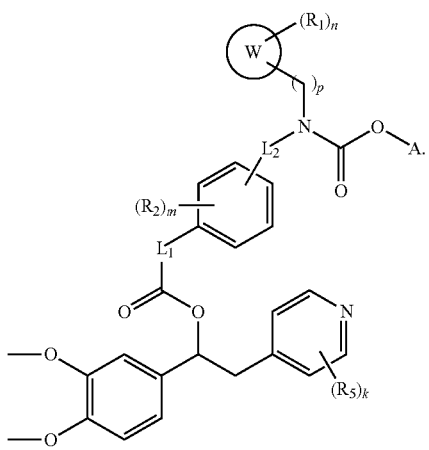

(ID)

4. A compound N-oxide, deuterated derivative, or a pharmaceutically acceptable salt according to claim 1, which is represented by formula (IA):

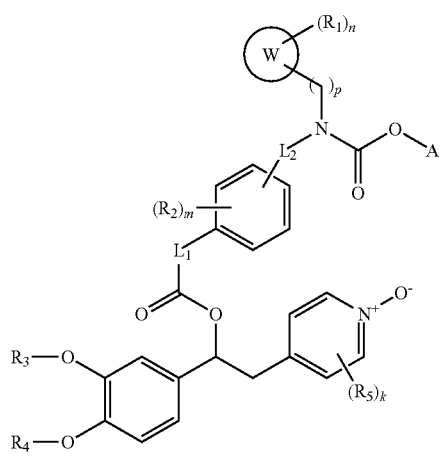

(IA)

5. A compound, N-oxide, deuterated derivative, or a pharmaceutically acceptable salt according to claim 1, which is represented by formula (IE):

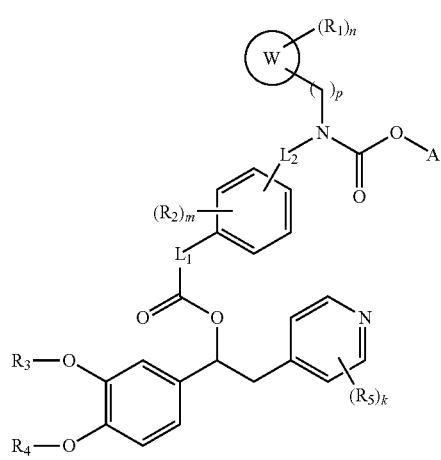

(IE)

wherein $L_2$ and $L_1$ are located in the ortho, meta or para position on the phenyl ring they are linked to;

$L_1$ is selected from a group $(CH_2)_t$ wherein t is 0 or an integer ranging from 1 to 3; and L₂ is:
(CH₂)_q wherein q is an integer ranging from 1 to 3,
divalent meta-benzyl (m-C₆H₄—CH₂—),
divalent para-benzyl (p-C₆H₄—CH₂—),
divalent meta-methyleneoxy-benzyl (m-CH₂—O—C₆H₄—CH₂—), or
divalent para-methylenoxy-benzyl (p-CH₂—O—C₆H₄—CH₂—), wherein the carbon chain atom of the benzyl group is linked to the nitrogen atom and the respective aromatic carbon atom or the methylene carbon atom of the methylene oxy group is linked to the phenyl group.

6. A compound, N-oxide, deuterated derivative, or a pharmaceutically acceptable salt according to claim 1, which has the absolute configuration of carbon (1) shown in formula (I)':

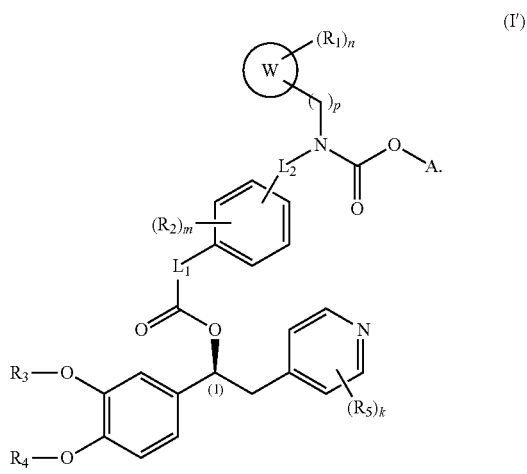

(I')

7. A compound, N-oxide, deuterated derivative, or a pharmaceutically acceptable salt according to claim 1 which is a compound selected from the group consisting of:
- (1S)-2-(3,5-dichloro-1-oxido-pyridin-1-ium-4-yl)-1-(3,4-dimethoxyphenyl)ethyl]3-[(4-fluoro-N-[(3R)-quinuclidin-3-yl]oxycarbonyl-anilino)methyl]benzoate;
- [(1S)-2-(3,5-dichloro-1-oxido-pyridin-1-ium-4-yl)-1-(3,4-dimethoxyphenyl)ethyl]3-[(2-fluoro-N-[(3R)-quinuclidin-3-yl]oxycarbonyl-anilino)methyl]benzoate;
- [(1S)-2-(3,5-dichloro-1-oxido-pyridin-1-ium-4-yl)-1-(3,4-dimethoxyphenyl)ethyl]3-[(3-fluoro-N-[(3R)-quinuclidin-3-yl]oxycarbonyl-anilino)methyl]benzoate;
- [(1S)-2-(3,5-dichloro-1-oxido-pyridin-1-ium-4-yl)-1-(3,4-dimethoxyphenyl)ethyl]3-[(2-methoxy-N-[(3R)-quinuclidin-3-yl]oxycarbonyl-anilino)methyl]benzoate;
- [(1S)-2-(3,5-dichloro-1-oxido-pyridin-1-ium-4-yl)-1-(3,4-dimethoxyphenyl)ethyl]3-[(3-methoxy-N-[(3R)-quinuclidin-3-yl]oxycarbonyl-anilino)methyl]benzoate;
- [(1S)-2-(3,5-dichloro-1-oxido-pyridin-1-ium-4-yl)-1-(3,4-dimethoxyphenyl)ethyl]3-[(4-methoxy-N-[(3R)-quinuclidin-3-yl]oxycarbonyl-anilino)methyl]benzoate;
- [(1S)-2-(3,5-dichloro-1-oxido-pyridin-1-ium-4-yl)-1-(3,4-dimethoxyphenyl)ethyl]4-[(N-[(3R)-quinuclidin-3-yl]oxycarbonylanilino)methyl]benzoate;
- [(1S)-2-(3,5-dichloro-1-oxido-pyridin-1-ium-4-yl)-1-(3,4-dimethoxyphenyl)ethyl]4-[(2-fluoro-N-[(3R)-quinuclidin-3-yl]oxycarbonyl-anilino)methyl]benzoate;
- [(1S)-2-(3,5-dichloro-1-oxido-pyridin-1-ium-4-yl)-1-(3,4-dimethoxyphenyl)ethyl]4-[(4-fluoro-N-[(3R)-quinuclidin-3-yl]oxycarbonyl-anilino)methyl]benzoate;
- [(1S)-2-(3,5-dichloro-1-oxido-pyridin-1-ium-4-yl)-1-(3,4-dimethoxyphenyl)ethyl]4-[(2-methoxy-N-[(3R)-quinuclidin-3-yl]oxycarbonyl-anilino)methyl]benzoate;
- [(1S)-2-(3,5-dichloro-1-oxido-pyridin-1-ium-4-yl)-1-(3,4-dimethoxyphenyl)ethyl]4-[(3-methoxy-N-[(3R)-quinuclidin-3-yl]oxycarbonyl-anilino)methyl]benzoate;
- [(1S)-2-(3,5-dichloro-1-oxido-pyridin-1-ium-4-yl)-1-(3,4-dimethoxyphenyl)ethyl]4-[(2-methyl-N-[(3R)-quinuclidin-3-yl]oxycarbonyl-anilino)methyl]benzoate;
- [(1S)-2-(3,5-dichloro-1-oxido-pyridin-1-ium-4-yl)-1-(3,4-dimethoxyphenyl)ethyl]3-[(N-[(3R)-quinuclidin-3-yl]oxycarbonylanilino)methyl]benzoate;
- [(1R)-2-(3,5-dichloro-1-oxido-pyridin-1-ium-4-yl)-1-(3,4-dimethoxyphenyl)ethyl]3-[(N-[(3R)-quinuclidin-3-yl]oxycarbonylanilino)methyl]benzoate;
- [(1S)-2-(3,5-dichloro-1-oxido-pyridin-1-ium-4-yl)-1-(3,4-dimethoxyphenyl)ethyl]4-[(3-fluoro-N-[(3R)-quinuclidin-3-yl]oxycarbonyl-anilino)methyl]benzoate;
- [(1R)-2-(3,5-dichloro-1-oxido-pyridin-1-ium-4-yl)-1-(3,4-dimethoxyphenyl)ethyl]4-[(3-fluoro-N-[(3R)-quinuclidin-3-yl]oxycarbonyl-anilino)methyl]benzoate;
- [(1S)-2-(3,5-dichloro-1-oxido-pyridin-1-ium-4-yl)-1-(3,4-dimethoxyphenyl)ethyl]4-[(4-methoxy-N-[(3R)-quinuclidin-3-yl]oxycarbonyl-anilino)methyl]benzoate;
- [(1R)-2-(3,5-dichloro-1-oxido-pyridin-1-ium-4-yl)-1-(3,4-dimethoxyphenyl)ethyl]4-[(4-methoxy-N-[(3R)-quinuclidin-3-yl]oxycarbonyl-anilino)methyl]benzoate;
- [2-(3,5-dichloro-1-oxido-pyridin-1-ium-4-yl)-1-(3,4-dimethoxyphenyl)ethyl]3-[(N-[(3R)-quinuclidin-3-yl]oxycarbonylanilino)methyl]benzoate;
- [(1S)-2-(3,5-dichloro-1-oxido-pyridin-1-ium-4-yl)-1-(3,4-dimethoxyphenyl)ethyl]3-bromo-5-[(2-fluoro-N-[(3R)-quinuclidin-3-yl]oxycarbonyl-anilino)methyl]benzoate;
- [(1S)-2-(3,5-dichloro-1-oxido-pyridin-1-ium-4-yl)-1-(3,4-dimethoxyphenyl)ethyl]2-[4-[(N-[(3R)-quinuclidin-3-yl]oxycarbonylanilino)methyl]phenyl]acetate;
- [(1S)-1-[3-(cyclopropylmethoxy)-4-(difluoromethoxy)phenyl]-2-(3,5-dichloro-1-oxido-pyridin-1-ium-4-yl)ethyl]2-[4-[(N-[(3R)-quinuclidyl]oxycarbonylanilino)methyl]phenyl]acetate;
- [(1S)-2-(3,5-dichloro-1-oxido-pyridin-1-ium-4-yl)-1-(3,4-dimethoxyphenyl)ethyl]2-[4-[(2-fluoro-N-[(3R)-quinuclidin-3-yl]oxycarbonyl-anilino)methyl]phenyl]acetate;
- [(1S)-2-(3,5-dichloro-1-oxido-pyridin-1-ium-4-yl)-1-(3,4-dimethoxyphenyl)ethyl]3-[(3-chloro-N-[(3R)-quinuclidin-3-yl]oxycarbonyl-anilino)methyl]benzoate;
- [(1S)-2-(3,5-dichloro-1-oxido-pyridin-1-ium-4-yl)-1-(3,4-dimethoxyphenyl)ethyl]3-[(2,3-difluoro-N-[(3R)-quinuclidin-3-yl]oxycarbonyl-anilino)methyl]benzoate;
- [(1S)-2-(3,5-dichloro-1-oxido-pyridin-1-ium-4-yl)-1-(3,4-dimethoxyphenyl)ethyl]3-[(2,5-difluoro-N-[(3R)-quinuclidin-3-yl]oxycarbonyl-anilino)methyl]benzoate;
- [(1S)-2-(3,5-dichloro-1-oxido-pyridin-1-ium-4-yl)-1-(3,4-dimethoxyphenyl)ethyl]3-[(3-methyl-N-[(3R)-quinuclidin-3-yl]oxycarbonyl-anilino)methyl]benzoate;
- [(1S)-2-(3,5-dichloro-1-oxido-pyridin-1-ium-4-yl)-1-(3,4-dimethoxyphenyl)ethyl]3-[[N-[(3R)-quinuclidin-3-yl]oxycarbonyl-3-(trifluoromethyl)anilino]methyl]benzoate;
- [(1S)-2-(3,5-dichloro-1-oxido-pyridin-1-ium-4-yl)-1-(3,4-dimethoxyphenyl)ethyl]3-[(2-methyl-N-[(3R)-quinuclidin-3-yl]oxycarbonyl-anilino)methyl]benzoate;

[(1S)-2-(3,5-dichloro-1-oxido-pyridin-1-ium-4-yl)-1-(3,4-dimethoxyphenyl)ethyl]3-[(3-cyano-N-[(3R)-quinuclidin-3-yl]oxycarbonyl-anilino)methyl]benzoate;

[(1S)-2-(3,5-dichloro-1-oxido-pyridin-1-ium-4-yl)-1-[4-(difluoromethoxy)-3-methoxy-phenyl]ethyl]3-[(2-fluoro-N-[(3R)-quinuclidin-3-yl]oxycarbonyl-anilino)methyl]benzoate;

[(1S)-2-(3,5-dichloro-1-oxido-pyridin-1-ium-4-yl)-1-[4-(difluoromethoxy)-3-isopropoxy-phenyl]ethyl]3-[(2-fluoro-N-[(3R)-quinuclidin-3-yl]oxycarbonyl-anilino)methyl]benzoate;

[(1S)-2-(3,5-dichloro-1-oxido-pyridin-1-ium-4-yl)-1-[4-(difluoromethoxy)-3-ethoxy-phenyl]ethyl]3-[(2-fluoro-N-[(3R)-quinuclidin-3-yl]oxycarbonyl-anilino)methyl]benzoate;

[(1S)-2-(3,5-dichloro-1-oxido-pyridin-1-ium-4-yl)-1-[4-(difluoromethoxy)-3-methoxy-phenyl]ethyl]3-[(3-fluoro-N-[(3R)-quinuclidin-3-yl]oxycarbonyl-anilino)methyl]benzoate;

[(1S)-2-(3,5-dichloro-1-oxido-pyridin-1-ium-4-yl)-1-[4-(difluoromethoxy)-3-isopropoxy-phenyl]ethyl]3-[(3-fluoro-N-[(3R)-quinuclidin-3-yl]oxycarbonyl-anilino)methyl]benzoate;

[(1S)-2-(3,5-dichloro-1-oxido-pyridin-1-ium-4-yl)-1-[4-(difluoromethoxy)-3-ethoxy-phenyl]ethyl]3-[(3-fluoro-N-[(3R)-quinuclidin-3-yl]oxycarbonyl-anilino)methyl]benzoate;

[(1S)-2-(3,5-dichloro-1-oxido-pyridin-1-ium-4-yl)-1-[4-(difluoromethoxy)-3-methoxy-phenyl]ethyl]4-[(2-methoxy-N-[(3R)-quinuclidin-3-yl]oxycarbonyl-anilino)methyl]benzoate;

[(1S)-2-(3,5-dichloro-1-oxido-pyridin-1-ium-4-yl)-1-[4-(difluoromethoxy)-3-isopropoxy-phenyl]ethyl]4-[(2-methoxy-N-[(3R)-quinuclidin-3-yl]oxycarbonyl-anilino)methyl]benzoate;

[(1S)-2-(3,5-dichloro-1-oxido-pyridin-1-ium-4-yl)-1-[4-(difluoromethoxy)-3-ethoxy-phenyl]ethyl]4-[(2-methoxy-N-[(3R)-quinuclidin-3-yl]oxycarbonyl-anilino)methyl]benzoate;

[(1S)-2-(3,5-dichloro-1-oxido-pyridin-1-ium-4-yl)-1-(3,4-dimethoxyphenyl)ethyl]4-[(2,3-difluoro-N-[(3R)-quinuclidin-3-yl]oxycarbonyl-anilino)methyl]benzoate;

[(1S)-2-(3,5-dichloro-1-oxido-pyridin-1-ium-4-yl)-1-(3,4-dimethoxyphenyl)ethyl]4-[(2,4-difluoro-N-[(3R)-quinuclidin-3-yl]oxycarbonyl-anilino)methyl]benzoate;

[(1S)-2-(3,5-dichloro-1-oxido-pyridin-1-ium-4-yl)-1-(3,4-dimethoxyphenyl)ethyl]4-[(2,5-difluoro-N-[(3R)-quinuclidin-3-yl]oxycarbonyl-anilino)methyl]benzoate;

[(1S)-2-(3,5-dichloro-1-oxido-pyridin-1-ium-4-yl)-1-(3,4-dimethoxyphenyl)ethyl]4-[(2,5-difluoro-N-[(3R)-quinuclidin-3-yl]oxycarbonyl-anilino)methyl]benzoate;

[(1S)-2-(3,5-dichloro-1-oxido-pyridin-1-ium-4-yl)-1-(3,4-dimethoxyphenyl)ethyl]4-[(3-methyl-N-[(3R)-quinuclidin-3-yl]oxycarbonyl-anilino)methyl]benzoate;

[(1S)-2-(3,5-dichloro-1-oxido-pyridin-1-ium-4-yl)-1-(3,4-dimethoxyphenyl)ethyl]4-[(3-methyl-N-[(3R)-quinuclidin-3-yl]oxycarbonyl-anilino)methyl]benzoate;

[(1S)-2-(3,5-dichloro-1-oxido-pyridin-1-ium-4-yl)-1-(3,4-dimethoxyphenyl)ethyl]4-[(3-cyano-N-[(3R)-quinuclidin-3-yl]oxycarbonyl-anilino)methyl]benzoate;

[(1S)-2-(3,5-dichloro-1-oxido-pyridin-1-ium-4-yl)-1-(3,4-dimethoxyphenyl)ethyl]2-fluoro-4-[(2-fluoro-N-[(3R)-quinuclidin-3-yl]oxycarbonyl-anilino)methyl]benzoate;

[(1S)-2-(3,5-dichloro-1-oxido-pyridin-1-ium-4-yl)-1-(3,4-dimethoxyphenyl)ethyl]2-fluoro-4-[(N-[(3R)-quinuclidin-3-yl]oxycarbonylanilino)methyl]benzoate;

[(1S)-2-(3,5-dichloro-1-oxido-pyridin-1-ium-4-yl)-1-(3,4-dimethoxyphenyl)ethyl]3-fluoro-5-[(2-fluoro-N-[(3R)-quinuclidin-3-yl]oxycarbonyl-anilino)methyl]benzoate;

[(1S)-2-(3,5-dichloro-1-oxido-pyridin-1-ium-4-yl)-1-(3,4-dimethoxyphenyl)ethyl]3-fluoro-4-[(2-fluoro-N-[(3R)-quinuclidin-3-yl]oxycarbonyl-anilino)methyl]benzoate;

[(1S)-2-(3,5-dichloro-1-oxido-pyridin-1-ium-4-yl)-1-[4-(difluoromethoxy)-3-(trideuteriomethoxy)phenyl]ethyl]3-[(2-fluoro-N-[(3R)-quinuclidin-3-yl]oxycarbonyl-anilino)methyl]benzoate;

[(1S)-2-(3,5-dichloro-1-oxido-pyridin-1-ium-4-yl)-1-[4-(difluoromethoxy)-3-(trideuteriomethoxy)phenyl]ethyl]3-[(3-fluoro-N-[(3R)-quinuclidin-3-yl]oxycarbonyl-anilino)methyl]benzoate;

[(1S)-2-(3,5-dichloro-1-oxido-pyridin-1-ium-4-yl)-1-[4-(difluoromethoxy)-3-(trideuteriomethoxy)phenyl]ethyl]4-[(2-methoxy-N-[(3R)-quinuclidin-3-yl]oxycarbonyl-anilino)methyl]benzoate;

[(1S)-2-(3,5-dichloro-1-oxido-pyridin-1-ium-4-yl)-1-(3,4-dimethoxyphenyl)ethyl]4-[[2-pyridyl-[(3R)-quinuclidin-3-yl]oxycarbonyl-amino]methyl]benzoate;

[(1S)-1-[3-(cyclopropylmethoxy)-4-(difluoromethoxy)phenyl]-2-(3,5-dichloro-1-oxido-pyridin-1-ium-4-yl)ethyl]4-[[2-pyridyl-[(3R)-quinuclidin-3-yl]oxycarbonyl-amino]methyl]benzoate;

[(1S)-2-(3,5-dichloro-1-oxido-pyridin-1-ium-4-yl)-1-(3,4-dimethoxyphenyl)ethyl]4-[[3-pyridyl-[(3R)-quinuclidin-3-yl]oxycarbonyl-amino]methyl]benzoate;

[(1S)-1-[3-(cyclopentoxy)-4-(difluoromethoxy)phenyl]-2-(3,5-dichloro-1-oxido-pyridin-1-ium-4-yl)ethyl]3-[(2-fluoro-N-[(3R)-quinuclidin-3-yl]oxycarbonyl-anilino)methyl]benzoate;

[(1S)-1-[3-(cyclopentoxy)-4-(difluoromethoxy)phenyl]-2-(3,5-dichloro-1-oxido-pyridin-1-ium-4-yl)ethyl]4-[(2-fluoro-N-[(3R)-quinuclidin-3-yl]oxycarbonyl-anilino)methyl]benzoate;

[(1S)-2-(3,5-dichloro-1-oxido-pyridin-1-ium-4-yl)-1-(3,4-dimethoxyphenyl)ethyl]3-[[3-[(N-[(3R)-quinuclidin-3-yl]oxycarbonylanilino)methyl]phenoxy]methyl]benzoate;

[(1S)-2-(3,5-dichloro-1-oxido-pyridin-1-ium-4-yl)-1-(3,4-dimethoxyphenyl)ethyl]4-[[3-[(N-[(3R)-quinuclidin-3-yl]oxycarbonylanilino)methyl]phenoxy]methyl]benzoate;

[(1S)-2-(3,5-dichloro-1-oxido-pyridin-1-ium-4-yl)-1-(3,4-dimethoxyphenyl)ethyl]3-[[4-[(N-[(3R)-quinuclidin-3-yl]oxycarbonylanilino)methyl]phenoxy]methyl]benzoate;

[(1S)-2-(3,5-dichloro-1-oxido-pyridin-1-ium-4-yl)-1-(3,4-dimethoxyphenyl)ethyl]4-[[4-[(N-[(3R)-quinuclidin-3-yl]oxycarbonylanilino)methyl]phenoxy]methyl]benzoate;

[(1S)-1-[3-(cyclopropylmethoxy)-4-(difluoromethoxy)phenyl]-2-(3,5-dichloro-1-oxido-pyridin-1-ium-4-yl)ethyl]4-[(2-fluoro-N-[(3R)-quinuclidin-3-yl]oxycarbonyl-anilino)methyl]benzoate;

[(1S)-2-(3,5-dichloro-1-oxido-pyridin-1-ium-4-yl)-1-[4-(difluoromethoxy)-3-isopropoxy-phenyl]ethyl]4-[[2-pyridyl-[(3R)-quinuclidin-3-yl]oxycarbonyl-amino]methyl]benzoate;

[(1S)-2-(3,5-dichloro-1-oxido-pyridin-1-ium-4-yl)-1-[4-(difluoromethoxy)-3-(trideuteriomethoxy)phenyl]ethyl]4-[(2-fluoro-N-[(3R)-quinuclidin-3-yl]oxycarbonyl-anilino)methyl]benzoate;

[(1S)-2-(3,5-dichloro-1-oxido-pyridin-1-ium-4-yl)-1-[4-(difluoromethoxy)-3-methoxy-phenyl]ethyl]4-[(2-fluoro-N-[(3R)-quinuclidin-3-yl]oxycarbonyl-anilino)methyl]benzoate;

[(1S)-2-(3,5-dichloro-1-oxido-pyridin-1-ium-4-yl)-1-[4-(difluoromethoxy)-3-ethoxy-phenyl]ethyl]4-[(2-fluoro-N-[(3R)-quinuclidin-3-yl]oxycarbonyl-anilino)methyl]benzoate;

[(1S)-2-(3,5-dichloro-1-oxido-pyridin-1-ium-4-yl)-1-[4-(difluoromethoxy)-3-isopropoxy-phenyl]ethyl]4-[(2-fluoro-N-[(3R)-quinuclidin-3-yl]oxycarbonyl-anilino)methyl]benzoate;

[(1S)-2-(3,5-dichloro-1-oxido-pyridin-1-ium-4-yl)-1-(3,4-dimethoxyphenyl)ethyl]2-fluoro-5-[(2-fluoro-N-[(3R)-quinuclidin-3-yl]oxycarbonyl-anilino)methyl]benzoate;

[(1S)-2-(3,5-dichloro-1-oxido-pyridin-1-ium-4-yl)-1-(3,4-dimethoxyphenyl)ethyl]4-[2-(2-fluoro-N-[(3R)-quinuclidin-3-yl]oxycarbonyl-anilino)ethyl]benzoate;

[2-(3,5-dichloro-4-pyridyl)-1-(3,4-dimethoxyphenyl)ethyl]4-[(2-fluoro-N-[(3R)-quinuclidin-3-yl]oxycarbonyl-anilino)methyl]benzoate;

[2-(3,5-dichloro-4-pyridyl)-1-(3,4-dimethoxyphenyl)ethyl]3-[(2-fluoro-N-[(3R)-quinuclidin-3-yl]oxycarbonyl-anilino)methyl]benzoate;

[(1S)-2-(3,5-dichloro-1-oxido-pyridin-1-ium-4-yl)-1-(3,4-dimethoxyphenyl)ethyl]3-[(2-fluoro-N-[(3R)-quinuclidin-3-yl]oxycarbonyl-anilino)methyl]-5-methyl-benzoate;

[(1S)-1-[3-(cyclopropylmethoxy)-4-(difluoromethoxy)phenyl]-2-(3,5-dichloro-1-oxido-pyridin-1-ium-4-yl)ethyl]2-[3-[(N-[(3R)-quinuclidin-3-yl]oxycarbonylanilino)methyl]phenyl]acetate;

[(1S)-2-(3,5-dichloro-1-oxido-pyridin-1-ium-4-yl)-1-(3,4-dimethoxyphenyl)ethyl]2-[3-[(2-fluoro-N-[(3R)-quinuclidin-3-yl]oxycarbonyl-anilino)methyl]phenyl]acetate;

[(1R)-1-[3-(cyclopropylmethoxy)-4-methoxy-phenyl]-2-(3,5-dichloro-1-oxido-pyridin-1-ium-4-yl)ethyl]4-[(2-fluoro-N-[(3R)-quinuclidin-3-yl]oxycarbonyl-anilino)methyl]benzoate;

[(1S)-1-[3-(cyclopropylmethoxy)-4-methoxy-phenyl]-2-(3,5-dichloro-1-oxido-pyridin-1-ium-4-yl)ethyl]4-[(2-fluoro-N-[(3R)-quinuclidin-3-yl]oxycarbonyl-anilino)methyl]benzoate;

[(1R)-1-[3,4-bis(difluoromethoxy)phenyl]-2-(3,5-dichloro-1-oxido-pyridin-1-ium-4-yl)ethyl]3-[(2-fluoro-N-[(3R)-quinuclidin-3-yl]oxycarbonyl-anilino)methyl]benzoate;

[(1S)-1-[3,4-bis(difluoromethoxy)phenyl]-2-(3,5-dichloro-1-oxido-pyridin-1-ium-4-yl)ethyl]3-[(2-fluoro-N-[(3R)-quinuclidin-3-yl]oxycarbonyl-anilino)methyl]benzoate;

[(1R)-1-[3,4-bis(difluoromethoxy)phenyl]-2-(3,5-dichloro-1-oxido-pyridin-1-ium-4-yl)ethyl]4-[(2-fluoro-N-[(3R)-quinuclidin-3-yl]oxycarbonyl-anilino)methyl]benzoate;

[(1S)-1-[3,4-bis(difluoromethoxy)phenyl]-2-(3,5-dichloro-1-oxido-pyridin-1-ium-4-yl)ethyl]4-[(2-fluoro-N-[(3R)-quinuclidin-3-yl]oxycarbonyl-anilino)methyl]benzoate;

[(1R)-1-[3-(cyclopentoxy)-4-methoxy-phenyl]-2-(3,5-dichloro-1-oxido-pyridin-1-ium-4-yl)ethyl]4-[(2-fluoro-N-[(3R)-quinuclidin-3-yl]oxycarbonyl-anilino)methyl]benzoate;

[(1S)-1-[3-(cyclopentoxy)-4-methoxy-phenyl]-2-(3,5-dichloro-1-oxido-pyridin-1-ium-4-yl)ethyl]4-[(2-fluoro-N-[(3R)-quinuclidin-3-yl]oxycarbonyl-anilino)methyl]benzoate;

[(1R)-1-[3-(cyclopentoxy)-4-methoxy-phenyl]-2-(3,5-dichloro-1-oxido-pyridin-1-ium-4-yl)ethyl]3-[(2-fluoro-N-[(3R)-quinuclidin-3-yl]oxycarbonyl-anilino)methyl]benzoate;

[(1R)-1-[3-(cyclopropylmethoxy)-4-methoxy-phenyl]-2-(3,5-dichloro-1-oxido-pyridin-1-ium-4-yl)ethyl]3-[(2-fluoro-N-[(3R)-quinuclidin-3-yl]oxycarbonyl-anilino)methyl]benzoate;

[(1R)-1-[3-(cyclopentoxy)-4-methoxy-phenyl]-2-(3,5-dichloro-1-oxido-pyridin-1-ium-4-yl)ethyl]4-[[2-pyridyl-[(3R)-quinuclidin-3-yl]oxycarbonyl-amino]methyl]benzoate;

[(1S)-1-[3-(cyclopentoxy)-4-methoxy-phenyl]-2-(3,5-dichloro-1-oxido-pyridin-1-ium-4-yl)ethyl]4-[[2-pyridyl-[(3R)-quinuclidin-3-yl]oxycarbonyl-amino]methyl]benzoate;

[(1S)-1-[3-(cyclopentoxy)-4-methoxy-phenyl]-2-(3,5-dichloro-1-oxido-pyridin-1-ium-4-yl)ethyl]4-[[3-pyridyl-[(3R)-quinuclidin-3-yl]oxycarbonyl-amino]methyl]benzoate;

[(1R)-1-[3-(cyclopentoxy)-4-methoxy-phenyl]-2-(3,5-dichloro-1-oxido-pyridin-1-ium-4-yl)ethyl]4-[[3-pyridyl-[(3R)-quinuclidin-3-yl]oxycarbonyl-amino]methyl]benzoate;

[(1S)-1-[3-(cyclopropylmethoxy)-4-methoxy-phenyl]-2-(3,5-dichloro-1-oxido-pyridin-1-ium-4-yl)ethyl]4-[[3-pyridyl-[(3R)-quinuclidin-3-yl]oxycarbonyl-amino]methyl]benzoate;

[(1R)-1-[3-(cyclopropylmethoxy)-4-methoxy-phenyl]-2-(3,5-dichloro-1-oxido-pyridin-1-ium-4-yl)ethyl]4-[[3-pyridyl-[(3R)-quinuclidin-3-yl]oxycarbonyl-amino]methyl]benzoate;

[(1S)-1-[3-(cyclopropylmethoxy)-4-methoxy-phenyl]-2-(3,5-dichloro-1-oxido-pyridin-1-ium-4-yl)ethyl]4-[[2-pyridyl-[(3R)-quinuclidin-3-yl]oxycarbonyl-amino]methyl]benzoate;

[(1R)-1-[3-(cyclopropylmethoxy)-4-methoxy-phenyl]-2-(3,5-dichloro-1-oxido-pyridin-1-ium-4-yl)ethyl]4-[[2-pyridyl-[(3R)-quinuclidin-3-yl]oxycarbonyl-amino]methyl]benzoate;

[(1S)-2-(3,5-dichloro-1-oxido-pyridin-1-ium-4-yl)-1-(3,4-dimethoxyphenyl)ethyl]3-[(2-chloro-N-[(3R)-quinuclidin-3-yl]oxycarbonyl-anilino)methyl]benzoate;

[(1S)-2-(3,5-dichloro-1-oxido-pyridin-1-ium-4-yl)-1-(3,4-dimethoxyphenyl)ethyl]3-[(2,4-difluoro-N-[(3R)-quinuclidin-3-yl]oxycarbonyl-anilino)methyl]benzoate;

[(1S)-2-(3,5-dichloro-1-oxido-pyridin-1-ium-4-yl)-1-(3,4-dimethoxyphenyl)ethyl]4-fluoro-3-[(2-fluoro-N-[(3R)-quinuclidin-3-yl]oxycarbonyl-anilino)methyl]benzoate;

[(1S)-2-(3,5-dichloro-1-oxido-pyridin-1-ium-4-yl)-1-(3,4-dimethoxyphenyl)ethyl]4-fluoro-3-[(N-[(3R)-quinuclidin-3-yl]oxycarbonylanilino)methyl]benzoate;

[(1S)-2-(3,5-dichloro-1-oxido-pyridin-1-ium-4-yl)-1-(3,4-dimethoxyphenyl)ethyl]4-[(2-fluoro-4-methoxy-N-[(3R)-quinuclidin-3-yl]oxycarbonyl-anilino)methyl]benzoate;

[(1S)-2-(3,5-dichloro-1-oxido-pyridin-1-ium-4-yl)-1-(3,4-dimethoxyphenyl)ethyl]4-[[2-(difluoromethoxy)-N-[(3R)-quinuclidin-3-yl]oxycarbonyl-anilino]methyl]benzoate;

[(1S)-2-(3,5-dichloro-1-oxido-pyridin-1-ium-4-yl)-1-(3,4-dimethoxyphenyl)ethyl]4-[(2-fluoro-6-methoxy-N-[(3R)-quinuclidin-3-yl]oxycarbonyl-anilino)methyl]benzoate;

[(1S)-2-(3,5-dichloro-1-oxido-pyridin-1-ium-4-yl)-1-(3,4-dimethoxyphenyl)ethyl]4-[(2-hydroxy-N-[(3R)-quinuclidin-3-yl]oxycarbonyl-anilino)methyl]benzoate;

[(1S)-2-(3,5-dichloro-1-oxido-pyridin-1-ium-4-yl)-1-(3,4-dimethoxyphenyl)ethyl]4-[(3-hydroxy-N-[(3R)-quinuclidin-3-yl]oxycarbonyl-anilino)methyl]benzoate;

[(1S)-2-(3,5-dichloro-1-oxido-pyridin-1-ium-4-yl)-1-(3,4-dimethoxyphenyl)ethyl]4-[[(5-fluoro-3-pyridyl)-[(3R)-quinuclidin-3-yl]oxycarbonyl-amino]methyl]benzoate;

[(1S)-2-(3,5-dichloro-1-oxido-pyridin-1-ium-4-yl)-1-(3,4-dimethoxyphenyl)ethyl]4-[[(4-fluoro-2-pyridyl)-[(3R)-quinuclidin-3-yl]oxycarbonyl-amino]methyl]benzoate;

[(1S)-2-(3,5-dichloro-1-oxido-pyridin-1-ium-4-yl)-1-(3,4-dimethoxyphenyl)ethyl]4-[[3-(dimethylcarbamoyl)-N-[(3R)-quinuclidin-3-yl]oxycarbonyl-anilino]methyl]benzoate;

[(1S)-2-(3,5-dichloro-1-oxido-pyridin-1-ium-4-yl)-1-(3,4-dimethoxyphenyl)ethyl]4-[[(2-methoxy-3-pyridyl)-[(3R)-quinuclidin-3-yl]oxycarbonyl-amino]methyl]benzoate;

[(1S)-2-(3,5-dichloro-1-oxido-pyridin-1-ium-4-yl)-1-(3,4-dimethoxyphenyl)ethyl]4-[[(5-methoxy-3-pyridyl)-[(3R)-quinuclidin-3-yl]oxycarbonyl-amino]methyl]benzoate;

[(1S)-2-(3,5-dichloro-1-oxido-pyridin-1-ium-4-yl)-1-(3,4-dimethoxyphenyl)ethyl]4-[[(6-hydroxy-3-pyridyl)-[(3R)-quinuclidin-3-yl]oxycarbonyl-amino]methyl]benzoate;

[(1S)-2-(3,5-dichloro-1-oxido-pyridin-1-ium-4-yl)-1-(3,4-dimethoxyphenyl)ethyl]4-[(2-cyano-N-[(3R)-quinuclidin-3-yl]oxycarbonyl-anilino)methyl]benzoate;

[(1S)-1-[3-(cyclopropylmethoxy)-4-(difluoromethoxy)phenyl]-2-(3,5-dichloro-1-oxido-pyridin-1-ium-4-yl)ethyl]4-[[3-pyridyl-[(3R)-quinuclidin-3-yl]oxycarbonyl-amino]methyl]benzoate;

[(1S)-2-(3,5-dichloro-1-oxido-pyridin-1-ium-4-yl)-1-[4-(difluoromethoxy)-3-isopropoxy-phenyl]ethyl]4-[[3-pyridyl-[(3R)-quinuclidin-3-yl]oxycarbonyl-amino]methyl]benzoate;

[1-[3-(cyclopropylmethoxy)-4-methoxy-phenyl]-2-(3,5-dichloro-1-oxido-pyridin-1-ium-4-yl)ethyl]4-[[3-pyridyl-[(3R)-quinuclidin-3-yl]oxycarbonyl-amino]methyl]benzoate;

[1-[3-(cyclopentoxy)-4-methoxy-phenyl]-2-(3,5-dichloro-1-oxido-pyridin-1-ium-4-yl)ethyl]4-[[3-pyridyl-[(3R)-quinuclidin-3-yl]oxycarbonyl-amino]methyl]benzoate;

[(1S)-2-(3,5-dichloro-1-oxido-pyridin-1-ium-4-yl)-1-(3,4-dimethoxyphenyl)ethyl]4-3-[(2-fluoro-N-[(3R)-quinuclidin-3-yl]oxycarbonyl-anilino)methyl]phenyl]benzoate;

[(1S)-2-(3,5-dichloro-1-oxido-pyridin-1-ium-4-yl)-1-(3,4-dimethoxyphenyl)ethyl]3-[3-[(2-fluoro-N-[(3R)-quinuclidin-3-yl]oxycarbonyl-anilino)methyl]phenyl]benzoate;

[(1S)-2-(3,5-dichloro-1-oxido-pyridin-1-ium-4-yl)-1-(3,4-dimethoxyphenyl)ethyl]4-[4-[(2-fluoro-N-[(3R)-quinuclidin-3-yl]oxycarbonyl-anilino)methyl]phenyl]benzoate;

[(1S)-2-(3,5-dichloro-1-oxido-pyridin-1-ium-4-yl)-1-(3,4-dimethoxyphenyl)ethyl]3-[4-[(2-fluoro-N-[(3R)-quinuclidin-3-yl]oxycarbonyl-anilino)methyl]phenyl]benzoate;

[(1S)-2-(3,5-dichloro-1-oxido-pyridin-1-ium-4-yl)-1-(3,4-dimethoxyphenyl)ethyl]4-[[[(3R)-quinuclidin-3-yl]oxycarbonyl-thiazol-2-yl-amino]methyl]benzoate;

[(1S)-2-(3,5-dichloro-1-oxido-pyridin-1-ium-4-yl)-1-(3,4-dimethoxyphenyl)ethyl]4-[[1H-indazol-7-yl-[(3R)-quinuclidin-3-yl]oxycarbonyl-amino]methyl]benzoate;

[(1S)-2-(3,5-dichloro-1-oxido-pyridin-1-ium-4-yl)-1-(3,4-dimethoxyphenyl)ethyl]4-[[1H-indazol-7-yl-[(3R)-quinuclidin-3-yl]oxycarbonyl-amino]methyl]benzoate;

[(1S)-2-(3,5-dichloro-1-oxido-pyridin-1-ium-4-yl)-1-(3,4-dimethoxyphenyl)ethyl]4-[[1H-indol-7-yl-[(3R)-quinuclidin-3-yl]oxycarbonyl-amino]methyl]benzoate;

[(1S)-1-[3-(cyclopropylmethoxy)-4-(difluoromethoxy)phenyl]-2-(3,5-dichloro-1-oxido-pyridin-1-ium-4-yl)ethyl]4-[(2-hydroxy-N-[(3R)-quinuclidin-3-yl]oxycarbonyl-anilino)methyl]benzoate;

[(1S)-1-[3-(cyclopropylmethoxy)-4-(difluoromethoxy)phenyl]-2-(3,5-dichloro-1-oxido-pyridin-1-ium-4-yl)ethyl]3-[(2-hydroxy-N-[(3R)-quinuclidin-3-yl]oxycarbonyl-anilino)methyl]benzoate;

[(1S)-2-(3,5-dichloro-1-oxido-pyridin-1-ium-4-yl)-1-(3,4-dimethoxyphenyl)ethyl]4-[[3-(difluoromethyl)-N-[(3R)-quinuclidin-3-yl]oxycarbonyl-anilino]methyl]benzoate;

[(1S)-2-(3,5-dichloro-1-oxido-pyridin-1-ium-4-yl)-1-(3,4-dimethoxyphenyl)ethyl]4-[(3-fluoro-5-hydroxy-N-[(3R)-quinuclidin-3-yl]oxycarbonyl-anilino)methyl]benzoate;

[(1S)-2-(3,5-dichloro-1-oxido-pyridin-1-ium-4-yl)-1-(3,4-dimethoxyphenyl)ethyl]4-[(2-methoxy-3-hydroxy-N-[(3R)-quinuclidin-3-yl]oxycarbonyl-anilino)methyl]benzoate;

[(1S)-2-(3,5-dichloro-1-oxido-pyridin-1-ium-4-yl)-1-(3,4-dimethoxyphenyl)ethyl]4-[(2-methyl-3-hydroxy-N-[(3R)-quinuclidin-3-yl]oxycarbonyl-anilino)methyl]benzoate;

[(1S)-2-(3,5-dichloro-1-oxido-pyridin-1-ium-4-yl)-1-(3,4-dimethoxyphenyl)ethyl]4-[(2-chloro-5-hydroxy-N-[(3R)-quinuclidin-3-yl]oxycarbonyl-anilino)methyl]benzoate;

[(1S)-2-(3,5-dichloro-1-oxido-pyridin-1-ium-4-yl)-1-(3,4-dimethoxyphenyl)ethyl]4-[(2-fluoro-5-hydroxy-N-[(3R)-quinuclidin-3-yl]oxycarbonyl-anilino)methyl]benzoate;

[(1S)-2-(3,5-dichloro-1-oxido-pyridin-1-ium-4-yl)-1-(3,4-dimethoxyphenyl)ethyl]4-[(5-hydroxy-2-methyl-N-[(3R)-quinuclidin-3-yl]oxycarbonyl-anilino)methyl]benzoate;

[(1S)-2-(3,5-dichloro-1-oxido-pyridin-1-ium-4-yl)-1-(3,4-dimethoxyphenyl)ethyl]4-[(2-chloro-3-hydroxy-N-[(3R)-quinuclidin-3-yl]oxycarbonyl-anilino)methyl]benzoate;

[(1S)-2-(3,5-Dichloro-1-oxido-pyridin-1-ium-4-yl)-1-(3,4-dimethoxyphenyl)ethyl]3-[(3-hydroxy-N-[(3R)-quinuclidin-3-yl]oxycarbonyl-anilino)methyl]benzoate;

[(1S)-2-(3,5-dichloro-1-oxido-pyridin-1-ium-4-yl)-1-(3,4-dimethoxyphenyl)ethyl]3-[(2,6-difluoro-N-[(3R)-quinuclidin-3-yl]oxycarbonyl-anilino)methyl]benzoate;

[(1S)-1-[3-(cyclopropylmethoxy)-4-(difluoromethoxy)phenyl]-2-(3,5-dichloro-1-oxido-pyridin-1-ium-4-yl)ethyl]3-[(3-fluoro-N-[(3R)-quinuclidin-3-yl]oxycarbonyl-anilino)methyl]benzoate;

[(1S)-2-(3,5-dichloro-1-oxido-pyridin-1-ium-4-yl)-1-(3,4-dimethoxyphenyl)ethyl]3-[[2-pyridyl-[(3R)-quinuclidin-3-yl]oxycarbonyl-amino]methyl]benzoate;

[(1S)-2-(3,5-dichloro-1-oxido-pyridin-1-ium-4-yl)-1-(3,4-dimethoxyphenyl)ethyl]4-[(2-chloro-N-[(3R)-quinuclidin-3-yl]oxycarbonyl-anilino)methyl]benzoate;

[(1S)-2-(3,5-dichloro-1-oxido-pyridin-1-ium-4-yl)-1-(3,4-dimethoxyphenyl)ethyl]4-[(2,6-difluoro-N-[(3R)-quinuclidin-3-yl]oxycarbonyl-anilino)methyl]benzoate;

[(1S)-2-(3,5-dichloro-1-oxido-pyridin-1-ium-4-yl)-1-(3,4-dimethoxyphenyl)ethyl]3-[[3-pyridyl-[(3R)-quinuclidin-3-yl]oxycarbonyl-amino]methyl]benzoate;

[(1S)-2-(3,5-dichloro-1-oxido-pyridin-1-ium-4-yl)-1-(3,4-dimethoxyphenyl)ethyl]3-[(2-fluoro-4-hydroxy-N-[(3R)-quinuclidin-3-yl]oxycarbonyl-anilino)methyl]benzoate;

[(1S)-2-(3,5-dichloro-1-oxido-pyridin-1-ium-4-yl)-1-(3,4-dimethoxyphenyl)ethyl]3-[(4-hydroxy-N-[(3R)-quinuclidin-3-yl]oxycarbonyl-anilino)methyl]benzoate;

[(1S)-2-(3,5-dichloro-1-oxido-pyridin-1-ium-4-yl)-1-(3,4-dimethoxyphenyl)ethyl]3-[[4-(methanesulfonamido)-N-[(3R)-quinuclidin-3-yl]oxycarbonyl-anilino]methyl]benzoate;

[(1S)-2-(3,5-dichloro-1-oxido-pyridin-1-ium-4-yl)-1-(3,4-dimethoxyphenyl)ethyl]3-[(3-tert-butyl-N-[(3R)-quinuclidin-3-yl]oxycarbonyl-anilino)methyl]benzoate;

[(1S)-2-(3,5-dichloro-1-oxido-pyridin-1-ium-4-yl)-1-[4-(difluoromethoxy)-3-propoxy-phenyl]ethyl]4-[(2-fluoro-N-[(3R)-quinuclidin-3-yl]oxycarbonyl-anilino)methyl]benzoate;

[(1S)-2-(3,5-dichloro-1-oxido-pyridin-1-ium-4-yl)-1-[4-(difluoromethoxy)-3-propoxy-phenyl]ethyl]4-[(3-pyridyl-N-[(3R)-quinuclidin-3-yl]oxycarbonyl-anilino)methyl]benzoate;

[(1S)-2-(3,5-dichloro-1-oxido-pyridin-1-ium-4-yl)-1-(3,4-dimethoxyphenyl)ethyl]3-[[3-(methanesulfonamido)-N-[(3R)-quinuclidin-3-yl]oxycarbonyl-anilino]methyl]benzoate;

[(1S)-2-(3,5-dichloro-1-oxido-pyridin-1-ium-4-yl)-1-(3,4-dimethoxyphenyl)ethyl]4-[[4-(methanesulfonamido)-N-[(3R)-quinuclidin-3-yl]oxycarbonyl-anilino]methyl]benzoate;

[(1S)-2-(3,5-dichloro-1-oxido-pyridin-1-ium-4-yl)-1-(3,4-dimethoxyphenyl)ethyl]4-[[2-(cyclopropylmethoxy)-N-[(3R)-quinuclidin-3-yl]oxycarbonyl-anilino]methyl]benzoate;

[(1S)-2-(3,5-dichloro-1-oxido-pyridin-1-ium-4-yl)-1-(3,4-dimethoxyphenyl)ethyl]4-[[2-(cyclopropylmethoxy)-N-[(3R)-quinuclidin-3-yl]oxycarbonyl-anilino]methyl]benzoate;

[(1S)-2-(3,5-dichloro-1-oxido-pyridin-1-ium-4-yl)-1-(3,4-dimethoxyphenyl)ethyl]4-[(2-fluoro-6-hydroxy-N-[(3R)-quinuclidin-3-yl]oxycarbonyl-anilino)methyl]benzoate;

[(1S)-2-(3,5-dichloro-1-oxido-pyridin-1-ium-4-yl)-1-(3,4-dimethoxyphenyl)ethyl]4-[[3-(hydroxymethyl)-N-[(3R)-quinuclidin-3-yl]oxycarbonyl-anilino]methyl]benzoate;

[(1S)-2-(3,5-dichloro-1-oxido-pyridin-1-ium-4-yl)-1-(3,4-dimethoxyphenyl)ethyl]4-[(2-carbamoyl-N-[(3R)-quinuclidin-3-yl]oxycarbonyl-anilino)methyl]benzoate;

[(1S)-2-(3,5-dichloro-1-oxido-pyridin-1-ium-4-yl)-1-(3,4-dimethoxyphenyl)ethyl]4-[(2,3-dihydroxy-N-[(3R)-quinuclidin-3-yl]oxycarbonyl-anilino)methyl]benzoate;

[(1S)-2-(3,5-dichloro-1-oxido-pyridin-1-ium-4-yl)-1-(3,4-dimethoxyphenyl)ethyl]4-[(2,3-dihydroxy-N-[(3R)-quinuclidin-3-yl]oxycarbonyl-anilino)methyl]benzoate;

[(1S)-2-(3,5-dichloro-1-oxido-pyridin-1-ium-4-yl)-1-(3,4-dimethoxyphenyl)ethyl]4-[[[(3R)-quinuclidin-3-yl]oxycarbonyl-(1H-tetrazol-5-yl)amino]methyl]benzoate;

[(1S)-1-[3-(cyclopropylmethoxy)-4-(difluoromethoxy)phenyl]-2-(3,5-dichloro-1-oxido-pyridin-1-ium-4-yl)ethyl]3-[(2-fluoro-N-[(3R)-quinuclidin-3-yl]oxycarbonyl-anilino)methyl]benzoate;

[(1S)-1-[3-(cyclopropylmethoxy)-4-(difluoromethoxy)phenyl]-2-(3,5-dichloro-1-oxido-pyridin-1-ium-4-yl)ethyl]3-[(N-[(3R)-quinuclidin-3-yl]oxycarbonyl-anilino)methyl]benzoate; and

[(1S)-1-[3-(cyclopropylmethoxy)-4-(difluoromethoxy)phenyl]-2-(3,5-dichloro-1-oxido-pyridin-1-ium-4-yl)ethyl]2-hydroxy-3-[(2-hydroxy-N-[(3R)-quinuclidin-3-yl]oxycarbonyl-anilino)methyl]benzoate or a pharmaceutically acceptable salt of said compound.

8. A pharmaceutical composition, comprising a compound, N-oxide, deuterated derivative, or a pharmaceutically acceptable salt according to claim 1 and one or more pharmaceutically acceptable carriers.

9. A pharmaceutical composition according to claim 8, further comprising another active ingredient.

10. A method for the treatment of a disease of the respiratory tract characterized by airway obstruction, comprising administering an effective amount of a compound, N-oxide, deuterated derivative, or a pharmaceutically acceptable salt according to claim 1 to a subject in need thereof.

11. A method according to claim 10, wherein said disease of the respiratory tract is asthma or COPD.

12. An inhalation device comprising a pharmaceutical composition according to claim 8.

13. A kit, comprising a pharmaceutical composition according to claim 8 and a device which is a single- or multi-dose dry powder inhaler, a metered dose inhaler, or a nebulizer.

* * * * *